US009890373B2

(12) United States Patent
Nakata et al.

(10) Patent No.: US 9,890,373 B2
(45) Date of Patent: Feb. 13, 2018

(54) MODIFIED ISOPRENE SYNTHASE

(71) Applicant: AJINOMOTO CO., INC., Tokyo (JP)

(72) Inventors: Kunio Nakata, Kawasaki (JP); Yoshinori Tajima, Kawasaki (JP); Uno Tagami, Kawasaki (JP); Takashi Oku, Kobe (JP); Yasuhiro Kashima, Kobe (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 15/159,140

(22) Filed: May 19, 2016

(65) Prior Publication Data

US 2016/0257944 A1 Sep. 8, 2016

Related U.S. Application Data

(63) Continuation of application No. PCT/JP2014/080980, filed on Nov. 21, 2014.

(30) Foreign Application Priority Data

Nov. 22, 2013 (JP) ................................ 2013-242261

(51) Int. Cl.

| | |
|---|---|
| ***C12N 9/88*** | (2006.01) |
| ***C08F 36/08*** | (2006.01) |
| ***C12N 15/09*** | (2006.01) |
| ***C12P 5/02*** | (2006.01) |
| ***C08K 3/04*** | (2006.01) |
| ***C08K 3/22*** | (2006.01) |
| ***C12P 5/00*** | (2006.01) |

(52) U.S. Cl.

CPC ................ *C12N 9/88* (2013.01); *C08F 36/08* (2013.01); *C08K 3/04* (2013.01); *C08K 3/22* (2013.01); *C12N 15/09* (2013.01); *C12P 5/007* (2013.01); *C12P 5/026* (2013.01); *C12Y 402/03027* (2013.01); *C08K 2003/2296* (2013.01); *C12Y 402/03007* (2013.01)

(58) Field of Classification Search

None

See application file for complete search history.

(56) References Cited

U.S. PATENT DOCUMENTS

| | | | | |
|---|---|---|---|---|
| 8,173,410 | B2 | 5/2012 | Bott et al. | |
| 8,288,148 | B2 | 10/2012 | Cervin et al. | |
| 8,709,785 | B2 | 4/2014 | Cervin et al. | |
| 8,895,277 | B2 * | 11/2014 | Beatty ................. | C07K 14/415 435/167 |
| 8,916,370 | B2 | 12/2014 | Bott et al. | |
| 8,962,296 | B2 * | 2/2015 | Hayashi ......... | C12Y 402/03027 435/167 |
| 9,260,727 | B2 | 2/2016 | Cervin et al. | |
| 2010/0196977 | A1 | 8/2010 | Chotani et al. | |
| 2011/0039323 | A1 | 2/2011 | Singsaas et al. | |
| 2011/0045563 | A1 | 2/2011 | Melis | |
| 2011/0076743 | A1 | 3/2011 | Beck et al. | |
| 2013/0045891 | A1 | 2/2013 | Beck et al. | |
| 2013/0295632 | A1 | 11/2013 | Rife et al. | |
| 2013/0330709 | A1 | 12/2013 | Beatty et al. | |
| 2013/0330796 | A1 | 12/2013 | Beck et al. | |
| 2015/0191712 | A1 | 7/2015 | Bott et al. | |

FOREIGN PATENT DOCUMENTS

| | | | |
|---|---|---|---|
| JP | 2011-505841 | A | 3/2011 |
| JP | 2011-518564 | A | 6/2011 |
| JP | 2012-516677 | A | 7/2012 |
| WO | 2013/016591 | A1 | 1/2013 |
| WO | 2013/166320 | A1 | 11/2013 |
| WO | 2013/179722 | A1 | 12/2013 |

OTHER PUBLICATIONS

International Search Report in PCT/JP2014/080980 dated Feb. 6, 2015.

Kesselmeier, J. et al., "Biogenic Volatile Organic Compounds (VOC); An Overview on Emission, Physiology and Ecology", Journal of Atmospheric Chemistry, vol. 33, pp. 23-88, (1999).

Monson, R. K. et al., "Relationships among Isoprene Emission Rate, Photosynthesis, and Isoprene Synthase Activity as Influenced by Temperature" Plant Physiol., vol. 98, pp. 1175-1180, (1992).

Kuzma, J. et al., "Leaf Isoprene Emission rate is Dependent on Leaf Development and the Level of Isoprene Synthase", Plant Physiol., vol. 101, pp. 435-440, (1993).

European Search Report dated May 16, 2017, in European Patent Application No. 14864940.3.

Peter C. Harley et al., "Isoprene Emission from Velvet Bean Leaves", Interactions among Nitrogen Availability, Growth Photon Flux Density, and Leaf Development, Plant Physiol vol. 105, May 1, 1994, pp. 279-285, XP055368428.

* cited by examiner

*Primary Examiner* — Hope Robinson

(74) *Attorney, Agent, or Firm* — Oblon, McClelland, Maier & Neustadt, L.L.P.

(57) ABSTRACT

The present application relates to a modified isoprene synthase that has an isoprene synthetic activity and has at least one mutation of an amino acid residue in the amino acid sequence of SEQ ID NO: 4, an amino acid sequence having one or several amino acid substitutions, deletions, insertions or additions in the amino acid sequence of SEQ ID NO: 4, or an amino acid sequence having 90% or more identity to the amino acid sequence of SEQ ID NO: 4. The modified isoprene synthase is useful for preparing isoprene monomers in improved yields.

9 Claims, 2 Drawing Sheets pstS-attTn7-KKDyI-glmS rc
9175 bp pstS-attTn7-Ptac-KKDyI-glmS Tet(S) rc
7464 bp

MODIFIED ISOPRENE SYNTHASE

CROSS REFERENCES TO RELATED APPLICATIONS

This application is a continuation of International Patent Application No. PCT/JP2014/080980, filed on Nov. 21, 2014, and claims priority to Japanese Patent Application No. 2013-242261, filed on Nov. 22, 2013, both of which are incorporated herein by reference in their entireties.

BACKGROUND OF THE INVENTION

Field of the Invention

The present invention relates to modified isoprene synthases, polynucleotides which encode such an isoprene synthase, and methods of producing isoprene with such an isoprene synthase.

Discussion of the Background

Natural rubbers are very important raw materials in the tire industry and rubber industries. While demands for rubbers will expand in motorization mainly in developing countries in future, increase of farm plantations is not easy due to regulation to deforestation and competition with palms. Thus, it is predicted that the increase of natural rubber yields is difficult to be anticipated and the balance of demands and supplies will become tight. Synthesized polyisoprene is available as a material in place of the natural rubber, and its raw material monomer, isoprene (2-methyl-1,3-butadiene), is obtained by extracting from a C5 fraction obtained by cracking of naphtha. However in recent years, with lightening in the field of crackers, the production amount of isoprene has tended to decrease, and its supply has been apprehended. Also in recent years, due to strong influence of variation in oil prices, establishment of a system for inexpensively producing isoprene derived from non-oil resource has been required for stably securing an isoprene monomer.

For such a demand, methods of producing the isoprene monomer using a transformant obtained by integrating an isolated isoprene synthase gene derived from kudzu or poplar and its mutant into a bacterium for fermentation production, and the like have been disclosed (see Japanese Laid-Open Publication No. 2011-505841, Japanese Laid-Open Publication No. 2011-518564, US Patent Application Publication No. 2011/0076743, US Patent Application Publication No. 2013/0045891, US Patent Application Publication No. 2013/0295632, US Patent Application Publication No. 2013/0330709, US Patent Application Publication No. 2013/0330796, US Patent Application Publication No. 2013/0295632, US Patent Application Publication No. 2011/0045563, US Patent Application Publication No. 2011/0039323, International Publication WO 2013/016591, Kesselmeier J. et al., Journal of Atmospheric Chemistry, vol. 33, pages 23-88, 1999, Monson R. K. et al., Plant Physiol., vol. 98, pages 1175-1180, 1992, and Kuzma J. et al., Plant Physiol., vol. 101, pages 435-440, 1993, all of which are incorporated herein by reference in their entireties).

There remains, however, a need for improved transformants.

SUMMARY OF THE INVENTION

Accordingly, it is one object of the present invention to provide novel isoprene synthases.

It is another object of the present invention to provide novel polynucleotides which encode such an isoprene synthase.

It is another object of the present invention to provide novel methods of producing isoprene with such an isoprene synthase.

It is another object of the present invention to achieve a high productivity of isoprene monomer by using a further improved enzyme.

It is another object of the present invention to provide an enzyme and the like useful for establishing an excellent isoprene monomer production system These and other objects, which will become apparent during the following detailed description, have been achieved by the inventors' discovery of a modified isoprene synthase having an excellent isoprene monomer productivity by mutating an amino acid residue of isoprene synthase derived from *Mucuna* (*Mucuna bracteata*).

Namely, the present invention is as follows.

(1) A modified isoprene synthase that has a mutation(s) of an amino acid residue(s) corresponding to one or more amino acid residues selected from the following:

S2, F31, L35, L67, I90, V97, L114, Q123, D124, V125, K127, R128, K130, D131, G134, C137, V144, V187, R202, L224, L247, S248, L249, T257, K259, R264, D265, R266, E269, C286, K292, T298, I300, D301, Y304, D305, E312, F316, E321, V325, I328, C338, L340, C370, E371, C373, E379, S383, K386, I388, A390, Y394, S401, S402, G404, V405, L414, C416, C440, R444, N447, R458, T461, T462, T466, E471, C480, K481, R484, K492, V499, P505, F508, I518, S519, H520, C521, Y523, and G530 in any amino acid sequence of (a) the amino acid sequence of SEQ ID NO:4, (b) an amino acid sequence having one or several amino acid substitutions, deletions, insertions or additions in the amino acid sequence of SEQ ID NO:4, or (c) an amino acid sequence having 90% or more identity to the amino acid sequence of SEQ ID NO:4, and has an isoprene synthetic activity.

(2) The modified isoprene synthase according to (1), wherein said mutation is selected from the group consisting of S2A, F31E, F31K, L35E, L35K, L67E, 190E, V97E, L114E, Q123C, D124E, V125E, K127D, K127E, K127N, K127R, R128K, K130G, D131C, G134P, C137E, C137I, C137L, C137M, C137S, V144E, V187E, R202D, R202N, L224E, L247D, L247E, L247Q, S248E, S248K, S248R, L249E, L249K, L249R, L249T, T257L, K259D, K259E, K259N, K259Q, K259R, R264F, R264M, R264T, D265E, D265N, D265Q, D265R, R266N, R266Q, E269D, E269I, E269Y, C286V, C286N, K292L, T298I, I300N, D301R, Y304F, D305R, E312I, E312R, F316E, E321D, V325K, I328E, C338V, C338L, L340K, C370E, C370N, C370K, C370V, E371D, C373V, C373Y, E379T, S383I, K386R, I388C, A390C, Y394F, S401T, S402L, G404A, G404M, V405C, L414C, C416E, C440S, R444T, N447L, N447R, R458Q, T461R, T462M, T462S, T466F, T466C, T466W, T466M, T466Y, T466H, T466P, T466Q, T466N, T466A, E471C, C480N, C480Y, C480V, K481E, R484K, K492E, V499I, P505H, F508C, F508Q, F508R, I518C, I518S, S519N, H520N, C521N, C521S, C521V, C521E, C521I, Y523I, Y523L, and G530K.

(3) The modified isoprene synthase according to (1) or (2), further having a signal sequence at N-terminus.

(4) The modified isoprene synthase according to (3), which has a mutation(s) of an amino acid residue(s) corresponding to one or more amino acid residues selected from the following:

S45, F74, L78, L110, I133, V140, L157, Q166, D167, V168, K170, R171, K173, D174, G177, C180, V187, V230, R245, L267, L290, S291, L292, T300, K302, R307, D308, R309, E312, C329, K335, T341, I343, D344, Y347, D348, E355, F359, E364, V368, I371, C381, L383, C413, E414, C416, E422, S426, K429, I431, A433, Y437, S444, S445, G447, V448, L457, C459, C483, R487, N490, R501, T504, T505, T509, E514, C523, K524, R527, K535, V542, P548, F551, I561, S562, H563, C564, Y566, and G573 in any amino acid sequence of (d) the amino acid sequence of SEQ ID NO:2, (e) an amino acid sequence having one or several amino acid substitutions, deletions, insertions or additions in the amino acid sequence of SEQ ID NO:2, or (f) an amino acid sequence having 90% or more identity to the amino acid sequence of SEQ ID NO:2, and has an isoprene synthetic activity.

(5) The modified isoprene synthase according to (4), wherein said mutation is selected from the group consisting of S45A, F74E, F74K, L78E, L78K, L110E, I133E, V140E, L157E, Q166C, D167E, V168E, K170D, K170E, K170N, K170R, R171K, K173G, D174C, G177P, C180E, C180I, C180L, C180M, C180S, C180M, V187E, V230E, R245D, R245N, L267E, L290D, L290E, L290Q, S291E, S291K, S291R, L292E, L292K, L292R, L292T, T300L, K302D, K302E, K302N, K302Q, K302R, R307F, R307M, R307T, D308E, D308N, D308Q, D308R, R309N, R309Q, E312D, E312I, E312Y, C329V, C329N, K335L, T341I, I343N, D344R, Y347F, D348R, E355I, E355R, F359E, E364D, V368K, I371E, C381V, C381L, L383K, C413E, C413N, C413K, C413V, E414D, C416V, C416Y, E422T, S426I, K429R, I431C, A433C, Y437F, S444T, S445L, G447A, G447M, V448C, L457C, C459E, C483S, R487T, N490L, N490R, R501Q, T504R, T505M, T505S, T509F, T509C, T509W, T509M, T509Y, T509H, T509P, T509Q, T509N, T509A, E514C, C523N, C523Y, C523V, K524E, R527K, K535E, V542I, P548H, F551C, F551Q, F551R, I561C, I561S, S562N, H563N, C564N, C564S, C564V, C564E, C564I, Y566I, Y566L, and G573K.

(6) A polynucleotide encoding the modified isoprene synthase according to any one of (1) to (5).

(7) An expression vector comprising the polynucleotide according to (6).

(8) A host cell comprising an expression unit of a polynucleotide encoding the modified isoprene synthase according to any one of (1) to (5).

(9) The host cell according to (8), wherein said host cell has an ability to synthesize dimethylallyl diphosphate via a methylerythritol phosphate pathway.

(10) The host cell according to (9), wherein said host cell is an *Escherichia coli*.

(11) The host cell according to any one of (8) to (10), wherein said host cell has an ability to synthesize dimethylallyl diphosphate via both a mevalonate pathway and a methylerythritol phosphate pathway.

(12) The host cell according to (8), wherein said host cell is a microorganism belonging to the genus *Corynebacterium*, the genus *Pantoea*, the genus *Enterobacter* or the genus *Saccharomyces*.

(13) A method for producing a modified isoprene synthase, comprising producing the modified isoprene synthase using the host cell according to any one of (8) to (12).

(14) A method for producing a modified isoprene monomer, comprising producing the isoprene monomer from dimethylallyl diphosphate in the presence of the modified isoprene synthase according to any one of (1) to (5).

(15) The method according to (14), wherein the isoprene monomer is produced by cultivation of the host cell according to any one of (8) to (12) in a medium.

(16) The method according to (15), wherein the dimethylallyl diphosphate is supplied from a carbon source in medium by cultivation of said host cell.

(17) A method for producing an isoprene polymer, comprising (I) and (II):

(I) producing an isoprene monomer by the method according to any one of (14) to (16), and (II) polymerizing the isoprene monomer to form the isoprene polymer.

(18) A polymer derived from an isoprene monomer produced by the method according to any one of (14) to (16).

(19) A rubber composition comprising the polymer according to (18).

(20) A tire produced by the use of the rubber composition according to (19).

According to the present invention, an excellent isoprene monomer production system can be established.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
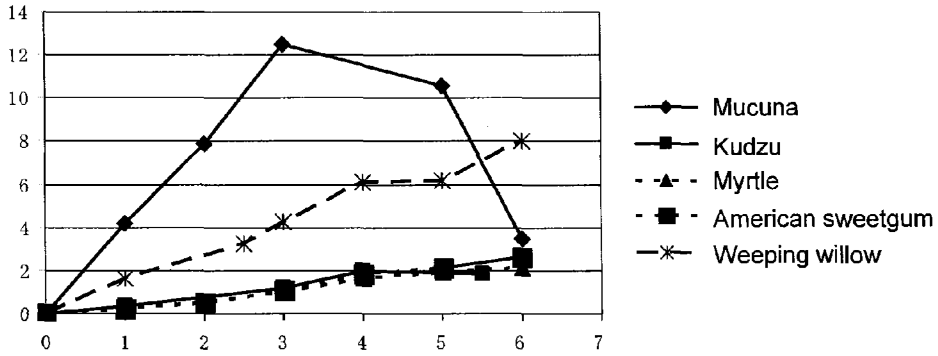
FIG. 1 shows the amounts of isoprene generated per unit weight of dry leaves from various plants.

The present invention provides a modified isoprene synthase.

Isoprene synthase is an enzyme that converts dimethylallyl diphosphate into isoprene. The modified isoprene synthase of the present invention can be derived from *Mucuna*. The isoprene synthase derived from *Mucuna* is a protein encoded by an amino acid sequence of SEQ ID NO:4 (a mature protein in which a signal sequence has been removed) or a protein encoded by an amino acid sequence of SEQ ID NO:2 (a protein having the signal sequence). The isoprene synthase derived from *Mucuna* may delete a methionine residue artificially added to an N-terminus of the amino acid sequence of SEQ ID NO:4.

In one embodiment, the modified isoprene synthase of the present invention can be a mutant of isoprene synthase having no signal sequence at the N-terminus. The isoprene synthase having no signal sequence at N-terminus is one comprising any amino acid sequence of:

(a) the amino acid sequence of SEQ ID NO:4;

(b) an amino acid sequence having one or several amino acid substitutions, deletions, insertions or additions in the amino acid sequence of SEQ ID NO:4; or (c) an amino acid sequence having 90% or more identity to the amino acid sequence of SEQ ID NO:4;

and having an isoprene synthetic activity.

In the present invention, the term isoprene synthetic activity refers to an activity to convert dimethylallyl diphosphate into isoprene (the same shall apply hereinafter).

The modified isoprene synthase of the present invention may have the signal sequence at the N-terminus. In another embodiment, the modified isoprene synthase of the present invention is a mutant of isoprene synthase having the signal sequence at the N-terminus. Examples of the signal sequence may include transit signal sequences such as a chloroplast transit signal sequence (e.g., a sequence composed of amino acid residues at positions 1 to 44 in the amino acid sequence of SEQ ID NO:2) and secretory signal sequences. Examples of the isoprene synthase having the signal sequence at the N-terminus may include those that have a mutation(s) of an amino acid residue(s) corresponding to one or more amino acid residues selected from the followings in any amino acid sequence of (d) the amino acid sequence of SEQ ID NO:2;

(e) an amino acid sequence having one or several amino acid substitutions, deletions, insertions or additions in the amino acid sequence of SEQ ID NO:2; or (f) an amino acid sequence having 90% or more identity to the amino acid sequence of SEQ ID NO:2;

and have an isoprene synthetic activity.

The isoprene synthase of each of the above (b) and (d) may comprise a mutation (e.g., substitution, deletion, insertion, and addition) of one or several amino acid residues. The number of mutation is, for example, 1 to 50, preferably 1 to 40, more preferably 1 to 30, still more preferably 1 to 20, and most preferably 1 to 10 (e.g., 1, 2, 3, 4, or 5).

The isoprene synthase of each of the above (c) and (f) may comprise an amino acid sequence having 90% or more identity to the amino acid sequences represented by SEQ ID NO:4 and SEQ ID NO:2. The amino acid sequence percent identity may be preferably 92% or more, more preferably 95% or more, further preferably 97% or more, and most preferably 98% or more, or 99% or more.

The identity of the amino acid sequences can be determined, for example, using the algorithm BLAST (Pro. Natl. Acad. Sci. USA, 90, 5873 (1993) which is incorporated herein by reference in its entirety) by Karlin and Altschul, and the FASTA algorithm (Methods Enzymol., 183, 63 (1990) which is incorporated herein by reference in its entirety) by Pearson. The program referred to as BLASTP was developed based on the algorithm BLAST (see http (colon)//www(dot)ncbi(dot)nlm(dot)nih(dot)gov). Thus, the identity of the amino acid sequences may be calculated using this program with default setting. Also, for example, a numerical value obtained by calculating similarity as a percentage at a setting of "unit size to compare=2" using the full length of a polypeptide portion encoded in ORF with the software GENETYX Ver. 7.0.9 from Genetyx Corporation employing the Lipman-Pearson method may be used as the identity of the amino acid sequences. Alternatively, the homology may be a value (Identity) calculated using a parameter of default setting (Gap penalty=10, Extend penalty=0.5, Matrix=EBLOSUM62) in a NEEDLE program (J Mol Biol 1970; 48: 443-453, which is incorporated herein by reference in its entirety) search. The lowest value among the values derived from these calculations may be employed as the identity of the amino acid sequences.

A position of an amino acid residue into which a mutation can be introduced in the amino acid sequence of any of the above (b), (c), (d), and (f) is known to those skilled in the art, and, for example, an additional mutation can be introduced with reference to an alignment of amino acid sequences. Specifically, a person skilled in the art can recognize a correlation between structure and function, since a person skilled in the art can 1) compare the amino acid sequences of multiple homologs (known isoprene synthases), 2) clarify regions that are relatively conserved and regions that are not relatively conserved, and then 3) predict regions capable of playing a functionally important role and regions incapable of playing a functionally important role from the regions that are relatively conserved and the regions that are not relatively conserved, respectively.

When the additional mutation of the amino acid residue is substitution, the substitution of the amino acid residue may be conservative substitution. The term "conservative substitution" refers to substitution of a certain amino acid residue with an amino acid residue having a similar side chain. Families of amino acid residues having similar side chains are well-known in the art. Examples of such families may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a branched side chain at position β (e.g., threonine, valine, isoleucine), amino acids having an aromatic side chain (e.g., tyrosine, phenylalanine, tryptophan, histidine), amino acids having a hydroxyl group-containing (e.g., alcoholic, phenolic) side chain (e.g., serine, threonine, tyrosine), and amino acids having a sulfur-containing side chain (e.g., cysteine, methionine). Preferably, the conservative substitution of the amino acids may be the substitution between aspartic acid and glutamic acid, the substitution among arginine, lysine and histidine, the substitution between tryptophan and phenylalanine, the substitution between phenylalanine and valine, the substitution among leucine, isoleucine and alanine, and the substitution between glycine and alanine.

In the modified isoprene synthase of the present invention, at least one amino acid residue is mutated so as to improve an amount of isoprene to be produced. Examples of mutations of amino acid residues may include substitution, deletion, addition and insertion, and the substitution is preferred. An amino acid residue to be mutated is L-alanine (A), L-asparagine (N), L-cysteine (C), L-glutamine (Q), L-isoleucine (I), L-leucine (L), L-methionine (M), L-phenylalanine (F), L-proline (P), L-serine (S), L-threonine (T), L-tryptophan (W), L-tyrosine (Y), L-valine (V), L-aspartic acid (D), L-glutamic acid (E), L-arginine (R), L-histidine (H) or L-lysine (K) that is a naturally occurring L-α-amino acid, or glycine (G). When the mutation is substitution, addition or insertion, an amino acid residue after the substitution, addition or insertion corresponds to the amino acid residue to be mutated as described above. Hereinafter, "L" and "a" may be omitted in description of amino acids.

The modified isoprene synthase of the present invention comprising a mutation of an amino acid residue for improving the amount of isoprene to be produced may comprise the mutation(s) of the amino acid residue(s) corresponding to one or more amino acid residues selected from S2, F31, L35, L67, I90, V97, L114, Q123, D124, V125, K127, R128, K130, D131, G134, C137, V144, V187, R202, L224, L247, S248, L249, T257, K259, R264, D265, R266, E269, C286, K292, T298, I300, D301, Y304, D305, E312, F316, E321, V325, I328, C338, L340, C370, E371, C373, E379, S383, K386, I388, A390, Y394, S401, S402, G404, V405, L414, C416, C440, R444, N447, R458, T461, T462, T466, E471, C480, K481, R484, K492, V499, P505, F508, I518, S519, H520, C521, Y523, and G530 in the amino acid sequences of (a) to (c) above. Because the amino acid sequences of (a) to (c) above may have the signal sequence at the N-terminus and may have the mutation such as deletion and substitution, the above position can alter depending on the presence or absence of the signal sequence and its length, the presence or absence of the mutation, and the like. For example, when the amino acid sequences of (a) to (c) above having the signal sequence at the N-terminus are the amino acid sequences of (d) to (f) above, the modified isoprene synthase of the present invention comprising a mutation of an amino acid residue for improving the amount of isoprene to be produced may comprise the mutation(s) of the amino acid residue(s) corresponding to one or more amino acid residues selected from S45, F74, L78, L110, I133, V140, L157, Q166, D167, V168, K170, R171, K173, D174, G177, C180, V187, V230, R245, L267, L290, S291, L292, T300, K302, R307, D308, R309, E312, C329, K335, T341, I343, D344, Y347, D348, E355, F359, E364, V368, I371, C381, L383, C413, E414, C416, E422, S426, K429, I431, A433, Y437, S444, S445, G447, V448, L457, C459, C483, R487, N490, R501, T504, T505, T509, E514, C523, K524, R527, K535, V542, P548, F551, I561, S562, H563, C564, Y566, and G573 in the amino acid sequences of (d) to (f) above. The modified isoprene synthase of the present invention may comprise a plurality of (e.g., 1 to 10, 1 to 5, 1 to 3, or 1 or 2) the mutations at above positions in combination. A mutation of an amino acid residue(s) in certain embodiments described later may also comprise a plurality of the same mutations as above at positions described above.

In one embodiment, the mutation of the amino acid residue for improving the amount of isoprene to be produced is introduced so that an isoprene synthetic activity is enhanced relative to the isoprene synthase derived from *Mucuna* (hereinafter referred to as isoprene synthase before modification if necessary). Examples of the mutation of the amino acid residue for enhancing the isoprene synthetic activity may include mutations of amino acid residues corresponding to one or more amino acid residues selected from F31, L35, L67, I90, V97, D124, V125, K127, R128, K130, D131, G134, C137, R202, L247, S248, L249, T257, K259, R264, D265, R266, E269, C286, K292, T298, D301, D305, E312, F316, E321, V325, I328, L340, C370, E371, C373, E379, S383, K386, A390, S401, S402, G404, R444, N447, R458, T461, T462, E471, C480, K481, R484, K492, V499, P505, F508, I518, S519, H520, C521, Y523, and G530 in the amino acid sequences of (a) to (c) above. Alternatively, when the amino acid sequence of (a) to (c) above having the signal sequence at the N-terminus is the amino acid sequence of (d) to (f) above, the modified isoprene synthase of the present invention comprising a mutation of an amino acid residue for improving the amount of isoprene to be produced may be those comprising the mutation(s) of the amino acid residue(s) corresponding to one or more amino acid residues selected from F74, L78, L110, I133, V140, D167, V168, K170, R171, K173, D174, G177, C180, R245, L290, S291, L292, T300, K302, R307, D308, R309, E312, C329, K335, T341, D344, D348, E355, F359, E364, V368, I371, L383, C413, E414, C416, E422, S426, K429, A433, S444, S445, G447, R487, N490, R501, T504, T505, E514, C523, K524, R527, K535, V542, P548, F551, I561, S562, H563, C564, Y566, and G573 in the amino acid sequence of (d) to (f) above. The extent of enhancement of the isoprene synthetic activity of the modified isoprene synthase relative to the isoprene synthase before the modification (e.g., SEQ ID NO:4 or SEQ ID NO:2) is not particularly limited as long as the activity is enhanced relative to that of the isoprene synthase before the modification, and is, for example, 1.1 fold or more, preferably 1.2 fold or more, more preferably 1.3 fold or more, still more preferably 1.5 fold or more, and most preferably 2 fold or more.

More specifically, the modified isoprene synthase comprising a mutation of an amino acid residue for enhancing the isoprene synthetic activity may be those comprising the mutation(s) of the amino acid residue(s) corresponding to one or more amino acid residues selected from F31E, F31K, L35E, L35K, L67E, 190E, V97E, D124E, V125E, K127D, K127E, K127N, K127R, R128K, K130G, D131C, G134P, C137E, C137I, C137L, C137M, C137S, R202D, R202N, L247D, L247E, L247Q, S248E, S248K, S248R, L249E, L249K, L249R, L249T, T257L, K259D, K259E, K259N, K259Q, K259R, R264F, R264M, R264T, D265E, D265N, D265Q, D265R, R266N, R266Q, E269D, E269I, E269Y, C286N, K292L, T298I, D301R, D305R, E312I, E312R, F316E, E321D, V325K, I328E, L340K, C370V, E371D, C373Y, E379T, K386R, A390C, S401T, S402L, G404A, G404M, R444T, N447L, N447R, R458Q, T461R, T462M, E471C, C480N, C480Y, K481E, R484K, K492E, V499I, P505H, F508C, F508Q, F508R, I518C, I518S, S519N, H520N, C521N, Y523I, Y523L, and G530K in the amino acid sequences of (a) to (c) above. Alternatively, when the amino acid sequence of (a) to (c) above having the signal sequence at the N-terminus is the amino acid sequence of (d) to (f) above, the modified isoprene synthase of the present invention comprising a mutation of an amino acid residue for improving the amount of isoprene to be produced may be those comprising the mutation(s) of the amino acid residue(s) corresponding to one or more amino acid residues selected from F74E, F74K, L78E, L78K, L110E, I133E, V140E, D167E, V168E, K170D, K170E, K170N, K170R, R171K, K173G, D174C, G177P, C180E, C180I, C180L, C180M, C180S, R245D, R245N, L290D, L290E, L290Q, S291E, S291K, S291R, L292E, L292K, L292R, L292T, T300L, K302D, K302E, K302N, K302Q, K302R, R307F, R307M, R307T, D308E, D308N, D308Q, D308R, R309N, R309Q, E312D, E312I, E312Y, C329N, K335L, T341I, D344R, D348R, E355I, E355R, F359E, E364D, V368K, I371E, L383K, C413V, E414D, C416Y, E422T, K429R, A433C, S444T, S445L, G447A, G447M, R487T, N490L, N490R, R501Q, T504R, T505M, E514C, C523N, C523Y, K524E, R527K, K535E, V542I, P548H, F551C, F551Q, F551R, I561C, I561S, S562N, H563N, C564N, Y566I, Y566L, and G573K in the amino acid sequence of (d) to (f) above.

In another embodiment, the mutation of amino acid residue for improving the amount of isoprene to be produced is introduced so that enzyme stability is improved relative to the isoprene synthase before the modification. Improvement of the enzyme stability can be confirmed, for example, by comparing an accumulation rate of isoprene by the modified isoprene synthase with that by the isoprene synthase before the modification, as described later in the examples. Examples of the mutations of amino acid residues for improving the enzyme stability may include the mutation(s) of the amino acid residue(s) corresponding to one or more amino acid residues selected from S2, V97, L114, Q123, V125, D131, C137, V144, V187, L224, C286, T298, I300, C338, C370, C373, S383, I388, A390, V405, L414, C416, C440, E471, C480, K481, I518, and C521 in the amino acid sequences of (a) to (c) above. Alternatively, when the amino acid sequence of (a) to (c) above having the signal sequence at the N-terminus is the amino acid sequence of (d) to (f) above, the modified isoprene synthase of the present invention comprising a mutation of an amino acid residue for improving the enzyme stability may be those comprising the mutation(s) of the amino acid residue(s) corresponding to one or more amino acid residues selected from S45, V140, L157, Q166, V168, D174, C180, V187, V230, L267, C329, T341, I343, C381, C413, C416, S426, I431, A433, V448, L457, C459, C483, E514, C523, K524, I561, and C564 in the amino acid sequences of (d) to (f) above. The extent of the improvement of the enzyme stability of the modified isoprene synthase relative to the isoprene synthase before the modification (e.g., SEQ ID NO:4 or SEQ ID NO:2) is not particularly limited as long as the enzyme stability is improved relative to the isoprene synthase before the modification, and is, for example, 1.1 fold or more, preferably 1.3 fold or more, more preferably 1.5 fold or more, still more preferably 2 fold or more, and most preferably 3 fold or more.

More specifically, the modified isoprene synthase comprising a mutation of an amino acid residue for improving the enzyme stability may be those comprising the mutation(s) of the amino acid residue(s) corresponding to one or more amino acid residues selected from S2A, V97E, L114E, Q123C, V125E, D131C, C137E, C137I, C137M, C137S, V144E, V187E, L224E, C286V, C286N, T298I, I300N, C338V, C338L, C370V, C370E, C370N, C370K, C373V, C373Y, S383I, I388C, A390C, V405C, L414C, C416E, C440S, E471C, C480N, C480V, C480Y, K481E, I518C, C521E, C521I, C521S, C521N, and C521V in the amino acid sequences of (a) to (c) above. Alternatively, when the amino acid sequence of (a) to (c) above having the signal sequence at the N-terminus is the amino acid sequence of (d) to (f) above, the modified isoprene synthase of the present invention comprising a mutation of an amino acid residue for improving the enzyme stability may those comprising the mutation(s) of the amino acid residue(s) corresponding to one or more amino acid residues selected from S45A, V140E, L157E, Q166C, V168E, D174C, C180E, C180I, C180M, C180S, V187E, V230E, L267E, C329V, C329N, T341I, I343N, C381V, C381L, C413V, C413E, C413N, C413K, C416V, C416Y, S426I, I431C, A433C, V448C, L457C, C459E, C483S, E514C, C523N, C523V, C523Y, K524E, I561C, C564E, C564I, C564S, C564N, and C564V in the amino acid sequences of (d) to (f) above.

In still another embodiment, the mutation of the amino acid residue for improving the amount of isoprene to be produced is introduced so that the amount of isoprene to be produced in a host is improved relative to that by the isoprene synthase before the modification. The improvement of the amount of isoprene to be produced in the host is accomplished, for example, by enhancing the isoprene synthetic activity and/or improving the enzyme stability. Examples of the mutation of the amino acid residue for improving the amount of isoprene to be produced in the host may include mutations of amino acid residues corresponding to one or more amino acid residues selected from Y304, Y394, T462, and T466 in the amino acid sequences of (a) to (c) above. Alternatively, when the amino acid sequence of (a) to (c) above having the signal sequence at the N-terminus is the amino acid sequence of (d) to (f) above, the modified isoprene synthase of the present invention comprising the mutation of the amino acid residue for improving the amount of isoprene to be produced in the host may be those comprising mutations of amino acid residues corresponding to one or more amino acid residues selected from Y347, Y437, T505, and T509 in the amino acid sequences of (d) to (f) above. The extent of the improvement of the amount of isoprene to be produced by the modified isoprene synthase in the host relative to that by the isoprene synthase before the modification (e.g., SEQ ID NO: 4 or SEQ ID NO:2) is not particularly limited as long as the amount of isoprene to be produced in the host is improved relative to that by the isoprene synthase before the modification, and is, for example 1.02 fold or more, preferably 1.05 fold or more, more preferably 1.07 fold or more, still more preferably 1.1 fold or more, and most preferably 1.15 fold or more.

More specifically, the modified isoprene synthase comprising the mutation of the amino acid residue for improving the amount of isoprene to be produced in the host may be those comprising a mutation(s) of an amino acid residue(s) corresponding to one or more amino acid residues selected from Y304F, Y394F, T462S, T466F, T466C, T466W, T466M, T466Y, T466H, T466P, T466Q, T466N, and T466A in the amino acid sequences of (a) to (c) above. Alternatively, when the amino acid sequence of (a) to (c) above having the signal sequence at the N-terminus is the amino acid sequence of (d) to (f) above, the modified isoprene synthase of the present invention comprising a mutation of an amino acid residue for improving the amount of isoprene to be produced in the host may be those comprising the mutation(s) of the amino acid residue(s) corresponding to one or more amino acid residues selected from Y347F, Y437F, T505S, T509F, T509C, T509W, T509M, T509Y, T509H, T509P, T509Q, T509N, and T509A in the amino acid sequences of (d) to (f) above.

The modified isoprene synthase of the present invention may have another peptide component (e.g., a tag moiety) at C-terminus or N-terminus. Examples of the other peptide component which may be added to the modified isoprene synthase of the present invention may include peptide components that make purification of an objective protein easy (e.g., tag moieties such as histidine tag and Strep-tag II; proteins commonly used for the purification of an objective protein, such as glutathione-S-transferase and a maltose binding protein), peptide components that enhance solubility of an objective protein (e.g., Nus-tag), peptide components that work as a chaperon (e.g., a trigger factor), and peptide components as a protein or a protein domain having another function or a linker linking them.

The present invention also provides a polynucleotide encoding the modified isoprene synthase of the present invention. The polynucleotide of the present invention may be DNA or RNA, but is preferably DNA.

The modified isoprene synthase of the present invention can be prepared using a transformant of the present invention that expresses the modified isoprene synthase of the present invention, or using a cell-free system, and the like. The transformant of the present invention can be made, for example, by making an expression vector of the present invention and then transforming a host cell with this expression vector.

The present invention provides an expression vector. The expression vector of the present invention comprises a polynucleotide of the present invention or a polynucleotide encoding a protein of the present invention.

Examples of the expression vector of the present invention may include cellular system vectors that express the protein in a host or cell-free system vectors that utilize a protein translation system. The expression vector may also be a plasmid, a viral vector, a phage, an integrative vector, or an artificial chromosome. The integrative vector may be a vector of a type entirely incorporated into genome in a host cell. Alternatively, the integrative vector may be a vector of a type in which only a portion (e.g., an expression unit described later) of which is incorporated into the genome in the host cell. The expression vector may further be a DNA vector or an RNA vector.

A known expression vector suitable for a host is used as the cellular system vector. Examples thereof may include ColE-based plasmids typified by pBR322 derivatives, pACYC-based plasmid having a p15A origin, pSC-based plasmids, and F factor-derived mini F plasmids such as Bac-based plasmids in *Escherichia coli* (*E. coli*). In addition, expression vectors having a tryptophan promoter such as trc and tac, a lac promoter, a T7 promoter, a T5 promoter, a T3 promoter, an SP6 promoter, an arabinose inducible promoter, a cold shock promoter, a tetracycline inducible promoter, or the like may also be included.

Examples of the cell-free system vector may include an expression vector having the T7 promoter and an expression vector having the T3 promoter included in the cellular system vectors; vectors such as pEU-based plasmids having an SP6 promoter or the T7 promoter for synthesizing a wheat protein in the cell-free system, and the like.

In protein synthesis using the cell-free system vector, first cDNA of an objective protein is transcribed to synthesize mRNA using a transcription system. Such a transcription system may include a known system where cDNA is transcribed using RNA polymerase. Examples of the RNA polymerase may include T7 RNA polymerase.

Then, mRNA is translated to synthesize the protein using a cell-free protein synthesis system that is a translation system. This system includes ribosome, a translation initiation factor, a translation extension factor, a dissociation factor, amino-acyl tRNA synthetase, and the like, which are elements necessary for the translation. Such a protein translation system may include an *Escherichia coli* extract, a rabbit reticulocyte extract, and a wheat germ extract.

Further, a rearrangement type cell-free protein synthesis system consisting of factors obtained by independently purifying elements necessary for the above translation may be included.

Protein synthesis using the cellular system vector will be described layer in Transformants.

A protein synthesized using the cellular system vector or the cell-free system vector may be purified. A purification method may include methods using salting out and various chromatographic methods. When an expression vector is designed to express a tag sequence such as a histidine tag attached at the N-terminus or C-terminus of an objective protein, a purification method by an affinity column using a substance such as nickel or cobalt having affinity for this tag is employed. In addition, the purity of the protein of the present invention can be enhanced by purifying with appropriate combination of ion-exchange chromatography, gel filtration chromatography, and the like.

The expression vector of the present invention further comprises a homologous promoter or a heterologous promoter operably linked to the above polynucleotide. The term "homologous promoter" refers to a natural promoter of an isoprene synthase gene derived from *Mucuna*. The term "heterologous promoter" refers to promoters other than the natural promoter of the isoprene synthase gene derived from *Mucuna*. Therefore, examples of the heterologous promoter may include promoters of genes derived from *Mucuna* other than the isoprene synthase gene derived from *Mucuna*, promoters derived from organisms other than *Mucuna* (e.g., microorganisms, animals, insects, and plants), promoters derived from viruses, and artificially synthesized promoters. A promoter commonly used for production of a foreign protein may also be used as the heterologous promoter.

The expression vector of the present invention may further comprise a terminator downstream of the above polynucleotide. Examples of such a terminator may include a T7 terminator, a fd phage terminator, a T4 terminator, a terminator of a tetracycline resistant gene, and a terminator of an *Escherichia coli* trpA gene.

The expression vector of the present invention may further comprise a ribosome binding site (e.g., Shine-Dalgarno sequence) upstream of an initiation codon.

The expression vector of the present invention may further comprise a polynucleotide encoding a drug resistant gene. Examples of the drug resistant gene may include resistant genes to drugs such as tetracycline, ampicillin, kanamycin, hygromycin, and phosphinothricin.

The expression vector of the present invention may further comprise one or more regions that allow for homologous recombination with genome of a host cell when introduced into the host cell. For example, the expression vector of the present invention may be designed such that an expression unit comprising the polynucleotide of the present invention is located between a pair of homologous regions (e.g., homology arm homologous to a certain sequence in host genome, loxP, FRT). The expression unit refers to a unit that comprises a given polynucleotide to be expressed and a promoter (e.g., homologous promoter, heterologous promoter) operably linked thereto and allows for transcription of the polynucleotide. The expression unit may further comprise elements such as the terminator, the ribosome binding site and the drug resistant gene described above.

The transformant of the present invention is a host cell that can produce the modified isoprene synthase of the present invention or can express the polynucleotide of the present invention to produce the modified isoprene synthase. Specifically, the transformant of the present invention is a host cell comprising the expression unit comprising the polynucleotide of the present invention. Examples of the host cell comprising the expression unit comprising the polynucleotide of the present invention may include a host cell in which the expression vector of the present invention has been entirely introduced and a host cell in which the expression unit in the expression vector of the present invention has been introduced into its genome. The host cell is not particularly limited as long as it can express the modified isoprene synthase of the present invention. The host cell may be homogeneous or heterogeneous to the modified isoprene synthase of the present invention and the polynucleotide of the present invention, but is preferably heterogeneous. The host cell may also be homogeneous or heterogeneous to the above promoter, but is preferably heterogeneous. Examples of the host cell may include animal cells, plant cells, insect cells and microbial cells, and are preferably the microbial cells. More preferably, the host cell used for the present invention is a bacterial cell or a fungal cell. The bacterial cell may be Gram-positive or Gram-negative.

Examples of the gram-positive bacterium may include bacteria belonging to the genera *Bacillus, Listeria, Staphylococcus, Streptococcus, Enterococcus, Clostridium, Corynebacterium*, and *Streptomyces*. Bacteria belonging to the genera *Bacillus* and *Corynebacterium* are preferable.

Examples of the bacteria belonging to the genus *Bacillus* may include *Bacillus subtilis, Bacillus anthracis*, and *Bacillus cereus. Bacillus subtilis* is more preferable.

Examples of the bacteria belonging to genus the *Corynebacterium* may include *Corynebacterium glutamicum, Corynebacterium efficiens*, and *Corynebacterium callunae. Corynebacterium glutamicum* is more preferable.

Examples of the gram-negative bacterium may include bacteria belonging to the genera *Escherichia, Pantoea, Salmonella*, Vivrio, *Serratia*, and *Enterobacter*. The bacteria belonging to the genera *Escherichia, Pantoea* and *Enterobacter* are preferable.

*Escherichia coli* is preferable as the bacteria belonging to the genus *Escherichia.*

Examples of the bacteria belonging to the genus *Pantoea* may include *Pantoea ananatis, Pantoea stewartii, Pantoea agglomerans*, and *Pantoea citrea. Pantoea ananatis* and *Pantoea citrea* are preferable. Strains exemplified in EP 0 952 221, which is incorporated herein by reference in its entirety, may be used as the bacteria belonging to the genus *Pantoea*. Examples of representative strains of the bacteria belonging to genus *Pantoea* may include *Pantoea ananatis* AJ13355 strain (FERM BP-6614) and *Pantoea ananatis* AJ13356 strain (FERM BP-6615), both of which are disclosed in EP 0 952 221, which is incorporated herein by reference in its entirety.

Examples of the bacteria belonging to the genus *Enterobacter* may include *Enterobacter agglomerans* and *Enterobacter aerogenes. Enterobacter aerogenes* is preferable. The bacterial strains exemplified in EP 0 952 221, which is incorporated herein by reference in its entirety, may be used as the bacteria belonging to the genus *Enterobacter*. Examples of representative strains of the bacteria belonging to the genus *Enterobacter* may include *Enterobacter agglomerans* ATCC12287 strain, *Enterobacter aerogenes* TACC 13048 strain, *Enterobacter aerogenes* NBRC 12010 strain (Biotechnol. Bioeng., 2007 Mar. 27; 98(2): 340-348, which is incorporated herein by reference in its entirety), and *Enterobacter aerogenes* AJ110637 (FERM BP-10955). The *Enterobacter aerogenes* AJ110637 strain was deposited to International Patent Organism Depositary (IPOD), National Institute of Advanced Industrial Science and Technology (AIST) (Chuo No. 6, Higashi 1-1-1, Tsukuba City, Ibaraki Pref., JP, Postal code 305-8566) as of Aug. 22, 2007, with the deposit number of FERM P-21348 and was transferred to the international deposition based on Budapest Treaty on Mar. 13, 2008, and the receipt number FERM BP-10955 was given thereto.

Examples of the fungus may include microorganisms belonging to the genera *Saccharomyces, Schizosaccharomyces, Yarrowia, Trichoderma, Aspergillus, Fusarium*, and *Mucor*. The microorganisms belonging to the genera *Saccharomyces, Schizosaccharomyces, Yarrowia*, or *Trichoderma* are preferable.

Examples of the microorganisms belonging to the genus *Saccharomyces* may include *Saccharomyces carlsbergensis, Saccharomyces cerevisiae, Saccharomyces diastaticus, Saccharomyces douglasii, Saccharomyces kluyveri, Saccharomyces norbensis*, and *Saccharomyces oviformis. Saccharomyces cerevisiae* is preferable.

*Schizosaccharomyces pombe* is preferable as a microorganism belonging to the genus *Schizosaccharomyces.*

*Yarrowia lypolytica* is preferable as a microorganism belonging to the genus *Yarrowia.*

Examples of the microorganisms belonging to the genus *Trichoderma* may include *Trichoderma harzianum, Trichoderma koningii, Trichoderma longibrachiatum, Trichoderma reesei*, and *Trichoderma viride. Trichoderma reesei* is preferable.

In addition, the host used for the present invention is not particularly limited as long as the host has an ability to synthesize dimethylallyl diphosphate (DMAPP) via a mevalonate (MVA) pathway and/or a methylerythritol phosphate (MEP) pathway that are involved in synthesis of dimethylallyl diphosphate that is a substrate of the isoprene synthase, and may be an insect cell, an animal cell, a plant cell, and so forth.

In the transformant of the present invention, the pathway to synthesize dimethylallyl diphosphate (DMAPP) that is the substrate of the isoprene synthase may be further enhanced. For such an enhancement, an expression unit that expresses an isopentenyl-diphosphate delta isomerase having an ability to convert isopentenyl diphosphate (IPP) into dimethylallyl diphosphate (DMAPP) may be introduced into the transformant of the present invention by the above-described expression vector. An expression unit that expresses one or more enzymes involved in the mevalonate pathway and/or methylerythritol phosphate pathway associated with formation of IPP and/or DMAPP may also be introduced into the transformant of the present invention by the above-described expression vector. The expression unit for such an enzyme may further include a plurality of enzymes (e.g., one, two, three, or four or more) involved in the mevalonate pathway and/or the methylerythritol phosphate pathway, and may be, for example, an expression vector for polycistronic mRNA. The origin of the one or more enzymes involved in the mevalonate pathway and/or the methylerythritol phosphate pathway may be homologous or heterologous to the host. When the origin of the enzyme involved in the mevalonate pathway and/or the methylerythritol phosphate pathway is heterologous to the host, for example, the host may be a bacterium as described above (e.g., *Escherichia coli*) and the enzyme involved in the mevalonate pathway may be derived from a fungus (e.g., *Saccharomyces cerevisiae*). In addition, when the host inherently produces the enzyme involved in the methylerythritol phosphate pathway, the expression vector to be introduced into the host may express an enzyme involved in the mevalonate pathway.

Examples of isopentenyl-diphosphate delta isomerase (EC: 5.3.3.2) may include Idi1p (ACCESSION ID NP_015208), AT3G02780 (ACCESSION ID NP_186927), AT5G16440 (ACCESSION ID NP_197148) and Idi (ACCESSION ID NP_417365).

Examples of the enzymes involved in the mevalonate (MVA) pathway may include mevalonate kinase (EC: 2.7.1.36; example 1, Erg12p, ACCESSION ID NP_013935; example 2, AT5G27450, ACCESSION ID NP_001190411), phosphomevalonate kinase (EC: 2.7.4.2; example 1, Erg8p, ACCESSION ID NP_013947; example 2, AT1G31910, ACCESSION ID NP_001185124), diphosphomevalonate decarboxylase (EC: 4.1.1.33; example 1, Mvd1p, ACCESSION ID NP_014441; example 2, AT2G38700, ACCESSION ID NP_181404; example 3, AT3G54250, ACCESSION ID NP_566995), acetyl-CoA-C-acetyltransferase (EC: 2.3.1.9; example 1, Erg10p, ACCESSION ID NP_015297; example 2, AT5G47720, ACCESSION ID NP_001032028; example 3, AT5G48230, ACCESSION ID NP_568694), hydroxymethylglutaryl-CoA synthase (EC: 2.3.3.10; example 1, Erg13p, ACCESSION ID NP_013580; example 2, AT4G11820, ACCESSION ID NP_192919; example 3, MvaS, ACCESSION ID AAG02438), hydroxymethylglutaryl-CoA reductase (EC: 1.1.1.34; example 1, Hmg2p, ACCESSION ID NP_013555; example 2, Hmg1p, ACCESSION ID NP_013636; example 3, AT1G76490, ACCESSION ID NP_177775; example 4, AT2G17370, ACCESSION ID NP_179329, EC: 1.1.1.88, example, MvaA, ACCESSION ID P13702), and acetyl-CoA-C-acetyltransferase/hydroxymethylglutaryl-CoA reductase (EC: 2.3.1.9/1.1.1.34, example, MvaE, ACCESSION ID AAG02439).

Examples of the enzymes involved in the methylerythritol phosphate (MEP) pathway may include 1-deoxy-D-xylulose-5-phosphate synthase (EC: 2.2.1.7, example 1, Dxs, ACCESSION ID NP_414954; example 2, AT3G21500, ACCESSION ID NP_566686; example 3, AT4G15560, ACCESSION ID NP_193291; example 4, AT5G11380, ACCESSION ID NP_001078570), 1-deoxy-D-xylulose-5-phosphate reductoisomerase (EC: 1.1.1.267; example 1, Dxr, ACCESSION ID NP_414715; example 2, AT5G62790, ACCESSION ID NP_001190600), 4-diphosphocytidyl-2-C-methyl-D-erythritol synthase (EC: 2.7.7.60; example 1, IspD, ACCESSION ID NP_417227; example 2, AT2G02500, ACCESSION ID NP_565286), 4-diphosphocytidyl-2-C-methyl-D-erythritol kinase (EC: 2.7.1.148; example 1, IspE, ACCESSION ID NP_415726; example 2, AT2G26930, ACCESSION ID NP_180261), 2-C-methyl-D-erythritol-2,4-cyclodiphosphate synthase (EC: 4.6.1.12; example 1, IspF, ACCESSION ID NP_417226; example 2, AT1G63970, ACCESSION ID NP_564819), 1-hydroxy-2-methyl-2-(E)-butenyl-4-diphosphate synthase (EC: 1.17.7.1; example 1, IspG, ACCESSION ID NP_417010; example 2, AT5G60600, ACCESSION ID NP_001119467), and 4-hydroxy-3-methyl-2-butenyl diphosphate reductase (EC: 1.17.1.2; example 1, IspH, ACCESSION ID NP_414570; example 2, AT4G34350, ACCESSION ID NP_567965).

Introduction of the expression unit, in which the gene is incorporated, into the host (transformation) can be carried out using known methods regarding the expression vector. Examples of such a method may include a competent cell method using a microbial cell treated with calcium and an electroporation method. The gene may be introduced by infecting the microbial cell with a phage vector rather than the plasmid vector.

Further, a gene encoding the enzyme involved in the mevalonate pathway or the methylerythritol phosphate pathway that synthesizes dimethylallyl diphosphate that is the substrate of the isoprene synthase may also be introduced into the transformant of the present invention.

Examples of such an enzyme may include 1-deoxy-D-xylose-5-phosphate synthase that converts a pyruvate and D-glycelaldehyde-3-phosphate into 1-deoxy-D-xylose-5-phosphate, and isopentyl diphosphate isomerase that converts isopentenyl diphosphate into dimethylallyl diphosphate.

The protein of the present invention may be extracted or purified from the transformant of the present invention, and isoprene may be produced by culturing the transformant that expresses the protein of the present invention.

Method of Producing Isoprene Monomer and Isoprene Polymer

The present invention provides a method of producing an isoprene monomer. The method of producing an isoprene monomer of the present invention includes producing an isoprene monomer from dimethylallyl diphosphate in the presence of the protein of the present invention.

The method of producing the isoprene monomer of the present invention is not particularly limited as long as it is performed under the presence of the protein of the present invention, and it can be performed, for example, by utilizing an enzyme reaction system that uses the protein itself of the present invention (e.g., purified protein) or by culturing the transformant of the present invention that produces the protein of the present invention. Preferably, the method is performed by culturing the transformant of the present invention. When the transformant of the present invention is used in the method of producing the isoprene monomer of the present invention, dimethylallyl diphosphate that is a raw material of the isoprene monomer is efficiently supplied from a carbon source in a culture medium by the transformant of the present invention. The transformant of the present invention produces the isoprene monomer mainly as an outgas from the carbon source in the culture medium. Thus, the isoprene monomer is recovered by collecting gas produced from the transformant. Dimethylallyl diphosphate that is the substrate of the isoprene synthase is synthesized from the carbon source in the culture medium via the mevalonate pathway or the methylerythritol phosphate pathway in the host.

The culture medium for culturing the transformant of the present invention preferably contains the carbon source to be converted into isoprene. The carbon source may include carbohydrates such as monosaccharides, disaccharides, oligosaccharides, and polysaccharides; invert sugars obtained by hydrolyzing sucrose; glycerol; compounds having one carbon atom (hereinafter referred to as a C1 compound) such as methanol, formaldehyde, formate, carbon monoxide, and carbon dioxide; oils such as corn oil, palm oil and soybean oil; acetate; animal fats; animal oils; fatty acids such as saturated fatty acids and unsaturated fatty acids; lipids; phospholipids; glycerolipids; glycerine fatty acid esters such as monoglyceride, diglyceride and triglyceride; polypeptides such as microbial proteins and plant proteins; renewable carbon sources such as hydrolyzed biomass carbon sources; yeast extracts, or combinations thereof. For a nitrogen source, inorganic ammonium salts such as ammonium sulfate, ammonium chloride, and ammonium phosphate, organic nitrogen such as hydrolyzed soybeans, ammonia gas, ammonia water, and the like can be used. It is desirable to include required substances such as vitamin B1 and L-homoserine, or yeast extract and the like in an appropriate amount as an organic trace nutrient source. In addition thereto, potassium phosphate, magnesium sulfate, iron ion, manganese ion, and the like may be added in small amounts if necessary. The culture medium used in the present invention may be a natural medium or a synthesized medium as long as the culture medium contains a carbon source, a nitrogen source, inorganic ions, and optionally other organic trace ingredients.

Examples of the monosaccharides may include triose such as ketotriose (dihydroxyacetone) and aldotriose (glyceraldehyde); tetrose such as ketotetrose (erythrulose) and aldotetrose (erythrose, threose); pentose such as ketopentose (ribulose, xylulose), aldopentose (ribose, arabinose, xylose, lyxose) and deoxysaccharide (deoxyribose); hexose such as ketohexose (psychose, fructose, sorbose, tagatose), aldohexose (allose, altrose, glucose, mannose, gulose, idose, galactose, tallose), and deoxysaccharide (fucose, fucrose, rhamnose); and heptose such as sedoheptulose. C6 sugars such as fructose, mannose, galactose and glucose; and C5 sugars such as xylose and arabinose are preferable.

Examples of the disaccharides may include sucrose, lactose, maltose, trehalose, turanose, and cellobiose. Sucrose and lactose are preferable.

Examples of the oligosaccharides may include trisaccharides such as raffinose, melezitose and maltotriose; tetrasaccharides such as acarbose and stachyose; and other oligosaccharides such as fructooligosaccharide (FOS), galactooligosaccharide (GOS) and mannan-oligosaccharide (MOS).

Examples of the polysaccharides may include glycogen, starch (amylose, amylopectin), cellulose, dextrin, and glucan (β1,3-glucan). Starch and cellulose are preferable.

Examples of the microbial protein may include polypeptides obtainable from a yeast or bacterium. Examples of the plant protein may include polypeptides obtainable from soybean, corn, canola, Jatropha, palm, peanut, sunflower, coconut, mustard, cotton seed, palm kernel oil, olive, safflower, sesame, and linseed.

Examples of the lipid may include substances containing one or more saturated or unsaturated fatty acids of C4 or more.

The oil is preferably a lipid that contains one or more saturated or unsaturated fatty acids of C4 or more and is liquid at room temperature, and examples of the oil may include lipids obtainable from soybean, corn, canola, Jatropha, palm, peanut, sunflower, coconut, mustard, cotton seed, Palm kernel oil, olive, safflower, sesame, linseed, oily microbial cells, Chinese tallow tree, and a combination of two or more thereof.

Examples of the fatty acid may include compounds represented by a formula RCOOH ("R" represents a hydrocarbon group).

The unsaturated fatty acid is a compound having at least one double bond between two carbon atoms in "R", and examples of the unsaturated fatty acid may include oleic acid, vaccenic acid, linoleic acid, palmitelaidic acid and arachidonic acid.

The saturated fatty acid is a compound where the "R" is a saturated aliphatic group, and examples of the saturated fatty acid may include docosanoic acid, eicosanoic acid, octadecanoic acid, hexadecanoic acid, tetradecanoic acid, and dodecanoic acid.

Among them, those containing one or more C2 to C22 fatty acids are preferable as the fatty acid, and those containing C12 fatty acid, C14 fatty acid, C16 fatty acid, C18 fatty acid, C20 fatty acid and C22 fatty acid are more preferable.

The carbon source may include salts and derivatives of these fatty acids and salts of these derivatives. Examples of the salt may include lithium salts, potassium salts, and sodium salts.

Examples of the carbon source may also include combinations of carbohydrate such as glucose with the lipid(s), the oil(s), the fats, the fatty acid(s) and glycerin fatty acid(s) ester(s).

Examples of the renewable carbon source may include hydrolyzed biomass carbon sources.

Examples of the biomass carbon source may include cellulose-based substrates such as waste materials of woods, papers and pulps, leafy plants, and fruit pulps; and partial plants such as stalks, grain particles, roots, and tubers.

Examples of the plants to be used as the biomass carbon source may include corn, wheat, rye, sorghum, triticale, rice, millet, barley, cassava, legumes such as peas, potato, sweet potato, banana, sugar cane, and tapioca.

When the renewable carbon source such as biomass is added to the culture medium, the carbon source is preferably pretreated. Examples of the pretreatment may include an enzymatic pretreatment, a chemical pretreatment, and a combination of the enzymatic pretreatment and the chemical pretreatment.

It is preferred that the renewable carbon source is entirely or partially hydrolyzed before being added to the culture medium.

Examples of the carbon source may also include a yeast extract and a combination of the yeast extract with the other carbon source such as glucose. The combination of the yeast extract with the C1 compound such as carbon dioxide and methanol is preferable.

In the method of culturing the transformant according to the present invention, it is preferable that the cell is cultured in a standard medium containing saline and nutrients.

The culture medium is not particularly limited, and examples of the culture medium may include ready-made general media that are commercially available such as Luria Bertani (LB) broth, Sabouraud dextrose (SD) broth, and yeast medium (YM) broth. The medium suitable for the cultivation of the specific host can be selected appropriately for the use.

It is desirable to include appropriate minerals, salts, supplemental elements, buffers, and ingredients known for those skilled in the art to be suitable for the cultivation and to facilitate the production of isoprene in addition to the appropriate carbon source in the cell medium.

It is preferable to add the sugar, a metal salt, an antimicrobial substance, and the like to the medium in order to maintain the expression of the protein of the present invention in the transformant of the present invention.

The culture condition for the transformant of the present invention is not particularly limited as long as the protein of the present invention can be expressed, and a standard cell culture condition can be used.

The culture temperature is preferably 20 to 37° C., the gas composition is preferably about 6 to about 84% of $CO_2$ concentration, and the pH value is preferably about 5 to about 9.

It is preferable that the culturing is performed under an aerobic, oxygen-free, or anaerobic condition depending on a nature of the host.

Examples of methods of culturing the transformant include a method using a known fermentation method such as a batch cultivation method, a feeding cultivation method, or a continuous cultivation method.

In the batch cultivation method, a medium composition is added at start of the fermentation, the host is inoculated in the medium composition, and the transformant is cultured while pH and an oxygen concentration are controlled.

In the cultivation of the transformant by the batch cultivation method, the growth of the transformant starts from a mild induction phase, passes through a logarithmic growth phase and finally goes to a stationary phase in which a growth speed is reduced or stopped. Isoprene is produced by the transformant in the logarithmic growth phase and the stationary phase.

In the feeding cultivation method, in addition to the above batch method, the carbon source is gradually added according to the progress of a fermentation process. The feeding cultivation method is effective when the amount of the carbon source is to be restricted in the medium because metabolism of the transformant tends to be reduced due to catabolite suppression. The feed cultivation can be performed using a restricted amount or an excessive amount of the carbon source such as glucose.

In the continuous cultivation method, a certain amount of the medium is continuously supplied to a bioreactor at a constant rate while the same amount of the medium is removed. In the continuous cultivation method, the culture can be kept constantly at a high concentration and the transformant in the culture medium is generally in the logarithmic growth phase.

The nutrition can be supplemented by entirely or partly exchanging the medium appropriately, and accumulation of metabolic byproducts that potentially have adverse effects on the growth of the transformant, and the accumulation of dead cells can be prevented.

Examples of the promoter possessed by the expression vector or expression unit of the present invention may include a constitutive promoter or an inducible promoter. When the expression vector or the expression unit of the present invention has the inducible promoter such as a lac promoter, the expression of the protein of the present invention may be induced by, for example, adding IPTG (isopropyl-β-thiogalactopyranoside) into the culture medium.

Examples of the method of evaluating the amount of isoprene monomer produced by culturing the transformant of the present invention may include a method in which a gas phase is collected by a headspace method and this gas phase is analyzed by gas chromatography.

In detail, the isoprene monomer in a headspace which is obtained by culturing the transformant in a sealed vial with shaking the culture medium is analyzed by standard gas chromatography. Then, an area calculated by a curve measured by gas chromatography is converted into the amount of the isoprene monomer produced with the transformant using a standard curve.

Examples of the method of collecting the isoprene monomer obtained by culturing the transformant of the present invention may include gas stripping, fractional distillation, or dissociation of the isoprene monomer adsorbed to a solid phase by heat or vacuum, or extraction with a solvent.

In the gas stripping, isoprene gas is continuously removed from the outgas. Such removal of the isoprene gas can be performed by various methods. Examples of the removal may include adsorption to a solid phase, separation into a liquid phase, and a method in which the isoprene gas is directly condensed.

The isoprene monomer can be collected by a single step or multiple steps. When the isoprene monomer is collected by the single step, the isoprene monomer is converted into the liquid phase simultaneously with separating the isoprene monomer from the outgas. The isoprene monomer can also be directly condensed from the outgas to make the liquid phase. When the isoprene monomer is collected by the multiple stages, the isoprene monomer is separated from off-gas and subsequently converted into the liquid phase. For example, the isoprene monomer is adsorbed to a solid phase, and extracted from the solid phase with the solvent.

Exemplary methods of collecting the isoprene monomer may comprise further purifying the isoprene monomer. Examples of the purification may include separation from a liquid phase extract by distillation and various chromatographic methods.

The protein of the present invention is more excellent in ability to produce isoprene than conventional isoprene synthase. Thus, the isoprene monomer can be produced efficiently using the transformant that expresses the protein of the present invention.

The present invention further provides a method of producing an isoprene polymer. The method of producing the isoprene polymer according to the present invention comprises the following (I) and (II):

(I) producing an isoprene monomer by the method of the present invention; and (II) polymerizing the isoprene monomer to form an isoprene polymer.

The step (I) can be performed in the same manner as in the method of producing the isoprene monomer according to the present invention described above. The polymerization of the isoprene monomer in the step (II) can be performed by any method such as addition polymerization known in the art (e.g., synthesis methods in organic chemistry).

The rubber composition of the present invention comprises a polymer derived from isoprene produced by a method for producing isoprene according to the present invention. The polymer derived from isoprene may be a homopolymer (i.e., isoprene polymer) or a heteropolymer comprising isoprene and one or more monomer units other than the isoprene (e.g., a copolymer such as a block copolymer). Preferably, the polymer derived from isoprene is a homopolymer (i.e., isoprene polymer) produced by a method for producing isoprene polymer according to the present invention. The rubber composition of the present invention may further comprise one or more polymers other than the above polymer, one or more rubber components, and/or other components. The rubber composition of the present invention can be manufactured using a polymer derived from isoprene. For example, the rubber composition of the present invention can be prepared by mixing a polymer derived from isoprene with one or more polymers other than the above polymer, one or more rubber components, and/or other components such as a reinforcing filler, a crosslinking agent, a vulcanization accelerator, and an antioxidant.

The tire of the present invention is manufactured using the rubber composition of the present invention. The rubber composition of the present invention may be applied to any portion of the tire without limitation, which may be selected as appropriate depending on the application thereof. For example, the rubber composition of the present invention may be used in a tread, a base tread, a sidewall, a side reinforcing rubber and a bead filler of a tire. The tire can be manufactured by a conventional method. For example, a carcass layer, a belt layer, a tread layer, which are composed of unvulcanized rubber, and other members used for the production of usual tires may be successively laminated on a tire molding drum, then the drum may be withdrawn to obtain a green tire. Thereafter, the green tire may be heated and vulcanized in accordance with an ordinary method, to thereby obtain a desired tire (e.g., a pneumatic tire).

Other features of the invention will become apparent in the course of the following descriptions of exemplary embodiments which are given for illustration of the invention and are not intended to be limiting thereof.

EXAMPLES

Example 1: Design of Modified Enzyme of Isoprene Synthase (IspS) (1) and Analysis of Modified Enzyme of Isoprene Synthase Using Crude Purification Solution (1-1) Design of Modified Enzyme of IspS For efficient screening of modified enzymes, rational modification was carried out exploiting information on steric structure. A gene of IspSM that was isoprene synthetase derived from *Mucuna* was utilized as an isoprene synthase (IspS) gene. IspSM is an enzyme encoded by a gene where a chloroplast transit signal was deleted in the IspS gene derived from *Mucuna* (its nucleotide and amino acid sequences are represented by SEQ ID NO:1 and SEQ ID NO:2, respectively) and its codon usage was optimized for *E. coli*. A nucleotide sequence of a polynucleotide encoding IspSM and an amino acid sequence of IspSM are represented by SEQ ID NO:3 and SEQ ID NO:4, respectively. Since a steric structure of IspSM is unknown, a model structure of IspSM was acquired by a homology modeling method using a steric structure of the isoprene synthase derived from *Populus×canescnes* (PDB code: 3n0g) as a template.

Two points were focused on in high functionality of IspS. A first one is to improve affinity between IspS and a dimethylallyl pyrophosphate (DMAPP) molecule that is a substrate thereof. According to the reference of Schnitzler (J. P. Schnitzler et al, Planta., 2005, 222, 777, which is incorporated herein by reference in its entirety), a Km value between IspS derived from *Populus×canescnes* and DMAPP that is the substrate thereof is known to be of the order of mM. A substrate affinity in a common enzymatic reaction is of the order of μM. Thus, it was thought that there was room to improve the substrate affinity of IspS. In general, it is known that affinity and specificity between an enzyme and a substrate can be altered by modifying an amino acid residue(s) present in the vicinity of a substrate binding site (Practical Application of Protein Engineering, edited by Kimitsuna Watanabe et al., CMC Publishing, which is incorporated herein by reference in entirety). Thus, in order to improve the affinity between IspS and DMAPP, a residue positioned in the vicinity of a DMAPP binding site was subjected to modification. Hereinafter, this line is referred to as Concept (1). A second one is to enhance stability of IspS. It is known that the stability of an enzyme is closely associated with a steric structure of an enzyme molecule. From the model structure of IspS derived from *Mucuna* (IspSM), it has been predicted that IspSM has no intermolecular disulfide bond in its molecule and has a highly hydrophobic region on its molecular surface. As reported in the reference (e.g., M. Matsumura et al, Nature, 1989, 342, 291-293, which is incorporated herein by reference in its entirety), it is known that an enzyme is further stabilized by modifying a free Cys residue and introducing a hydrophilic residue to the molecular surface. It has been suggested from the model structure that an N terminal region of IspS does not form a constant structure. From this, it has been anticipated that the stability of IspS can be enhanced by modifying the N-terminal region itself and altering the number of residues. The report of Ray Fall et al. has suggested that IspS forms a dimer upon expressing its function. Thus, it has been anticipated that a dimer structure can be stabilized by focusing on an intermolecular interaction of IspS with one another (GM. Silver et al, J. Biol. Chem., 1995, 270, 13010, which is incorporated herein by reference in its entirety).

Hereinafter, the modification of the free Cys residue and optimization of the vicinity of the free Cys residue are referred to as Concept (2), as well as introduction of the hydrophilic residue to the molecular surface, optimization of the N-terminal residue of IspS and stabilization of the dimeric structure of the IspS molecule are referred to as Concept (3).

(1-1-1) Amino Acids after Modification

Amino acids were selected from acidic residues (D, E), basic residues (R, K), neutral residues (N, Q), hydrophilic residues (M, S) and aromatic residues (Y, F) with focusing on two points. For a first point, amino acids that were close to amino acids before the modification in bulkiness were selected with reference to the truth table for physicochemical natures of amino acids (e.g., M. J. Zvelebil et al, J. Mol. Biol., 1987, 195, 57, which is incorporated herein by reference in its entirety) and BLOSSUM table that were indicators of amino acid homology (S. Henikoff et al, Proc. Natl. Acad. USA., 1992, 89, 10915, which is incorporated herein by reference in its entirety). For a second point, information on steric structure was visually inspected and when a space filling rate in the vicinity of a modified residue is low, amino acids suitable for filling the space were selected.

(1-1-2) Selection of Residues to be Modified

In Concept (1), amino acid residues, a side chain of which was directed toward a DMAPP molecule were selected as subjects for modification among amino acid residues present within the shortest 7 Å from total atoms composing the DMAPP molecule in the model steric structure of IspSM. Modified enzymes in Concept (1) correspond to modified enzymes of numbers 1 to 88 shown in Table 1-1.

Then, in Concept (2), all nine Cys residues present as free thiol (i.e., C137, C286, C338, C370, C373, C440, C446, C480, C521) were selected as subjects for the modification. Also a case where the modification of the Cys residue had not worked successfully was supposed, and amino acid residues positioned in the vicinity of free thiol and in the distance capable of making a hydrogen bond with the residue were also selected as subjects for the modification. Modified enzymes in Concept (2) correspond to modified enzymes of numbers 89 to 178 shown in Table 1-2.

Finally in Concept (3), Val residues that were present on the molecular surface and were hydrophobic and in particular potentially brought about no large change in the steric structure in the model steric structure of IspSM were selected as subjects for the modification. It has been described that N-terminal residues are involved in resistance to protease and substitution thereof with an amino acid such as Gly having a small side chain enhances the resistance (A. Bachmair et al, Science, 234, 179-186(1986) and J. W. Tobias et al, Science, 254, 1374-1377(1991), both of which are incorporated herein by reference in their entireties). Thus, Gly and Ala and the like were selected and modified according to the reference information. Further, for the stabilization by dimerization of an IspS molecule, residues present in a dimer interface and capable of forming a disulfide bond were selected from the information on steric structure. Modified enzymes in Concept (3) correspond to modified enzymes of numbers 179 to 211 shown in Table 1-3.

(1-2) Construction of Plasmid for Expressing Modified Enzyme of IspSM

A plasmid for expressing the isoprene synthase derived from *Mucuna* in a large amount was constructed by the following procedures. For a vector portion, PCR with pCold-TF (supplied from TaKaRa Bio, catalog #3365, sequence information: GenBank/EMBL/DDBJ accession ID AB213654) as a template was carried out using synthesized oligonucleotides shown in pCold-TF PCR primer 1 and pCold-TF PCR primer 2 as primers. PCR with pUC57-IspSM [see (Reference Example 3-3)] as the template was carried out using IspSM primer 1 and IspSM primer 2 as the primers. PrimeStar HS (supplied from TaKaRa Bio, catalog #R010A) was used as polymerase for PCR method, and a reaction solution was prepared according to a composition attached to the kit. A cycle of 95° C. for 10 seconds, 55° C. for 5 seconds, and 72° C. for 6 minutes was used as a reaction condition, and the cycle was repeated 30 times. These resulting DNA fragments were ligated using In-Fusion HD Cloning Kit (supplied from Clontech, catalog #639648). The constructed plasmid was designated as pCold-TF-IspSM (SEQ ID NO:9). The polynucleotide consisting of the nucleotide residues at positions 1663 to 3318 in the nucleotide sequence of SEQ ID NO:9 encodes IspSM.

Primers Used for PCR

```
pCold-TF PCR primer-1
                                     (SEQ ID NO: 5)
5'-CCTACCTTCGATACCACCACTACC-3'

pCold-TF PCR primer-2
                                     (SEQ ID NO: 6)
5'-TAGGTAATCTCTGCTTAAAAGCACAGAATC-3'

IspSM primer-1
                                     (SEQ ID NO: 7)
5'-GGTAGTGGTGGTATCGAAGGTAGGATGTCCGCCGTTTCAAGCCA-3'

IspSM primer-2
                                     (SEQ ID NO: 8)
5'-GATTCTGTGCTTTTAAGCAGAGATTACCTATTAGTTAATCGGGAACG
GGTCAA-3'
```

(1-3) Preparation of Expression Plasmid

A plasmid encoding the designed modified enzyme was acquired by the following methods. The plasmid pCold-TF-IspSM for expression prepared by the aforementioned method was used as a template, synthesized oligonucleotides for introducing an amino acid mutation shown in Tables 1-1 to 1-3 described later were prepared for each modified enzyme, and PCR was carried out using these oligonucleotides as primers. PrimeStar HS (supplied from TaKaRa Bio) was used as polymerase for the PCR method, and a reaction solution was prepared according to a composition attached to the kit. A cycle of 95° C. for 10 seconds, 55° C. for 5 seconds, and 72° C. for 6 minutes was used for PCR, and the cycle was repeated 30 times. The solution after PCR was digested with DpnI (Toyobo) at 37° C. for 2 hours. Subsequently, *E. coli* competent cells (Ecos competent cell DH-5α supplied from Nippon Gene, catalog #310-06231) were added thereto, and after heat shock at 42° C. for 45 seconds, seeded onto an LB plate, (a) 10 g/L of Bacto tryptone, (b) 5 g/L of yeast extract, (c) 10 g/L of NaCl, (d) 100 mg/L of ampicillin, (d) 30 g/L of agar, (a) and (b) from Becton Dickinson and Company, (c) and (d) from Nacalai Tesque, containing 100 mg/L of ampicillin (Nacalai Tesque). Stationary cultivation at 37° C. for 14 hours was carried out in the plate. Then, a formed colony was inoculated to 2 mL of an LB medium, (a) 10 g/L of Bacto tryptone, (b) 5 g/L of yeast extract, (c) 10 g/L of NaCl, (d) 100 mg/L of ampicillin, (a) and (b) from Becton Dickinson and Company, (c) and (d) from Nacalai Tesque, and cultured at 37° C. for 4 hours with shaking at 120 rpm. Microbial cells were collected by centrifugation at 14,000×g for one minute, and then pCold-TF-IspSM having the introduced mutation (hereinafter described as pCold-TF-mIspSM) was collected using Fast-gene mini prep kit (Nippon Genetics). Subsequently, according to standard methods, a sequencing reaction by BigDye terminator ver3.1 (Applied Biosystems), and it was confirmed by a DNA sequencer 3130×1 (ABI) that the objective mutation had been introduced.

(1-4) Preparation of Modified Enzyme Crude Purified Solution

*E. coli* BL21 (DE3) (supplied from Life Technologies) was transformed with plasmid DNA of vector pCold-TF-mIspSM encoding the modified enzyme prepared in the aforementioned methods using the heat shock method. After the transformation, the cells were seeded on an LB plate, and the stationary cultivation was carried out at 37° C. for 14 hours. A formed colony was inoculated to 5 mL of the LB medium, and cultured at 37° C. for 4 hours with shaking at 120 rpm. Subsequently, 100 mL of the LB medium was added to a 250 ml volume Sakaguchi flask, the resulting cultured medium in total volume was inoculated thereto, and microbial cells were cultured at 37° C. with shaking at 120 ppm. When OD660 exceeded 1, IPTG (Nacalai Tesque) at a final concentration of 1 mM was added, and the cultivation with shaking at 120 ppm was carried out at 15° C. for 14 hours. Then, 30 mL of the resulting cultured medium was centrifuged at 5000×g for 10 minutes, and a supernatant was discarded. 1 mL of disruption buffer (50 mM sodium phosphate, 500 mM NaCl, pH 8.0, Nacalai Tesque) was added to microbial cells obtained here, which were then suspended. Subsequently, about 0.9 mL of beads for disruption (YBG01, diameter 0.1 mm) and 0.9 mL of the microbial cell suspension were placed in a 2 ml volume tube exclusive to a multibead shocker. And the microbial cells were disrupted in the multibead shocker (MB701 (S) model, Yasui Kikai) under a condition of 2500 rpm, 4° C. and 20 cycles of ON for 30 seconds and OFF for 30 seconds. Then, 200 mL of His-select nickel affinity gel (Sigma) was added to a 1.5 mL tube, resin was washed with the disruption buffer, and then, a disruption supernatant in total amount was added. After incubation at 4° C. for 14 hours, 1 mL of cleavage reaction buffer (25 mM tris-HCl, 10 mM $MgCl_2$, pH 8.0) was added for washing. After tapping, centrifugation at 14,000×g for one minute was carried out, and a supernatant was discarded. The same manipulation was repeated one more time, then 200 μL of the cleavage reaction buffer was added, 1 μL of Factor Xa (Merck) was added, and the stationary cultivation was carried out at 4° C. for 14 hours. Subsequently, the centrifugation at 14,000×g for one minute was carried out, and a supernatant was collected to use as a crude purified solution of mIspSM.

(1-5) Comparison of Amounts of Isoprene Produced by Respective Modified Enzymes

On ice, 46 μL of the crude purified solution of each modified enzyme was placed in a 0.2 mL volume PCR tube (Nippon Genetics), and 4 μL of 40 mM DMAPP (Cayman, catalog #63180) was added thereto. After lightly tapping, a hole was made on a cap. Next, this tube was placed in a 20 mL vial (Perkin Elmer), and immediately tightly sealed with a cap for a head space vial with a butyl rubber septum (Perkin Elmer). A reaction for producing isoprene was carried out at 37° C. for 20 minutes. After cooling at 4° C. for 10 minutes, the reaction mixture was further incubated at room temperature for 10 minutes. After termination of the reaction, the concentration of isoprene in the head space of the vial was measured by gas chromatography based on the condition described in Reference Example (4-3). Measured by gas chromatography. In order to narrow down effective modified enzymes, an amount of isoprene converted by each modified enzyme was divided by an amount of isoprene converted by the isoprene synthase derived from *Mucuna* which deletes a chloroplast transit signal (hereinafter referred to as wild type IspSM as needed) to calculate a relative activity value. Their results are shown in Table 1-1 to Table 1-3. Of 211 modified enzymes analyzed, 116 modified enzymes lost their activity. Of the remaining modified enzymes, those having the relative activity value of 30% or more were assessed as promising modified enzymes, which were 68 modified enzymes. Their results are shown in Tables 2-1 and 2-2.

TABLE 1-1

Activity values of modified enzymes produced based on Concept (1)

| No. | Modified enzyme | Activity* |
|---|---|---|
| 1 | R264D | 0% |
| 2 | R264Y | 0% |
| 3 | R264I | 0% |
| 4 | F294I | 0% |

TABLE 1-1-continued

Activity values of modified enzymes produced based on Concept (1)

| No. | Modified enzyme | Activity* |
|---|---|---|
| 5 | F294Y | 2% |
| 6 | F294R | 13% |
| 7 | F294Q | 0% |
| 8 | V297I | 0% |
| 9 | V297F | 0% |
| 10 | V297Y | 0% |
| 11 | V297D | 0% |
| 12 | T298I | 236% |
| 13 | T298F | 0% |
| 14 | T298Y | 0% |
| 15 | T298D | 0% |
| 16 | D301Q | 0% |
| 17 | D301M | 0% |
| 18 | D301Y | 0% |
| 19 | D302E | 2% |
| 20 | D302Q | 0% |
| 21 | Y304E | 0% |
| 22 | Y304Q | 0% |
| 23 | Y304R | 0% |
| 24 | Y304I | 0% |
| 25 | Y304F | 0% |
| 26 | D305Q | 0% |
| 27 | D305K | 0% |
| 28 | D305M | 0% |
| 29 | D348E | 185% |
| 30 | D348Q | 0% |
| 31 | F376D | 0% |
| 32 | F376R | 0% |
| 33 | F376Q | 29% |
| 34 | E379D | 0% |
| 35 | E379R | 0% |
| 36 | E379M | 0% |
| 37 | S383I | 35% |
| 38 | S383R | 0% |
| 39 | S383E | 10% |
| 40 | S383F | 0% |
| 41 | S383M | 220% |
| 42 | Y394Q | 0% |
| 43 | Y394M | 0% |
| 44 | A398I | 0% |
| 45 | A398R | 0% |
| 46 | A398E | 0% |
| 47 | A398F | 0% |
| 48 | A398S | 0% |
| 49 | S401E | 0% |
| 50 | S401N | 0% |
| 51 | S401K | 0% |
| 52 | S401F | 0% |
| 53 | S401Y | 0% |
| 54 | S402E | 0% |
| 55 | S402N | 0% |
| 56 | S402K | 0% |
| 57 | S402F | 0% |
| 58 | S402Y | 0% |
| 59 | S402I | 0% |
| 60 | S403E | 0% |
| 61 | S403N | 0% |
| 62 | S403K | 0% |
| 63 | S403F | 0% |
| 64 | S403Y | 0% |
| 65 | F443I | 0% |
| 66 | F443Y | 2% |
| 67 | F443R | 0% |
| 68 | R444K | 0% |
| 69 | R444E | 0% |
| 70 | R444Y | 0% |
| 71 | N447S | 0% |
| 72 | N447Q | 0% |
| 73 | N447E | 0% |
| 74 | T451S | 5% |
| 75 | T451E | 30% |
| 76 | T451N | 0% |
| 77 | E455D | 15% |
| 78 | E455Q | 11% |
| 79 | E455M | 5% |

TABLE 1-1-continued

Activity values of modified enzymes produced based on Concept (1)

| No. | Modified enzyme | Activity* |
|---|---|---|
| 80 | E460I | 0% |
| 81 | E460R | 0% |
| 82 | E460Q | 0% |
| 83 | E460Y | 5% |
| 84 | T462Q | 9% |
| 85 | T462E | 0% |
| 86 | T462S | 23% |
| 87 | N463E | 0% |
| 88 | N463Y | 0% |

*Activity value relative to wild type

TABLE 1-2

Activity values of Modified enzymes produced based on Concept (2)

| No. | Modified enzyme | Activity* |
|---|---|---|
| 89 | F129C | 0% |
| 90 | D131C | 124% |
| 91 | C137S | 58% |
| 92 | C137M | 70% |
| 93 | C137T | 1% |
| 94 | C137I | 164% |
| 95 | C137K | 240% |
| 96 | C137E | 208% |
| 97 | C286I | 55% |
| 98 | C286V | 1504% |
| 99 | C286E | 0% |
| 100 | C286K | 0% |
| 101 | C286N | 56% |
| 102 | V290C | 23% |
| 103 | V290S | 0% |
| 104 | V290M | 0% |
| 105 | V290T | 0% |
| 106 | I300N | 113% |
| 107 | F316C | 0% |
| 108 | V320C | 902% |
| 109 | C338L | 90% |
| 110 | C338V | 99% |
| 111 | C338F | 0% |
| 112 | C338Y | 1% |
| 113 | C338E | 0% |
| 114 | C338K | 0% |
| 115 | V346C | 18% |
| 116 | V346S | 39% |
| 117 | V346M | 118% |
| 118 | V346T | 0% |
| 119 | C370E | 234% |
| 120 | C370K | 85% |
| 121 | C370N | 201% |
| 122 | C370V | 255% |
| 123 | C373F | 181% |
| 124 | C373Y | 224% |
| 125 | C373W | 0% |
| 126 | C373V | 1391% |
| 127 | S399C | 0% |
| 128 | V405E | 40% |
| 129 | L414C | 979% |
| 130 | C416E | 157% |
| 131 | C416K | 197% |
| 132 | C416F | 0% |
| 133 | C416Y | 123% |
| 134 | C416W | 0% |
| 135 | C416I | 0% |
| 136 | V436E | 0% |
| 137 | R437E | 0% |
| 138 | C440M | 0% |
| 139 | C440S | 231% |
| 140 | C440T | 0% |
| 141 | C440I | 0% |
| 142 | C440V | 0% |

TABLE 1-2-continued

Activity values of Modified enzymes produced based on Concept (2)

| No. | Modified enzyme | Activity* |
|---|---|---|
| 143 | I442E | 0% |
| 144 | F443C | 17% |
| 145 | C446E | 26% |
| 146 | C446K | 0% |
| 147 | C446N | 52% |
| 148 | C446S | 0% |
| 149 | C446Y | 21% |
| 150 | C446I | 5% |
| 151 | C446V | 101% |
| 152 | S452C | 52% |
| 153 | S464C | 25% |
| 154 | I465C | 2% |
| 155 | A479E | 0% |
| 156 | A479K | 0% |
| 157 | A479D | 1% |
| 158 | C480D | 4% |
| 159 | C480K | 0% |
| 160 | C480Y | 62% |
| 161 | C480R | 6% |
| 162 | C480N | 67% |
| 163 | C480V | 42% |
| 164 | K481E | 58% |
| 165 | K481D | 0% |
| 166 | F508C | 141% |
| 167 | M515C | 0% |
| 168 | I518C | 214% |
| 169 | S519C | 11% |
| 170 | H520C | 0% |
| 171 | C521E | 265% |
| 172 | C521V | 244% |
| 173 | C521K | 0% |
| 174 | C521N | 93% |
| 175 | C521S | 102% |
| 176 | C521I | 112% |
| 177 | C521V | 244% |
| 178 | Y523C | 0% |

*Activity value relative to wild type

TABLE 1-3

Activity value of Modified enzymes produced base on Concept (3)

| No. | Modified enzyme | Relative activity |
|---|---|---|
| 179 | S2K | 0% |
| 180 | S2E | 0% |
| 181 | S2G | 0% |
| 182 | S2A | 62% |
| 183 | V55E | 45% |
| 184 | V76E | 45% |
| 185 | V97E | 75% |
| 186 | L114E | 41% |
| 187 | V121E | 0% |
| 188 | Q123C | 69% |
| 189 | V125E | 75% |
| 190 | V144E | 60% |
| 191 | V187E | 80% |
| 192 | V191E | 40% |
| 193 | L224E | 42% |
| 194 | V236E | 40% |
| 195 | V270E | 0% |
| 196 | V290E | 0% |
| 197 | L313E | 0% |
| 198 | V320E | 0% |
| 199 | V346E | 0% |
| 200 | L354E | 0% |
| 201 | I388C | 41% |
| 202 | I388C/Q123C | 101% |
| 203 | I388C/N360C | 40% |
| 204 | V400E | 40% |
| 205 | V405C | 35% |
| 206 | V436C | 25% |

TABLE 1-3-continued

Activity value of Modified enzymes produced base on Concept (3)

| No. | Modified enzyme | Relative activity |
|---|---|---|
| 207 | R437C | 0% |
| 208 | I442C | 35% |
| 209 | E471C | 145% |
| 210 | E471C/A390C | 205% |
| 211 | L529E | 0% |

TABLE 2-1

List of Modified enzymes exhibiting relative activity of 30% or more (No. 1)

| No. | Modified enzyme | Relative activity | Concept |
|---|---|---|---|
| 1 | C286V | 1504% | (2) |
| 2 | C373V | 1391% | (2) |
| 3 | L414C | 979% | (2) |
| 4 | V320C | 902% | (2) |
| 5 | C521E | 265% | (2) |
| 6 | C370V | 255% | (2) |
| 7 | C521V | 244% | (2) |
| 8 | C137K | 240% | (2) |
| 9 | T298I | 236% | (1) |
| 10 | C370E | 234% | (2) |
| 11 | C440S | 231% | (2) |
| 12 | C373Y | 224% | (2) |
| 13 | S383M | 220% | (1) |
| 14 | I518C | 214% | (2) |
| 15 | C137E | 208% | (2) |
| 16 | E471C/A390C | 205% | (3) |
| 17 | C370N | 201% | (2) |
| 18 | C416K | 197% | (2) |
| 19 | D348E | 185% | (1) |
| 20 | C373F | 181% | (2) |
| 21 | C137I | 164% | (2) |
| 22 | C416E | 157% | (2) |
| 23 | E471C | 145% | (3) |
| 24 | F508C | 141% | (2) |
| 25 | D131C | 124% | (2) |
| 26 | C416Y | 123% | (2) |
| 27 | V346M | 118% | (2) |
| 28 | I300N | 113% | (2) |
| 29 | C521I | 112% | (2) |
| 30 | C521S | 102% | (2) |
| 31 | C446V | 101% | (2) |
| 32 | I388C/Q123C | 101% | (3) |
| 33 | C338V | 99% | (2) |

TABLE 2-2

List of Modified enzymes exhibiting relative activity of 30% or more (No. 2)

| No. | Modified enzyme | Relative activity | Concept |
|---|---|---|---|
| 34 | C521N | 93% | (2) |
| 35 | C338L | 90% | (2) |
| 36 | C370K | 85% | (2) |
| 37 | V187E | 80% | (3) |
| 38 | V97E | 75% | (3) |
| 39 | V125E | 75% | (3) |
| 40 | C137M | 70% | (2) |
| 41 | Q123C | 69% | (3) |
| 42 | C480N | 67% | (2) |
| 43 | C480Y | 62% | (2) |
| 44 | S2A | 62% | (3) |
| 45 | V144E | 60% | (3) |
| 46 | C137S | 58% | (2) |
| 47 | K481E | 58% | (2) |
| 48 | C286N | 56% | (2) |
| 49 | C286I | 55% | (2) |
| 50 | S452C | 52% | (2) |

TABLE 2-2-continued

| List of Modified enzymes exhibiting relative activity of 30% or more (No. 2) | | | |
|---|---|---|---|
| No. | Modified enzyme | Relative activity | Concept |
| 51 | C446N | 52% | (2) |
| 52 | V55E | 45% | (3) |
| 53 | V76E | 45% | (3) |
| 54 | C480V | 42% | (2) |
| 55 | L224E | 42% | (3) |
| 56 | L114E | 41% | (3) |
| 57 | I388C | 41% | (3) |
| 58 | I388C/N360C | 40% | (3) |
| 59 | V405E | 40% | (2) |
| 60 | V191E | 40% | (3) |
| 61 | V236E | 40% | (3) |
| 62 | V400E | 40% | (3) |
| 63 | V346S | 39% | (2) |
| 64 | V405C | 35% | (3) |
| 65 | I442C | 35% | (3) |
| 66 | S383I | 35% | (1) |
| 67 | T451E | 30% | (1) |

(1-6) Semi-Quantitative Evaluation of Ability of Modified Enzyme to Convert into Isoprene The aforementioned comparison of the amounts of isoprene produced by respective modified enzymes is a qualitative analysis, and thus, an enzyme concentration of mIspSM is not controlled. Thus, for 36 of 68 promising modified enzymes, the crude purified solution of mIspSM was developed on 4 to 12% NuPAGE (Life Technologies, catalog #NPO323BOX), and a band derived from each modified enzyme was quantified as a band intensity using a gel analyzer (BioRad). The band intensity derived from each modified enzyme was divided by a band intensity derived from the wild type to calculate a relative intensity. An amount of isoprene converted from DMAPP by mIspSM for 20 minutes was quantified by the same method as in the aforementioned comparison of the amounts of isoprene produced by respective modified enzymes. Hereinafter, the amount of isoprene produced by the reaction for 20 minutes is referred to as an amount of isoprene produced in an early phase. Further, in order to evaluate the enzyme stability of mIspSM, an amount of isoprene produced for a long period of time was quantified and referred to as an ability to accumulate isoprene. In order to evaluate the ability to accumulate isoprene, a reaction mixture composed of 4 μL of crude purified mIspSM solution, 41 μL of reaction buffer (50 mM Tris-HCl, 20 mM $MgCl_2$, pH 8.0) and 4 μL of 40 mM DMAPP was reacted at 37° C. for 17 hours. Subsequently, the produced isoprene was quantified by gas chromatography based on the condition described Reference Example (4-3). The resulting amount of isoprene produced in the early phase was divided by the band intensity to calculate a specific amount of isoprene produced in the early phase (Formula 1). The resulting ability to accumulate isoprene was divided by the band intensity to calculate a specific ability to accumulate isoprene (Formula 2). For the specific amount of isoprene produced in the early phase, a ratio was calculated so as to compare the modified enzymes with the wild type enzyme (Formula 3). For the specific ability to accumulate isoprene, a ratio was calculated so as to compare the modified enzymes with the wild type enzyme (Formula 4).

(Specific amount of isoprene produced in early phase)=(Amount of isoprene after reaction for 20 minutes)/(Band intensity)   Formula 1:

(Specific ability to accumulate isoprene)=(Amount of isoprene after reaction for 17 hours)/(Band intensity)   Formula 2:

(Ratio of modified enzyme to wild type for amount of isoprene produced in early phase)=(Formula 1 for modified enzyme)/(Formula 1 for wild type)   Formula 3:

(Ratio of modified enzyme to wild type for ability to accumulate isoprene)=(Formula 2 for modified enzyme)/(Formula 2 for wild type)   Formula 4:

The results are shown in Table 3. Those where the ratio of the modified enzyme to the wild type for the amount of isoprene produced in the early phase or the ratio of the modified enzyme to the wild type for the ability to accumulate isoprene was 1.1 fold or more were defined as effective modified enzymes. The modified enzymes where both ratios had increased were C446N, V97E, D131C, C137I, C137S, E471C/A390C, T298I, V125E, and I518C, the modified enzymes where only the ratio of the modified enzyme to the wild type for the ability to accumulate isoprene had increased were C521V, C521E, C480V, C286I, D348E, C370V, I300N, C521I, C286V, C137M, C137K, and C286N, and those where only the ratio of the modified enzyme to the wild type for the amount of isoprene produced in the early phase had increased were C480Y, C346M, C521N, and S383M.

TABLE 3

| Ratio of mIspSM to wild type for activity and isoprene accumulation | | | | |
|---|---|---|---|---|
| Modified enzyme | Ratio for activity* | Ratio for accumulation* | Effective modified enzyme | Effective function |
| C521V | 0.9 | 22.5 | Yes | Accum.* |
| C521E | 0.3 | 16.7 | Yes | Accum.* |
| C480V | 0.7 | 9.4 | Yes | Accum.* |
| C286I | 0.8 | 7.4 | Yes | Accum.* |
| D348E | 0.2 | 6.3 | Yes | Accum.* |
| C370V | 0.9 | 5.8 | Yes | Accum.* |
| C446N | 1.3 | 5 | Yes | Accum./Early pro.* |
| V97E | 2.2 | 4.9 | Yes | Accum./Early pro.* |
| I300N | 0.9 | 4.7 | Yes | Accum.* |
| C521I | 0.4 | 4.5 | Yes | Accum.* |
| C286V | 0.7 | 4.5 | Yes | Accum.* |
| D131C | 2.4 | 4.2 | Yes | Accum./Early pro.* |
| C137I | 2.3 | 3.8 | Yes | Accum./Early pro.* |
| C137M | 0.4 | 3.4 | Yes | Accum.* |
| C137S | 1.8 | 2.9 | Yes | Accum./Early pro.* |
| E471C/ A390C | 1.3 | 2.3 | Yes | Accum./Early pro.* |
| C137K | 0.9 | 2.2 | Yes | Accum.* |
| T298I | 1.1 | 1.9 | Yes | Accum./Early pro.* |
| V125E | 1.2 | 1.5 | Yes | Accum./Early pro.* |
| C286N | 1 | 1.4 | Yes | Accumulation |
| I518C | 1.2 | 1.1 | Yes | Accum./Early pro.* |
| S2A | 0.9 | 1 | No | |
| L114E | 0.4 | 0.9 | No | |
| C480N | 0.5 | 0.9 | No | |
| C480Y | 1.5 | 0.9 | Yes | Early pro.* |
| V346M | 1.1 | 0.9 | Yes | Early pro.* |
| C521S | 0.4 | 0.9 | No | |
| C373Y | 0.3 | 0.9 | No | |
| C338L | 0.9 | 0.8 | No | |
| Q123C | 0.2 | 0.7 | No | |

TABLE 3-continued

Ratio of mIspSM to wild type for activity and isoprene accumulation

| Modified enzyme | Ratio for activity* | Ratio for accumulation* | Effective modified enzyme | Effective function |
|---|---|---|---|---|
| C521N | 3.7 | 0.7 | Yes | Early pro.* |
| K481E | 1 | 0.7 | No | |
| L224E | 0.1 | 0.6 | No | |
| V346S | 0.4 | 0.5 | No | |
| C440S | 0.4 | 0.4 | No | |
| S383M | 1.1 | 0.4 | Yes | Early pro.* |

*Ratio for activity: Ratio of mIspSM to wild type for amount of isoprene produced in early phase

*Ratio for accumulation: Ratio of mIspSM to wild type for ability to accumulate isoprene

*Accum.: Ability of accumulation

*Early pro.: Amount of early production

"Yes" in columns for the effective modified enzyme indicates the effective modified enzyme where the value calculated in Formula 3 or Formula 4 is 1.1 folds or more in the modified enzyme as compared with the wild type.

"No" in columns for the effective modified enzyme indicates a non-effective modified enzyme where the value calculated in Formula 3 or Formula 4 is less than 1.1 folds in the modified enzyme as compared with the wild type. The ability of accumulation in columns for the effective function indicates that the value calculated in Formula 3 is 1.1 folds or more, and the amount of early production indicates that the value calculated in Formula 3 is 1.1 folds or more.

Example 2: Design of Modified Enzymes of Isoprene Synthase (IspS) and Analysis of Modified Enzymes of Isoprene Synthase by Fermentation Method Using Transformants (2-1) Construction of Plasmid for Expressing Mutant IspSM A mutation was introduced into an IspSM gene by the following procedures. PCR with pSTV-Ptac-IspSM as a template was carried out using primers for mutation introduction and PrimeStar polymerase (supplied from TaKaRa Bio). The nucleotide sequence of the polynucleotide encoding IspSM and its amino acid sequence are represented by SEQ ID NO:3 and 4, respectively as described in Example 1. A reaction solution was prepared according to a composition attached to the kit, and a cycle of 98° C. for 10 seconds, 54° C. for 20 seconds and 72° C. for 300 seconds was repeated 40 times. As a result, a PCR product of the IspSM gene having the introduced mutation was obtained. The resulting PCR product was purified followed by treatment with a restriction enzyme DpnI (TaKaRa Bio). *E. coli* JM109 was transformed with the PCR product after treatment with DpnI by a heat shock method, then applied onto an LB plate containing 60 mg/L of chloramphenicol, and cultured at 37° C. for 16 to 24 hours. Subsequently, a transformant exhibiting resistance to chloramphenicol was obtained from the resulting plate. Plasmid extraction was carried out from the resulting transformant according to standard methods. Subsequently, in order to confirm that the mutation was introduced into an objective position as designed in the plasmid, a nucleotide sequence was analyzed by a sequencer. It was thus confirmed that amino acid substitution had occurred in the IspSM protein. Positions of the amino acid substitution in the IspSM protein and names for the plasmids for expressing mutant IspSM were described in Table 4.

TABLE 4

Positions of the amino acid substitution in the IspSM protein and names for the plasmids for expressing mutant IspSM

| Names for plasmids for expressing mutant IspSM | Positions of amino acid substitution in IspSM protein |
|---|---|
| pSTV-Ptac-IspSM (Y304F) | Y304F |
| pSTV-Ptac-IspSM (Y394F) | Y394F |
| pSTV-Ptac-IspSM (T462S) | T462S |
| pSTV-Ptac-IspSM (T466F) | T466F |
| pSTV-Ptac-IspSM (T466C) | T466C |
| pSTV-Ptac-IspSM (T466W) | T466W |
| pSTV-Ptac-IspSM (T466M) | T466M |
| pSTV-Ptac-IspSM (T466Y) | T466Y |
| pSTV-Ptac-IspSM (T466H) | T466H |
| pSTV-Ptac-IspSM (T466P) | T466P |
| pSTV-Ptac-IspSM (T466Q) | T466Q |
| pSTV-Ptac-IspSM (T466N) | T466N |
| pSTV-Ptac-IspSM (T466A) | T466A |

(2-2) Introduction of Plasmid for Expressing Mutant IspSM into Ptac-KKDyI Strain Competent cells of MG1655 Ptac-KKDyI strain (see Reference Example (7-4)) were prepared, and then each of pSTV-Ptac-IspSM, pSTV-Ptac-IspSM (Y304F), pSTV-Ptac-IspSM (Y394F), pSTV-Ptac-IspSM (T462S), pSTV-Ptac-IspSM (T466F), pSTV-Ptac-IspSM (T466C), pSTV-Ptac-IspSM (T466W), pSTV-Ptac-IspSM (T466M), pSTV-Ptac-IspSM (T466Y), pSTV-Ptac-IspSM (T466H), pSTV-Ptac-IspSM (T466P), pSTV-Ptac-IspSM (T466Q), pSTV-Ptac-IspSM (T466N), or pSTV-Ptac-IspSM (T466A) was introduced thereto by an electroporation method. Culture medium containing the transformant was evenly applied onto an LB plate containing 60 mg/L of chloramphenicol, and cultured at 37° C. for 16 to 24 hours. Subsequently, a transformant with resistance to chloramphenicol was obtained from the resulting plate. A strain where pSTV-Ptac-IspSM, pSTV-Ptac-IspSM (Y304F), pSTV-Ptac-IspSM (Y394F), pSTV-Ptac-IspSM (T462S), pSTV-Ptac-IspSM (T466F), pSTV-Ptac-IspSM (T466C), pSTV-Ptac-IspSM (T466W), pSTV-Ptac-IspSM (T466M), pSTV-Ptac-IspSM (T466Y), or pSTV-Ptac-IspSM (T466H) had been introduced into MG1655 Ptac-KKDyI strain was designated as Ptac-KKDyI/IspSM, Ptac-KKDyI/IspSM (Y304F), Ptac-KKDyI/IspSM (Y394F), Ptac-KKDyI/IspSM (T462S), Ptac-KKDyI/IspSM (T466F), Ptac-KKDyI/IspSM (T466C), Ptac-KKDyI/IspSM (T466W), Ptac-KKDyI/IspSM (T466M), Ptac-KKDyI/IspSM (T466Y), Ptac-KKDyI/IspSM (T466H), Ptac-KKDyI/IspSM (T466P), Ptac-KKDyI/IspSM (T466Q), Ptac-KKDyI/IspSM (T466N), or Ptac-KKDyI/IspSM (T466A).

(2-3) Comparison of Ability to Produce Isoprene in Strains Having Introduced Mutant IspSM Each of the pSTV-Ptac-IspSM and the MG1655 Ptac-KKDyI strain having each introduced mutant IspSM were evenly applied onto an LB plate containing 60 mg/L of chloramphenicol, and cultured at 37° C. for 18 hours. One loopful of microbial cells from the resulting plate was inoculated to 1 mL of M9 glucose medium (containing mevalonic acid) in a headspace vial (supplied from Perkin Elmer, 22 mL, CREAR CRIMP TOP VIAL cat#B0104236), and subsequently cultured with shaking for 24 hours. A composition of the M9 glucose medium (containing mevalonic acid) was described in Table 5. DMAPP (dimethylallyl diphosphate) is supplied from a carbon source (mevalonic acid) in the medium by culturing the above transformant in this medium. $OD_{600}$ values at the end of the culture, amounts of produced isoprene, and relative values of production by Ptac-KKDyI/IspSM were described in Table 6. A concentration of isoprene in the headspace in the vial was measured by gas chromatography. A condition for the gas chromatography is described below.

TABLE 5

| Composition of M9 glucose medium (containing mevalonic acid) | |
|---|---|
| Glucose | 2.0 (g/L) |
| $Na_2HPO_4$ | 6.0 (g/L) |
| $KH_2PO_4$ | 3.0 (g/L) |
| $NH_4Cl$ | 1.0 (g/L) |
| Mevalonic acid (ADEKA) | 1.0 (g/L) |
| 1M $MgSO_4$ (autoclaved) | 1.0 ml |
| 1M $CaCl_2$ (autoclaved) | 0.1 ml |

Chloramphenicol was added at a final concentration of 60 mg/L.

A total volume was adjusted to 1 L, and then filter sterilization was carried out.

TABLE 6

$OD_{600}$ values, amounts of produced isoprene (mg/L), and relative values as compared to production by Ptac-KKDyI/IspSM

| Bacterial strain name | OD600 | Isoprene production (mg/L) | Relative value[a)] (Isoprene production) |
|---|---|---|---|
| Ptac-KKDyI/IspSM | 3.07 ± 0.09 | 38.94 ± 1.95 | 1.00 |
| Ptac-KKDyI/IspSM(Y304F) | 3.28 ± 0.09 | 40.03 ± 0.77 | 1.03 |
| Ptac-KKDyI/IspSM(Y394F) | 3.28 ± 0.09 | 40.25 ± 1.97 | 1.03 |
| Ptac-KKDyI/IspSM(T462S) | 3.64 ± 0.02 | 43.08 ± 1.48 | 1.10 |
| Ptac-KKDyI/IspSM(T466F) | 3.12 ± 0.06 | 48.65 ± 5.17 | 1.25 |
| Ptac-KKDyI/IspSM(T466C) | 3.22 ± 0.04 | 47.74 ± 2.47 | 1.23 |
| Ptac-KKDyI/IspSM(T466W) | 3.35 ± 0.04 | 47.01 ± 1.68 | 1.21 |
| Ptac-KKDyI/IspSM(T466M) | 3.32 ± 0.19 | 45.81 ± 2.51 | 1.18 |
| Ptac-KKDyI/IspSM(T466Y) | 3.11 ± 0.06 | 44.63 ± 3.03 | 1.15 |
| Ptac-KKDyI/IspSM(T466H) | 3.31 ± 0.10 | 42.74 ± 2.24 | 1.10 |
| Ptac-KKDyI/IspSM(T466P) | 3.38 ± 0.15 | 41.61 ± 3.10 | 1.07 |
| Ptac-KKDyI/IspSM(T466Q) | 3.23 ± 0.06 | 40.97 ± 2.35 | 1.05 |
| Ptac-KKDyI/IspSM(T466N) | 3.33 ± 0.16 | 39.74 ± 6.44 | 1.02 |
| Ptac-KKDyI/IspSM(T466A) | 3.32 ± 0.05 | 39.56 ± 3.60 | 1.02 |

[a)]A relative value is shown when an amount of isoprene produced by Ptac-KKDyI/IspSM is 1.

As a result, a larger amount (mg/L) of isoprene than that produced by Ptac-KKDyI/IspSM strain was observed in all of evaluated strains having the introduced mutant IspSM (Table 6).

Reference Example 1: Evaluation of Ability to Produce Isoprene in Plants 1-1) Measurement of Amount of Isoprene Formed Per Unit Weight of Dry Leaves First, an amount of isoprene formed per 1 g of dry leaves in the plant was measured for evaluating an ability to produce isoprene in plants. *Mucuna* (*Mucuna bracteata*), Weeping willow (*Salix babylonica*), American sweetgum (*Liquidambar styraciflua*), Myrtle (*Myrtus communis*), and Kudzu (*Pueraria lobata*) were used as the plants.

In the measurement of an amount of formed isoprene, a gas replaceable desiccator (trade name: Vacuum Desiccator, manufactured by AS ONE Corporation) was housed in an incubator (trade name: Growth Chamber MLR-351H, manufactured by SANYO), and the incubator was set to a high temperature induction condition (an illuminance of 100 μmol $E/m^2/s$ at 40° C.) while a fan for stirring the gas, which was provided in the gas replaceable desiccator, was driven to stir an atmosphere in space in the gas replaceable desiccator. After the temperature of the atmosphere in the gas replaceable desiccator reached 40° C., a plant body of *Mucuna* planted in a planter was housed therein and kept for 3 hours in a state where the gas replaceable desiccator was sealed. Then, a gas component released from *Mucuna* was aspirated from the space in the gas replaceable desiccator by an aspiration pump through a silicon tube, an adsorption tube and a gas collection tube. Thereby, water vapor (water content) contained in the gas component released from *Mucuna* was adsorbed and separated in the adsorption tube, the gas component from which the water vapor had been separated was led to the gas collection tube, and the gas component was collected in the gas collection tube. Subsequently, isoprene contained in the gas component collected in the gas collection tube was quantitatively analyzed using gas chromatograph (trade name: GC-FID6890, manufactured by Agilent).

For the weight of dry leaves, a leaf area of a fresh individual leaf, and a dry weight when the fresh individual leaf is dried by a dryer at 80° C. for 8 hours establish a very good positive correlation. Thus, a formula for converting from the leaf area to the dry weight was derived, and the dry weight was estimated from the entire leaf area from the plant body of *Mucuna* used for the measurement of an amount of formed isoprene.

The amount of formed isoprene per 1 g of the dry leaf was obtained by dividing the amount of formed isoprene from the entire plant body of *Mucuna* by the estimated weight of the entire plant body.

As a result, it was demonstrated that *Mucuna* was excellent in amount of formed isoprene per unit weight of the dry leaf (FIG. 1).

1-2) Measurement of Amount of Formed Isoprene Per Amount of Total Protein

Then, the amount of formed isoprene per amount of total protein extracted from leaves of various plants was measured. *Mucuna* (samples 1 and 2), Weeping willow, American sweetgum, Myrtle, and Kudzu were used as the plants.

For extraction of the protein, a buffer solution (50 mM Tris-HCl, 20 mM MgCl, 5% glycerol, 0.02% TRITON® X100, pH 8.0) was made, and 10% POLYCLAR® AT, 20 mM DTT, protease complete tablet (one tablet/50 mL), and 1 mM benzamidine HCl (final concentrations, each) were added just before the use, and was used as a protein extraction buffer. 50 mL of the protein extraction buffer was added to 5 g of the sample, then the mixture was ground well in a cold mortar on ice and filtrated though doubly overlapped Miracloth. A filtrate was centrifuged at 12,000 G for 20 minutes and 40,000 G for 40 minutes to obtain a supernatant, and the supernatant was used as a crude extract.

Subsequently, this crude extract was fractionated with ammonium sulfate. Proteins precipitated in a range of 40% to 55% of final concentrations of ammonium sulfate were centrifuged at 40,000 G for 40 minutes, and an obtained pellet was re-dissolved in the protein extraction buffer to obtain an ammonium sulfate fraction.

A total (ammonium sulfate fraction) protein mass was calculated by measuring the ammonium sulfate fraction using Bradford assay. A Bradford reagent was reacted with the standard protein, bovine serum albumin, and absorbance at a wavelength of 595 nm was measured using a spectrophotometer. A standard curve for the protein was made using the obtained absorbance values. The absorbance at a wavelength of 595 nm was also measured in the ammonium sulfate fraction diluted to 50 times, and the amount of the total (ammonium sulfate fraction) protein was estimated from the standard curve for the standard protein.

In the measurement of the amount of formed isoprene, 100 µL of the crude extract or 100 µL of a crude enzyme solution boiled at 100° C. was placed in a 4 mL glass vial, and then 2 µL of a 0.5 M $MgCl_2$ solution and 5 µL of a 0.2 M DMAPP solution were added thereto. The vial was tightly closed with a screw cap with a septum, and then the vial was gently vortexed and set in an incubator at 40° C. After 0.5, 1 and 2 hours, 0.5 to 2 mL of a gas layer in a headspace was sampled by a gas-tight syringe, and the amount of formed isoprene was measured using gas chromatograph (trade name: GC-FID6890, manufactured by Agilent). The amount of formed isoprene using the crude enzyme after 0.5, 1 and 2 hours was calculated by subtracting a measured value in the case of using the crude enzyme solution boiled at 100° C. from a measured value in the case of using the crude enzyme. An enzymatic activity per 1 mg of the total protein (specific activity) was calculated from the amount of the formed isoprene per one hour. The amount of formed isoprene was measured with keeping the amount of DMAPP that was the substrate of the isoprene synthase constant.

Figure 2:
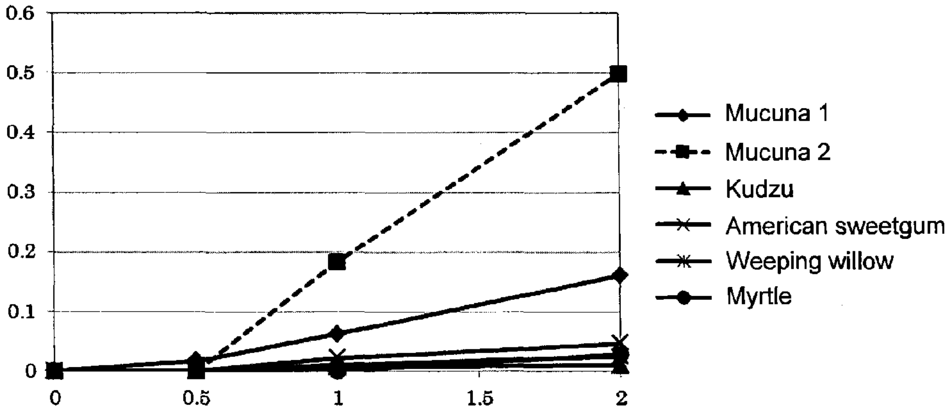
FIG. 2 shows the amounts of isoprene generated per total protein mass extracted from leaves of various plants.

As a result, it was demonstrated that *Mucuna* was excellent in amount of formed isoprene per amount of total protein (FIG. 2, Table 7). As described above, it was shown that *Mucuna* was excellent in ability to produce isoprene.

TABLE 7

Amount of formed isoprene per amount of total protein (index numbers relative to case of Kudzu)

|  | 0 hour* | 0.5 hour* | 1 hour* | 2 hours* | Specific activity index (Value from Kudzu was set to 1) |
| --- | --- | --- | --- | --- | --- |
| Mucuna 1 | 0 | 16.947 | 61.895 | 160.632 | 16.87842808 |
| Mucuna 2 | 0 | 0 | 183.587 | 449.514 | 47.23274141 |
| American sweetgum | 0 | 0 | 22.063 | 46.132 | 4.847325838 |
| Weeping willow | 0 | 0 | 9.756 | 24.39 | 2.562782389 |
| Myrtle | 0 | 0 | 0 | 27.451 | 2.884417358 |
| Kudzu | 0 | 0 | 6.662 | 9.517 | 1 |

*Unit is µg isoprene/mg protein

Reference Example 2: Cloning of Isoprene Synthase Gene Derived from *Mucuna*

2-1) Evaluation of Sampling Time

Isoprene gas released from leaves of *Mucuna* illuminated with light for 1, 2, 3 and 5 hours at temperature of 40° C. was sampled and the amount of produced isoprene was quantified by gas chromatography described later, and production of 4, 8, 12 and 10 µg of isoprene/g DW leaf was confirmed. Thus, it was confirmed that an optimal light illumination time was 3 hours.

2-2) Extraction of Total RNA Lysis Solution

A total RNA was extracted from leaves of *Mucuna* with total RNA lysis solution according to the following procedures.

(1) The leaves of *Mucuna* illuminated with light for 3 hours at temperature of 40° C. were sampled.

(2) 100 mg of leaf tissue was pulverized in a mortar with rapidly freezing the leaf tissue with liquid nitrogen, then the leaf tissue together with the liquid nitrogen was dispensed in an RNA-free 2 mL Eppendorf tube, and the liquid nitrogen was gasified.

(3) To this Eppendorf tube, 450 µL of a dissolution buffer RLT (containing 2-mercaptoethanol) attached to RNEASY® Plant Kit (manufactured by Qiagen), and mixed vigorously with Vortex to obtain a leaf tissue lysate.

(4) This leaf tissue lysate was applied to QIA shredder spin column attached to RNEASY® Plant Kit, and centrifuged at 15,000 rpm for 2 minutes.

(5) A supernatant alone of a column eluate was transferred to a new RNA-free 2 mL Eppendorf tube, then special grade ethanol in a half volume of the supernatant was added to the supernatant, and the obtained solution was mixed by pipetting to obtain about 650 µL of a solution.

(6) This solution was applied to RNEASY® spin column attached to RNEASY® Plant Kit, centrifuged at 10,000 rpm for 15 seconds, and a filtrate was discarded.

(7) 700 µL of RW1 buffer attached to RNEASY® Plant Kit was added to this RNEASY® spin column, centrifuged at 10,000 rpm for 15 seconds, and a filtrate was discarded.

(8) 500 µL of BPE buffer attached to RNEASY® Plant Kit was added to this RNEASY® spin column, centrifuged at 10,000 rpm for 15 seconds, and a filtrate was discarded.

(9) 500 µL of BPE buffer was again added to this RNEASY® spin column, centrifuged at 10,000 rpm for 2 minutes, and a filtrate was discarded.

(10) This RNEASY® spin column was set to a 2 mL collective tube attached to RNEASY® Plant Kit, centrifuged at 15,000 rpm for one minute, and a filtrate was discarded.

(11) This RNEASY® spin column was set to a 1.5 mL collective tube attached to RNEASY® Plant Kit.

(12) RNA-free distilled water attached to RNEASY® Plant Kit was directly added to a membrane of this RNEASY® spin column using a Pipetman, centrifuged at 10,000 rpm for one minute, and total RNA was collected. This step was repeated twice to obtain about 100 µg of total RNA.

2-3) Analysis of Nucleotide Sequence of Isoprene Synthase Gene Derived from *Mucuna*

Quality of RNA in the extracted total RNA solution was checked using nano-chips for RNA provided by BioAnalyzer (Agilent Technologies, Inc.), and it was confirmed that the solution was not contaminated with genomic DNA and RNA was not decomposed in the solution.

This total RNA was converted into a double strand using reverse transcriptase, and then fragmented using a nebulizer. Nucleotide sequences of 198,179 fragments having a poly A sequence at a 3' end were analyzed using 454 titanium FLX high performance sequencer (manufactured by Roche Applied Science). Overlapped sequences in the obtained fragment sequences were aligned to obtain 13,485 contig sequences. BLAST search was performed for these contig sequences, and 6 contig sequences having the homology (identity of nucleotide sequences) to registered and known isoprene synthase gene sequences from Kudzu and Poplar were extracted. These sequences were further analyzed in detail, and 3 sequences in these 6 contig sequences were found to be derived from the same gene. Thus, a partial sequence of the isoprene synthase gene derived from *Mucuna* was obtained. 5' RACE was performed based on this partial sequence to obtain a full length nucleotide sequence of the isoprene synthase gene derived from *Mucuna*, which was represented by SEQ ID NO:1.

Reference Example 3: Preparation of Expression Plasmid for Isoprene Synthase Derived from Various Plants 3-1) Chemical Synthesis of Isoprene Synthase Derived from *Pueraria montana* Var. *Lobata* (Kudzu)

The nucleotide sequence and the amino acid sequence of the isoprene synthase derived from *Pueraria montana* var. *lobata* were already known (ACCESSION: AAQ84170: *P. montana* var. *lobata* isoprene synthase (IspS)). The amino acid sequence of the IspS protein derived from *P. montana* and the nucleotide sequence of its gene are represented by SEQ ID NO:10 and SEQ ID NO:11, respectively. The IspS gene was optimized for codon usage frequency in *E. coli* in order to efficiently express the IspS gene in *E. coli*, and further designed to cut off the chloroplast localization signal. The designed gene was designated as IspSK. A nucleotide sequence of IspSK is represented by SEQ ID NO:12. The IspSK gene was chemically synthesized, then cloned into pUC57 (manufactured by GenScript), and the resulting plasmid was designated as pUC5-IspSK.

3-2) Chemical Synthesis of Isoprene Synthase Derived from *Populus alba*×*Populus tremula* (Poplar)

The nucleotide sequence and the amino acid sequence of the isoprene synthase derived from *P. alba*×*P. tremula* were already known (ACCESSION: CAC35696: *P. alba*×*P. tremula* (Poplar) isoprene synthase). The amino acid sequence of the IspS protein derived from *P. alba*×*P. tremula* and the nucleotide sequence of its gene are represented by SEQ ID NO:13 and SEQ ID NO:14, respectively. An IspS gene that was optimized for the codon usage frequency in *E. coli* in the same manner as above and in which the chloroplast localization signal was cut off was designed and designated as IspSP. A nucleotide sequence of IspSP is represented by SEQ ID NO:15. The IspSP gene was chemically synthesized, then cloned into pUC57 (manufactured by GenScript), and the resulting plasmid was designated as pUC57-IspSP.

3-3) Chemical Synthesis of Isoprene Synthase Derived from *Mucuna*

Based on the nucleotide sequence of the isoprene synthase derived from *Mucuna*, an IspS gene that was optimized for the codon usage frequency in *E. coli* was designed in the same manner as above. One in which the chloroplast localization signal had been conferred was designated as IspSM (L), and one in which the chloroplast localization signal had been cut off was designated as IspSM. Nucleotide sequences for IspSM (L) and IspSM are represented by SEQ ID NO:16 and SEQ ID NO:3, respectively. The IspSM gene and the IspSM (L) gene were chemically synthesized, then cloned into pUC57 (manufactured by GenScript), and the resulting plasmids were designated as pUC57-IspSM and pUC57-IspSM (L).

3-4) Construction of Expression Plasmid, pSTV28-Ptac-Ttrp

An expression plasmid pSTV28-Ptac-Ttrp for expressing IspS derived from various plants in *E. coli* was constructed. First, a DNA fragment comprising a tac promoter (synonym: Ptac) region (deBoer, et al., (1983) Proc. Natl. Acad. Sci. U.S.A., 80, 21-25) and a terminator region of tryptophan operon (synonym: Ttrp) derived from *E. coli* (Wu et al., (1978) Proc. Natl. Acad. Sci. U.S.A., 75, 442-5446) and having a KpnI site at a 5' terminus and a BamHI site at a 3' end was synthesized chemically (the nucleotide sequence of Ptac-Ttrp is represented by SEQ ID NO:17). The resulting Ptac-Ttrp DNA fragment was digested with KpnI and BamHI, and ligated to pSTV28 (manufactured by Takara Bio Inc.) similarly digested with KpnI and BamHI by a ligation reaction with DNA ligase. The resulting plasmid was designated as pSTV28-Ptac-Ttrp (its nucleotide sequence is represented by SEQ ID NO:18). This plasmid can amplify the expression of the IspS gene by cloning the IspS gene downstream of Ptac.

3-5) Construction of Plasmid for Expressing IspS Gene Derived from Various Plants Plasmids for expressing the IspSK gene, the IspSP gene, the IspSM gene and the IspSM (L) gene in *E. coli* were constructed by the following procedure. PCR was performed with Prime Star polymerase (manufactured by Takara Bio Inc.) using synthesized oligonucleotides consisting of the nucleotide sequences represented by SEQ ID NOs:19 and 20 as primers with pUC57-IspSK as a template, synthesized oligonucleotides consisting of the nucleotide sequences represented by SEQ ID NOs:21 and 22 as primers with pUC57-IspSP as a template, synthesized oligonucleotides consisting of the nucleotide sequences represented by SEQ ID NOs:23 and 24 as primers with pUC57-IspSM as a template, or further synthesized oligonucleotides consisting of the nucleotide sequences represented by SEQ ID NOs:25 and 26 as primers with pUC57-IspSM (L) as a template. A reaction solution was prepared according to a composition attached to the kit, and a reaction at 98° C. for 10 seconds, 54° C. for 20 seconds and 68° C. for 120 seconds was performed in 40 cycles. As a result, a PCR product containing the IspSK gene, the IspSP gene, the IspSM gene or the IspSM (L) gene was obtained. Likewise, PCR was performed with Prime Star polymerase (manufactured by Takara Bio Inc.) using synthesized oligonucleotides consisting of the nucleotide sequences represented by SEQ ID NOs:27 and 28 as primers with pSTV28-Ptac-Ttrp as a template, A reaction solution was prepared according to a composition attached to the kit, and a reaction at 98° C. for 10 seconds, 54° C. for 20 seconds and 68° C. for 210 seconds was performed in 40 cycles. As a result, a PCR product containing pSTV28-Ptac-Ttrp was obtained. Subsequently, the purified IspSK gene, IspSP gene, IspSM gene, and IspSM (L) gene fragments were ligated to the PCR product for pSTV28-Ptac-Ttrp using In-Fusion HD Cloning Kit (manufactured by Clontech). The resulting plasmids for expressing the IspSK gene, the IspSP gene, IspSM gene and IspSM (L) gene were designated as pSTV28-Ptac-IspSK, pSTV28-Ptac-IspSP, pSTV28-Ptac-IspSM, and pSTV28-Ptac-IspSM (L), respectively.

TABLE 8

Primer sequences used for construction of plasmids for expressing IspS genes derived from various plants

| Subject for amplification | Sequence name | Sequence (5'-) |
|---|---|---|
| IspSK | Ptac-IspS(K)F | GATAACAATTTCACACAAT AATTTTGTTTAACTTTAAG AAGGAGATATAATGTGTGC GACCTCTTCTCAATTTACT CAG (SEQ ID NO: 19) |

TABLE 8-continued

Primer sequences used for construction of plasmids for expressing IspS genes derived from various plants

| Subject for amplification | Sequence name | Sequence (5'-) |
|---|---|---|
| IspSK | IspS(K)R-MCSR | ACGGCCAGTGAATTCTTAGACATACATCAGCTGGTTAATCGG (SEQ ID NO: 20) |
| IspSP | Ptac-IspS(P)F | GATAACAATTTCACACAATAATTTTGTTTAACTTTAAGAAGGAGATATAATGTGCTCTGTTTCTACCGAGAACGTTTCC (SEQ ID NO: 21) |
| IspSP | IspS(P)R-MCSR | ACGGCCAGTGAATTCTTAACGTTCGAACGGCAGAATCGGTTCG (SEQ ID NO: 22) |
| IspSM | Ptac-IspS(M)F | GATAACAATTTCACACAATAATTTTGTTTAACTTTAAGAAGGAGATATAATGTCCGCCGTTTCAAGCCA (SEQ ID NO: 23) |
| IspSM | IspS(M)R-MCSR | ACGGCCAGTGAATTCTTAGTTAATCGGGAACGGGT (SEQ ID NO: 24) |
| IspSM(L) | Ptac-IspS(M(L))F | GATAACAATTTCACACAATAATTTTGTTTAACTTTAAGAAGGAGATATAATGGCTACCAACCCGTCCTGTCTGTCAACC (SEQ ID NO: 25) |
| IspSM(L) | IspS(M(L))R-MCSR | ACGGCCAGTGAATTCTCAGTTAATCGGGAACGGGT (SEQ ID NO: 26) |
| pSTV28-Ptac-Ttrp | pSTV28-F | GTGTGAAATTGTTATCCGCTCACAATTCC (SEQ ID NO: 27) |
| pSTV28-Ptac-Ttrp | pSTV28-R | GAATTCACTGGCCGTCGTTTTACAACG (SEQ ID NO: 28) |

Reference Example 4: Measurement of Enzymatic Activity of Isoprene Synthase Derived from Various Plants Using Crude Enzyme Extract Derived from *E. coli*

4-1) Construction of *E. coli* MG1655 Strain Having Ability to Produce Isoprene

Competent cells of *E. coli* MG1655 strain (ATCC 700926) were prepared, and then pSTV28-Ptac-Ttrp, pSTV28-Ptac-IspSK, pSTV28-Ptac-IspSP, pSTV28-Ptac-IspSM, or further pSTV28-Ptac-IspSM (L) was introduced therein by an electroporation method. A suspension of the cells was evenly applied onto an LB plate containing 60 mg/L of chloramphenicol, and cultured at 37° C. for 18 hours. Subsequently, transformants that were resistant to chloramphenicol were obtained from the resulting plate. A strain in which pSTV28-Ptac-Ttrp, pSTV28-Ptac-IspSK, pSTV28-Ptac-IspSP, pSTV28-Ptac-IspSM, or further pSTV28-Ptac-IspSM (L) was introduced into *E. coli* MG1655 strain were designated as MG1655/pSTV28-Ptac-Ttrp, MG1655/pSTV28-Ptac-IspSK, MG1655/pSTV28-Ptac-IspSP, MG1655/pSTV28-Ptac-IspSM, or further MG1655/pSTV28-Ptac-IspSM (L) strain, respectively.

4-2) Method of Preparing Crude Enzyme Extract

Microbial cells of MG1655/pSTV28-Ptac-Ttrp, MG1655/pSTV28-Ptac-IspSK, MG1655/pSTV28-Ptac-IspSP, MG1655/pSTV28-Ptac-IspSM, or MG1655/pSTV28-Ptac-IspSM (L) strain were evenly applied onto the LB plate containing 60 mg/L of chloramphenicol, and cultured at 37° C. for 18 hours. The microbial cells corresponding to 1/6 of the resulting plate were inoculated to a Sakaguchi flask in which 20 mL of LB containing 60 mg/L of chloramphenicol had been added, and cultured at 37° C. for 6 hours. The microbial cells from the culture medium were centrifuged at 5000 rpm at 4° C. for 5 minutes, and washed twice with ice-cold isoprene synthase buffer (50 mM Tris-HCl, pH 8.0, 20 mM $MgCl_2$, 5% glycerol). The washed microbial cells were suspended in 1.8 mL of the same buffer. About 0.9 mL of beads for disruption (YBG01, diameter 0.1 mm) and 0.9 mL of the microbial cell suspension were placed in a 2 mL tube specific for a multibead shocker, and the microbial cells were disrupted using the multibead shocker manufactured by Yasui Kikai Corporation at 2500 rpm at 4° C. for 3 cycles of ON for 30 seconds/OFF for 30 seconds. After the disruption, the tube was centrifuged at 20,000 g at 4° C. for 20 minutes, and a supernatant was used as a crude enzyme extract.

4-3) Measurement of Isoprene Synthase Activity

The crude enzyme extract from MG1655/pSTV28-Ptac-Ttrp, MG1655/pSTV28-Ptac-IspSK, MG1655/pSTV28-Ptac-IspSP, MG1655/pSTV28-Ptac-IspSM, or MG1655/pSTV28-Ptac-IspSM (L) strain (containing 2 mg as amount of total protein) together with the isoprene buffer in a total volume of 0.5 mL was placed in a headspace vial (22 mL CLEAR CRIMP TOP VIAL (cat #B0104236) manufactured by Perkin Elmer), then 0.025 mL of a 0.5 M $MgCl_2$ solution and 0.01 mL of a 0.2 M DMAPP (manufactured by Cayman, catalog No. 63180) solution were added thereto, and the mixture was lightly vortexed. Then immediately, the vial was tightly sealed with a cap with a butyl rubber septum for the headspace vial (CRIMPS (cat #B0104240) manufactured by Perkin Elmer), and kept at 37° C. for 2 hours.

After completion of the reaction, a concentration of isoprene in the headspace of the vial was measured by gas chromatography. An analysis condition for the gas chromatography will be described below.

Headspace sampler (manufactured by Perkin Elmer, Turbo Matrix 40)
Temperature for keeping vial warm: 40° C.
Time period for keeping vial warm: 30 minutes
Pressurization time: 3.0 minutes
Injection time: 0.02 minute
Needle temperature: 70° C.
Transfer temperature: 80° C.
Carrier gas pressure (high purity helium): 124 kPa
Gas chromatography (manufactured by Shimadzu Corporation, GC-2010 Plus AF)
Column (Rxi (registered trademark)-1 ms: length 30 m, internal diameter 0.53 mm, liquid phase film thickness 1.5 μm, cat #13370)
Column temperature: 37° C.
Pressure: 24.8 kPa
Column flow: 5 mL/minute
Influx method: Split 1:0 (actually measured 1:18)
Transfer flow: 90 mL
GC injection volume: 1.8 mL (transfer flow×injection time)
Injection volume of sample into column: 0.1 mL
Inlet temperature: 250° C.

Detector: FID (hydrogen 40 mL/minute, air 400 mL/minute, makeup gas helium 30 mL/minute)

Detector temperature: 250° C.

Preparation of Isoprene Standard Sample

A reagent isoprene (specific gravity 0.681) was diluted to 10, 100, 1000, 10000 and 100000 times with cold methanol to prepare standard solutions for addition. Subsequently, 1 μL of each standard solution for addition was added to a headspace vial in which 1 mL of water had been added, and used as a standard sample.

The amount of formed isoprene after the reaction of each microbial strain for 2 hours is described in Table 9.

TABLE 9

Amount of formed isoprene after reaction for 2 hours

| Name of microbial strain | Amount of formed isoprene (mg/L) |
|---|---|
| MG1655/pSTV28-Ptac-Ttrp | 0.10 ± 0.01 |
| MG1655/pSTV28-Ptac-IspSK | 0.45 ± 0.02 |
| MG1655/pSTV28-Ptac-IspSM | 28.93 ± 6.04 |
| MG1655/pSTV28-Ptac-IspSM(L) | 5.06 ± 0.13 |
| MG1655/pSTV28-Ptac-IspSP | 0.10 ± 0.01 |

From the result in Table 9, the amount of formed isoprene was larger in order of MG1655/pSTV28-Ptac-IspSM, MG1655/pSTV28-Ptac-IspSM (L) and MG1655/pSTV28-Ptac-IspSK strains, and was almost equal in MG1655/pSTV28-Ptac-IspSP and MG1655/pSTV28-Ptac-Ttrp strains. From the above result, the crude enzyme extract from the strain introduced with the isoprene synthase derived from *Mucuna* exhibited the highest activity to form isoprene.

Reference Example 5: Effects of Introduction of Isoprene Synthase Derived from Various Plants on *E. coli* MG1655 Strain From the result of the crude enzymatic activity in Reference Example 4, the highest activity was confirmed in the isoprene synthase derived from *Mucuna* that deleted the chloroplast localization signal. Thus, an ability to produce isoprene from glucose was compared in all isoprene synthase-introduced strains in which the chloroplast localization signal had been deleted. Microbial cells of MG1655/pSTV28-Ptac-Ttrp, MG1655/pSTV28-Ptac-IspSK, MG1655/pSTV28-Ptac-IspSP, or MG1655/pSTV28-Ptac-IspSM strain were evenly applied onto the LB plate containing 60 mg/L of chloramphenicol, and cultured at 37° C. for 18 hours. One loopful of the microbial cells from the resulting plate was inoculated to 1 mL of M9 glucose medium in a headspace vial. The vial was tightly sealed with the cap with the butyl rubber septum for the headspace vial (CRIMPS (cat #B0104240) manufactured by Perkin Elmer), and the microbial cells were cultured at 30° C. for 24 hours using a reciprocal shaking cultivation apparatus (120 rpm). A composition of the M9 glucose medium is as described in Table 10.

TABLE 10

Composition of M9 glucose medium

| | |
|---|---|
| Glucose | 1.0 g/L |
| $Na_2HPO_4$ | 6.0 g/L |
| $KH_2PO_4$ | 3.0 g/L |
| NaCl | 0.5 g/L |
| $NH_4Cl$ | 1.0 g/L |

TABLE 10-continued

Composition of M9 glucose medium

| | |
|---|---|
| 1M $MgSO_4$ (autoclaved) | 1.0 mL |
| 1M $CaCl_2$ (autoclaved) | 0.1 mL |

Further, chloramphenicol was added at a final concentration of 60 mg/L. The volume was adjusted to 1 L and the medium was then sterilized by filtration.

After completion of the cultivation, the concentration of isoprene in the headspace in the vial was measured by the gas chromatography. An OD value was also measured at 600 nm using a spectrophotometer (HITACHI U-2900). The concentration of isoprene and the OD value in each microbial strain at the time of completing the cultivation are described in Table 11.

TABLE 11

OD value, and amount (μg/L) of isoprene produced by MG1655/pSTV28-Ptac-Ttrp, MG1655/pSTV28-Ptac-IspSK, MG1655/pSTV28-Ptac-IspSP and MG1655/pSTV28-Ptac-IspSM strains at the time of completing cultivation

| Name of microbial strain | OD value | Amount (μg/L) of formed isoprene |
|---|---|---|
| MG1655/pSTV28-Ptac-Ttrp | 1.68 ± 0.04 | ND |
| MG1655/pSTV28-Ptac-IspSK | 1.60 ± 0.09 | 43 ± 6 |
| MG1655/pSTV28-Ptac-IspSM | 1.45 ± 0.03 | 56 ± 7 |
| MG1655/pSTV28-Ptac-IspSP | 1.59 ± 0.07 | 26 ± 3 |

From the results in Table 11, it was found that the amount of produced isoprene was larger in order of MG1655/pSTV28-Ptac-IspSM, MG1655/pSTV28-Ptac-IspSK, MG1655/pSTV28-Ptac-IspSP and MG1655/pSTV28-Ptac-Ttrp strains. From the above results, the strain introduced with the isoprene synthase derived from *Mucuna* exhibited the highest activity to produce isoprene in the wild strains.

Reference Example 6: Effects of Introduction of Isoprene Synthase Derived from Various Plants on *E. coli* MG1655 Strain in which MEP (Methylerythritol) Pathway is Enhanced 6-1) Construction of Plasmid for Expressing dxs Gene (pMW219-dxs)

It was already reported that the amount of formed isoprene was enhanced (Appl. Microbiol. Biotechnol., (2011) 90, 1915-1922, which is incorporated herein by reference in its entirety), when the expression of a dxs (1-deoxy-D-xylulose-5-phosphate synthase) gene that constitutes the MEP pathway was enhanced in *E. coli* strain in which the isoprene synthase was introduced. Thus, it was confirmed whether an ability to produce isoprene was also different due to an origin of the isoprene synthase in the strain in which the expression of the dxs gene was enhanced. The entire genomic nucleotide sequence of *E. coli* K-12 strain was already shown (GenBank Accession No. U00096) (Science, (1997) 277, 1453-1474, which is incorporated herein by reference in its entirety). pMW219 (manufactured by Nippon Gene Co., Ltd.) was used for amplifying the gene. This plasmid can increase an expression level of an objective gene when isopropyl-β-thiogalactopyranoside (IPTG) is added by introducing the objective gene into a multicloning site. Synthesized oligonucleotides were synthesized from the nucleotide sequences represented by SEQ ID NOs:29 and 30 based on the nucleotide sequence of the dxs gene in the genomic nucleotide sequence of *E. coli*. Subsequently, PCR was performed with Prime Star polymerase (manufactured by Takara Bio Inc.) using the synthesized oligonucleotides consisting of the nucleotide sequences represented by SEQ ID NOs:29 and 30 as the primers with MR1655 strain genomic DNA as the template. A reaction solution was prepared according to the composition attached to the kit, and a reaction at 98° C. for 10 seconds, 54° C. for 20 seconds and 68° C. for 120 seconds was performed in 40 cycles. As a result, a PCR product containing the dxs gene was obtained. Likewise, PCR was performed with Prime Star polymerase (manufactured by Takara Bio Inc.) using the synthesized oligonucleotides consisting of the nucleotide sequences represented by SEQ ID NOs:31 and 32 as the primers with pMW219 as the template. A reaction solution was prepared according to the composition attached to the kit, and a reaction at 98° C. for 10 seconds, 54° C. for 20 seconds and 68° C. for 240 seconds was performed in 40 cycles. As a result, a PCR product containing pMW219 was obtained. Subsequently, the purified dxs gene fragment was ligated to the PCR product of pMW219 using In-Fusion HD Cloning Kit (manufactured by Clontech). The resulting plasmid for expressing the dxs gene was designated as pMW219-dxs.

TABLE 12

Primer sequences used for construction of plasmid for expressing dxs gene

| Sequence name | Sequence (5'-) |
|---|---|
| dxs-F | CAGGAAACAGCTATGAGTTTTGA TATTGCCAAATACCCGAC (SEQ ID NO: 29) |
| dxs-R | GCTGCCACTCCTGCTATACTCGT CATAC (SEQ ID NO: 30) |
| pMW219-F | CATAGCTGTTTCCTGTGTGAAAT TGTTATC (SEQ ID NO: 31) |
| pMW219-R | AGCAGGAGTGGCAGCGAATTCGA GCTCGGTACCCGGGGAT (SEQ ID NO: 32) |

6-2) Introduction of pMW219-dxs into *E. coli* MG1655 Strain Having Ability to Produce Isoprene Competent cells of MG1655/pSTV28-Ptac-Ttrp, MG1655/pSTV28-Ptac-IspSK, MG1655/pSTV28-Ptac-IspSM, or further MG1655/pSTV28-Ptac-IspSP strain were prepared, and pMW219-dxs was introduced therein by an electroporation method. The cells were evenly applied onto the LB plate containing 60 mg/L of chloramphenicol and 50 mg/L of kanamycin hydrochloride, and the cells were cultured at 37° C. for 18 hours. Transformants that were resistant to chloramphenicol and kanamycin were obtained from the resulting LB plates. Strains in which pMW219-dxs had been introduced into MG1655/pSTV28-Ptac-Ttrp, MG1655/pSTV28-Ptac-IspSK, MG1655/pSTV28-Ptac-IspSM, or further MG1655/pSTV28-Ptac-IspSP strain were designated as MG1655/pSTV28-Ptac-Ttrp/pMW219-dxs, MG1655/pSTV28-Ptac-IspSK/pMW219-dxs, MG1655/pSTV28-Ptac-IspSM/pMW219-dxs, or further MG1655/pSTV28-Ptac-IspSP/pMW219-dxs strain, respectively.

6-3) Effects of Introduction of Isoprene Synthase Derived from Various Plants on *E. coli* MG1655 Strain in which Expression of DXS is Enhanced MG1655/pSTV28-Ptac-Ttrp/pMW219-dxs, MG1655/pSTV28-Ptac-IspSK/pMW219-dxs, MG1655/pSTV28-Ptac-IspSM/pMW219-dxs, or further MG1655/pSTV28-Ptac-IspSP/pMW219-dxs strain were evenly applied onto the LB plate containing 60 mg/L of chloramphenicol and 50 mg/L of kanamycin hydrochloride, and were cultured at 37° C. for 18 hours. Subsequently, the cultivation in the headspace vial was evaluated as described in Reference Example 5. The amount (μg/L) of produced isoprene and the OD value upon completion of the cultivation are described in Table 13.

TABLE 13

Amount (μg/L) of produced isoprene and OD value when the cultivation was completed in various strains having enhanced isoprene synthase which are prepared from *E. coli* MG1655 strain having enhanced DXS as host

| Name of microbial strain | OD value | Amount (μg/L) of produced isoprene |
|---|---|---|
| MG1655/pSTV28-Ptac-Ttrp/pMW219-dxs | 1.46 ± 0.04 | ND |
| MG1655/pSTV28-Ptac-IspSK/pMW219-dxs | 1.13 ± 0.02 | 101 ± 28 |
| MG1655/pSTV28-Ptac-IspSM/pMW219-dxs | 1.76 ± 0.06 | 126 ± 23 |
| MG1655/pSTV28-Ptac-IspSP/pMW219-dxs | 2.21 ± 0.12 | 42 ± 17 |

From the results in Table 13, the amount of produced isoprene was larger in order of MG1655/pSTV28-Ptac-IspSM/pMW219-dxs, MG1655/pSTV28-Ptac-IspSK/pMW219-dxs, MG1655/pSTV28-Ptac-IspSP/pMW219-dxs and MG1655/pSTV28-Ptac-Ttrp/pMW219-dxs strains. From the above results, the strain introduced with the isoprene synthase derived from *Mucuna* also exhibited the highest ability to produce isoprene in the MEP pathway-enhanced strains.

Reference Example 7: Effects of Introduction of Isoprene Synthase Derived from Various Plants on *E. coli* MG1655 Strain in which MVA (Mevalonate) Pathway is Introduced 7-1) Cloning Gene Downstream of Mevalonate Pathway which is Derived from Yeast A downstream region of the mevalonate pathway was obtained from *Saccharomyces cerevisiae* (WO2009076676, *Saccharomyces* Genome database http(colon)//www(dot)yeastgenome(dot)org/# Nucleic Acids Res., January 2012; 40: D700-D705, which are incorporated herein by reference in their entireties). An ERG12 gene encoding mevalonate kinase, an ERG8 gene encoding phosphomevalonate kinase, an ERG19 gene encoding diphosphomevalonate decarboxylase, and an IDI1 gene encoding isopentenyl-diphosphate delta isomerase were amplified by PCR with genomic DNA of *S. cerevisiae* as the template using the primer shown below (Table 14). Prime Star Max Premix sold by Takara Bio Inc. was used for a PCR enzyme, and the reaction was performed at 98° C. for 2 minutes and for 30 cycles of 98° C. for 10 seconds, 55° C. for 5 seconds and 72° C. for 5 seconds/kb. Cloning and construction of an expression vector were performed by introducing the PCR fragment into the pSTV28-Ptac-Ttrp vector (SEQ ID NO:18) treated with the restriction enzyme SmaI by an in-fusion cloning method. *E. coli* DH5α was transformed with the expression vector, clones having assumed sequence length from each gene were selected, a plasmid was extracted according to standard methods, and its sequence was confirmed. The nucleotide sequences of these amplified genes and the amino acid sequences of the enzymes encoded by these genes are available on *Saccharomyces* Genome database http(colon)//www(dot)yeastgenome(dot)org/#.

TABLE 14

Primer sequences used for cloning of genes downstream of mevalonate pathway

| Amplified gene | Sequence name | Sequence (5'-) |
|---|---|---|
| ERG12 | MVK-IFS_5742-33-1 | ACACAAGGAGACTCC CATGTCATTACCGTT CTTAACTTCT (SEQ ID NO: 33) |
| ERG12 | MVK-IFA_5742-33-2 | GGAACTGGCGGCTCC CGGGTTATTATGAAG TCCATGGTAAATTCG T (SEQ ID NO: 34) |
| ERG8 | PMK-IFS_5742-33-3 | ACACAAGGAGACTCC CATGTCAGAGTTGAG AGCCTTCA (SEQ ID NO: 35) |
| ERG8 | PMK-IFA_5742-33-4 | GGAACTGGCGGCTCC CGGGTTATTATTTAT CAAGATAAGTTTCCG G (SEQ ID NO: 36) |
| ERG19 | MVD-IFS_5742-33-5 | ACACAAGGAGACTCC CATGACCGTTTACAC AGCATCC (SEQ ID NO: 37) |
| ERG19 | MVD-IFA_5742-33-6 | GGAACTGGCGGCTCC CGGGTTATTATTCCT TTGGTAGACCAGTCT T (SEQ ID NO: 38) |
| IDI1 | yIDI-IFS_5742-33-7 | ACACAAGGAGACTCC CATGCCCCATGGTGC AGTATC (SEQ ID NO: 39) |
| IDI1 | yIDI-IFA_5742-33-8 | GGAACTGGCGGCTCC CGGGTTATTATAGCA TTCTATGAATTTGCC TGTC (SEQ ID NO: 40) |

7-2) Construction of Artificial Operon Downstream of Mevalonate Pathway

A sequence in which the gene encoding the mevalonate kinase and the gene encoding the phosphomevalonate kinase were arranged in straight was constructed by the in-fusion cloning method. The ERG12 gene encoding the mevalonate kinase and the ERG8 gene encoding the phosphomevalonate kinase were amplified by PCR with genomic DNA from *Saccharomyces cerevisiae* as the template using the primers shown in Table 15. KOD plus sold by Toyobo was used for the PCR enzyme, and the reaction was performed at 94° C. for 2 minutes and for 30 cycles of 94° C. for 15 seconds, 45° C. for 30 seconds and 68° C. for 1 minute/kb. The cloning and the construction of an expression vector were performed by inserting the PCR fragment into pUC118 vector treated with the restriction enzyme SmaI by the in-fusion cloning method. *E. coli* JM109 was transformed with the expression vector, clones having assumed sequence length of each gene were selected, a plasmid was extracted according to standard methods, and its sequence was confirmed. The produced plasmid was designated as pUC-mvk-pmk. The nucleotide sequence of pUC-mvk-pmk is represented by SEQ ID NO:41.

TABLE 15

Primer sequences used for ligating mevalonate kinase and phosphomevalonate kinase

| Amplified gene | Sequence name | Sequence (5'-) |
|---|---|---|
| ERG12 | KKS1-6038-2-1 | TCGAGCTCGGTACCC ATGTCATTACCGTTC TTAACTTCT (SEQ ID NO: 42) |
| ERG12 | KKA1-6038-2-2 | TTAAGGGTGCAGGCC TATCGCAAATTAGCT TATGAAGTCCATGGT AAATTCGT (SEQ ID NO: 43) |
| ERG8 | KKS2-6083-2-3 | GGCCTGCACCCTTAA GGAGGAAAAAAACAT GTCAGAGTTGAGAGC CTTCA (SEQ ID NO: 44) |
| ERG8 | KKA2-6083-2-4 | CTCTAGAGGATCCCC TTATTTATCAAGATA AGTTTCCGG (SEQ ID NO: 45) |

A sequence in which a gene encoding diphosphomevalonate decarboxylase and a gene encoding isopentenyl-diphosphate delta isomerase were arranged in straight was constructed by the in-fusion cloning method. The ERG19 gene encoding the diphosphomevalonate decarboxylase and the IDI1 gene encoding the isopentenyl-diphosphate delta isomerase were amplified by PCR with genomic DNA of *Saccharomyces cerevisiae* as the template using the primers shown in Table 16. KOD plus sold by Toyobo was used for the PCR enzyme, and the reaction was performed at 94° C. for 2 minutes and for 30 cycles of 94° C. for 15 seconds, 45° C. for 30 seconds and 68° C. for 1 minute/kb, and then at 68° C. for 10 minutes. The cloning and the construction of an expression vector were performed by inserting the PCR fragment into TWV228 vector treated with the restriction enzyme SmaI by the in-fusion cloning method. *E. coli* DH5α was transformed with the expression vector, clones having assumed sequence length of each gene were selected, a plasmid was extracted according to standard methods, and its sequence was confirmed. The produced plasmid was designated as pTWV-dmd-yidi. The nucleotide sequence of pTWV-dmd-yidi is represented by SEQ ID NO:46.

TABLE 16

Primer sequences used for ligating diphosphomevalonate decarboxylase and isopentenyl-diphosphate delta isomerase

| Amplified gene | Sequence name | Sequence (5'-) |
|---|---|---|
| ERG19 | DyIS1-6083-2-5 | TCGAGCTCGGTACCC ATGACCGTTTACACA GCATCC (SEQ ID NO: 47) |

TABLE 16-continued

Primer sequences used for ligating diphosphomevalonate decarboxylase and isopentenyl-diphosphate delta isomerase

| Amplified gene | Sequence name | Sequence (5'-) |
|---|---|---|
| ERG19 | DyIA1-6083-2-6 | TTTTTTTACCTCCTA AGGGCGATGCAGCGA ATTGATCTTATTCCT TTGGTAGACCAGTCT T (SEQ ID NO: 48) |
| IDI1 | DyIS2-6083-2-7 | TAGGAGGTAAAAAAA AATGACTGCCGACAA CAATAGTATGCCCCA TGGTGCAGTATC (SEQ ID NO: 49) |
| IDI1 | DyIA2-6083-2-8 | CTCTAGAGGATCCCC TTATAGCATTCTATG AATTTGCCTGTC (SEQ ID NO: 50) |

A sequence in which the gene encoding the mevalonate kinase, the gene encoding the phosphomevalonate kinase, the gene encoding the diphosphomevalonate decarboxylase and the gene encoding the isopentenyl-diphosphate delta isomerase were arranged in straight was constructed by the in-fusion cloning method. An expression vector in which these four enzyme genes were arranged in straight was constructed by amplifying the gene encoding the mevalonate kinase and the gene encoding the phosphomevalonate kinase by PCR with pUC-mvk-pmk as the template using the primers shown in Table 17 and amplifying the gene encoding the diphosphomevalonate decarboxylase and the gene encoding the isopentenyl-diphosphate delta isomerase by PCR with pTWV-dmd-yidi as the template using the primers shown in Table 17, followed by cloning the amplified products into pTrcHis2B vector by the in-fusion cloning method. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. The PCR fragment was inserted into pTrcHis2B vector treated with the restriction enzymes NcoI and PstI to construct the expression vector. *E. coli* JM109 was transformed with the expression vector, clones having an objective sequence length were selected, a plasmid was extracted according to standard methods, and its sequence was confirmed. The constructed expression vector was designated as pTrc-KKDyI (β). The nucleotide sequence of pTrc-KKDyI (β) is represented by SEQ ID NO:51.

TABLE 17

Primer sequences used for amplifying genes for constructing pTrc-KKDyI (β)

| Template plasmid | Sequence name | Sequence (5'-) |
|---|---|---|
| pUC-mvk-pmk | KKDS2_6038-3-2 | GAGGAATAAACCATG TCATTACCGTTCTTA ACTTCT (SEQ ID NO: 52) |

TABLE 17-continued

Primer sequences used for amplifying genes for constructing pTrc-KKDyI (β)

| Template plasmid | Sequence name | Sequence (5'-) |
|---|---|---|
| pUC-mvk-pmk | KKMyIA_6038-2-9 | AAGGGCGAATTCTGC ATGCAGCTACCTTAA GTTATTTATCAAGAT AAGTTTCCGG (SEQ ID NO: 53) |
| pTWV-dmd-yidi | KMS_6038-6-1 | GCAGAATTCGCCCTT AAGGAGGAAAAAAAA ATGACCGTTTACACA GCATCC (SEQ ID NO: 54) |
| pTWV-dmd-yidi | KDyIA_6038-3-3 | CCATATGGTACCAGC TGCAGTTATAGCATT CTATGAATTTGCCTG TC (SEQ ID NO: 55) |

7-3) Fixation of Downstream Region of Mevalonate Pathway on Chromosome

The sequence in which the gene encoding the mevalonate kinase, the gene encoding the phosphomevalonate kinase, the gene encoding the diphosphomevalonate decarboxylase and the gene encoding the isopentenyl-diphosphate delta isomerase were arranged in straight was expressed on a chromosome. A glucose isomerase promoter was used for the expression of the gene, and a transcription termination region of aspA gene in *E. coli* was used for the termination of the transcription (WO2010/031062, which is incorporated herein by reference in its entirety). A translocation site of Tn7 was used as a chromosomal site to be fixed (Mol Gen Genet., 1981; 183 (2): 380-7, which is incorporated herein by reference in its entirety). A cat gene was used as a drug marker after the fixation of the chromosome. A Tn7 downstream region in the chromosome region to be fixed was amplified by PCR with genomic DNA of *E. coli* as the template using the primers shown in Table 18. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. A cat gene region containing a λ phage attachment site was amplified by PCR with pMW118-attL-Cm-attR plasmid as the template using the primers shown in Table 18 (WO2010/027022, which is incorporated herein by reference in its entirety). Prime Star HS DNA polymerase sold by Takara Bio Inc. was used for the PCR enzyme, and the reaction was carried out at 95° C. for 3 minutes followed by in 2 cycles of 95° C. for 1 minute, 34° C. for 30 seconds and 72° C. for 40 seconds, 2 cycles of 95° C. for 30 seconds, 50° C. for 30 seconds and 72° C. for 40 seconds, and then at 72° C. for 5 minutes. A sequence downstream of the mevalonate pathway to which a promoter and a transcription termination region had been added (hereinafter abbreviated as KKDyI) was amplified with pTrc-KKDyI (β) as the template using the primers shown in Table 18. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. A vector was constructed using these PCR products and pMW219 treated with the restriction enzyme SmaI by the in-fusion cloning method. *E. coli* JM109 was transformed with the expression vector, clones having an objective sequence length were selected, a plasmid was extracted according to standard methods, and its sequence was confirmed. The resulting plasmid was designated as pMW219-KKDyI-TaspA. The nucleotide sequence of pMW219-KKDyI-TaspA is represented by SEQ ID NO:56.

Subsequently, a Tn7 upstream region in the chromosome region to be fixed was amplified by PCR with the genomic DNA of *E. coli* as the template using the primers shown in Table 19. Prime Star HS DNA polymerase sold by Takara Bio Inc. was used for the PCR enzyme, and the reaction was carried out at 98° C. for 2 minutes followed by in 30 cycles of 98° C. for 10 seconds, 52° C. for 5 seconds and 72° C. for 1 minute/kb, and then at 72° C. for 10 minutes. A vector was constructed using the PCR product and pMW219-KKDyI-TaspA treated with the restriction enzyme SalI by the in-fusion cloning method. *E. coli* JM109 was transformed with the expression vector, clones having an objective sequence length were selected, a plasmid was extracted according to standard methods, and its sequence was confirmed. The resulting plasmid was designated as pMW-Tn7-Pgi-KKDyI-TaspA-Tn7. The sequence of the constructed plasmid is represented by SEQ ID NO:57.

Figure 3:
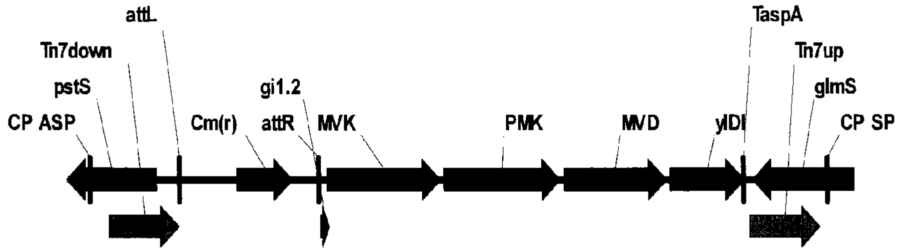
FIG. 3 shows an outline of mevalonic acid pathway downstream and its surrounding region in chromosome fixation.

Subsequently, a chromosome having a region including the chloramphenicol resistance gene, the glucose isomerase promoter, the operon downstream of the mevalonate pathway, and the aspA gene transcription termination region was fixed using λ-Red method. A fragment for chromosome fixation was prepared by extracting the plasmid pMW-Tn7-Pgi-KKDyI-TaspA-Tn7 and then treating it with the restriction enzymes PvuI and SalI followed by purifying it. *E. coli* MG1655 containing a plasmid pKD46 having a temperature-sensitive replication capacity (hereinafter referred to as MG1655/pKD46) was used for the electroporation. The plasmid pKD46 (Proc. Natl. Acad. Sci. USA, 2000, vol. 97, No. 12, p 6640-6645, which is incorporated herein by reference in its entirety) contains a DNA fragment of total 2154 nucleotides (GenBank/EMBL Accession No. J02459, 31088th to 33241st) of λ phage containing λ Red system genes (λ, β, exo genes) controlled by an arabinose-inducible ParaB Promoter. After the electroporation, a colony that had acquired the resistance to chloramphenicol was obtained, subsequently genomic DNA was extracted, and it was confirmed by PCR using the primers shown in Table 20 that the objective region was fixed on the chromosome. Further, the sequence of the objective region was confirmed by confirming the sequence of the PCR fragment. The nucleotide sequence of the mevalonate pathway downstream and its proximal region fixed on the chromosome is represented by SEQ ID NO:58, and its construction outline is shown in FIG. 3. The resulting mutant was designated as MG1655 cat-Pgi-KKDyI.

The drug marker in MG1655 cat-Pgi-KKDyI was removed by the following procedure. Competent cells of MG1655 cat-Pgi-KKDyI was made, and then pMW-int-xis was introduced therein. pMW-int-xis is a plasmid containing a gene encoding integrase (Int) of the λ phage and a gene encoding excisionase (Xis) of the λ phage and having the temperature-sensitive replication capacity (WO2007/037460, JP Publication No. 2005-058827, which are incorporated herein by reference in their entireties).

The chloramphenicol-resistant gene located in a region sandwiched with attL and attR that are the attachment site of the λ phage is dropped off from the chromosome by introducing pMW-int-xis. As a result, it is known that the host loses the resistance to chloramphenicol. And, a chloramphenicol-sensitive strain was obtained from the resulting colony, and subsequently cultured on the LB medium at 42° C. for 6 hours. The cultured microbial cells were applied onto the LB plate medium to allow colonies to appear. A colony that had lost the resistance to ampicillin was selected from these colonies to remove the drug resistance. The mutant obtained as above was designated as MG1655 Pgi-KKDyI.

TABLE 18

Primers for making PCR fragments used for construction of pMW219-KKDyI-TaspA

| Template DNA | Amplified region | Sequence name | Sequence (5'-) |
|---|---|---|---|
| *E. coli* genome | Tn7 downstream | Tn7dS_6038-7-1 | TCGAGCTCGGTACCCTGTTTTTCCACTCTTCGTTCACTTT (SEQ ID NO: 59) |
| *E. coli* genome | Tn7 downstream | Tn7dA_6038-7-2 | AGGCTTCATTTTAATCAAACATCCTGCCAACTC (SEQ ID NO: 60) |
| pMW-attL-Cm-attR | attL-cat-attR | Tn7dattLcmS_6038-7-4 | ATTAAAATGAAGCCTGCTTTTTTAT (SEQ ID NO: 61) |
| pMW-attL-Cm-attR | attL-cat-attR | PgiattRcmA_6038-7-5 | GGCATCGTCAAGGGCCGCTCAAGTTAGTATAA (SEQ ID NO: 62) |
| pTrc-KKDyI(β) | KKDyI | gi1.2-MVK-S_6038-7-6 | GCCCTTGACGATGCCACATCCTGAGCAAATAATTCAACCACTAATTGTGAGCGGATAACACAAGGAGGAAACAGCTATGTCATTACCGTTCTTAACTTC (SEQ ID NO: 63) |

TABLE 18-continued

Primers for making PCR fragments used for construction of pMW219-KKDyI-TaspA

| Template DNA | Amplified region | Sequence name | Sequence (5'-) |
|---|---|---|---|
| pTrc-KKDyI(β) | KKDyI | pMW-TaspA-yIDIA_6038-7-7 | CTCTAGAGGATCCCCGGCCCCAAGAAAAAAGGCACGTCATCTGACGTGCCTTTTTTATTTGTAGACGCGTTGTTATAGCATTCTATGAATTTGCCT (SEQ ID NO: 64) |

TABLE 19

Primers for making PCR fragments used for construction of pMW-Tn7-Pgi-KKDyI-TaspA-Tn7

| Template DNA | Amplified region | Sequence name | Sequence (5'-) |
|---|---|---|---|
| *E. coli* genome | Tn7 upstream | Tn7upSv02_6038-24-1 | ATCCTCTAGAGTCGAAAGAAAAATGCCCCGCTTACG (SEQ ID NO: 64) |
| *E. coli* genome | Tn7 upstream | Tn7upAv02_6038-24-2 | ATGCCTGCAGGTCGACTGTCACAGTCTGGCGAAACCG (SEQ ID NO: 65) |

TABLE 20

PCR primers for confirming chromosome fixation of mevalonate pathway downstream

| Sequence name | Sequence (5'-) |
|---|---|
| Tn7v02-F_6038-22-5 | ACGAACTGCTGTCGAAGGTT (SEQ ID NO: 67) |
| Tn7v02-R_6038-22-6 | GGTGTACGCCAGGTTGTTCT (SEQ ID NO: 68) |

7-4) Substitution of Promoter Downstream of Mevalonate Pathway on Chromosome

The promoter of the operon downstream of the mevalonate pathway on the chromosome was substituted by the λ-red method. A genomic fragment having attL-Tet-attR-Ptac was used as the template for PCR. This is one in which the tac promoter, and attL and attR that are the attachment sites for a tetracycline resistant drug marker and the λ, phage are aligned. This sequence is represented by SEQ ID NO:69. A PCR fragment was prepared using the promoter shown in Table 21. LA-Taq polymerase sold by Takara Bio Inc. was used for the PCR enzyme, and the reaction was carried out at 92° C. for 1 minute, then for 40 cycles of 92° C. for 10 seconds, 50° C. for 20 seconds and 72° C. for 1 minute/kb, and further at 72° C. for 7 minutes. The PCR product was purified. MG1655 Pgi-KKDyI containing the plasmid pKD46 (hereinafter referred to as MG1655 Pgi-KKDyI/pKD46) having the temperature-sensitive replication capacity was used for the electroporation. The plasmid pKD46 (Proc. Natl. Acad. Sci. USA, 2000, vol. 97, No. 12, p 6640-6645, which is incorporated herein by reference in its entirety) contains a DNA fragment of total 2154 nucleotides (GenBank/EMBL Accession No. J02459, 31088th to 33241st) of λ phage containing λ Red system genes (λ, β, exo genes) controlled by an arabinose-inducible ParaB Promoter. The plasmid pKD46 is required for incorporating the PCR product into MG1655 Pgi-KKDyI.

Competent cells for the electroporation were prepared as follows. MG1655 Pgi-KKDyI/pKD46 cultured in the LB medium containing 100 mg/L of ampicillin at 30° C. overnight were diluted to 100 times with 5 mL of LB medium containing ampicillin and L-arabinose (1 mM). The resulting cells in diluted suspension were grown until OD600 reached about 0.6 with ventilating at 30° C., and subsequently washed three times with ice-cold 10% glycerol solution to use for the electroporation. The electroporation was performed using 504 of the competent cells and about 100 ng of the PCR product. The cells after the electroporation in 1 mL of SOC medium (Molecular Cloning: Laboratory Manuals, 2nd Edition, Sambrook, J. et al., Cold Spring Harbor Laboratory Press (1989), which is incorporated herein by reference in its entirety) were cultured at 37° C. for one hour, and subjected to a plate culture on LB agar medium at 37° C. to select a chloramphenicol-resistant transformant. Subsequently, in order to remove the pKD46 plasmid, the transformant was subcultured on the LB agar medium containing tetracycline at 37° C. The ampicillin resistance was examined in the obtained colonies, and an ampicillin-resistant strain having no pKD46 was obtained. A mutant containing the tac promoter substitution that could be distinguished by the tetracycline-resistant gene was obtained. The obtained mutant was designated as MG1655 tet-Ptac-KKDyI.

Figure 4:
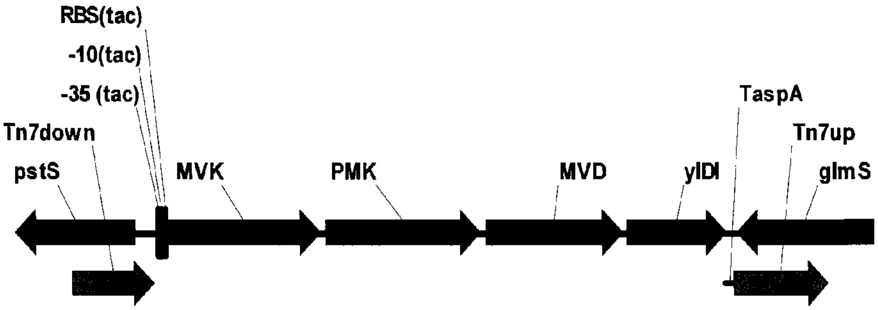
FIG. 4 shows an outline of mevalonic acid pathway downstream and its surrounding region controlled by a tac promoter on a chromosome.

The antibiotic marker was removed by the following procedure. Competent cells of MG1655 tet-Ptac-KKDyI were made, and then pMW-int-xis was introduced therein. pMW-int-xis is a plasmid containing the genes encoding integrase (Int) and excisionase (Xis) of the λ phage and having the temperature-sensitive replication capacity (WO2007/037460, JP Publication No. 2005-058827, which are incorporated herein by reference in their entireties). The tetracycline-resistant gene located in a region sandwiched with attL and attR that are the attachment site of the λ phage is dropped off from the chromosome by introducing pMW-int-xis. As a result, it is known that the host loses the resistance to tetracycline. Thus, a tetracycline-sensitive strain was obtained from the resulting colonies. Cells of this strain were cultured on the LB medium at 42° C. for 6 hours, and the cultured cells were applied onto the LB plate medium to allow colonies to appear. A clone that had lost the resistance to ampicillin was selected to remove the drug resistance. The resulting mutant was designated as MG1655 Ptac-KKDyI. The nucleotide sequence of the mevalonate pathway downstream and its proximal region controlled by the tac promoter on the chromosome is represented by SEQ ID NO:70, and its outline is shown in FIG. 4.

TABLE 21

Primers for making PCR fragments for promoter substitution

| Sequence name | Sequence (5'-) |
|---|---|
| APtacKKDyIv03_6038-36-5 | gataaagtatcagtctgatttaa ataagcgttgatattcagtcaat tactgaagcctgatttttatac (SEQ ID NO: 71) |
| SPtacKKDyIv02_6038-36-3 | tcaccaaaaataataacctttcc cggtgcagaagttaagaacggta atgaCATggcagtctccttgtgt ga (SEQ ID NO: 72) |

7-5) Introduction of Isoprene Synthase Derived from Various Plants into MG1655 Ptac-KKDyI Strain Competent cells of MG1655 Ptac-KKDyI strain were prepared, and then pSTV28-Ptac-Ttrp, pSTV28-Ptac-IspSK, pSTV28-Ptac-IspSM, or further pSTV28-Ptac-SP was introduced therein. The cells were evenly applied onto the LB plate containing 60 mg/L of chloramphenicol, and the cells were cultured at 37° C. for 18 hours. Transformants that exhibited the chloramphenicol resistance were obtained from the resulting plate. A strain in which pSTV28-Ptac-Ttrp, pSTV28-Ptac-IspSK, pSTV28-Ptac-IspSM, or pSTV28-Ptac-IspSP had been introduced into MG1655 Ptac-KKDyI strain was designated as MG1655 Ptac-KKDyI/pSTV28-Ptac-Ttrp, MG1655 Ptac-KKDyI/pSTV28-Ptac-IspSK, MG1655 Ptac-KKDyI/pSTV28-Ptac-IspSM, or MG1655 Ptac-KKDyI/pSTV28-Ptac-IspSP, respectively.

7-6) Effects of Introduction of Isoprene Synthase Derived from Various Plants on MG1655 Strain in which MVA Pathway is Enhanced Microbial cells of MG1655 Ptac-KKDyI/pSTV28-Ptac-Ttrp, MG1655 Ptac-KKDyI/pSTV28-Ptac-IspSK, MG1655 Ptac-KKDyI/pSTV28-Ptac-IspSM, or further MG1655 Ptac-KKDyI/pSTV28-Ptac-IspSP strain were evenly applied onto the LB plate containing 60 mg/L of chloramphenicol, and the cells were cultured at 37° C. for 18 hours. One loopful of the microbial cells from the resulting LB plate was inoculated to 1 mL of M9 glucose (containing mevalonic acid) medium in a headspace vial (22 mL CLEAR CRIMP TOP VIAL (cat #B0104236) manufactured by Perkin Elmer), and subsequently the cultivation was evaluated according to the method described in Reference Example 2. A composition of the M9 glucose (containing mevalonic acid) medium is described in Table 22. The amount of produced isoprene and the OD value upon completion of the cultivation are described in Table 23.

TABLE 22

Composition of M9 glucose (containing mevalonic acid) medium

| | |
|---|---|
| Glucose | 2.0 g/L |
| $Na_2HPO_4$ | 6.0 g/L |
| $KH_2PO_4$ | 3.0 g/L |
| NaCl | 0.5 g/L |
| $NH_4Cl$ | 1.0 g/L |
| Mevalonic acid (manufactured by ADEKA) | 1.0 g/L |
| 1M $MgSO_4$ (autoclaved) | 1.0 mL |
| 1M $CaCl_2$ (autoclaved) | 0.1 mL |

Chloramphenicol was added at a final concentration of 60 mg/L.

A total volume was adjusted to 1 L, and the medium was sterilized by filtration.

TABLE 23

Amount (mg/L) of produced isoprene and OD value when cultivation of MG1655 Ptac-KKDyI/pSTV28-Ptac-Ttrp, MG1655 Ptac-KKDyI/pSTV28-Ptac-IspSK, MG1655 Ptac-KKDyI/pSTV28-Ptac-IspSM, or further MG1655 Ptac-KKDyI/pSTV28-Ptac-IspSP was completed

| Name of microbial strain | OD value | Amount (mg/L) of produced isoprene |
|---|---|---|
| MG1655 Ptac-KKDyI/pSTV28-Ptac-Ttrp | 2.08 ± 0.07 | 0.07 ± 0.01 |
| MG1655 Ptac-KKDyI/pSTV28-Ptac-IspSK | 2.48 ± 0.13 | 30.96 ± 3.04 |
| MG1655 Ptac-KKDyI/pSTV28-Ptac-IspSM | 2.48 ± 0.09 | 57.13 ± 15.00 |
| MG1655 Ptac-KKDyI/pSTV28-Ptac-IspSP | 1.95 ± 0.09 | 0.52 ± 0.01 |

From the results in Table 23, the amount of produced isoprene was larger in order of MG1655 Ptac-KKDyI/pSTV28-Ptac-IspSM, MG1655 Ptac-KKDyI/pSTV28-Ptac-IspSK, MG1655 Ptac-KKDyI/pSTV28-Ptac-IspSP, and MG1655 Ptac-KKDyI/pSTV28-Ptac-Ttrp strains. From the above results, the strain introduced with the isoprene synthase derived from *Mucuna* also exhibited the highest ability to produce isoprene in the strains introduced with the MVA pathway.

Example 3: Selection and Modification of Amino Acids to be Subjected to Modification with Focusing on Specified Matter (3-1) Selection and Modification of Amino Acids to be Subjected to Modification with Focusing on Interaction with Substrate Hereinafter, amino acid residues are shown based on the amino acid sequence of SEQ ID NO:4. Residues that interacted with DMAPP that was the substrate were computed using the steric structure model constructed in Example 1 and simulation software Molgero Molecular Viewer (Molegro). As a result, an electromagnetic interaction with the substrate was predicted in total 47 residues of K259, R264, D265, R266, E269, K288, K292, F294, V297, D301, D302, D305, D311, E312, E321, K336, K367, E371, K374, F376, E379, K381, K386, K393, D396, S401, S402, S403, R437, F443, R444, N447, D448, E455, E457, R458, E460, E471, E476, K481, R484, E490, K492, K493, Y523, D533, and K541. Results obtained by computing using Molgero Molecular Viewer are shown in Table 24.

The higher activity value than that in the wild type was observed by modification of D131C in Example 1 (Table 1-2). Based on this result, the charged residues K127 and K130 that positioned in the vicinity of the D131 residue were selected and subjected to modification. Among the residues present in the vicinity of the substrate DMAPP, T451E, T451S, E455D, E455Q, E455M, T462Q, and T462S still retained their activity after the modification in Example 1 although their activity was reduced as compared with that in the wild type (Table 1-1). On the basis of this fact, T451, E455 and T462 were selected and subjected to modification. T461 and L407 present in the vicinity of these residues were selected and subjected to modification.

The amino acid residues after the modification were selected from acidic residues (D, E), basic residues (R, K), neutral residues (N, Q), hydrophilic residues (M, S) and aromatic residues (Y, F) with focusing on two points. A first one is bulkiness, and amino acids close to amino acids before the modification were selected with reference to the truth table for physicochemical natures of amino acids (e.g., M. J. Zvelebil et al, J. Mol. Biol., 1987, 195, 57, which is incorporated herein by reference in its entirety) and BLOSSUM table that was indicators of amino acid homology (S. Henikoff et al, Proc. Natl. Acad. USA., 1992, 89, 10915, which is incorporated herein by reference in its entirety). For a second point, the information on steric structure was visually inspected and when a space filling rate in the vicinity of an introduced modified residue is low, amino acids suitable for filling the space were selected.

(3-2) Selection of Amino Acid Residue to be Subjected to Modification and Modification Thereof with Focusing on Optimization of Cys Residues and Optimization of Surrounding Environment of Cys Residues Based on optimization of Cys residues and optimization of surrounding environment of Cys residues, which was Concept shown in Example 1, 7 (C137, C286, C370, C373, C440, C480, C521) of total 9 Cys residues were substituted with Gly residues in order to alter motility of molecules in the vicinity of the Cys residue.

Surrounding residues that interacted with the Cys residue or surrounding residues capable of interacting with the Cys residue by modification were selected and subjected to the modification. With reference to the model structure, the presence of 22 residues of D131, L256, I299, Y304, F316, V320, E321, F376, S399, G404, V405, Y412, L414, V415, L449, S452, I465, P505, F508, I518, S519, and H520 was confirmed. These residues were modified in consideration of surrounding chemical environment.

(3-3) Selection of Amino Acid Residue to be Subjected to Modification and Modification Thereof with Focusing on Enhancement of Hydrophilicity on Enzyme Surface and Formation of Intermolecular Disulfide Bond Among hydrophobic residues present on the molecular surface, Val residues (V106, V187, V289, V306, V325), Leu residues (L35, L67, L163, L310, L340, L377, L529) and Ile residues (I190, I328, I387, I388) not involved in packing, as well as Phe residues (F31, F129) and Gly residues (G528, G530) were selected and subjected to modification. Subsequently, Gly residues (G134, G135, G157, G160, G182) present on a loop were selected and substituted with Pro residues in order to control molecular motility. Next, residues present on a helix (D124, R128, L247, T257, R264, E269, K292, F294, V297, T298, G404, L407, F443, V499) were selected in order to enhance stability of an IspS molecule by stabilizing a helix structure. Finally, S162 for forming an intermolecular disulfide bond and R202 for forming an intramolecular disulfide bond were selected and substituted with Cys residue.

(3-4) Selection of Amino Acid Residues to be Subjected to Modification and Modification Thereof with Reference to Bornyl Synthase.

The substrate affinity of IspS derived from kudzu and poplar is known to be of the order of mM. From similarity on their primary sequences, the substrate affinity of IspSM was also predicted to be of the order of mM. On the other hand, bornyl synthase (EC5.5.1.8) having the similarity on their steric structure has a substrate affinity of the order of μM (Croteasu R. et al, J. Biol. Chem., 1986, 261(29), 13438-45, which is incorporated herein by reference in its entirety). As a result of comparing the model structure of IspSM with the steric structure of bornyl synthase, differences were observed in a J-K loop and an N-terminal region. In more detail, residues that interacted with the N-terminus of bornyl synthase were 5248 and R249, and they corresponded to 5248 and L249 on IspSM. Thus, these residues were substituted with K, E, R or T, and the formation of interaction with the N-terminus was examined.

(3-5) Method of Measuring Activity

Respective modified enzymes were prepared according to Example 1 (1-4) herein. The obtained crude purified solution was diluted to 0.026 mg/mL of protein with a solution composed of 25 mM Tris-HCl (pH 7.5) and 10 mM $MgCl_2$. Subsequently, 10 μL of the crude purified solution was mixed with 0.1 mL of a substrate solution composed of 4 mM DMAPP, 25 mM Tris-HCl (pH 7.5) and 10 mM $MgCl_2$. The mixed solution was incubated at 37° C. for 60 minutes to allow isoprene synthase to act upon DMAPP to produce isoprene and pyrophosphoric acid. Subsequently, 204 of 20 mg/mL activated charcoal suspension was mixed with the reaction solution, which was immediately transferred on ice to stop the reaction. The 20 mg/mL activated charcoal suspension was prepared by suspending activated charcoal powder washed with hydrochloric acid (Nacalai Tesque) in distilled water in 100 folds amount, then filtering it with glass filter, washing the residue by adding distilled water in 2000 folds amount with aspirating, and suspending its powder obtained by completely drying in a dryer at 60° C. in distilled water at a final concentration of 20 mg/mL. The mixed solution after stopping the reaction was centrifuged at 20,000×g at 4° C. for 10 minutes. A supernatant was diluted to one tenth with 0.1 M Tris-HCl (pH 7.5) and centrifuged again at ×g at 4° C. for 10 minutes. Then 50 μL of a supernatant was dispensed in each well in a 96-well plate (supplied from Sanplatec, #3719), and mixed with 50 μL of a chromogenic solution (Piper pyrophosphate assay kit, Life Technologies, #P22061). Subsequently, the mixture was incubated at 37° C. for 60 minutes, and then absorbance at 570 nm was measured using a plate reader (BioRad, Model 680). A solution composed of 0.1 M Tris-HCl (pH 7.5) and 1 mM $MgCl_2$ was used as a blank in place of the enzyme solution. Simultaneously, a standard curve for pyrophosphoric acid concentrations was prepared using a series of solutions in which 50 μL of the chromogenic solution (Piper pyrophosphate assay kit, Life Technologies, #P22061) had been added to 0, 10, 20, 30, 40 or 50 μM pyrophosphoric acid solution dissolved in 0.1 M Tris-HCl (pH 7.5) and 2 mM $MgCl_2$. The concentration of pyrophosphoric acid produced by each modified enzyme was calculated using a value obtained by correcting an actual measured value with a blank value and using the standard curve.

(3-6) Results

The activity was measured in total 292 mutants. Results are shown in Tables 25-1 to 25-6. The activity that was 1.1 fold or more higher than the activity in the wild type enzyme was observed in 79 modified enzymes (F31E, F31K, L35E, L35K, L67E, 190E, D124E, K127D, K127E, K127N, K127R, R128K, K130G, G134P, C137L, R202D, R202N, L247D, L247E, L247Q, S248E, S248K, S248R, L249E, L249K, L249R, L249T, T257L, K259D, K259E, K259N, K259Q, K259R, R264F, R264M, R264T, D265E, D265N, D265Q, D265R, R266N, R266Q, E269D, E269I, E269Y, K292L, D301R, D305R, E312I, E312R, F316E, E321D, V325K, I328E, L340K, E371D, E379T, K386R, S401T, S402L, G404A, G404M, R444T, N447L, N447R, R458Q, T461R, T462M, R484K, K492E, V499I, P505H, F508Q, F508R, I518S, S519N, H520N, Y523I, Y523L, G530K). In particular, modified enzymes F31K, K127E, C137L, L247D, L249E, S248K, L249R, L249T, R264F, F316E, G404M, Y523I, Y523L, and G530K were demonstrated to have high activity which was 3 folds or higher than the activity in the wild type enzyme. These effective modified enzymes are summarized as lists, and shown in Tables 26-1 and 26-2.

TABLE 24

Results of computation by Molegro Molecular Viewer

| Number | Residue | Total | EPair | EElec (r > 4.5) | EElec (r < 4.5) |
|---|---|---|---|---|---|
| 1 | R444 | −22.5 | −7.2 | −3.6 | −11.7 |
| 2 | R264 | −5.8 | −1.9 | −3.8 | |
| 3 | N447 | −4.5 | −4.5 | | |
| 4 | S402 | −3.6 | −3.6 | | |
| 5 | F376 | −2.8 | −2.8 | | |
| 6 | S401 | −2.5 | −2.5 | | |
| 7 | F294 | −2.3 | −2.3 | | |
| 8 | R458 | −2.3 | 0 | −2.3 | |
| 9 | F443 | −2 | −2 | | |
| 10 | S403 | −1.6 | −1.6 | | |
| 11 | R266 | −1.5 | 0 | −1.5 | |
| 12 | K374 | −0.9 | 0 | −0.9 | |
| 13 | R437 | −0.9 | 0 | −0.9 | |
| 14 | K381 | −0.9 | 0 | −0.9 | |
| 15 | R484 | −0.7 | 0 | −0.7 | |
| 16 | K386 | −0.7 | 0 | −0.7 | |
| 17 | K393 | −0.6 | 0 | −0.6 | |
| 18 | K367 | −0.6 | 0 | −0.6 | |
| 19 | V297 | −0.5 | −0.5 | | |
| 20 | K292 | −0.4 | 0 | −0.4 | |
| 21 | K493 | −0.4 | 0 | −0.4 | |
| 22 | Y523 | −0.4 | −0.4 | | |
| 23 | K481 | −0.4 | 0 | −0.4 | |
| 24 | K259 | −0.4 | 0 | −0.4 | |
| 25 | K336 | −0.3 | 0 | −0.3 | |
| 26 | K541 | −0.3 | 0 | −0.3 | |
| 27 | K288 | −0.3 | 0 | −0.3 | |
| 28 | K492 | −0.3 | 0 | −0.3 | |
| 29 | D311 | 0.3 | 0 | 0.3 | |
| 30 | E471 | 0.4 | 0 | 0.4 | |
| 31 | E490 | 0.7 | 0 | 0.7 | |
| 32 | E321 | 0.7 | 0 | 0.7 | |
| 33 | E476 | 0.7 | 0 | 0.7 | |
| 34 | D265 | 0.7 | 0 | 0.7 | |
| 35 | E457 | 0.8 | 0 | 0.8 | |
| 36 | E312 | 0.8 | 0 | 0.8 | |
| 37 | D533 | 0.8 | 0 | 0.8 | |
| 38 | E371 | 0.8 | 0 | 0.8 | |

EPair, EElec (r>4.5) and EElec (r<4.5) represent energy due to charge pairing, energy of electrostatic interaction that occurs in distance of 4.5 Å or more and energy of electrostatic interaction that occurs in distance within 4.5 Å, respectively. Total is defined as total sum of these energies. A blank column indicates that the energy was zero computationally.

TABLE 25-1

Activity changes in isoprene synthase mutants (No. 1)

| Number | Mutation | Fold |
|---|---|---|
| 1 | K127R | 2.3 |
| 2 | K127E | 3.4 |
| 3 | K127D | 2.4 |
| 4 | K127N | 1.4 |
| 5 | K127Q | ND |
| 6 | K127Y | ND |
| 7 | K130D | ND |
| 8 | K130N | ND |
| 9 | K130Q | ND |
| 10 | K130Y | 0.2 |
| 11 | R202E | 0.3 |
| 12 | R202K | 0.3 |
| 13 | R202D | 1.3 |
| 14 | R202Q | 0.7 |

TABLE 25-1-continued

Activity changes in isoprene synthase mutants (No. 1)

| Number | Mutation | Fold |
|---|---|---|
| 15 | R202N | 1.3 |
| 16 | W250E | 0.2 |
| 17 | W250D | ND |
| 18 | W250Q | ND |
| 19 | W250N | ND |
| 20 | K259R | 1.8 |
| 21 | K259E | 2.5 |
| 22 | K259D | 2.3 |
| 23 | K259Q | 2 |
| 24 | K259N | 1.5 |
| 25 | D265E | 1.4 |
| 26 | D265Q | 2.6 |
| 27 | D265N | 1.7 |
| 147 | D131I | 0.2 |
| 148 | C137G | ND |
| 149 | C137L | 3 |
| 150 | L256E | 0.3 |
| 151 | L256K | 0.1 |
| 152 | C286G | 1 |
| 153 | I299E | ND |
| 154 | I299R | 0.7 |
| 155 | I299M | ND |
| 156 | Y304S | ND |
| 157 | Y304W | ND |
| 158 | F316S | 0.5 |
| 159 | F316E | 3.1 |
| 160 | F316N | ND |
| 161 | F316R | ND |
| 162 | V320M | ND |
| 163 | V320S | ND |
| 164 | V320I | ND |
| 165 | E321C | ND |
| 166 | E321S | 1 |
| 167 | E321N | ND |
| 168 | C370G | ND |
| 169 | C373G | ND |
| 170 | F376I | ND |
| 171 | F376H | ND |
| 172 | F376Y | 0.8 |
| 173 | C388G | ND |

Fold: Scale factor of activity change in mutant enzyme compared with wild type enzyme.
ND (Not Detected): indicates that no significant activity was observed in the mutant enzyme.

TABLE 25-2

Activity changes of isoprene synthase mutants (No. 2)

| Number | Mutation | Fold |
|---|---|---|
| 28 | D265K | 0.2 |
| 29 | D265R | 1.4 |
| 30 | R266K | 0.2 |
| 31 | R266E | 0.8 |
| 32 | R266Q | 1.2 |
| 33 | R266N | 2.6 |
| 34 | K288R | 0.3 |
| 35 | K288Q | 0.6 |
| 36 | K288N | 1 |
| 37 | K288E | 0.8 |
| 38 | F294L | 0.6 |
| 39 | F294W | ND |
| 40 | V297E | 0.4 |
| 41 | D301R | 1.6 |
| 42 | D301T | ND |
| 43 | D305R | 1.2 |
| 44 | D305T | ND |
| 45 | D311E | 0.6 |
| 46 | D311Q | 0.6 |
| 47 | D311N | 0.4 |
| 48 | D311K | 0.5 |
| 49 | D311R | 0.7 |
| 50 | D311I | 0.6 |
| 51 | E312D | 0.2 |

TABLE 25-2-continued

Activity changes of isoprene synthase mutants (No. 2)

| Number | Mutation | Fold |
|---|---|---|
| 52 | E312Q | 0.6 |
| 53 | E312N | 0.7 |
| 54 | E312K | 0.7 |
| 174 | S399N | ND |
| 175 | S399M | ND |
| 176 | G404N | 0.3 |
| 177 | G404M | 3 |
| 178 | V405N | 0.9 |
| 179 | V405M | 0.5 |
| 180 | Y412N | ND |
| 181 | Y412M | ND |
| 182 | L414N | 0.6 |
| 183 | L414M | ND |
| 184 | V415N | ND |
| 185 | V415M | ND |
| 186 | C416G | ND |
| 187 | C416M | ND |
| 188 | C416L | ND |
| 189 | L449N | 0.4 |
| 190 | L449I | 0.5 |
| 191 | S452E | ND |
| 192 | S452I | ND |
| 193 | S452N | 0.8 |
| 194 | I465S | 0.4 |
| 195 | I465N | ND |
| 196 | I465M | ND |
| 197 | C446G | ND |
| 198 | C480G | ND |
| 199 | P505Q | 0.3 |
| 200 | P505R | 1 |

Fold: Scale factor of activity change in mutant enzyme compared with wild type enzyme.
ND (Not Detected): indicates that no significant activity was observed in the mutant enzyme.

TABLE 25-3

Activity changes in isoprene synthase mutants (No. 3)

| Number | Mutation | Fold |
|---|---|---|
| 55 | E312I | 1.4 |
| 56 | E312R | 1.8 |
| 57 | E321D | 2.9 |
| 58 | E321Q | 0.5 |
| 59 | E321N | 0.5 |
| 60 | E321K | 0.5 |
| 61 | E321R | 0.9 |
| 62 | E321I | 0.7 |
| 63 | K336D | 0.5 |
| 64 | K336Q | 0.7 |
| 65 | K336N | 0.6 |
| 66 | K336E | 0.9 |
| 67 | K336L | 0.6 |
| 68 | K367R | 0.9 |
| 69 | K367Q | 0.6 |
| 70 | K367E | 0.5 |
| 71 | E371D | 1.3 |
| 72 | E371Q | 0.6 |
| 73 | E371K | 0.6 |
| 74 | E371R | 0.5 |
| 75 | E371L | 0.4 |
| 76 | K374R | 0.4 |
| 77 | K374Q | 0.6 |
| 78 | K374N | 0.6 |
| 79 | K374E | 1 |
| 80 | E379T | 2.2 |
| 81 | K381R | 0.2 |
| 201 | P505H | 1.3 |
| 202 | F508Q | 1.8 |
| 203 | F508R | 1.2 |
| 204 | F508H | 0.3 |
| 205 | I518S | 2.1 |
| 206 | I518N | 0.6 |
| 207 | I518L | 0.3 |

TABLE 25-3-continued

Activity changes in isoprene synthase mutants (No. 3)

| Number | Mutation | Fold |
|---|---|---|
| 208 | S519M | ND |
| 209 | S519N | 2.1 |
| 210 | H520N | 1.8 |
| 211 | H520M | ND |
| 212 | C521G | ND |
| 213 | F31E | 2.8 |
| 214 | F31K | 3.6 |
| 215 | L35E | 1.9 |
| 216 | L35K | 2.8 |
| 217 | L67E | 2.4 |
| 218 | I90E | 1.1 |
| 219 | V106E | 0.1 |
| 220 | S122G | 0.1 |
| 221 | S122D | ND |
| 222 | S122E | ND |
| 223 | D124E | 1.3 |
| 224 | R128K | 1.6 |
| 225 | F129G | 0.7 |
| 226 | F129D | 0.4 |
| 227 | F129E | 0.1 |

Fold: Scale factor of activity change in mutant enzyme compared with wild type enzyme.
ND (Not Detected): indicates that no significant activity was observed in the mutant enzyme.

TABLE 25-4

Activity changes in isoprene synthase mutants (No. 4)

| Number | Mutation | Fold |
|---|---|---|
| 82 | K381Q | 0.8 |
| 83 | K381N | 0.6 |
| 84 | K381E | 0.7 |
| 85 | K381L | 0.9 |
| 86 | K386R | 1.1 |
| 87 | K386Q | 1 |
| 88 | K386D | 0.7 |
| 89 | K393R | 0.7 |
| 90 | K393L | 0.8 |
| 91 | K393N | 0.5 |
| 92 | K393E | 0.6 |
| 93 | K393D | 0.7 |
| 94 | D396E | 0.7 |
| 95 | D396Q | 0.2 |
| 96 | D396N | 0.4 |
| 97 | D396K | 0.3 |
| 98 | D396R | 0.4 |
| 99 | S401R | 0.9 |
| 100 | S401T | 2.2 |
| 101 | S402L | 1.2 |
| 102 | S402W | ND |
| 103 | L407F | 0.2 |
| 104 | R437K | 1 |
| 105 | R437E | 0.4 |
| 106 | R437L | 0.5 |
| 107 | F443L | 0.8 |
| 108 | F443W | 0.5 |
| 228 | K130G | 2.2 |
| 229 | G134P | 1.1 |
| 230 | G135P | 0.5 |
| 231 | G157P | 0.3 |
| 232 | G160P | 0.3 |
| 233 | S162C | 0.6 |
| 234 | L163E | ND |
| 235 | L163K | 0.1 |
| 236 | G182P | 0.3 |
| 237 | V187K | 0.1 |
| 238 | R202C | ND |
| 239 | L247E | 1.6 |
| 240 | L247D | 4.8 |
| 241 | L247Q | 1.5 |
| 242 | L247N | 0.4 |
| 243 | T257L | 2.5 |
| 244 | R264K | ND |

TABLE 25-4-continued

| Activity changes in isoprene synthase mutants (No. 4) | | |
|---|---|---|
| Number | Mutation | Fold |
| 245 | R264M | 2.9 |
| 246 | R264F | 3.5 |
| 247 | R264T | 1.3 |
| 248 | E269Y | 2.8 |
| 249 | E269I | 2.8 |
| 250 | E269D | 1.7 |
| 251 | V289K | 0.3 |
| 252 | K292A | 1 |
| 253 | K292I | 0.7 |
| 254 | K292L | 1.3 |

Fold: Scale factor of activity change in mutant enzyme compared with wild type enzyme.
ND (Not Detected): indicates that no significant activity was observed in the mutant enzyme.

TABLE 25-5

| Activity changes in isoprene synthase mutants (No. 5) | | |
|---|---|---|
| Number | Mutation | Fold |
| 109 | R444T | 2.3 |
| 110 | N447R | 1.4 |
| 111 | N447T | 0.3 |
| 112 | N447I | ND |
| 113 | N447W | 0.5 |
| 114 | N447Y | ND |
| 115 | N447L | 1.1 |
| 116 | D448E | 0.9 |
| 117 | D448L | 0.8 |
| 118 | D448K | 0.8 |
| 119 | T451Q | 0.3 |
| 120 | E455H | 0.1 |
| 121 | R458K | 0.9 |
| 122 | R458Q | 1.2 |
| 123 | R458N | 0.5 |
| 124 | R458E | 0.5 |
| 125 | R458D | 0.4 |
| 126 | T461R | 1.3 |
| 127 | T462M | 2.1 |
| 128 | E476R | 0.5 |
| 129 | R484K | 1.3 |
| 130 | R484Q | 0.1 |
| 131 | R484L | 0.1 |
| 132 | K492R | 0.2 |
| 133 | K492Q | 0.1 |
| 134 | K492L | 0.3 |
| 135 | K492E | 1.1 |
| 255 | F294I | 0.6 |
| 256 | V297L | 0.8 |
| 257 | T298V | 0.9 |
| 258 | T298L | 1 |
| 259 | V306E | ND |
| 260 | V306K | ND |
| 261 | L310E | 0.7 |
| 262 | V325E | 0.5 |
| 263 | V325K | 1.1 |
| 264 | I328E | 1.2 |
| 265 | L340K | 1.2 |
| 266 | L377R | 1 |
| 267 | I387K | ND |
| 268 | I388K | 0.2 |
| 269 | G404A | 2.7 |
| 270 | L407Y | ND |
| 271 | F443I | 0.3 |
| 272 | V499I | 1.6 |
| 273 | G528K | ND |
| 274 | G528E | ND |
| 275 | G528R | 0.2 |
| 276 | G528T | ND |
| 277 | L529K | ND |

TABLE 25-5-continued

| Activity changes in isoprene synthase mutants (No. 5) | | |
|---|---|---|
| Number | Mutation | Fold |
| 278 | L529R | ND |
| 279 | L529T | ND |
| 280 | G530K | 3 |
| 281 | G530E | 0.1 |

Fold: Scale factor of activity change in mutant enzyme compared with wild type enzyme.
ND (Not Detected): indicates that no significant activity was observed in the mutant enzyme.

TABLE 25-6

| Activity changes in isoprene synthase mutants (No. 6) | | |
|---|---|---|
| Number | Mutation | Fold |
| 136 | K492D | 1 |
| 137 | K493R | 0.5 |
| 138 | K493Q | 0.8 |
| 139 | K493L | 0.8 |
| 140 | K493E | 0.5 |
| 141 | K493D | 0.3 |
| 142 | Y523I | 3.2 |
| 143 | Y523L | 3 |
| 144 | Y523W | 1 |
| 145 | D131Q | 0.1 |
| 146 | D131S | 0.1 |
| 282 | G530R | ND |
| 283 | G530T | 0.1 |
| 284 | I96K | 0.1 |
| 285 | S248K | 3.9 |
| 286 | S248E | 1.7 |
| 287 | S248R | 1.1 |
| 288 | S248T | 0.5 |
| 289 | L249K | 1.7 |
| 290 | L249E | 3.4 |
| 291 | L249R | 3.2 |
| 292 | L249T | 3.5 |

Fold: Scale factor of activity change in mutant enzyme compared with wild type enzyme.
ND (Not Detected): indicates that no significant activity was observed in the mutant enzyme.

TABLE 26-1

| List of effective mutants (No. 1) | | |
|---|---|---|
| Number | Mutation | Fold |
| 1 | K127R | 2.3 |
| 2 | K127E | 3.4 |
| 3 | K127D | 2.4 |
| 4 | K127N | 1.4 |
| 13 | R202D | 1.3 |
| 15 | R202N | 1.3 |
| 20 | K259R | 1.8 |
| 21 | K259E | 2.5 |
| 22 | K259D | 2.3 |
| 23 | K259Q | 2 |
| 24 | K259N | 1.5 |
| 25 | D265E | 1.4 |
| 26 | D265Q | 2.6 |
| 27 | D265N | 1.7 |
| 29 | D265R | 1.4 |
| 32 | R266Q | 1.2 |
| 33 | R266N | 2.6 |
| 41 | D301R | 1.6 |
| 43 | D305R | 1.2 |
| 55 | E312I | 1.4 |
| 56 | E312R | 1.8 |
| 57 | E321D | 2.9 |
| 71 | E371D | 1.3 |
| 80 | E379T | 2.2 |
| 86 | K386R | 1.1 |
| 100 | S401T | 2.2 |

TABLE 26-1-continued

| List of effective mutants (No. 1) | | |
|---|---|---|
| Number | Mutation | Fold |
| 101 | S402L | 1.2 |
| 201 | P505H | 1.3 |
| 202 | F508Q | 1.8 |
| 203 | F508R | 1.2 |
| 205 | I518S | 2.1 |
| 209 | S519N | 2.1 |
| 210 | H520N | 1.8 |
| 213 | F31E | 2.8 |
| 214 | F31K | 3.6 |
| 215 | L35E | 1.9 |
| 216 | L35K | 2.8 |
| 217 | L67E | 2.4 |
| 218 | I90E | 1.1 |
| 223 | D124E | 1.3 |
| 224 | R128K | 1.6 |
| 228 | K130G | 2.2 |
| 229 | G134P | 1.1 |
| 239 | L247E | 1.6 |
| 240 | L247D | 4.8 |
| 241 | L247Q | 1.5 |
| 243 | T257L | 2.5 |
| 245 | R264M | 2.9 |
| 246 | R264F | 3.5 |
| 247 | R264T | 1.3 |
| 248 | E269Y | 2.8 |
| 249 | E269I | 2.8 |
| 250 | E269D | 1.7 |
| 254 | K292L | 1.3 |

Fold: Scale factor of activity change in mutant enzyme compared with wild type enzyme.

TABLE 26-2

| List of effective mutants (No. 2) | | |
|---|---|---|
| Number | Mutation | Fold |
| 109 | R444T | 2.3 |
| 110 | N447R | 1.4 |
| 115 | N447L | 1.1 |
| 122 | R458Q | 1.2 |
| 126 | T461R | 1.3 |
| 127 | T462M | 2.1 |
| 129 | R484K | 1.3 |
| 135 | K492E | 1.1 |
| 142 | Y523I | 3.2 |
| 143 | Y523L | 3 |
| 149 | C137L | 3 |
| 159 | F316E | 3.1 |
| 177 | G404M | 3 |
| 263 | V325K | 1.1 |
| 264 | I328E | 1.2 |
| 265 | L340K | 1.2 |
| 269 | G404A | 2.7 |
| 272 | V499I | 1.6 |
| 280 | G530K | 3 |
| 285 | S248K | 3.9 |
| 286 | S248E | 1.7 |
| 287 | S248R | 1.1 |
| 289 | L249K | 1.7 |
| 290 | L249E | 3.4 |
| 291 | L249R | 3.2 |
| 292 | L249T | 3.5 |

Fold: Scale factor of activity change in mutant enzyme compared with wild type enzyme.

Example 4: Quantitative Evaluation of Ability of Modified Enzyme to Convert into Isoprene Among 67 modified enzymes having the qualitative activity value of 30% or more relative to the wild type in Example 1 (1-5), 66 modified enzymes except C416K were evaluated for quantitative function. The function was specifically evaluated as follows. A concentration of each IspS mutant protein after simple purification was quantified by Bradford method. Subsequently, 1 μs of each IspS mutant was weighed and placed in a 0.2 mL volume PCR tube (Nippon Genetics) on ice. Then, 5 μL of reaction buffer (250 mM Tris-HCl, 200 mM $MgCl_2$, pH 8.0) was added thereto, and sterilized water was added so as to make 45 μL solution together with the enzyme solution. After gently tapping, 5 μL of 40 mM DMAPP (Cayman, catalog #63180) was added and mixed. The mixture was left stand at 37° C. for 10 minutes or 17 hours, and then an amount of produced isoprene was measured by GC. A relative value of the enzyme activity of each modified enzyme relative to the wild type IspS was calculated by dividing the amount of isoprene produced by each modified enzyme by the amount isoprene produced by wild type IspS. The relative value for a reaction time of 10 minutes was defined as an activity, and the relative activity for the reaction time of 18 hours was defined as an accumulation ability. The results are shown in Tables 27-1 to 27-3. The modified enzymes that exhibited 1.1 or more of the activity or the accumulation ability were 43 modified enzymes of S2A, V97E, L114E, Q123C, V125E, D131C, C137E, C137I, C137M, C137S, V144E, V187E, L224E, C286V, C286N, T298I, I300N, C338V, C338L, C370V, C370E, C370N, C370K, C373V, C373Y, S383I, I388C/Q123C, V405C, L414C, C416E, C440S, E471C/A390C, C480N, C480Y, C480V, K481E, F508C, I518C, C521E, C521V, C521I, C521S, and C521N. The mutants that were evaluated as the effective modified enzymes in Example 1 (1-6), but effectiveness of which could not be reproduced in Tables 27-1 to 27-3 are C137K, C286I, V346M, D348E, S383M, and C446N.

TABLE 27-1

| Activity evaluation of isoprene synthase mutants (No. 1) | | | | |
|---|---|---|---|---|
| Number | Mutant | Activity | Accumulation | Effective mutant |
| 1 | S2A | 0.9 | 1.5 | Yes |
| 2 | V55E | 0 | 0.1 | |
| 3 | V76E | 0 | 0.1 | |
| 4 | V97E | 0.8 | 4.4 | Yes |
| 5 | L114E | 0.6 | 1.8 | Yes |
| 6 | Q123C | 0.6 | 3.3 | Yes |
| 7 | V125E | 0.8 | 2.7 | Yes |
| 8 | D131C | 1.6 | 1.3 | Yes |
| 9 | C137K | 0.4 | 0.4 | |
| 10 | C137E | 1.1 | 3.4 | Yes |
| 11 | C137I | 0.6 | 1.2 | Yes |
| 12 | C137M | 1.5 | 5 | Yes |
| 13 | C137S | 0.7 | 2.2 | Yes |
| 14 | V144E | 0.6 | 1.5 | Yes |
| 15 | V187E | 0.3 | 1.8 | Yes |
| 16 | V191E | 0 | 0.1 | |
| 17 | L224E | 0.7 | 3.3 | Yes |
| 18 | V236E | 0.3 | 0.3 | |
| 19 | C286V | 0.5 | 4.6 | Yes |
| 20 | C286N | 1.6 | 3.8 | Yes |
| 21 | C286I | 0 | 0.2 | |
| 22 | T298I | 1.2 | 1.9 | Yes |
| 23 | I300N | 0.6 | 3.6 | Yes |
| 24 | V320C | 0.3 | 0.7 | |
| 25 | C338V | 0.7 | 4.2 | Yes |
| 26 | C338L | 0.2 | 1.1 | Yes |
| 27 | V346M | 0 | 0.1 | |

Activity: Relative activity for reaction time of 10 minutes.
Accumulation: Relative activity for reaction time of 18 hours.

TABLE 27-2

| Activity evaluation of isoprene synthase mutants (No. 2) | | | | |
|---|---|---|---|---|
| Number | Mutant | Activity | Accumulation | Effective mutant |
| 28 | V346S | 0 | 0.1 | |
| 29 | D348E | 0.5 | 0.4 | |
| 30 | C370V | 1.4 | 6.1 | Yes |
| 31 | C370E | 0.5 | 3.2 | Yes |
| 32 | C370N | 0.5 | 3.4 | Yes |
| 33 | C370K | 0.5 | 6 | Yes |
| 34 | C373V | 0.5 | 2.2 | Yes |
| 35 | C373Y | 1.2 | 3.3 | Yes |
| 36 | C373F | 0 | 0.1 | |
| 37 | S383M | 1 | 0.9 | |
| 38 | S383I | 0.2 | 1.4 | Yes |
| 39 | I388C/Q123C | 1 | 1.7 | Yes |
| 40 | I388C | 0.3 | 0.5 | |
| 41 | I388C/N360C | 0.2 | 0.3 | |
| 42 | V400E | 0.1 | 0.1 | |
| 43 | V405E | 0.5 | 0.3 | |
| 44 | V405C | 0.8 | 1.5 | Yes |
| 45 | L414C | 0.5 | 1.7 | Yes |
| 46 | C416E | 0.9 | 1.5 | Yes |
| 47 | C416Y | 0.5 | 0.3 | |
| 48 | C440S | 0.6 | 2.4 | Yes |
| 49 | I442C | 0 | 0.8 | |
| 50 | C446V | 0.2 | 0.5 | |
| 51 | C446N | 0.1 | 0.9 | |
| 52 | T451E | 0 | 0.1 | |
| 53 | S452C | 0.1 | 0.1 | |
| 54 | E471C/A390C | 0.5 | 2 | Yes |

Activity: Relative activity for reaction time of 10 minutes.
Accumulation: Relative activity for reaction time of 18 hours.

TABLE 27-3

| Activity evaluation of isoprene synthase mutants (No. 3) | | | | |
|---|---|---|---|---|
| Number | Mutant | Activity | Accumulation | Effective mutant |
| 55 | E471C | 0.3 | 0.2 | |
| 56 | C480N | 1.4 | 1.3 | Yes |
| 57 | C480Y | 0.8 | 2 | Yes |
| 58 | C480V | 1.1 | 4.4 | Yes |
| 59 | K481E | 1.3 | 5.4 | Yes |
| 60 | F508C | 2 | 0.3 | Yes |
| 61 | I518C | 0.4 | 2.9 | Yes |
| 62 | C521E | 1.6 | 9.4 | Yes |
| 63 | C521V | 0.7 | 2.4 | Yes |
| 64 | C521I | 0.5 | 1.4 | Yes |
| 65 | C521S | 1 | 1.8 | Yes |
| 66 | C521N | 0.5 | 1.9 | Yes |

Activity: Relative activity for reaction time of 10 minutes.
Accumulation: Relative activity for reaction time of 18 hours.

Example 5: Production of Polyisoprene

Isoprene is collected with a trap cooled with liquid nitrogen by passing the fermentation exhaust. Collected isoprene is mixed with 35 g of hexane (Sigma-Aldrich) and 10 g of silica gel (Sigma-Aldrich, catalog No. 236772) and 10 g of alumina (Sigma-Aldrich, catalog No. 267740) under a nitrogen atmosphere in 100 mL glass vessel that is sufficiently dried. Resulting mixture is left at room temperature for 5 hours. Then supernatant liquid is skimmed and is added into 50 ml glass vessel that is sufficiently dried.

Meanwhile, in a glove box under a nitrogen atmosphere, 40.0 μmol of tris[bis(trimethylsilyl)amido]gadolinium, 150.0 μmol of tributylaluminium, 40.0 μmol of bis[2-(diphenylphosphino)phenyl]amine, 40.0 μmol of triphenylcarbonium tetrakis(pentafluorophenyl)borate ($(Ph_3CBC_6F_5)_4$) are provided in a glass container, which is dissolved into 5 mL of toluene (Sigma-Aldrich, catalog No. 245511), to thereby obtain a catalyst solution. After that, the catalyst solution is taken out from the glove box and added to the monomer solution, which is then subjected to polymerization at 50° C. for 120 minutes.

After the polymerization, 1 mL of an isopropanol solution containing, by 5 mass %, 2,2'-methylene-bis(4-ethyl-6-t-butylphenol) (NS-5), is added to stop the reaction. Then, a large amount of methanol is further added to isolate the polymer, and the polymer is vacuum dried at 70° C. to obtain a polymer.

Example 6: Production of Rubber Compound

The rubber compositions formulated as shown in Table 28 are prepared, which are vulcanized at 145° C. for 35 minutes.

TABLE 28

| | Parts by mass |
|---|---|
| Polyisoprene | 100 |
| Stearic Acid | 2 |
| Carbon Black (HAF class) | 50 |
| Antioxidant (*1) | 1 |
| Zinc Oxide | 3 |
| Cure Accelerator (*2) | 0.5 |
| Sulfur | 1.5 |

(*1) N-(1,3-dimethylbutyl)-N'-p-phenylenediamine
(*2) N-cyclohexyl-2-benzothiazolesulfenamide Where a numerical limit or range is stated herein, the endpoints are included. Also, all values and subranges within a numerical limit or range are specifically included as if explicitly written out.

As used herein the words “a” and “an” and the like carry the meaning of “one or more.”

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A modified isoprene synthase, having an amino acid sequence at least 90 identical to the amino acid sequence of SEQ ID NO: 4, wherein the modified isoprene synthase has at least one mutation of an amino acid residue corresponding to at least one amino acid residue in SEQ ID NO: 4 selected from the group consisting of: C286, E321, C370, A390, E471, C480, I518, and C521, and the modified isoprene synthase has an isoprene synthetic activity.

2. The modified isoprene synthase of claim 1, wherein the at least one mutation in the modified isoprene synthase corresponds to at least one mutation in SEQ ID NO: 4 selected from the group consisting of: C286V, E321D, C370E, A390C, E471C, C480N, I518C, C521V, and C521I.

3. The modified isoprene synthase of claim 1, wherein the modified isoprene synthase further comprises a signal sequence at the N-terminus.

4. A modified isoprene synthase, having an amino acid sequence at least 90% identical to the amino acid sequence of SEQ ID NO: 2, wherein the modified isoprene synthase has at least one mutation of an amino acid residue corresponding to at least one amino acid residue in SEQ ID NO: 2 selected from the group consisting of: C329, E364, C413, A433, E514, C523, I561, and C564, and the modified isoprene synthase has an isoprene synthetic activity.

5. The modified isoprene synthase of claim 4, wherein the at least one mutation in the modified isoprene synthase corresponds to at least one mutation in SEQ ID NO: 2 selected from the group consisting of: C329V, E364D, A433C, E514C, C523N, I561C, C564V, and C564I.

6. The modified isoprene synthase of claim 1, wherein the amino acid sequence of the modified isoprene synthase has 95% or more identity to the amino acid sequence of SEQ ID NO: 4.

7. The modified isoprene synthase of claim 1, wherein the at least one mutation in the modified isoprene synthase corresponds to at least one mutation in SEQ ID NO: 4 selected from the group consisting of: C286I, C286V, E321D, C370K, A390C, E471C, C480N, I518C, C521V, and C521I.

8. The modified isoprene synthase of claim 1, wherein the at least one mutation in the modified isoprene synthase corresponds to at least two mutations in SEQ ID NO: 4 selected from the group consisting of: C286I, C286V, E321D, C370K, A390C, E471C, C480N, I518C, C521V, and C521I.

9. The modified isoprene synthase of claim 2, wherein the modified isoprene synthase further comprises a signal sequence at the N-terminus.

* * * * *

SEQUENCE LISTING

```
<160> NUMBER OF SEQ ID NOS: 72

<210> SEQ ID NO 1
<211> LENGTH: 1785
<212> TYPE: DNA
<213> ORGANISM: Mucuna bracteata
<220> FEATURE:
<221> NAME/KEY: CDS
```

```
<222> LOCATION: (1)..(1785)

<400> SEQUENCE: 1

atg gca acc aac cct tca tgc tta tct act cca ttt ttg tcc tcc aca       48
Met Ala Thr Asn Pro Ser Cys Leu Ser Thr Pro Phe Leu Ser Ser Thr
1               5                   10                  15

cca gca cta agt act aga ttt cca tta agt gag aac ttc aca caa aaa       96
Pro Ala Leu Ser Thr Arg Phe Pro Leu Ser Glu Asn Phe Thr Gln Lys
            20                  25                  30

aca tct ctt gtc aat ccc aaa cct tgg cca ctt att tct gca gtc agc      144
Thr Ser Leu Val Asn Pro Lys Pro Trp Pro Leu Ile Ser Ala Val Ser
        35                  40                  45

tct caa ttt agc caa ata gca gaa gat aat agt cgt cgt tca gct aat      192
Ser Gln Phe Ser Gln Ile Ala Glu Asp Asn Ser Arg Arg Ser Ala Asn
    50                  55                  60

tac cac cca aac ctc tgg gat ttt gaa ttt ctg cag tct ctc gaa aat      240
Tyr His Pro Asn Leu Trp Asp Phe Glu Phe Leu Gln Ser Leu Glu Asn
65                  70                  75                  80

gac tct aag atg gaa aag ctg gaa gag aaa gca aca aag ttg gag gag      288
Asp Ser Lys Met Glu Lys Leu Glu Glu Lys Ala Thr Lys Leu Glu Glu
                85                  90                  95

gaa gtg cga aac atg atg aac gaa gca aag aca gaa gca cta agc tta      336
Glu Val Arg Asn Met Met Asn Glu Ala Lys Thr Glu Ala Leu Ser Leu
            100                 105                 110

ttg gaa ttg ata gac gac gtc cag cgt ctg gga ttg acc tac aag ttt      384
Leu Glu Leu Ile Asp Asp Val Gln Arg Leu Gly Leu Thr Tyr Lys Phe
        115                 120                 125

gag aag gac ata atc aaa gcc ctt gag aag att gtt cca ttg gat gag      432
Glu Lys Asp Ile Ile Lys Ala Leu Glu Lys Ile Val Pro Leu Asp Glu
    130                 135                 140

agt ggg ctg cat gtt act tct ctc agc ttc cgt ata ctt aga caa cat      480
Ser Gly Leu His Val Thr Ser Leu Ser Phe Arg Ile Leu Arg Gln His
145                 150                 155                 160

ggc ttt gag gtt tcc caa gat gtg ttt aag aga ttt aag gac aag gag      528
Gly Phe Glu Val Ser Gln Asp Val Phe Lys Arg Phe Lys Asp Lys Glu
                165                 170                 175

gga ggt ttt tgt gct gaa ctt aaa gac gat gtt caa ggg ttg cta agt      576
Gly Gly Phe Cys Ala Glu Leu Lys Asp Asp Val Gln Gly Leu Leu Ser
            180                 185                 190

cta tat gaa gca tcc tat ctt ggt ttt gag gga gaa agt ctc tta gac      624
Leu Tyr Glu Ala Ser Tyr Leu Gly Phe Glu Gly Glu Ser Leu Leu Asp
        195                 200                 205

gag gca agg gca ttt tca ata aca cat ctc aag aac aac cta aac aaa      672
Glu Ala Arg Ala Phe Ser Ile Thr His Leu Lys Asn Asn Leu Asn Lys
    210                 215                 220

gga ata aac acc aaa gta gcc caa caa gtt agc cat gca ctg gaa ctt      720
Gly Ile Asn Thr Lys Val Ala Gln Gln Val Ser His Ala Leu Glu Leu
225                 230                 235                 240

cct tat cat cga aga ctg cat aga ctg gaa gca cga tgg ctc ctt gac      768
Pro Tyr His Arg Arg Leu His Arg Leu Glu Ala Arg Trp Leu Leu Asp
                245                 250                 255

aaa tat gaa cca aag gaa ccc cac cat cat tta cta cac gag ctt gca      816
Lys Tyr Glu Pro Lys Glu Pro His His His Leu Leu His Glu Leu Ala
            260                 265                 270

aag ttg gat ttc aat ttg gtc caa tca ttg tac cag aaa gag ttg cga      864
Lys Leu Asp Phe Asn Leu Val Gln Ser Leu Tyr Gln Lys Glu Leu Arg
        275                 280                 285

gaa ttg tca ctg tgg tgg agg gag att ggg ctc aca agc aag ttg gac      912
Glu Leu Ser Leu Trp Trp Arg Glu Ile Gly Leu Thr Ser Lys Leu Asp
    290                 295                 300
```

-continued

```
ttt gtt cga gac aga tta atg gaa gtg tac ttt tgg gcg ctg gga atg      960
Phe Val Arg Asp Arg Leu Met Glu Val Tyr Phe Trp Ala Leu Gly Met
305                 310                 315                 320

gca cct gat cct caa ttt agt gaa tgt cgt aaa gtc gtc act aaa atg     1008
Ala Pro Asp Pro Gln Phe Ser Glu Cys Arg Lys Val Val Thr Lys Met
                325                 330                 335

ttt ggg cta gtt act atc atc gat gat gta tat gac gtt tac ggt act     1056
Phe Gly Leu Val Thr Ile Ile Asp Asp Val Tyr Asp Val Tyr Gly Thr
            340                 345                 350

ttg gac gag cta caa ctc ttc acc gat gct gtt gag aga tgg gac gtg     1104
Leu Asp Glu Leu Gln Leu Phe Thr Asp Ala Val Glu Arg Trp Asp Val
        355                 360                 365

aat gcg ata aat aca ctt cca gac tat atg aaa ttg tgc tat tta gcc     1152
Asn Ala Ile Asn Thr Leu Pro Asp Tyr Met Lys Leu Cys Tyr Leu Ala
    370                 375                 380

ctt tat aac acc gtc aat gac aca gct tat agc atc ctt aaa gaa aag     1200
Leu Tyr Asn Thr Val Asn Asp Thr Ala Tyr Ser Ile Leu Lys Glu Lys
385                 390                 395                 400

gga cat aac aac att tct tat ttg aca aaa tct tgg tgt gag ttg tgc     1248
Gly His Asn Asn Ile Ser Tyr Leu Thr Lys Ser Trp Cys Glu Leu Cys
                405                 410                 415

aaa gca ttc ctc caa gaa gca aaa tgg tca aac aac aaa atc att cca     1296
Lys Ala Phe Leu Gln Glu Ala Lys Trp Ser Asn Asn Lys Ile Ile Pro
            420                 425                 430

gca ttc aac aag tac cta gac aat gca tcg gtg tcc tcc tct ggt gtg     1344
Ala Phe Asn Lys Tyr Leu Asp Asn Ala Ser Val Ser Ser Ser Gly Val
        435                 440                 445

gct ttg ctt gct cct tcc tac ttc tta gtg tgc caa gaa caa gac att     1392
Ala Leu Leu Ala Pro Ser Tyr Phe Leu Val Cys Gln Glu Gln Asp Ile
    450                 455                 460

tca gac caa gct ctt cat tcc tta act aat ttc cat ggc ctt gtg cgt     1440
Ser Asp Gln Ala Leu His Ser Leu Thr Asn Phe His Gly Leu Val Arg
465                 470                 475                 480

tca tca tgc acc att ttt agg ctt tgc aat gat ctg gct acc tca tcg     1488
Ser Ser Cys Thr Ile Phe Arg Leu Cys Asn Asp Leu Ala Thr Ser Ser
                485                 490                 495

gct gag cta gag aga ggt gaa aca aca aat tca atc aca tcg tac atg     1536
Ala Glu Leu Glu Arg Gly Glu Thr Thr Asn Ser Ile Thr Ser Tyr Met
            500                 505                 510

cat gag aat gag act tct gag gag caa gca tgt aag gag ttg aga aat     1584
His Glu Asn Glu Thr Ser Glu Glu Gln Ala Cys Lys Glu Leu Arg Asn
        515                 520                 525

ttg atc gat gca gag tgg aag aag atg aat gaa gag cga gtt tca aat     1632
Leu Ile Asp Ala Glu Trp Lys Lys Met Asn Glu Glu Arg Val Ser Asn
    530                 535                 540

tct aca ctc cca aaa gca ttt agg gaa ata gct att aac atg gct cgg     1680
Ser Thr Leu Pro Lys Ala Phe Arg Glu Ile Ala Ile Asn Met Ala Arg
545                 550                 555                 560

att tcc cat tgc aca tac caa tat gga gac gga ctt gga agg ccc gac     1728
Ile Ser His Cys Thr Tyr Gln Tyr Gly Asp Gly Leu Gly Arg Pro Asp
                565                 570                 575

tac acc aca gag aac agg ata aag ttg cta cta ata gac cct ttt cca     1776
Tyr Thr Thr Glu Asn Arg Ile Lys Leu Leu Leu Ile Asp Pro Phe Pro
            580                 585                 590

att aat tag                                                         1785
Ile Asn

<210> SEQ ID NO 2
<211> LENGTH: 594
```

<212> TYPE: PRT
<213> ORGANISM: Mucuna bracteata

<400> SEQUENCE: 2

```
Met Ala Thr Asn Pro Ser Cys Leu Ser Thr Pro Phe Leu Ser Ser Thr
1               5                   10                  15

Pro Ala Leu Ser Thr Arg Phe Pro Leu Ser Glu Asn Phe Thr Gln Lys
            20                  25                  30

Thr Ser Leu Val Asn Pro Lys Pro Trp Pro Leu Ile Ser Ala Val Ser
        35                  40                  45

Ser Gln Phe Ser Gln Ile Ala Glu Asp Asn Ser Arg Arg Ser Ala Asn
    50                  55                  60

Tyr His Pro Asn Leu Trp Asp Phe Glu Phe Leu Gln Ser Leu Glu Asn
65                  70                  75                  80

Asp Ser Lys Met Glu Lys Leu Glu Glu Lys Ala Thr Lys Leu Glu Glu
                85                  90                  95

Glu Val Arg Asn Met Met Asn Glu Ala Lys Thr Glu Ala Leu Ser Leu
            100                 105                 110

Leu Glu Leu Ile Asp Asp Val Gln Arg Leu Gly Leu Thr Tyr Lys Phe
        115                 120                 125

Glu Lys Asp Ile Ile Lys Ala Leu Glu Lys Ile Val Pro Leu Asp Glu
    130                 135                 140

Ser Gly Leu His Val Thr Ser Leu Ser Phe Arg Ile Leu Arg Gln His
145                 150                 155                 160

Gly Phe Glu Val Ser Gln Asp Val Phe Lys Arg Phe Lys Asp Lys Glu
                165                 170                 175

Gly Gly Phe Cys Ala Glu Leu Lys Asp Asp Val Gln Gly Leu Leu Ser
            180                 185                 190

Leu Tyr Glu Ala Ser Tyr Leu Gly Phe Glu Gly Glu Ser Leu Leu Asp
        195                 200                 205

Glu Ala Arg Ala Phe Ser Ile Thr His Leu Lys Asn Asn Leu Asn Lys
    210                 215                 220

Gly Ile Asn Thr Lys Val Ala Gln Gln Val Ser His Ala Leu Glu Leu
225                 230                 235                 240

Pro Tyr His Arg Arg Leu His Arg Leu Glu Ala Arg Trp Leu Leu Asp
                245                 250                 255

Lys Tyr Glu Pro Lys Glu Pro His His His Leu Leu His Glu Leu Ala
            260                 265                 270

Lys Leu Asp Phe Asn Leu Val Gln Ser Leu Tyr Gln Lys Glu Leu Arg
        275                 280                 285

Glu Leu Ser Leu Trp Trp Arg Glu Ile Gly Leu Thr Ser Lys Leu Asp
    290                 295                 300

Phe Val Arg Asp Arg Leu Met Glu Val Tyr Phe Trp Ala Leu Gly Met
305                 310                 315                 320

Ala Pro Asp Pro Gln Phe Ser Glu Cys Arg Lys Val Val Thr Lys Met
                325                 330                 335

Phe Gly Leu Val Thr Ile Ile Asp Asp Val Tyr Asp Val Tyr Gly Thr
            340                 345                 350

Leu Asp Glu Leu Gln Leu Phe Thr Asp Ala Val Glu Arg Trp Asp Val
        355                 360                 365

Asn Ala Ile Asn Thr Leu Pro Asp Tyr Met Lys Leu Cys Tyr Leu Ala
    370                 375                 380

Leu Tyr Asn Thr Val Asn Asp Thr Ala Tyr Ser Ile Leu Lys Glu Lys
385                 390                 395                 400
```

```
Gly His Asn Asn Ile Ser Tyr Leu Thr Lys Ser Trp Cys Glu Leu Cys
                405                 410                 415

Lys Ala Phe Leu Gln Glu Ala Lys Trp Ser Asn Asn Lys Ile Ile Pro
            420                 425                 430

Ala Phe Asn Lys Tyr Leu Asp Asn Ala Ser Val Ser Ser Ser Gly Val
        435                 440                 445

Ala Leu Leu Ala Pro Ser Tyr Phe Leu Val Cys Gln Glu Gln Asp Ile
    450                 455                 460

Ser Asp Gln Ala Leu His Ser Leu Thr Asn Phe His Gly Leu Val Arg
465                 470                 475                 480

Ser Ser Cys Thr Ile Phe Arg Leu Cys Asn Asp Leu Ala Thr Ser Ser
                485                 490                 495

Ala Glu Leu Glu Arg Gly Glu Thr Thr Asn Ser Ile Thr Ser Tyr Met
            500                 505                 510

His Glu Asn Glu Thr Ser Glu Glu Gln Ala Cys Lys Glu Leu Arg Asn
        515                 520                 525

Leu Ile Asp Ala Glu Trp Lys Lys Met Asn Glu Glu Arg Val Ser Asn
    530                 535                 540

Ser Thr Leu Pro Lys Ala Phe Arg Glu Ile Ala Ile Asn Met Ala Arg
545                 550                 555                 560

Ile Ser His Cys Thr Tyr Gln Tyr Gly Asp Gly Leu Gly Arg Pro Asp
                565                 570                 575

Tyr Thr Thr Glu Asn Arg Ile Lys Leu Leu Leu Ile Asp Pro Phe Pro
            580                 585                 590

Ile Asn


<210> SEQ ID NO 3
<211> LENGTH: 1656
<212> TYPE: DNA
<213> ORGANISM: Artificial Sequence
<220> FEATURE:
<223> OTHER INFORMATION: Polynucleotide encoding isoprene synthase
      without chloroplast-localization signal which is derived from
      Mucuna pururiens (IspSM gene)
<220> FEATURE:
<221> NAME/KEY: CDS
<222> LOCATION: (1)..(1656)

<400> SEQUENCE: 3

atg tcc gcc gtt tca agc cag ttc tct caa atc gcc gaa gac aat agc       48
Met Ser Ala Val Ser Ser Gln Phe Ser Gln Ile Ala Glu Asp Asn Ser
1               5                   10                  15

cgt cgc tca gca aat tat cat ccg aat ctg tgg gac ttt gaa ttt ctg       96
Arg Arg Ser Ala Asn Tyr His Pro Asn Leu Trp Asp Phe Glu Phe Leu
            20                  25                  30

cag tct ctg gaa aac gat agt aaa atg gaa aaa ctg gaa gaa aaa gcc      144
Gln Ser Leu Glu Asn Asp Ser Lys Met Glu Lys Leu Glu Glu Lys Ala
        35                  40                  45

acc aaa ctg gaa gaa gaa gtg cgt aac atg atg aat gaa gcg aaa acg      192
Thr Lys Leu Glu Glu Glu Val Arg Asn Met Met Asn Glu Ala Lys Thr
    50                  55                  60

gaa gcc ctg agc ctg ctg gaa ctg att gat gac gtc caa cgc ctg ggt      240
Glu Ala Leu Ser Leu Leu Glu Leu Ile Asp Asp Val Gln Arg Leu Gly
65                  70                  75                  80

ctg acc tac aaa ttc gaa aaa gat atc atc aaa gca ctg gaa aaa att      288
Leu Thr Tyr Lys Phe Glu Lys Asp Ile Ile Lys Ala Leu Glu Lys Ile
                85                  90                  95

gtc ccg ctg gac gaa tca ggt ctg cac gtg acg tct ctg agt ttt cgt      336
```

-continued

```
Val Pro Leu Asp Glu Ser Gly Leu His Val Thr Ser Leu Ser Phe Arg
            100                 105                 110

atc ctg cgc cag cat ggc ttc gaa gtt tcg caa gat gtc ttt aaa cgt      384
Ile Leu Arg Gln His Gly Phe Glu Val Ser Gln Asp Val Phe Lys Arg
        115                 120                 125

ttc aaa gac aaa gaa ggc ggt ttc tgc gcg gaa ctg aaa gat gac gtg      432
Phe Lys Asp Lys Glu Gly Gly Phe Cys Ala Glu Leu Lys Asp Asp Val
    130                 135                 140

cag ggt ctg ctg tcc ctg tat gaa gcc tca tac ctg ggt ttt gaa ggc      480
Gln Gly Leu Leu Ser Leu Tyr Glu Ala Ser Tyr Leu Gly Phe Glu Gly
145                 150                 155                 160

gaa tcc ctg ctg gat gaa gcg cgc gcc ttc tca att acc cac ctg aaa      528
Glu Ser Leu Leu Asp Glu Ala Arg Ala Phe Ser Ile Thr His Leu Lys
                165                 170                 175

aac aat ctg aac aaa ggc atc aat acg aaa gtg gca cag caa gtt agc      576
Asn Asn Leu Asn Lys Gly Ile Asn Thr Lys Val Ala Gln Gln Val Ser
            180                 185                 190

cat gct ctg gaa ctg ccg tat cac cgt cgc ctg cat cgt ctg gaa gca      624
His Ala Leu Glu Leu Pro Tyr His Arg Arg Leu His Arg Leu Glu Ala
        195                 200                 205

cgc tgg ctg ctg gat aaa tac gaa ccg aaa gaa ccg cat cac cat ctg      672
Arg Trp Leu Leu Asp Lys Tyr Glu Pro Lys Glu Pro His His His Leu
    210                 215                 220

ctg cac gaa ctg gcg aaa ctg gac ttt aat ctg gtt cag tcg ctg tat      720
Leu His Glu Leu Ala Lys Leu Asp Phe Asn Leu Val Gln Ser Leu Tyr
225                 230                 235                 240

caa aaa gaa ctg cgt gaa ctg agc ctg tgg tgg cgc gaa att ggt ctg      768
Gln Lys Glu Leu Arg Glu Leu Ser Leu Trp Trp Arg Glu Ile Gly Leu
                245                 250                 255

acc tct aaa ctg gat ttt gtg cgt gac cgc ctg atg gaa gtt tac ttc      816
Thr Ser Lys Leu Asp Phe Val Arg Asp Arg Leu Met Glu Val Tyr Phe
            260                 265                 270

tgg gca ctg ggc atg gct ccg gat ccg cag ttt agc gaa tgc cgt aaa      864
Trp Ala Leu Gly Met Ala Pro Asp Pro Gln Phe Ser Glu Cys Arg Lys
        275                 280                 285

gtg gtt acc aaa atg ttc ggt ctg gtc acg att atc gat gac gtc tat      912
Val Val Thr Lys Met Phe Gly Leu Val Thr Ile Ile Asp Asp Val Tyr
    290                 295                 300

gat gtg tac ggc acc ctg gac gaa ctg caa ctg ttc acg gat gcg gtc      960
Asp Val Tyr Gly Thr Leu Asp Glu Leu Gln Leu Phe Thr Asp Ala Val
305                 310                 315                 320

gaa cgc tgg gac gtg aac gcc atc aat acc ctg ccg gat tat atg aaa     1008
Glu Arg Trp Asp Val Asn Ala Ile Asn Thr Leu Pro Asp Tyr Met Lys
                325                 330                 335

ctg tgt tat ctg gcg ctg tac aac acc gtt aat gac acg gcc tat agc     1056
Leu Cys Tyr Leu Ala Leu Tyr Asn Thr Val Asn Asp Thr Ala Tyr Ser
            340                 345                 350

atc ctg aaa gaa aaa ggt cat aac aac atc tcg tac ctg acc aaa agc     1104
Ile Leu Lys Glu Lys Gly His Asn Asn Ile Ser Tyr Leu Thr Lys Ser
        355                 360                 365

tgg tgc gaa ctg tgt aaa gcg ttt ctg cag gaa gcc aaa tgg tct aac     1152
Trp Cys Glu Leu Cys Lys Ala Phe Leu Gln Glu Ala Lys Trp Ser Asn
    370                 375                 380

aac aaa atc atc ccg gca ttc aac aaa tac ctg gat aat gct agt gtt     1200
Asn Lys Ile Ile Pro Ala Phe Asn Lys Tyr Leu Asp Asn Ala Ser Val
385                 390                 395                 400

agc tct agt ggc gtc gca ctg ctg gct ccg tcc tac ttt ctg gtg tgt     1248
Ser Ser Ser Gly Val Ala Leu Leu Ala Pro Ser Tyr Phe Leu Val Cys
                405                 410                 415
```

-continued

```
cag gaa caa gat att tct gac cag gcg ctg cac agt ctg acc aac ttt      1296
Gln Glu Gln Asp Ile Ser Asp Gln Ala Leu His Ser Leu Thr Asn Phe
            420                 425                 430

cat ggt ctg gtt cgt tcc tca tgc acc atc ttc cgc ctg tgt aat gat      1344
His Gly Leu Val Arg Ser Ser Cys Thr Ile Phe Arg Leu Cys Asn Asp
        435                 440                 445

ctg gcg acg tcg agc gcc gaa ctg gaa cgt ggc gaa acc acg aac tcg      1392
Leu Ala Thr Ser Ser Ala Glu Leu Glu Arg Gly Glu Thr Thr Asn Ser
    450                 455                 460

att acc agc tat atg cac gaa aat gaa acg agt gaa gaa cag gca tgc      1440
Ile Thr Ser Tyr Met His Glu Asn Glu Thr Ser Glu Glu Gln Ala Cys
465                 470                 475                 480

aaa gaa ctg cgt aac ctg atc gat gct gaa tgg aag aaa atg aac gaa      1488
Lys Glu Leu Arg Asn Leu Ile Asp Ala Glu Trp Lys Lys Met Asn Glu
                485                 490                 495

gaa cgc gtg tcc aat tca acc ctg ccg aaa gcc ttt cgt gaa att gca      1536
Glu Arg Val Ser Asn Ser Thr Leu Pro Lys Ala Phe Arg Glu Ile Ala
            500                 505                 510

atc aat atg gct cgc att tcc cat tgt acg tat cag tac ggc gat ggt      1584
Ile Asn Met Ala Arg Ile Ser His Cys Thr Tyr Gln Tyr Gly Asp Gly
        515                 520                 525

ctg ggc cgc ccg gac tac acg acc gaa aac cgt att aaa ctg ctg ctg      1632
Leu Gly Arg Pro Asp Tyr Thr Thr Glu Asn Arg Ile Lys Leu Leu Leu
    530                 535                 540

att gac ccg ttc ccg att aac taa                                      1656
Ile Asp Pro Phe Pro Ile Asn
545                 550


<210> SEQ ID NO 4
<211> LENGTH: 551
<212> TYPE: PRT
<213> ORGANISM: Artificial Sequence
<220> FEATURE:
<223> OTHER INFORMATION: Synthetic Construct

<400> SEQUENCE: 4

Met Ser Ala Val Ser Ser Gln Phe Ser Gln Ile Ala Glu Asp Asn Ser
1               5                   10                  15

Arg Arg Ser Ala Asn Tyr His Pro Asn Leu Trp Asp Phe Glu Phe Leu
            20                  25                  30

Gln Ser Leu Glu Asn Asp Ser Lys Met Glu Lys Leu Glu Glu Lys Ala
        35                  40                  45

Thr Lys Leu Glu Glu Glu Val Arg Asn Met Met Asn Glu Ala Lys Thr
    50                  55                  60

Glu Ala Leu Ser Leu Leu Glu Leu Ile Asp Asp Val Gln Arg Leu Gly
65                  70                  75                  80

Leu Thr Tyr Lys Phe Glu Lys Asp Ile Ile Lys Ala Leu Glu Lys Ile
                85                  90                  95

Val Pro Leu Asp Glu Ser Gly Leu His Val Thr Ser Leu Ser Phe Arg
            100                 105                 110

Ile Leu Arg Gln His Gly Phe Glu Val Ser Gln Asp Val Phe Lys Arg
        115                 120                 125

Phe Lys Asp Lys Glu Gly Gly Phe Cys Ala Glu Leu Lys Asp Asp Val
    130                 135                 140

Gln Gly Leu Leu Ser Leu Tyr Glu Ala Ser Tyr Leu Gly Phe Glu Gly
145                 150                 155                 160

Glu Ser Leu Leu Asp Glu Ala Arg Ala Phe Ser Ile Thr His Leu Lys
                165                 170                 175
```

```
Asn Asn Leu Asn Lys Gly Ile Asn Thr Lys Val Ala Gln Gln Val Ser
            180                 185                 190

His Ala Leu Glu Leu Pro Tyr His Arg Arg Leu His Arg Leu Glu Ala
        195                 200                 205

Arg Trp Leu Leu Asp Lys Tyr Glu Pro Lys Glu Pro His His His Leu
    210                 215                 220

Leu His Glu Leu Ala Lys Leu Asp Phe Asn Leu Val Gln Ser Leu Tyr
225                 230                 235                 240

Gln Lys Glu Leu Arg Glu Leu Ser Leu Trp Trp Arg Glu Ile Gly Leu
                245                 250                 255

Thr Ser Lys Leu Asp Phe Val Arg Asp Arg Leu Met Glu Val Tyr Phe
            260                 265                 270

Trp Ala Leu Gly Met Ala Pro Asp Pro Gln Phe Ser Glu Cys Arg Lys
        275                 280                 285

Val Val Thr Lys Met Phe Gly Leu Val Thr Ile Ile Asp Asp Val Tyr
    290                 295                 300

Asp Val Tyr Gly Thr Leu Asp Glu Leu Gln Leu Phe Thr Asp Ala Val
305                 310                 315                 320

Glu Arg Trp Asp Val Asn Ala Ile Asn Thr Leu Pro Asp Tyr Met Lys
                325                 330                 335

Leu Cys Tyr Leu Ala Leu Tyr Asn Thr Val Asn Asp Thr Ala Tyr Ser
            340                 345                 350

Ile Leu Lys Glu Lys Gly His Asn Asn Ile Ser Tyr Leu Thr Lys Ser
        355                 360                 365

Trp Cys Glu Leu Cys Lys Ala Phe Leu Gln Glu Ala Lys Trp Ser Asn
    370                 375                 380

Asn Lys Ile Ile Pro Ala Phe Asn Lys Tyr Leu Asp Asn Ala Ser Val
385                 390                 395                 400

Ser Ser Ser Gly Val Ala Leu Leu Ala Pro Ser Tyr Phe Leu Val Cys
                405                 410                 415

Gln Glu Gln Asp Ile Ser Asp Gln Ala Leu His Ser Leu Thr Asn Phe
            420                 425                 430

His Gly Leu Val Arg Ser Ser Cys Thr Ile Phe Arg Leu Cys Asn Asp
        435                 440                 445

Leu Ala Thr Ser Ser Ala Glu Leu Glu Arg Gly Glu Thr Thr Asn Ser
    450                 455                 460

Ile Thr Ser Tyr Met His Glu Asn Glu Thr Ser Glu Glu Gln Ala Cys
465                 470                 475                 480

Lys Glu Leu Arg Asn Leu Ile Asp Ala Glu Trp Lys Lys Met Asn Glu
                485                 490                 495

Glu Arg Val Ser Asn Ser Thr Leu Pro Lys Ala Phe Arg Glu Ile Ala
            500                 505                 510

Ile Asn Met Ala Arg Ile Ser His Cys Thr Tyr Gln Tyr Gly Asp Gly
        515                 520                 525

Leu Gly Arg Pro Asp Tyr Thr Thr Glu Asn Arg Ile Lys Leu Leu Leu
    530                 535                 540

Ile Asp Pro Phe Pro Ile Asn
545                 550
```

<210> SEQ ID NO 5
<211> LENGTH: 24
<212> TYPE: DNA
<213> ORGANISM: Artificial Sequence
<220> FEATURE:
<223> OTHER INFORMATION: pCold-TF PCR Primer 1

<400> SEQUENCE: 5
cctaccttcg ataccaccac tacc 24

<210> SEQ ID NO 6
<211> LENGTH: 30
<212> TYPE: DNA
<213> ORGANISM: Artificial Sequence
<220> FEATURE:
<223> OTHER INFORMATION: pCold-TF PCR Primer 2

<400> SEQUENCE: 6
taggtaatct ctgcttaaaa gcacagaatc 30

<210> SEQ ID NO 7
<211> LENGTH: 44
<212> TYPE: DNA
<213> ORGANISM: Artificial Sequence
<220> FEATURE:
<223> OTHER INFORMATION: IspSM PCR Primer 1

<400> SEQUENCE: 7
ggtagtggtg gtatcgaagg taggatgtcc gccgtttcaa gcca 44

<210> SEQ ID NO 8
<211> LENGTH: 53
<212> TYPE: DNA
<213> ORGANISM: Artificial Sequence
<220> FEATURE:
<223> OTHER INFORMATION: IspSM PCR Primer 2

<400> SEQUENCE: 8
gattctgtgc ttttaagcag agattaccta ttagttaatc gggaacgggt caa 53

<210> SEQ ID NO 9
<211> LENGTH: 7365
<212> TYPE: DNA
<213> ORGANISM: Artificial Sequence
<220> FEATURE:
<223> OTHER INFORMATION: pCold-TF vector carrying ispSM gene
(pCold-TF-IspSM)

<400> SEQUENCE: 9
aaggaatggt gtggccgatt aatcataaat atgaaaaata attgttgcat cacccgccaa 60
tgcgtggctt aatgcacatc aaattgtgag cggataacaa tttgatgtgc tagcgcatat 120
ccagtgtagt aaggcaagtc ccttcaagag ttatcgttga taccccctcgt agtgcacatt 180 cctttaacgc ttcaaaatct gtaaagcacg ccatatcgcc gaaaggcaca cttaattatt 240
aagaggtaat acaccatgaa tcacaaagtg catcatcatc atcatcacat gcaagtttca 300
gttgaaacca ctcaaggcct tggccgccgt gtaacgatta ctatcgctgc tgacagcatc 360
gagaccgctg ttaaaagcga gctggtcaac gttgcgaaaa aagtacgtat tgacggcttc 420
cgcaagggca aagtgccaat gaatatcgtt gctcagcgtt atggcgcgtc tgtacgccag 480
gacgttctgg gtgacctgat gagccgtaac ttcattgacg ccatcattaa agaaaaaatc 540
aatccggctg gcgcaccgac ttatgttccg ggcgaataca agctgggtga agacttcact 600
tactctgtag agtttgaagt ttatccggaa gttgaactgc aaggtctgga agcgatcgaa 660
gttgaaaaac cgatcgttga agtgaccgac gctgacgttg acggcatgct ggatactctg 720
cgtaaacagc aggcgacctg gaaagaaaaa gacggcgctg ttgaagcaga agaccgcgtg 780
accatcgact tcaccggttc tgtagacggc gaagagttcg aaggcggtaa agcgtctgat 840

```
ttcgtactgg cgatgggcca gggtcgtatg atcccgggct ttgaagacgg tatcaaaggc    900
cacaaagctg gcgaagagtt caccatcgac gtgaccttcc cggaagaata ccacgcagaa    960
aacctgaaag gtaaagcagc gaaattcgct atcaacctga agaaagttga agagcgtgaa   1020
ctgccggaac tgaccgcaga gttcatcaaa cgtttcggcg ttgaagatgg ttccgtagaa   1080
ggtctgcgcg ctgaagtgcg taaaaacatg gagcgcgagc tgaagagcgc catccgtaac   1140
cgcgttaagt ctcaggcgat cgaaggtctg gtaaaagcta acgacatcga cgtaccggct   1200
gcgctgatcg acagcgaaat cgacgttctg cgtcgccagg ctgcacagcg tttcggtggc   1260
aacgaaaaac aagctctgga actgccgcgc gaactgttcg aagaacaggc taaacgccgc   1320
gtagttgttg gcctgctgct gggcgaagtt atccgcacca acgagctgaa agctgacgaa   1380
gagcgcgtga aaggcctgat cgaagagatg gcttctgcgt acgaagatcc gaaagaagtt   1440
atcgagttct acagcaaaaa caaagaactg atggacaaca tgcgcaatgt tgctctggaa   1500
gaacaggctg ttgaagctgt actggcgaaa gcgaaagtga ctgaaaaaga aaccactttc   1560
aacgagctga tgaaccagca ggcgtccgcg ggtctggaag ttctgttcca ggggccctcc   1620
gcgggtctgg tgccacgcgg tagtggtggt atcgaaggta ggatgtccgc cgtttcaagc   1680
cagttctctc aaatcgccga agacaatagc cgtcgctcag caaattatca tccgaatctg   1740
tgggactttg aatttctgca gtctctggaa aacgatagta aaatggaaaa actggaagaa   1800
aaagccacca aactggaaga agaagtgcgt aacatgatga atgaagcgaa aacggaagcc   1860
ctgagcctgc tggaactgat tgatgacgtc caacgcctgg gtctgaccta caaattcgaa   1920
aaagatatca tcaaagcact ggaaaaaatt gtcccgctgg acgaatcagg tctgcacgtg   1980
acgtctctga gttttcgtat cctgcgccag catggcttcg aagtttcgca agatgtcttt   2040
aaacgtttca aagacaaaga aggcggtttc tgcgcggaac tgaaagatga cgtgcagggt   2100
ctgctgtccc tgtatgaagc ctcatacctg ggttttgaag gcgaatccct gctggatgaa   2160
gcgcgcgcct tctcaattac ccacctgaaa aacaatctga acaaaggcat caatacgaaa   2220
gtggcacagc aagttagcca tgctctggaa ctgccgtatc accgtcgcct gcatcgtctg   2280
gaagcacgct ggctgctgga taaatacgaa ccgaaagaac cgcatcacca tctgctgcac   2340
gaactggcga aactggactt taatctggtt cagtcgctgt atcaaaaaga actgcgtgaa   2400
ctgagcctgt ggtggcgcga aattggtctg acctctaaac tggattttgt gcgtgaccgc   2460
ctgatggaag tttacttctg ggcactgggc atggctccgg atccgcagtt tagcgaatgc   2520
cgtaaagtgg ttaccaaaat gttcggtctg gtcacgatta tcgatgacgt ctatgatgtg   2580
tacggcaccc tggacgaact gcaactgttc acggatgcgg tcgaacgctg ggacgtgaac   2640
gccatcaata ccctgccgga ttatatgaaa ctgtgttatc tggcgctgta caacaccgtt   2700
aatgacacgg cctatagcat cctgaaagaa aaaggtcata acaacatctc gtacctgacc   2760
aaaagctggt gcgaactgtg taaagcgttt ctgcaggaag ccaaatggtc taacaacaaa   2820
atcatcccgg cattcaacaa atacctggat aatgctagtg ttagctctag tggcgtcgca   2880
ctgctggctc cgtcctactt tctggtgtgt caggaacaag atatttctga ccaggcgctg   2940
cacagtctga ccaactttca tggtctggtt cgttcctcat gcaccatctt ccgcctgtgt   3000
aatgatctgg cgacgtcgag cgccgaactg gaacgtggcg aaaccacgaa ctcgattacc   3060
agctatatgc acgaaaatga aacgagtgaa gaacaggcat gcaaagaact gcgtaacctg   3120
atcgatgctg aatggaagaa aatgaacgaa gaacgcgtgt ccaattcaac cctgccgaaa   3180
```

-continued

```
gcctttcgtg aaattgcaat caatatggct cgcatttccc attgtacgta tcagtacggc   3240
gatggtctgg gccgcccgga ctacacgacc gaaaaccgta ttaaactgct gctgattgac   3300
ccgttcccga ttaactaata ggtaatctct gcttaaaagc acagaatcta agatccctgc   3360
catttggcgg ggattttttt atttgttttc aggaaataaa taatcgatcg cgtaataaaa   3420
tctattatta tttttgtgaa gaataaattt gggtgcaatg agaatgcgca ggccctttcg   3480
tctcgcgcgt ttcggtgatg acggtgaaaa cctctgacac atgcagctcc cggagacggt   3540
cacagcttgt ctgtaagcgg atgccgggag cagacaagcc cgtcagggcg cgtcagcggg   3600
tgttggcggg tgtcggggct ggcttaacta tgcggcatca gagcagattg tactgagagt   3660
gcaccataaa attgtaaacg ttaatatttt gttaaaattc gcgttaaatt tttgttaaat   3720
cagctcattt tttaaccaat aggccgaaat cggcaaaatc ccttataaat caaaagaata   3780
gcccgagata gggttgagtg ttgttccagt ttggaacaag agtccactat taaagaacgt   3840
ggactccaac gtcaaagggc gaaaaaccgt ctatcagggc gatggcccac tacgtgaacc   3900
atcacccaaa tcaagttttt tggggtcgag gtgccgtaaa gcactaaatc ggaaccctaa   3960
agggagcccc cgatttagag cttgacgggg aaagccggcg aacgtggcga gaaaggaagg   4020
gaagaaagcg aaaggagcgg gcgctagggc gctggcaagt gtagcggtca cgctgcgcgt   4080
aaccaccaca cccgccgcgc ttaatgcgcc gctacagggc gcgtactatg gttgctttga   4140
cgtatgcggt gtgaaatacc gcacagatgc gtaaggagaa aataccgcat caggcgtcag   4200
gtggcacttt tcggggaaat gtgcgcggaa cccctatttg tttatttttc taaatacatt   4260
caaatatgta tccgctcatg agacaataac cctgataaat gcttcaataa tattgaaaaa   4320
ggaagagtat gagtattcaa catttccgtg tcgcccttat tccctttttt gcggcatttt   4380
gccttcctgt ttttgctcac ccagaaacgc tggtgaaagt aaaagatgct gaagatcagt   4440
tgggtgcacg agtgggttac atcgaactgg atctcaacag cggtaagatc cttgagagtt   4500
ttcgccccga agaacgtttt ccaatgatga gcacttttaa agttctgcta tgtggcgcgg   4560
tattatcccg tattgacgcc gggcaagagc aactcggtcg ccgcatacac tattctcaga   4620
atgacttggt tgagtactca ccagtcacag aaaagcatct tacggatggc atgacagtaa   4680
gagaattatg cagtgctgcc ataaccatga gtgataacac tgcggccaac ttacttctga   4740
caacgatcgg aggaccgaag gagctaaccg cttttttgca caacatgggg gatcatgtaa   4800
ctcgccttga tcgttgggaa ccggagctga atgaagccat accaaacgac gagcgtgaca   4860
ccacgatgcc tgtagcaatg gcaacaacgt tgcgcaaact attaactggc gaactactta   4920
ctctagcttc ccggcaacaa ttaatagact ggatggaggc ggataaagtt gcaggaccac   4980
ttctgcgctc ggcccttccg gctggctggt ttattgctga taaatctgga gccggtgagc   5040
gtgggtctcg cggtatcatt gcagcactgg ggccagatgg taagccctcc cgtatcgtag   5100
ttatctacac gacggggagt caggcaacta tggatgaacg aaatagacag atcgctgaga   5160
taggtgcctc actgattaag cattggtaac tgtcagacca agtttactca tatatacttt   5220
agattgattt aaaacttcat ttttaattta aaaggatcta ggtgaagatc ctttttgata   5280
atctcatgac caaaatccct taacgtgagt tttcgttcca ctgagcgtca gaccccgtag   5340
aaaagatcaa aggatcttct tgagatcctt tttttctgcg cgtaatctgc tgcttgcaaa   5400
caaaaaaacc accgctacca gcggtggttt gtttgccgga tcaagagcta ccaactcttt   5460
ttccgaaggt aactggcttc agcagagcgc agataccaaa tactgttctt ctagtgtagc   5520
cgtagttagg ccaccacttc aagaactctg tagcaccgcc tacatacctc gctctgctaa   5580
```

```
tcctgttacc agtggctgct gccagtggcg ataagtcgtg tcttaccggg ttggactcaa   5640

gacgatagtt accggataag gcgcagcggt cgggctgaac ggggggttcg tgcacacagc   5700

ccagcttgga gcgaacgacc tacaccgaac tgagatacct acagcgtgag ctatgagaaa   5760

gcgccacgct tcccgaaggg agaaaggcgg acaggtatcc ggtaagcggc agggtcggaa   5820

caggagagcg cacgagggag cttccagggg gaaacgcctg gtatctttat agtcctgtcg   5880

ggtttcgcca cctctgactt gagcgtcgat ttttgtgatg ctcgtcaggg gggcggagcc   5940

tatggaaaaa cgccagcaac gcggcctttt tacggttcct ggccttttgc tggccttttg   6000

ctcacatagt catgccccgc gcccaccgga aggagctgac tgggttgaag gctctcaagg   6060

gcatcggtcg agatcccggt gcctaatgag tgagctaact tacattaatt gcgttgcgct   6120

cactgcccgc tttccagtcg ggaaacctgt cgtgccagct gcattaatga atcggccaac   6180

gcgcggggag aggcggtttg cgtattgggc gccagggtgg tttttctttt caccagtgag   6240

acgggcaaca gctgattgcc cttcaccgcc tggccctgag agagttgcag caagcggtcc   6300

acgctggttt gccccagcag gcgaaaatcc tgtttgatgg tggttaacgg cgggatataa   6360

catgagctgt cttcggtatc gtcgtatccc actaccgaga tatccgcacc aacgcgcagc   6420

ccggactcgg taatggcgcg cattgcgccc agcgccatct gatcgttggc aaccagcatc   6480

gcagtgggaa cgatgccctc attcagcatt tgcatggttt gttgaaaacc ggacatggca   6540

ctccagtcgc cttcccgttc cgctatcggc tgaatttgat tgcgagtgag atatttatgc   6600

cagccagcca gacgcagacg cgccgagaca gaacttaatg ggcccgctaa cagcgcgatt   6660

tgctggtgac ccaatgcgac cagatgctcc acgcccagtc gcgtaccgtc ttcatgggag   6720

aaaataatac tgttgatggg tgtctggtca gagacatcaa gaaataacgc cggaacatta   6780

gtgcaggcag cttccacagc aatggcatcc tggtcatcca gcggatagtt aatgatcagc   6840

ccactgacgc gttgcgcgag aagattgtgc accgccgctt tacaggcttc gacgccgctt   6900

cgttctacca tcgacaccac cacgctggca cccagttgat cggcgcgaga tttaatcgcc   6960

gcgacaattt gcgacggcgc gtgcagggcc agactggagg tggcaacgcc aatcagcaac   7020

gactgtttgc ccgccagttg ttgtgccacg cggttgggaa tgtaattcag ctccgccatc   7080

gccgcttcca ctttttcccg cgttttcgca gaaacgtggc tggcctggtt caccacgcgg   7140

gaaacggtct gataagagac accggcatac tctgcgacat cgtataacgt tactggtttc   7200

acattcacca ccctgaattg actctcttcc gggcgctatc atgccatacc gcgaaaggtt   7260

ttgcgccatt cgatggtgtc cgggatctcg acgctctccc ttatgcgact cctgcattag   7320

gaagcagccc agtagtaggt tgaggccgtt gagcaccgcc gccgc                  7365
```

<210> SEQ ID NO 10
<211> LENGTH: 608
<212> TYPE: PRT
<213> ORGANISM: Pueraria lobata

<400> SEQUENCE: 10

```
Met Ala Thr Asn Leu Leu Cys Leu Ser Asn Lys Leu Ser Ser Pro Thr
1               5                   10                  15

Pro Thr Pro Ser Thr Arg Phe Pro Gln Ser Lys Asn Phe Ile Thr Gln
            20                  25                  30

Lys Thr Ser Leu Ala Asn Pro Lys Pro Trp Arg Val Ile Cys Ala Thr
        35                  40                  45

Ser Ser Gln Phe Thr Gln Ile Thr Glu His Asn Ser Arg Arg Ser Ala
```

```
    50                  55                  60

Asn Tyr Gln Pro Asn Leu Trp Asn Phe Glu Phe Leu Gln Ser Leu Glu
65                  70                  75                  80

Asn Asp Leu Lys Val Glu Lys Leu Glu Glu Lys Ala Thr Lys Leu Glu
                85                  90                  95

Glu Glu Val Arg Cys Met Ile Asn Arg Val Asp Thr Gln Pro Leu Ser
            100                 105                 110

Leu Leu Glu Leu Ile Asp Asp Val Gln Arg Leu Gly Leu Thr Tyr Lys
        115                 120                 125

Phe Glu Lys Asp Ile Ile Lys Ala Leu Glu Asn Ile Val Leu Leu Asp
    130                 135                 140

Glu Asn Lys Lys Asn Lys Ser Asp Leu His Ala Thr Ala Leu Ser Phe
145                 150                 155                 160

Arg Leu Leu Arg Gln His Gly Phe Glu Val Ser Gln Asp Val Phe Glu
                165                 170                 175

Arg Phe Lys Asp Lys Glu Gly Gly Phe Ser Gly Glu Leu Lys Gly Asp
            180                 185                 190

Val Gln Gly Leu Leu Ser Leu Tyr Glu Ala Ser Tyr Leu Gly Phe Glu
        195                 200                 205

Gly Glu Asn Leu Leu Glu Glu Ala Arg Thr Phe Ser Ile Thr His Leu
    210                 215                 220

Lys Asn Asn Leu Lys Glu Gly Ile Asn Thr Lys Val Ala Glu Gln Val
225                 230                 235                 240

Ser His Ala Leu Glu Leu Pro Tyr His Gln Arg Leu His Arg Leu Glu
                245                 250                 255

Ala Arg Trp Phe Leu Asp Lys Tyr Glu Pro Lys Glu Pro His His Gln
            260                 265                 270

Leu Leu Leu Glu Leu Ala Lys Leu Asp Phe Asn Met Val Gln Thr Leu
        275                 280                 285

His Gln Lys Glu Leu Gln Asp Leu Ser Arg Trp Trp Thr Glu Met Gly
    290                 295                 300

Leu Ala Ser Lys Leu Asp Phe Val Arg Asp Arg Leu Met Glu Val Tyr
305                 310                 315                 320

Phe Trp Ala Leu Gly Met Ala Pro Asp Pro Gln Phe Gly Glu Cys Arg
                325                 330                 335

Lys Ala Val Thr Lys Met Phe Gly Leu Val Thr Ile Ile Asp Asp Val
            340                 345                 350

Tyr Asp Val Tyr Gly Thr Leu Asp Glu Leu Gln Leu Phe Thr Asp Ala
        355                 360                 365

Val Glu Arg Trp Asp Val Asn Ala Ile Asn Thr Leu Pro Asp Tyr Met
    370                 375                 380

Lys Leu Cys Phe Leu Ala Leu Tyr Asn Thr Val Asn Asp Thr Ser Tyr
385                 390                 395                 400

Ser Ile Leu Lys Glu Lys Gly His Asn Asn Leu Ser Tyr Leu Thr Lys
                405                 410                 415

Ser Trp Arg Glu Leu Cys Lys Ala Phe Leu Gln Glu Ala Lys Trp Ser
            420                 425                 430

Asn Asn Lys Ile Ile Pro Ala Phe Ser Lys Tyr Leu Glu Asn Ala Ser
        435                 440                 445

Val Ser Ser Ser Gly Val Ala Leu Leu Ala Pro Ser Tyr Phe Ser Val
    450                 455                 460

Cys Gln Gln Gln Glu Asp Ile Ser Asp His Ala Leu Arg Ser Leu Thr
465                 470                 475                 480
```

-continued

Asp Phe His Gly Leu Val Arg Ser Ser Cys Val Ile Phe Arg Leu Cys
485 490 495

Asn Asp Leu Ala Thr Ser Ala Ala Glu Leu Glu Arg Gly Glu Thr Thr
500 505 510

Asn Ser Ile Ile Ser Tyr Met His Glu Asn Asp Gly Thr Ser Glu Glu
515 520 525

Gln Ala Arg Glu Glu Leu Arg Lys Leu Ile Asp Ala Glu Trp Lys Lys
530 535 540

Met Asn Arg Glu Arg Val Ser Asp Ser Thr Leu Leu Pro Lys Ala Phe
545 550 555 560

Met Glu Ile Ala Val Asn Met Ala Arg Val Ser His Cys Thr Tyr Gln
565 570 575

Tyr Gly Asp Gly Leu Gly Arg Pro Asp Tyr Ala Thr Glu Asn Arg Ile
580 585 590

Lys Leu Leu Leu Ile Asp Pro Phe Pro Ile Asn Gln Leu Met Tyr Val
595 600 605

<210> SEQ ID NO 11
<211> LENGTH: 1827
<212> TYPE: DNA
<213> ORGANISM: Pueraria lobata

<400> SEQUENCE: 11
atggcaacca accttttatg cttgtctaat aaattatcgt cccccacacc aacaccaagt 60
actagatttc cacaaagtaa gaacttcatc acacaaaaaa catctcttgc caatcccaaa 120
ccttggcgag ttatttgtgc tacgagctct caatttaccc aaataacaga acataatagt 180
cggcgttcag ctaattacca gccaaacctc tggaattttg aatttctgca gtctctggaa 240
aatgacctta aggtggaaaa actagaagag aaggcaacaa agctagagga ggaggtacga 300
tgcatgatca acagagtaga cacacaacca ttaagcttac tagaattgat cgacgatgtc 360
cagcgtctag gattgaccta caagtttgag aaggacataa tcaaagccct tgagaatatt 420
gttttgctgg atgagaataa gaaaaataaa agtgacctcc atgctactgc tctcagcttc 480
cgtttactta gacaacatgg ctttgaggtt tcccaagatg tgtttgagag atttaaggac 540
aaggagggag gtttcagtgg tgaacttaaa ggtgatgtgc aagggttgct gagtctatat 600
gaagcatcct atcttggctt tgagggagaa aatctcttgg aggaggcaag gacattttca 660
ataacacatc tcaagaacaa cctaaaagaa ggaataaaca ccaaagtggc agaacaagtt 720
agtcatgcac tggaacttcc ctatcatcaa agattgcata gactagaagc acgatggttc 780
cttgacaaat atgaaccaaa ggaaccccac catcagttac tactcgagct tgcaaagcta 840
gatttcaata tggtgcaaac attgcaccag aaagaactgc aagacctgtc aaggtggtgg 900
acggagatgg ggctagcaag caagctagac tttgtccgag acagattaat ggaagtgtat 960
ttttgggcgt tgggaatggc acctgatcct caattcggtg aatgtcgtaa agctgtcact 1020
aaaatgtttg gattggtcac catcatcgat gatgtatatg acgtttatgg tactttggat 1080
gagctacaac tcttcactga tgctgttgag agatgggacg tgaatgccat aaacacactt 1140
ccagactaca tgaagttgtg cttcctagca ctttataaca ccgtcaatga cacgtcttat 1200
agcatcctta aagaaaaagg acacaacaac ctttcctatt tgacaaaatc ttggcgtgag 1260
ttatgcaaag cattccttca agaagcaaaa tggtcgaaca acaaaatcat tccagcattt 1320
agcaagtacc tggaaaatgc atcggtgtcc tcctccggtg tggctttgct tgctccttcc 1380

-continued

```
tacttctcag tgtgccaaca acaagaagat atctcagacc atgctcttcg ttctttaact   1440

gatttccatg gccttgtgcg ctcctcatgc gtcattttca gactctgcaa tgatttggct   1500

acctcagcgg ctgagctaga gaggggtgag acgacaaatt caataatatc ttatatgcat   1560

gagaatgacg gcacttctga agagcaagca cgtgaggagt tgagaaaatt gatcgatgca   1620

gagtggaaga agatgaaccg agagcgagtt tcagattcta cactactccc aaaagctttt   1680

atggaaatag ctgttaacat ggctcgagtt tcgcattgca cataccaata tggagacgga   1740

cttggaaggc cagactacgc cacagagaat agaatcaagt tgctacttat agaccccttt   1800

ccaatcaatc aactaatgta cgtgtaa                                        1827
```

<210> SEQ ID NO 12
<211> LENGTH: 1695
<212> TYPE: DNA
<213> ORGANISM: Artificial Sequence
<220> FEATURE:
<223> OTHER INFORMATION: Polynucleotide having modified codons, which encodes isoprene synthase derived from Pueraria lobata (IspSK gene)

<400> SEQUENCE: 12

```
atgtgtgcga cctcttctca atttactcag attaccgagc ataattcccg tcgttccgca     60

aactatcagc caaacctgtg gaatttcgaa ttcctgcaat ccctggagaa cgacctgaaa    120

gtggaaaagc tggaggagaa agcgaccaaa ctggaggaag aagttcgctg catgatcaac    180

cgtgtagaca cccagccgct gtccctgctg gagctgatcg acgatgtgca gcgcctgggt    240

ctgacctaca aatttgaaaa agacatcatt aaagccctgg aaaacatcgt actgctggac    300

gaaaacaaaa agaacaaatc tgacctgcac gcaaccgctc tgtctttccg tctgctgcgt    360

cagcacggtt tcgaggtttc tcaggatgtt tttgagcgtt tcaaggataa agaaggtggt    420

ttcagcggtg aactgaaagg tgacgtccaa ggcctgctga gcctgtatga agcgtcttac    480

ctgggtttcg agggtgagaa cctgctggag gaggcgcgta ccttttccat cacccacctg    540

aagaacaacc tgaaagaagg cattaatacc aaggttgcag aacaagtgag ccacgccctg    600

gaactgccat atcaccagcg tctgcaccgt ctggaggcac gttggttcct ggataaatac    660

gaaccgaaag aaccgcatca ccagctgctg ctggagctgg cgaagctgga ttttaacatg    720

gtacagaccc tgcaccagaa agagctgcaa gatctgtccc gctggtggac cgagatgggc    780

ctggctagca aactggattt tgtacgcgac cgcctgatgg aagtttattt ctgggcactg    840

ggtatggcgc cagacccgca gtttggtgaa tgtcgcaaag ctgttactaa aatgtttggt    900

ctggtgacga tcatcgatga cgtgtatgac gtttatggca ctctggacga actgcaactg    960

ttcaccgatg ctgtagagcg ctgggacgtt aacgctatta acaccctgcc ggactatatg   1020

aaactgtgtt tcctggcact gtacaacacc gttaacgaca cgtcctattc tattctgaaa   1080

gagaaaggtc ataacaacct gtcctatctg acgaaaagct ggcgtgaact gtgcaaagcc   1140

tttctgcaag aggcgaaatg gtccaacaac aaaattatcc cggctttctc caagtacctg   1200

gaaaacgcca gcgtttcctc ctccggtgta gcgctgctgg cgccgtctta cttttccgta   1260

tgccagcagc aggaagacat ctccgaccac gcgctgcgtt ccctgaccga cttccatggt   1320

ctggtgcgtt ctagctgcgt tatcttccgc ctgtgcaacg atctggccac ctctgcggcg   1380

gagctggaac gtggcgagac taccaattct atcattagct acatgcacga aaacgatggt   1440

accagcgagg aacaggcccg cgaagaactg cgtaaactga tcgacgccga atggaaaaag   1500

atgaatcgtg aacgcgttag cgactccacc ctgctgccta aagcgttcat ggaaatcgca   1560
```

```
gttaacatgg cacgtgtttc ccactgcacc taccagtatg gcgatggtct gggtcgccca   1620

gactacgcga ctgaaaaccg catcaaactg ctgctgattg accctttccc gattaaccag   1680

ctgatgtatg tctaa                                                    1695


<210> SEQ ID NO 13
<211> LENGTH: 595
<212> TYPE: PRT
<213> ORGANISM: Populus nigra var. italic

<400> SEQUENCE: 13

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Phe Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Arg Ala Leu Asp Arg Phe Val Ser Ser Gly Gly Phe Asp Gly Val Thr
    130                 135                 140

Lys Thr Ser Leu His Ala Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Thr Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Arg Val Phe Ala Ile Ser His Leu Lys Glu Leu Ser Glu
    210                 215                 220

Glu Lys Ile Gly Lys Glu Leu Ala Glu Gln Val Asn His Ala Leu Glu
225                 230                 235                 240

Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Lys Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
```

```
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Ile Phe Ala Tyr Phe Ala Val Val Gln Asn Ile Lys
    450                 455                 460

Lys Glu Glu Ile Glu Asn Leu Gln Lys Tyr His Asp Ile Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Glu Leu Ala Thr Glu Ser Val Met Asn Leu
        515                 520                 525

Ile Asp Glu Thr Cys Lys Lys Met Asn Lys Glu Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595


<210> SEQ ID NO 14
<211> LENGTH: 1788
<212> TYPE: DNA
<213> ORGANISM: Populus nigra var. italic

<400> SEQUENCE: 14

atggcaactg aattattgtg cttgcaccgt ccaatctcac tgacacacaa actgttcaga      60

aatcccttac ctaaagtcat ccaggccact cccttaactt tgaaactcag atgttctgta     120

agcacagaaa acgtcagctt cacagaaaca gaaacagaag ccagacggtc tgccaattat     180

gaaccaaata gctgggatta tgattttttg ctgtcttcag acactgacga atcgattgaa     240

gtatacaaag acaaggccaa aaagctggag gctgaggtga gaagagagat taacaatgaa     300

aaggcagagt tttgactctg cttgaactg atagataatg tccaaaggtt aggattgggt      360

taccggttcg agagtgacat aaggagagcc ctcgacagat ttgtttcttc aggaggattt     420

gatggtgtta caaaaactag ccttcatgct actgctctta gcttcaggct tctcagacag     480

catggctttg aggtctctca agaagcgttc agtggattca aggatcaaaa tggcaatttc     540

ttggaaaacc ttaaggagga caccaaggca atactaagcc tatatgaagc ttcatttctt     600

gcattagaag gagaaaatat cttggatgag gccagggtgt ttgcaatatc acatctaaaa     660
```

gagctcagcg aagaaaagat tggaaaagag ctggccgaac aggtgaatca tgcattggag 720
cttccattgc atcgcaggac gcaaagacta gaagctgttt ggagtattga agcataccgt 780
aaaaaggaag atgcaaatca agtactgcta gaacttgcta tattggacta caacatgatt 840
caatcagtat accaaagaga tcttcgcgag acatcaaggt ggtggaggcg agtgggtctt 900
gcaacaaagt tgcattttgc taaagacagg ttaattgaaa gcttttactg ggcagttgga 960
gttgcgttcg aacctcaata cagtgattgc cgtaattcag tagcaaaaat gttttcattt 1020
gtaacaatca ttgatgatat ctatgatgtt tatggtactc tggatgagct ggagctattt 1080
acagatgctg ttgagagatg ggatgttaac gccatcaatg atcttccgga ttatatgaag 1140
ctctgcttcc tagctctcta caacactatc aatgagatag cttatgacaa tctgaaggac 1200
aagggggaaa acattcttcc atacctaaca aaagcgtggg cagatttatg caatgcattc 1260
ctacaagaag caaaatggct gtacaataag tccacaccaa catttgatga ctatttcgga 1320
aatgcatgga aatcatcctc agggcctctt caactaattt ttgcctactt tgccgtggtt 1380
caaaacatca agaaagagga aattgaaaac ttacaaaagt atcatgatat catcagtagg 1440
ccttcccaca tctttcgtct ttgcaacgac ctggcttcag catcggctga gatagcgaga 1500
ggtgaaactg cgaattccgt atcctgctac atgcgtacaa aaggcatttc tgaggaactt 1560
gctactgaat ccgtaatgaa tttgatcgac gaaacctgta aaaagatgaa caaagaaaag 1620
cttggtggct ctttgtttgc aaaacctttt gtcgaaacag ctattaacct tgcacggcaa 1680
tcccattgca cttatcataa cggagatgcg catacttcac cagacgagct aactaggaaa 1740
cgtgtcctgt cagtaatcac agagcctatt ctaccctttg agagataa 1788

<210> SEQ ID NO 15
<211> LENGTH: 1680
<212> TYPE: DNA
<213> ORGANISM: Artificial Sequence
<220> FEATURE:
<223> OTHER INFORMATION: Polynucleotide having modified codons, which
encodes isoprene synthase derived from Populus nigra var. italic
(IspSP gene)

<400> SEQUENCE: 15
atgtgctctg tttctaccga gaacgtttcc ttcactgaga cggaaaccga ggcacgtcgt 60
agcgcgaact acgagccgaa tagctgggac tacgatttcc tgctgtcttc cgatactgac 120
gaatctattg aggtgtacaa agacaaagca aagaaactgg aggctgaagt gcgccgcgaa 180
attaacaacg agaaagctga attcctgact ctgctggagc tgatcgataa cgtacagcgc 240
ctgggtctgg gttaccgctt cgaatctgat atccgtcgcg cactggatcg tttcgtaagc 300
agcggcggtt tcgatggcgt gaccaaaacg agcctgcacg ctaccgcgct gtccttccgt 360
ctgctgcgtc agcacggctt cgaagtttct caggaagcat tctccggttt caaagatcaa 420
aacggtaact tcctggaaaa cctgaaagaa gacactaagg cgatcctgag cctgtatgag 480
gcaagctttc tggccctgga gggtgagaac atcctggatg aggcgcgcgt attcgccatc 540
tcccatctga aagagctgtc tgaagagaaa atcggtaagg aactggcaga gcaggttaat 600
cacgcactgg aactgccgct gcatcgtcgt acccagcgtc tggaggcggt ttggtccatc 660
gaagcgtacc gcaaaaagga ggatgctaac caggttctgc tggaactggc catcctggac 720
tacaacatga tccagtccgt ttaccagcgt gatctgcgtg aaacctcccg ttggtggcgc 780
cgtgtgggcc tggcgaccaa actgcacttc gctaaggacc gcctgattga gtctttttac 840

```
tgggcagtcg gcgttgcgtt cgaacctcag tattctgact gccgtaacag cgttgcgaaa    900

atgttcagct tcgttactat tatcgacgac atctacgacg tttacggtac tctggacgag    960

ctggaactgt ttaccgacgc tgtcgaacgt tgggatgtta acgccatcaa cgatctgcct   1020

gactacatga aactgtgctt cctggcactg tataacacga tcaacgaaat tgcatacgac   1080

aacctgaaag acaaaggtga aaacatcctg ccgtacctga ctaaagcgtg ggcggatctg   1140

tgtaacgctt ttctgcaaga agcgaaatgg ctgtataaca aatccactcc gacctttgac   1200

gattatttcg gcaatgcctg gaaatccagc tctggcccgc tgcaactgat cttcgcttat   1260

tttgcggttg tccaaaacat caaaaaggag gaaattgaaa acctgcaaaa ataccacgat   1320

atcattagcc gtccttctca tatctttcgc ctgtgcaacg acctggcaag cgcgtccgca   1380

gagatcgcac gtggcgaaac cgctaactct gtttcctgct acatgcgcac caagggcatt   1440

tccgaagagc tggcaaccga gagcgtaatg aatctgatcg acgaaacctg taagaaaatg   1500

aacaaagaaa aactgggtgg ctccctgttc gctaaaccgt tcgtagagac tgctattaac   1560

ctggcacgtc agagccactg cacctaccac aatggtgacg cacatactag cccggatgaa   1620

ctgactcgta aacgtgtact gtctgttatc accgaaccga ttctgccgtt cgaacgttaa   1680


<210> SEQ ID NO 16
<211> LENGTH: 1785
<212> TYPE: DNA
<213> ORGANISM: Artificial Sequence
<220> FEATURE:
<223> OTHER INFORMATION: Polynucleotide which encodes isoprene synthase
      derived from Mucuna bracteata and which is fused with
      chloroplast-localization signal (IspSM(L) gene)

<400> SEQUENCE: 16

atggctacca acccgtcctg tctgtcaacc ccgttcctgt cttcaacccc ggctctgtcc     60

acccgcttcc cgctgtccga aaacttcacc cagaaaacga gcctggttaa cccgaaaccg    120

tggccgctga tttctgcggt cagctctcag tttagtcaaa tcgcggaaga taattctcgt    180

cgcagtgcca actatcatcc gaatctgtgg gattttgaat tcctgcagtc gctggaaaac    240

gacagcaaaa tggaaaaact ggaagaaaaa gcgaccaaac tggaagaaga agtgcgtaac    300

atgatgaatg aagcgaaaac ggaagccctg tctctgctgg aactgattga tgacgttcaa    360

cgcctgggtc tgacctacaa attcgaaaaa gatatcatca aagccctgga aaaaattgtc    420

ccgctggacg aatcaggtct gcacgtgacc tccctgtcat ttcgtatcct gcgccagcat    480

ggcttcgaag tttcgcaaga tgtctttaaa cgtttcaaag acaaagaagg cggtttctgc    540

gcagaactga aagatgacgt gcagggtctg ctgtctctgt atgaagctag ttacctgggt    600

tttgaaggcg aatccctgct ggatgaagcg cgcgccttct caattaccca cctgaaaaac    660

aatctgaaca aaggcatcaa tacgaaagtg gcacagcaag ttagtcatgc tctggaactg    720

ccgtatcacc gtcgcctgca tcgtctggaa gcccgctggc tgctggataa atacgaaccg    780

aaagaaccgc atcaccatct gctgcacgaa ctggcaaaac tggactttaa tctggttcag    840

tcgctgtatc aaaaagaact gcgtgaactg agcctgtggt ggcgcgaaat tggtctgacc    900

tctaaactgg attttgtgcg tgaccgcctg atggaagttt acttctgggc actgggcatg    960

gctccggatc cgcagtttag cgaatgccgt aaagtggtta ccaaaatgtt cggtctggtg   1020

acgattatcg atgacgtcta tgatgtgtac ggcaccctgg acgaactgca actgttcacg   1080

gatgcagtcg aacgctggga cgtgaacgct atcaataccc tgccggatta tatgaaactg   1140

tgttatctgg cactgtacaa caccgttaat gacacggctt acagcatcct gaaagaaaaa   1200
```

```
ggtcataaca acatctccta cctgaccaaa tcatggtgcg aactgtgtaa agcgtttctg   1260

caggaagcca aatggtctaa caataaaatt atcccggcgt tcaacaaata tctggataat   1320

gccagtgtta gttcctcagg cgtcgcactg ctggctccgt cctactttct ggtctgtcag   1380

gaacaagata tttcggacca ggcactgcac agcctgacca actttcatgg tctggttcgt   1440

tcgagctgca ccatcttccg cctgtgtaat gatctggcga cgtctagtgc cgaactggaa   1500

cgtggcgaaa ccacgaactc cattacctca tatatgcacg aaaatgaaac gagtgaagaa   1560

caggcgtgca aagaactgcg taacctgatc gatgccgaat ggaagaaaat gaacgaagaa   1620

cgcgtgtcga atagcaccct gccgaaagcc tttcgtgaaa ttgcaatcaa tatggctcgc   1680

atttcccatt gtacgtatca gtacggcgat ggtctgggcc gcccggacta cacgaccgaa   1740

aaccgcatta aactgctgct gattgacccg ttcccgatta actga                   1785
```

<210> SEQ ID NO 17
<211> LENGTH: 399
<212> TYPE: DNA
<213> ORGANISM: Artificial Sequence
<220> FEATURE:
<223> OTHER INFORMATION: Ptac-Ttrp

<400> SEQUENCE: 17

```
ggtaccagat ctccctgttg acaattaatc atcggctcta taatgtgtgg aatcgtgagc     60

ggataacaat ttcacacaag gagactcccg ggagccgcca gttccgctgg cggcatttta    120

actttcttta atgaagccgg aaaaatccta aattcattta atatttatct ttttaccgtt    180

tcgcttaccc cggtcgaacg tcaacttacg tcatttttcc gcccaacagt aatataatca    240

aacaaattaa tcccgcaaca taacaccagt aaaatcaata attttctcta agtcacttat    300

tcctcaggta attgttaata tatccagaat gttcctcaaa atatattttc cctctatctt    360

ctcgttgcgc ttaatttgac taattctcat tagggatcc                           399
```

<210> SEQ ID NO 18
<211> LENGTH: 3383
<212> TYPE: DNA
<213> ORGANISM: Artificial Sequence
<220> FEATURE:
<223> OTHER INFORMATION: Expression plasmid pSTV28-Ptac-Ttrp

<400> SEQUENCE: 18

```
cgtatggcaa tgaaagacgg tgagctggtg atatgggata gtgttcaccc ttgttacacc     60

gttttccatg agcaaactga aacgttttca tcgctctgga gtgaatacca cgacgatttc    120

cggcagtttc tacacatata ttcgcaagat gtggcgtgtt acggtgaaaa cctggcctat    180

ttccctaaag ggtttattga gaatatgttt ttcgtctcag ccaatccctg ggtgagtttc    240

accagttttg atttaaacgt ggccaatatg gacaacttct tcgcccccgt tttcaccatg    300

ggcaaatatt atacgcaagg cgacaaggtg ctgatgccgc tggcgattca ggttcatcat    360

gccgtttgtg atggcttcca tgtcggcaga atgcttaatg aattacaaca gtactgcgat    420

gagtggcagg gcggggcgta atttttttaa ggcagttatt ggtgccctta aacgcctggt    480

gctacgcctg aataagtgat aataagcgga tgaatggcag aaattcgaaa gcaaattcga    540

cccggtcgtc ggttcagggc agggtcgtta aatagccgct tatgtctatt gctggtttac    600

cggtttattg actaccggaa gcagtgtgac cgtgtgcttc tcaaatgcct gaggccagtt    660

tgctcaggct ctccccgtgg aggtaataat tgacgatatg atcatttatt ctgcctccca    720
```

-continued gagcctgata aaaacggtta gcgcttcgtt aatacagatg taggtgttcc acagggtagc 780
cagcagcatc ctgcgatgca gatccggaac ataatggtgc agggcgcttg tttcggcgtg 840
ggtatggtgg caggccccgt ggccgggga ctgttgggcg ctgccggcac ctgtcctacg 900
agttgcatga taaagaagac agtcataagt gcggcgacga tagtcatgcc ccgcgcccac 960
cggaaggagc taccggacag cggtgcggac tgttgtaact cagaataaga aatgaggccg 1020
ctcatggcgt tccaatacgc aaaccgcctc tccccgcgcg ttggccgatt cattaatgca 1080
gctggcacga caggtttccc gactggaaag cgggcagtga gcgcaacgca attaatgtga 1140
gttagctcac tcattaggca ccccaggctt tacactttat gcttccggct cgtatgttgt 1200
gtggaattgt gagcggataa caatttcaca caggaaacag ctatgaccat gattacgaat 1260
tcgagctcgg taccagatct ccctgttgac aattaatcat cggctctata atgtgtggaa 1320
tcgtgagcgg ataacaattt cacacaagga gactcccggg agccgccagt tccgctggcg 1380
gcattttaac tttctttaat gaagccggaa aaatcctaaa ttcatttaat atttatcttt 1440
ttaccgtttc gcttaccccg gtcgaacgtc aacttacgtc atttttccgc ccaacagtaa 1500
tataatcaaa caaattaatc ccgcaacata acaccagtaa aatcaataat tttctctaag 1560
tcacttattc ctcaggtaat tgttaatata tccagaatgt tcctcaaaat atattttccc 1620
tctatcttct cgttgcgctt aatttgacta attctcatta gggatcctct agagtcgacc 1680
tgcaggcatg caagcttggc actggccgtc gttttacaac gtcgtgactg ggaaaaccct 1740
ggcgttaccc aacttaatcg ccttgcagca catccccctt tcgccagctg gcgtaatagc 1800
gaagaggccc gcaccgatcg cccttcccaa cagttgcgca gcctgaatgg cgaatgagct 1860
tatcgatgat aagctgtcaa acatgagaat tacaacttat atcgtatggg gctgacttca 1920
ggtgctacat ttgaagagat aaattgcact gaaatctaga aatattttat ctgattaata 1980
agatgatctt cttgagatcg ttttggtctg cgcgtaatct cttgctctga aaacgaaaaa 2040
accgccttgc agggcggttt ttcgaaggtt ctctgagcta ccaactcttt gaaccgaggt 2100
aactggcttg gaggagcgca gtcaccaaaa cttgtccttt cagtttagcc ttaaccggcg 2160
catgacttca agactaactc ctctaaatca attaccagtg gctgctgcca gtggtgcttt 2220
tgcatgtctt tccgggttgg actcaagacg atagttaccg gataaggcgc agcggtcgga 2280
ctgaacgggg ggttcgtgca tacagtccag cttggagcga actgcctacc cggaactgag 2340
tgtcaggcgt ggaatgagac aaacgcggcc ataacagcgg aatgacaccg gtaaaccgaa 2400
aggcaggaac aggagagcgc acgagggagc cgccagggga aacgcctggt atctttatag 2460
tcctgtcggg tttcgccacc actgatttga gcgtcagatt tcgtgatgct tgtcaggggg 2520
gcggagccta tggaaaaacg gctttgccgc ggccctctca cttccctgtt aagtatcttc 2580
ctggcatctt ccaggaaatc tccgccccgt tcgtaagcca tttccgctcg ccgcagtcga 2640
acgaccgagc gtagcgagtc agtgagcgag gaagcggaat atatcctgta tcacatattc 2700
tgctgacgca ccggtgcagc ctttttctc ctgccacatg aagcacttca ctgacaccct 2760
catcagtgcc aacatagtaa gccagtatac actccgctag cgctgatgtc cggcggtgct 2820
tttgccgtta cgcaccaccc cgtcagtagc tgaacaggag ggacagctga tagaaacaga 2880
agccactgga gcacctcaaa aacaccatca tacactaaat cagtaagttg gcagcatcac 2940
ccgacgcact ttgcgccgaa taaatacctg tgacggaaga tcacttcgca gaataaataa 3000
atcctggtgt ccctgttgat accgggaagc cctgggccaa cttttggcga aaatgagacg 3060
ttgatcggca cgtaagaggt tccaactttc accataatga aataagatca ctaccgggcg 3120

-continued

```
tattttttga gttatcgaga ttttcaggag ctaaggaagc taaaatggag aaaaaaatca   3180

ctggatatac caccgttgat atatcccaat ggcatcgtaa agaacatttt gaggcatttc   3240

agtcagttgc tcaatgtacc tataaccaga ccgttcagct ggatattacg gcctttttaa   3300

agaccgtaaa gaaaaataag cacaagtttt atccggcctt tattcacatt cttgcccgcc   3360

tgatgaatgc tcatccggaa ttt                                           3383
```

```
<210> SEQ ID NO 19
<211> LENGTH: 79
<212> TYPE: DNA
<213> ORGANISM: Artificial Sequence
<220> FEATURE:
<223> OTHER INFORMATION: Primer for amplifying IspSK gene
      (Ptac-IspS(K)F)

<400> SEQUENCE: 19

gataacaatt tcacacaata attttgttta actttaagaa ggagatataa tgtgtgcgac     60

ctcttctcaa tttactcag                                                  79
```

```
<210> SEQ ID NO 20
<211> LENGTH: 42
<212> TYPE: DNA
<213> ORGANISM: Artificial Sequence
<220> FEATURE:
<223> OTHER INFORMATION: Primer for amplifying IspSK gene
      (IspS(K)R-MCSR)

<400> SEQUENCE: 20

acggccagtg aattcttaga catacatcag ctggttaatc gg                        42
```

```
<210> SEQ ID NO 21
<211> LENGTH: 79
<212> TYPE: DNA
<213> ORGANISM: Artificial Sequence
<220> FEATURE:
<223> OTHER INFORMATION: Primer for amplifying IspSP gene
      (Ptac-IspS(P)F)

<400> SEQUENCE: 21

gataacaatt tcacacaata attttgttta actttaagaa ggagatataa tgtgctctgt     60

ttctaccgag aacgtttcc                                                  79
```

```
<210> SEQ ID NO 22
<211> LENGTH: 43
<212> TYPE: DNA
<213> ORGANISM: Artificial Sequence
<220> FEATURE:
<223> OTHER INFORMATION: Primer for amplifying IspSP gene
      (IspS(P)R-MCSR)

<400> SEQUENCE: 22

acggccagtg aattcttaac gttcgaacgg cagaatcggt tcg                       43
```

```
<210> SEQ ID NO 23
<211> LENGTH: 69
<212> TYPE: DNA
<213> ORGANISM: Artificial Sequence
<220> FEATURE:
<223> OTHER INFORMATION: Primer for amplifying IspSM gene
      (Ptac-IspS(K)F)

<400> SEQUENCE: 23

gataacaatt tcacacaata attttgttta actttaagaa ggagatataa tgtccgccgt     60
```

ttcaagcca 69

<210> SEQ ID NO 24
<211> LENGTH: 35
<212> TYPE: DNA
<213> ORGANISM: Artificial Sequence
<220> FEATURE:
<223> OTHER INFORMATION: Primer for amplifying IspSM gene

<400> SEQUENCE: 24
acggccagtg aattcttagt taatcgggaa cgggt 35

<210> SEQ ID NO 25
<211> LENGTH: 79
<212> TYPE: DNA
<213> ORGANISM: Artificial Sequence
<220> FEATURE:
<223> OTHER INFORMATION: Primer for amplifying IspSM(L) gene

<400> SEQUENCE: 25
gataacaatt tcacacaata attttgttta actttaagaa ggagatataa tggctaccaa 60
cccgtcctgt ctgtcaacc 79

<210> SEQ ID NO 26
<211> LENGTH: 35
<212> TYPE: DNA
<213> ORGANISM: Artificial Sequence
<220> FEATURE:
<223> OTHER INFORMATION: Primer for amplifying IspSM(L) gene

<400> SEQUENCE: 26
acggccagtg aattctcagt taatcgggaa cgggt 35

<210> SEQ ID NO 27
<211> LENGTH: 29
<212> TYPE: DNA
<213> ORGANISM: Artificial Sequence
<220> FEATURE:
<223> OTHER INFORMATION: Primer for amplifying IpSTV28-Ptac-Ttrp
construct (pSTV28-F)

<400> SEQUENCE: 27
gtgtgaaatt gttatccgct cacaattcc 29

<210> SEQ ID NO 28
<211> LENGTH: 27
<212> TYPE: DNA
<213> ORGANISM: Artificial Sequence
<220> FEATURE:
<223> OTHER INFORMATION: Primer for amplifying pSTV28-Ptac-Ttrp
construct (pSTV28-R)

<400> SEQUENCE: 28
gaattcactg gccgtcgttt tacaacg 27

<210> SEQ ID NO 29
<211> LENGTH: 41
<212> TYPE: DNA
<213> ORGANISM: Artificial Sequence
<220> FEATURE:
<223> OTHER INFORMATION: Primer for amplifying dxs gene (dxs-F)

<400> SEQUENCE: 29
caggaaacag ctatgagttt tgatattgcc aaatacccga c 41

<210> SEQ ID NO 30
<211> LENGTH: 28
<212> TYPE: DNA
<213> ORGANISM: Artificial Sequence
<220> FEATURE:
<223> OTHER INFORMATION: Primer for amplifying dxs gene (dxs-R)

<400> SEQUENCE: 30
gctgccactc ctgctatact cgtcatac 28

<210> SEQ ID NO 31
<211> LENGTH: 30
<212> TYPE: DNA
<213> ORGANISM: Artificial Sequence
<220> FEATURE:
<223> OTHER INFORMATION: Primer for amplifying dxs gene (pMW219-F)

<400> SEQUENCE: 31
catagctgtt tcctgtgtga aattgttatc 30

<210> SEQ ID NO 32
<211> LENGTH: 40
<212> TYPE: DNA
<213> ORGANISM: Artificial Sequence
<220> FEATURE:
<223> OTHER INFORMATION: Primer for amplifying dxs gene (pMW219-R)

<400> SEQUENCE: 32
agcaggagtg gcagcgaatt cgagctcggt acccggggat 40

<210> SEQ ID NO 33
<211> LENGTH: 40
<212> TYPE: DNA
<213> ORGANISM: Artificial Sequence
<220> FEATURE:
<223> OTHER INFORMATION: Primer for amplifying ERG12 gene
(MVK-IFS_5742-33-1)

<400> SEQUENCE: 33
acacaaggag actcccatgt cattaccgtt cttaacttct 40

<210> SEQ ID NO 34
<211> LENGTH: 46
<212> TYPE: DNA
<213> ORGANISM: Artificial Sequence
<220> FEATURE:
<223> OTHER INFORMATION: Primer for amplifying ERG12 gene
(MVK-IFA_5742-33-2)

<400> SEQUENCE: 34
ggaactggcg gctcccgggt tattatgaag tccatggtaa attcgt 46

<210> SEQ ID NO 35
<211> LENGTH: 38
<212> TYPE: DNA
<213> ORGANISM: Artificial Sequence
<220> FEATURE:
<223> OTHER INFORMATION: Primer for amplifying ERG8 gene
(PMK-IFS_5742-33-3)

<400> SEQUENCE: 35
acacaaggag actcccatgt cagagttgag agccttca 38

<210> SEQ ID NO 36
<211> LENGTH: 46
<212> TYPE: DNA

<213> ORGANISM: Artificial Sequence
<220> FEATURE:
<223> OTHER INFORMATION: Primer for amplifying ERG8 gene
(PMK-IFA_5742-33-4)

<400> SEQUENCE: 36
ggaactggcg gctcccgggt tattatttat caagataagt ttccgg 46

<210> SEQ ID NO 37
<211> LENGTH: 37
<212> TYPE: DNA
<213> ORGANISM: Artificial Sequence
<220> FEATURE:
<223> OTHER INFORMATION: Primer for amplifying ERG19 gene
(MVD-IFS_5742-33-5)

<400> SEQUENCE: 37
acacaaggag actcccatga ccgtttacac agcatcc 37

<210> SEQ ID NO 38
<211> LENGTH: 46
<212> TYPE: DNA
<213> ORGANISM: Artificial Sequence
<220> FEATURE:
<223> OTHER INFORMATION: Primer for amplifying ERG19 gene
(MVD-IFA_5742-33-6

<400> SEQUENCE: 38
ggaactggcg gctcccgggt tattattcct ttggtagacc agtctt 46

<210> SEQ ID NO 39
<211> LENGTH: 36
<212> TYPE: DNA
<213> ORGANISM: Artificial Sequence
<220> FEATURE:
<223> OTHER INFORMATION: Primer for amplifying IDI1 gene
(yIDI-IFS_5742-33-7)

<400> SEQUENCE: 39
acacaaggag actcccatgc cccatggtgc agtatc 36

<210> SEQ ID NO 40
<211> LENGTH: 49
<212> TYPE: DNA
<213> ORGANISM: Artificial Sequence
<220> FEATURE:
<223> OTHER INFORMATION: Primer for amplifying IDI1 gene
(yIDI-IFA_5742-33-8)

<400> SEQUENCE: 40
ggaactggcg gctcccgggt tattatagca ttctatgaat ttgcctgtc 49

<210> SEQ ID NO 41
<211> LENGTH: 5892
<212> TYPE: DNA
<213> ORGANISM: Artificial Sequence
<220> FEATURE:
<223> OTHER INFORMATION: Nucleotide sequence of prepared plasmid
pUC-mvk-pmk

<400> SEQUENCE: 41
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gaattcgagc 240

-continued

```
tcggtaccca tgtcattacc gttcttaact tctgcaccgg gaaaggttat tatttttggt    300
gaacactctg ctgtgtacaa caagcctgcc gtcgctgcta gtgtgtctgc gttgagaacc    360
tacctgctaa taagcgagtc atctgcacca gatactattg aattggactt cccggacatt    420
agctttaatc ataagtggtc catcaatgat ttcaatgcca tcaccgagga tcaagtaaac    480
tcccaaaaat tggccaaggc tcaacaagcc accgatggct tgtctcagga actcgttagt    540
cttttggatc cgttgttagc tcaactatcc gaatccttcc actaccatgc agcgttttgt    600
ttcctgtata tgtttgtttg cctatgcccc catgccaaga atattaagtt ttctttaaag    660
tctactttac ccatcggtgc tgggttgggc tcaagcgcct ctatttctgt atcactggcc    720
ttagctatgg cctacttggg gggttaata ggatctaatg acttggaaaa gctgtcagaa    780
aacgataagc atatagtgaa tcaatgggcc ttcataggtg aaaagtgtat tcacggtacc    840
ccttcaggaa tagataacgc tgtggccact tatggtaatg ccctgctatt tgaaaaagac    900
tcacataatg gaacaataaa cacaaacaat tttaagttct tagatgattt cccagccatt    960
ccaatgatcc taacctatac tagaattcca aggtctacaa aagatcttgt tgctcgcgtt   1020
cgtgtgttgg tcaccgagaa atttcctgaa gttatgaagc caattctaga tgccatgggt   1080
gaatgtgccc tacaaggctt agagatcatg actaagttaa gtaaatgtaa aggcaccgat   1140
gacgaggctg tagaaactaa taatgaactg tatgaacaac tattggaatt gataagaata   1200
aatcatggac tgcttgtctc aatcggtgtt tctcatcctg gattagaact tattaaaaat   1260
ctgagcgatg atttgagaat tggctccaca aaacttaccg gtgctggtgg cggcggttgc   1320
tctttgactt tgttacgaag agacattact caagagcaaa ttgacagctt caaaaagaaa   1380
ttgcaagatg attttagtta cgagacattt gaaacagact tgggtgggac tggctgctgt   1440
ttgttaagcg caaaaaattt gaataaagat cttaaaatca aatccctagt attccaatta   1500
tttgaaaata aaactaccac aaagcaacaa attgacgatc tattattgcc aggaaacacg   1560
aatttaccat ggacttcata agctaatttg cgataggcct gcacccttaa ggaggaaaaa   1620
aacatgtcag agttgagagc cttcagtgcc ccagggaaag cgttactagc tggtggatat   1680
ttagttttag atacaaaata tgaagcattt gtagtcggat tatcggcaag aatgcatgct   1740
gtagcccatc cttacggttc attgcaaggg tctgataagt ttgaagtgcg tgtgaaaagt   1800
aaacaattta aagatgggga gtggctgtac catataagtc ctaaaagtgg cttcattcct   1860
gtttcgatag gcggatctaa gaacccttttc attgaaaaag ttatcgctaa cgtatttagc   1920
tactttaaac ctaacatgga cgactactgc aatagaaact tgttcgttat tgatattttc   1980
tctgatgatg cctaccattc tcaggaggat agcgttaccg aacatcgtgg caacagaaga   2040
ttgagttttc attcgcacag aattgaagaa gttcccaaaa cagggctggg ctcctcggca   2100
ggtttagtca cagttttaac tacagctttg gcctcctttt ttgtatcgga cctggaaaat   2160
aatgtagaca aatatagaga agttattcat aatttagcac aagttgctca ttgtcaagct   2220
cagggtaaaa ttggaagcgg gtttgatgta gcggcggcag catatggatc tatcagatat   2280
agaagattcc cacccgcatt aatctctaat ttgccagata ttggaagtgc tacttacggc   2340
agtaaactgg cgcatttggt tgatgaagaa gactggaata ttacgattaa aagtaaccat   2400
ttaccttcgg gattaacttt atggatgggc gatattaaga atggttcaga aacagtaaaa   2460
ctggtccaga aggtaaaaaa ttggtatgat tcgcatatgc cagaaagctt gaaaatatat   2520
acagaactcg atcatgcaaa ttctagattt atggatggac tatctaaact agatcgctta   2580
```

-continued

```
cacgagactc atgacgatta cagcgatcag atatttgagt ctcttgagag gaatgactgt   2640
acctgtcaaa agtatcctga aatcacagaa gttagagatg cagttgccac aattagacgt   2700
tcctttagaa aaataactaa agaatctggt gccgatatcg aacctcccgt acaaactagc   2760
ttattggatg attgccagac cttaaaagga gttcttactt gcttaatacc tggtgctggt   2820
ggttatgacg ccattgcagt gattactaag caagatgttg atcttagggc tcaaaccgct   2880
aatgacaaaa gatttttctaa ggttcaatgg ctggatgtaa ctcaggctga ctggggtgtt   2940
aggaaagaaa aagatccgga aacttatctt gataaataag ggatcctct agagtcgacc   3000
tgcaggcatg caagcttggc actggccgtc gttttacaac gtcgtgactg ggaaaaccct   3060
ggcgttaccc aacttaatcg ccttgcagca catccccctt tcgccagctg gcgtaatagc   3120
gaagaggccc gcaccgatcg cccttcccaa cagttgcgca gcctgaatgg cgaatggcgc   3180
ctgatgcggt attttctcct tacgcatctg tgcggtattt cacaccgcat acgtcaaagc   3240
aaccatagta cgcgccctgt agcggcgcat taagcgcggc gggtgtggtg gttacgcgca   3300
gcgtgaccgc tacacttgcc agcgccctag cgcccgctcc tttcgctttc ttcccttcct   3360
ttctcgccac gttcgccggc tttccccgtc aagctctaaa tcgggggctc cctttagggt   3420
tccgatttag tgctttacgg cacctcgacc ccaaaaaact tgatttgggt gatggttcac   3480
gtagtgggcc atcgccctga tagacggttt ttcgcccttt gacgttggag tccacgttct   3540
ttaatagtgg actcttgttc caaactggaa caacactcaa ccctatctcg ggctattctt   3600
ttgatttata agggattttg ccgatttcgg cctattggtt aaaaaatgag ctgatttaac   3660
aaaaatttaa cgcgaatttt aacaaaatat taacgtttac aattttatgg tgcactctca   3720
gtacaatctg ctctgatgcc gcatagttaa gccagccccg acacccgcca acacccgctg   3780
acgcgccctg acgggcttgt ctgctcccgg catccgctta cagacaagct gtgaccgtct   3840
ccgggagctg catgtgtcag aggttttcac cgtcatcacc gaaacgcgcg agacgaaagg   3900
gcctcgtgat acgcctattt ttataggtta atgtcatgat aataatggtt tcttagacgt   3960
caggtggcac ttttcgggga aatgtgcgcg gaacccctat ttgtttattt ttctaaatac   4020
attcaaatat gtatccgctc atgagacaat aaccctgata aatgcttcaa taatattgaa   4080
aaaggaagag tatgagtatt caacatttcc gtgtcgccct tattcccttt tttgcggcat   4140
tttgccttcc tgtttttgct cacccagaaa cgctggtgaa agtaaaagat gctgaagatc   4200
agttgggtgc acgagtgggt tacatcgaac tggatctcaa cagcggtaag atccttgaga   4260
gttttcgccc cgaagaacgt tttccaatga tgagcacttt taaagttctg ctatgtggcg   4320
cggtattatc ccgtattgac gccgggcaag agcaactcgg tcgccgcata cactattctc   4380
agaatgactt ggttgagtac tcaccagtca cagaaaagca tcttacggat ggcatgacag   4440
taagagaatt atgcagtgct gccataacca tgagtgataa cactgcggcc aacttacttc   4500
tgacaacgat cggaggaccg aaggagctaa ccgctttttt gcacaacatg ggggatcatg   4560
taactcgcct tgatcgttgg gaaccggagc tgaatgaagc cataccaaac gacgagcgtg   4620
acaccacgat gcctgtagca atggcaacaa cgttgcgcaa actattaact ggcgaactac   4680
ttactctagc ttcccggcaa caattaatag actggatgga ggcggataaa gttgcaggac   4740
cacttctgcg ctcggccctt ccggctggct ggtttattgc tgataaatct ggagccggtg   4800
agcgtgggtc tcgcggtatc attgcagcac tggggccaga tggtaagccc tcccgtatcg   4860
tagttatcta cacgacgggg agtcaggcaa ctatggatga acgaaataga cagatcgctg   4920
agataggtgc ctcactgatt aagcattggt aactgtcaga ccaagtttac tcatatatac   4980
```

tttagattga tttaaaactt catttttaat ttaaaaggat ctaggtgaag atcctttttg 5040
ataatctcat gaccaaaatc ccttaacgtg agttttcgtt ccactgagcg tcagaccccg 5100
tagaaaagat caaaggatct tcttgagatc cttttttttct gcgcgtaatc tgctgcttgc 5160
aaacaaaaaa accaccgcta ccagcggtgg tttgtttgcc ggatcaagag ctaccaactc 5220
tttttccgaa ggtaactggc ttcagcagag cgcagatacc aaatactgtc cttctagtgt 5280
agccgtagtt aggccaccac ttcaagaact ctgtagcacc gcctacatac ctcgctctgc 5340
taatcctgtt accagtggct gctgccagtg gcgataagtc gtgtcttacc gggttggact 5400
caagacgata gttaccggat aaggcgcagc ggtcgggctg aacggggggt tcgtgcacac 5460
agcccagctt ggagcgaacg acctacaccg aactgagata cctacagcgt gagctatgag 5520
aaagcgccac gcttcccgaa gggagaaagg cggacaggta tccggtaagc ggcagggtcg 5580
gaacaggaga gcgcacgagg gagcttccag ggggaaacgc ctggtatctt tatagtcctg 5640
tcgggtttcg ccacctctga cttgagcgtc gatttttgtg atgctcgtca ggggggcgga 5700
gcctatggaa aaacgccagc aacgcggcct ttttacggtt cctggccttt tgctggcctt 5760
ttgctcacat gttctttcct gcgttatccc ctgattctgt ggataaccgt attaccgcct 5820
ttgagtgagc tgataccgct cgccgcagcc gaacgaccga gcgcagcgag tcagtgagcg 5880
aggaagcgga ag 5892

<210> SEQ ID NO 42
<211> LENGTH: 39
<212> TYPE: DNA
<213> ORGANISM: Artificial Sequence
<220> FEATURE:
<223> OTHER INFORMATION: Primer for amplifying ERG12 gene (KKS1-6038-2-1)

<400> SEQUENCE: 42
tcgagctcgg tacccatgtc attaccgttc ttaacttct 39

<210> SEQ ID NO 43
<211> LENGTH: 53
<212> TYPE: DNA
<213> ORGANISM: Artificial Sequence
<220> FEATURE:
<223> OTHER INFORMATION: Primer for amplifying ERG12 gene (KKA1-6038-2-2)

<400> SEQUENCE: 43
ttaagggtgc aggcctatcg caaattagct tatgaagtcc atggtaaatt cgt 53

<210> SEQ ID NO 44
<211> LENGTH: 50
<212> TYPE: DNA
<213> ORGANISM: Artificial Sequence
<220> FEATURE:
<223> OTHER INFORMATION: Primer for amplifying ERG8 gene (KKS2-6083-2-3)

<400> SEQUENCE: 44
ggcctgcacc cttaaggagg aaaaaaacat gtcagagttg agagccttca 50

<210> SEQ ID NO 45
<211> LENGTH: 39
<212> TYPE: DNA
<213> ORGANISM: Artificial Sequence
<220> FEATURE:
<223> OTHER INFORMATION: Primer for amplifying ERG8 gene (KKA2-6083-2-4)

```
<400> SEQUENCE: 45

ctctagagga tccccttatt tatcaagata agtttccgg                          39


<210> SEQ ID NO 46
<211> LENGTH: 6135
<212> TYPE: DNA
<213> ORGANISM: Artificial Sequence
<220> FEATURE:
<223> OTHER INFORMATION: Nucleotide sequence of prepared plasmid
      pTWV-dmd-yidi

<400> SEQUENCE: 46

gacgaaaggg cctcgtgata cgcctatttt tataggttaa tgtcatgata ataatggttt     60

cttagacgtc aggtggcact tttcggggaa atgtgcgcgg aacccctatt tgtttatttt    120

tctaaataca ttcaaatatg tatccgctca tgagacaata accctgataa atgcttcaat    180

aatattgaaa aaggaagagt atgagtattc aacatttccg tgtcgccctt attccctttt    240

ttgcggcatt ttgccttcct gtttttgctc acccagaaac gctggtgaaa gtaaaagatg    300

ctgaagatca gttgggtgca cgagtgggtt acatcgaact ggatctcaac agcggtaaga    360

tccttgagag ttttcgcccc gaagaacgtt ttccaatgat gagcactttt aaagttctgc    420

tatgtggcgc ggtattatcc cgtattgacg ccgggcaaga gcaactcggt cgccgcatac    480

actattctca gaatgacttg gttgagtact caccagtcac agaaaagcat cttacggatg    540

gcatgacagt aagagaatta tgcagtgctg ccataaccat gagtgataac actgcggcca    600

acttacttct gacaacgatc ggaggaccga aggagctaac cgcttttttg cacaacatgg    660

gggatcatgt aactcgcctt gatcgttggg aaccggagct gaatgaagcc ataccaaacg    720

acgagcgtga caccacgatg cctgtagcaa tggcaacaac gttgcgcaaa ctattaactg    780

gcgaactact tactctagct tcccggcaac aattaataga ctggatggag gcggataaag    840

ttgcaggacc acttctgcgc tcggcccttc cggctggctg gtttattgct gataaatctg    900

gagccggtga gcgtgggtct cgcggtatca ttgcagcact ggggccagat ggtaagccct    960

cccgtatcgt agttatctac acgacgggga gtcaggcaac tatggatgaa cgaaatagac   1020

agatcgctga gataggtgcc tcactgatta agcattggta actgtcagac caagtttact   1080

catatatact ttagattgat ttaaaacttc atttttaatt taaaaggatc taggtgaaga   1140

tcctttttga taatctcatg accaaaatcc cttaacgtga gttttcgttc cactgagcgt   1200

cagaccccgt agaaaagatc aaaggatctt cttgagatcc tttttttctg cgcgtaatct   1260

gctgcttgca aacaaaaaaa ccaccgctac cagcggtggt ttgtttgccg gatcaagagc   1320

taccaactct ttttccgaag gtaactggct tcagcagagc gcagatacca aatactgtcc   1380

ttctagtgta gccgtagtta ggccaccact tcaagaactc tgtagcaccg cctacatacc   1440

tcgctctgct aatcctgtta ccagtggctg ctgccagtgg cgataagtcg tgtcttaccg   1500

ggttggactc aagacgatag ttaccggata aggcgcagcg gtcgggctga acggggggtt   1560

cgtgcacaca gcccagcttg gagcgaacga cctacaccga actgagatac ctacagcgtg   1620

agctatgaga aagcgccacg cttcccgaag ggagaaaggc ggacaggtat ccggtaagcg   1680

gcagggtcgg aacaggagag cgcacgaggg agcttccagg gggaaacgcc tggtatcttt   1740

atagtcctgt cgggtttcgc cacctctgac ttgagcgtcg atttttgtga tgctcgtcag   1800

gggggcggag cctatggaaa aacgccagca acgcggcctt tttacggttc ctggcctttt   1860

gctggccttt tgctcacatg ttctttcctg cgttatcccc tgattctgtg gataaccgta   1920
```

-continued ttaccgcctt tgagtgagct gataccgctc gccgcagccg aacgaccgag cgcagcgagt 1980
cagtgagcga ggaagcggaa gagcgcctga tgcggtattt tctccttacg catctgtgcg 2040
gtatttcaca ccgcatatgg tgcactctca gtacaatctg ctctgatgcc gcatagttaa 2100
gccagtatac actccgctat cgctacgtga ctgggtcatg gctgcgcccc gacacccgcc 2160
aacacccgct gacgcgccct gacgggcttg tctgctcccg gcatccgctt acagacaagc 2220
tgtgaccgtc tccgggagct gcatgtgtca gaggttttca ccgtcatcac cgaaacgcgc 2280
gaggcagctg cggtaaagct catcagcgtg gtcgtgaagc gattcacaga tgtctgcctg 2340
ttcatccgcg tccagctcgt tgagtttctc cagaagcgtt aatgtctggc ttctgataaa 2400
gcgggccatg ttaagggcgg tttttcctg tttggtcact gatgcctccg tgtaaggggg 2460
atttctgttc atgggggtaa tgataccgat gaaacgagag aggatgctca cgatacgggt 2520
tactgatgat gaacatgccc ggttactgga acgttgtgag ggtaaacaac tggcggtatg 2580
gatgcggcgg gaccagagaa aaatcactca gggtcaatgc cagcgcttcg ttaatacaga 2640
tgtaggtgtt ccacagggta gccagcagca tcctgcgatg cagatccgga acataatggt 2700
gcagggcgct gacttccgcg tttccagact ttacgaaaca cggaaaccga agaccattca 2760
tgttgttgct caggtcgcag acgttttgca gcagcagtcg cttcacgttc gctcgcgtat 2820
cggtgattca ttctgctaac cagtaaggca accccgccag cctagccggg tcctcaacga 2880
caggagcacg atcatgcgca cccgtggcca ggacccaacg ctgcccgaga tgcgccgcgt 2940
gcggctgctg gagatggcgg acgcgatgga tatgttctgc caagtaatgt gagttagctc 3000
actcattagg caccccaggc tttacacttt atgcttccgg ctcgtatgtt gtgtggaatt 3060
gtgagcggat aacaatttca cacaggaaac agctatgacc atgattacga attcgagctc 3120
ggtacccatg accgtttaca cagcatccgt taccgcaccc gtcaacatcg caacccttaa 3180
gtattggggg aaaagggaca cgaagttgaa tctgcccacc aattcgtcca tatcagtgac 3240
tttatcgcaa gatgacctca gaacgttgac ctctgcggct actgcacctg agtttgaacg 3300
cgacactttg tggttaaatg gagaaccaca cagcatcgac aatgaaagaa ctcaaaattg 3360
tctgcgcgac ctacgccaat taagaaagga aatggaatcg aaggacgcct cattgcccac 3420
attatctcaa tggaaactcc acattgtctc cgaaaataac tttcctacag cagctggttt 3480
agcttcctcc gctgctggct ttgctgcatt ggtctctgca attgctaagt tataccaatt 3540
accacagtca acttcagaaa tatctagaat agcaagaaag gggtctggtt cagcttgtag 3600
atcgttgttt ggcggatacg tggcctggga aatgggaaaa gctgaagatg gtcatgattc 3660
catggcagta caaatcgcag acagctctga ctggcctcag atgaaagctt gtgtcctagt 3720
tgtcagcgat attaaaaagg atgtgagttc cactcagggt atgcaattga ccgtggcaac 3780
ctccgaacta tttaaagaaa gaattgaaca tgtcgtacca aagagatttg aagtcatgcg 3840
taaagccatt gttgaaaaag atttcgccac ctttgcaaag gaaacaatga tggattccaa 3900
ctctttccat gccacatgtt tggactcttt ccctccaata ttctacatga atgacacttc 3960
caagcgtatc atcagttggt gccacaccat taatcagttt tacggagaaa caatcgttgc 4020
atacacgttt gatgcaggtc caaatgctgt gttgtactac ttagctgaaa atgagtcgaa 4080
actctttgca tttatctata aattgtttgg ctctgttcct ggatgggaca agaaatttac 4140
tactgagcag cttgaggctt tcaaccatca atttgaatca tctaacttta ctgcacgtga 4200
attggatctt gagttgcaaa aggatgttgc cagagtgatt ttaactcaag tcggttcagg 4260
cccacaagaa acaaacgaat ctttgattga cgcaaagact ggtctaccaa aggaataaga 4320

-continued tcaattcgct gcatcgccct taggaggtaa aaaaaaatga ctgccgacaa caatagtatg 4380
ccccatggtg cagtatctag ttacgccaaa ttagtgcaaa accaaacacc tgaagacatt 4440
ttggaagagt ttcctgaaat tattccatta caacaaagac ctaatacccg atctagtgag 4500
acgtcaaatg acgaaagcgg agaaacatgt ttttctggtc atgatgagga gcaaattaag 4560
ttaatgaatg aaaattgtat tgttttggat tgggacgata atgctattgg tgccggtacc 4620
aagaaagttt gtcatttaat ggaaaatatt gaaaagggtt tactacatcg tgcattctcc 4680
gtctttattt tcaatgaaca aggtgaatta cttttacaac aaagagccac tgaaaaaata 4740
actttccctg atctttggac taacacatgc tgctctcatc cactatgtat tgatgacgaa 4800
ttaggtttga agggtaagct agacgataag attaagggcg ctattactgc ggcggtgaga 4860
aaactagatc atgaattagg tattccagaa gatgaaacta agacaagggg taagtttcac 4920
tttttaaaca gaatccatta catggcacca agcaatgaac catggggtga acatgaaatt 4980
gattacatcc tattttataa gatcaacgct aaagaaaact tgactgtcaa cccaaacgtc 5040
aatgaagtta gagacttcaa atgggtttca ccaaatgatt tgaaaactat gtttgctgac 5100
ccaagttaca agtttacgcc ttggtttaag attatttgcg agaattactt attcaactgg 5160
tgggagcaat tagatgacct ttctgaagtg gaaaatgaca ggcaaattca tagaatgcta 5220
taaggggatc ctctagagtc gacctgcagg catgcaagct tggcactggc cgtcgtttta 5280
caacgtcgtg actgggaaaa ccctggcgtt acccaactta atcgccttgc agcacatccc 5340
cctttcgcca gctggcgtaa tagcgaagag gcccgcaccg atcgcccttc ccaacagttg 5400
cgcagcctga atggcgaatg gcgcctgatg cggtattttc tccttacgca tctgtgcggt 5460
atttcacacc gcatacgtca aagcaaccat agtacgcgcc ctgtagcggc gcattaagcg 5520
cggcgggtgt ggtggttacg cgcagcgtga ccgctacact tgccagcgcc ctagcgcccg 5580
ctcctttcgc tttcttccct tcctttctcg ccacgttcgc cggctttccc cgtcaagctc 5640
taaatcgggg gctcccttta gggttccgat ttagtgcttt acggcacctc gaccccaaaa 5700
aacttgattt gggtgatggt tcacgtagtg ggccatcgcc ctgatagacg gtttttcgcc 5760
ctttgacgtt ggagtccacg ttctttaata gtggactctt gttccaaact ggaacaacac 5820
tcaaccctat ctcgggctat tcttttgatt tataagggat tttgccgatt tcggcctatt 5880
ggttaaaaaa tgagctgatt taacaaaaat ttaacgcgaa ttttaacaaa atattaacgt 5940
ttacaatttt atggtgcact ctcagtacaa tctgctctga tgccgcatag ttaagccagc 6000
cccgacaccc gccaacaccc gctgacgcgc cctgacgggc ttgtctgctc ccggcatccg 6060
cttacagaca agctgtgacc gtctccggga gctgcatgtg tcagaggttt tcaccgtcat 6120
caccgaaacg cgcga 6135

<210> SEQ ID NO 47
<211> LENGTH: 36
<212> TYPE: DNA
<213> ORGANISM: Artificial Sequence
<220> FEATURE:
<223> OTHER INFORMATION: Primer for amplifying ERG19 gene (DyIS1-6083-2-5)

<400> SEQUENCE: 47
tcgagctcgg tacccatgac cgtttacaca gcatcc 36

<210> SEQ ID NO 48
<211> LENGTH: 61

<212> TYPE: DNA
<213> ORGANISM: Artificial Sequence
<220> FEATURE:
<223> OTHER INFORMATION: Primer for amplifying ERG19 gene
(DyIA1-6083-2-6)

<400> SEQUENCE: 48
tttttttacc tcctaagggc gatgcagcga attgatctta ttcctttggt agaccagtct 60
t 61

<210> SEQ ID NO 49
<211> LENGTH: 57
<212> TYPE: DNA
<213> ORGANISM: Artificial Sequence
<220> FEATURE:
<223> OTHER INFORMATION: Primer for amplifying IDI1 gene
(DyIS2-6083-2-7)

<400> SEQUENCE: 49
taggaggtaa aaaaaaatga ctgccgacaa caatagtatg ccccatggtg cagtatc 57

<210> SEQ ID NO 50
<211> LENGTH: 42
<212> TYPE: DNA
<213> ORGANISM: Artificial Sequence
<220> FEATURE:
<223> OTHER INFORMATION: Primer for amplifying IDI1 gene
(DyIA2-6083-2-8)

<400> SEQUENCE: 50
ctctagagga tccccttata gcattctatg aatttgcctg tc 42

<210> SEQ ID NO 51
<211> LENGTH: 9257
<212> TYPE: DNA
<213> ORGANISM: Artificial Sequence
<220> FEATURE:
<223> OTHER INFORMATION: Nucleotide sequence of prepared plasmid
pTrc-KKDyI(beta))

<400> SEQUENCE: 51
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgtcatt 420
accgttctta acttctgcac cgggaaaggt tattattttt ggtgaacact ctgctgtgta 480
caacaagcct gccgtcgctg ctagtgtgtc tgcgttgaga acctacctgc taataagcga 540
gtcatctgca ccagatacta ttgaattgga cttcccggac attagcttta atcataagtg 600
gtccatcaat gatttcaatg ccatcaccga ggatcaagta aactcccaaa aattggccaa 660
ggctcaacaa gccaccgatg gcttgtctca ggaactcgtt agtcttttgg atccgttgtt 720
agctcaacta tccgaatcct tccactacca tgcagcgttt tgtttcctgt atatgtttgt 780
ttgcctatgc cccccatgcca agaatattaa gttttcttta aagtctactt tacccatcgg 840
tgctgggttg ggctcaagcg cctctatttc tgtatcactg gccttagcta tggcctactt 900

-continued

```
ggggggggtta ataggatcta atgacttgga aaagctgtca gaaaacgata agcatatagt    960
gaatcaatgg gccttcatag gtgaaaagtg tattcacggt accccttcag gaatagataa   1020
cgctgtggcc acttatggta atgccctgct atttgaaaaa gactcacata atggaacaat   1080
aaacacaaac aattttaagt tcttagatga tttcccagcc attccaatga tcctaaccta   1140
tactagaatt ccaaggtcta caaaagatct tgttgctcgc gttcgtgtgt tggtcaccga   1200
gaaatttcct gaagttatga agccaattct agatgccatg ggtgaatgtg ccctacaagg   1260
cttagagatc atgactaagt taagtaaatg taaaggcacc gatgacgagg ctgtagaaac   1320
taataatgaa ctgtatgaac aactattgga attgataaga ataaatcatg gactgcttgt   1380
ctcaatcggt gtttctcatc ctggattaga acttattaaa aatctgagcg atgatttgag   1440
aattggctcc acaaaactta ccggtgctgg tggcggcggt tgctctttga ctttgttacg   1500
aagagacatt actcaagagc aaattgacag cttcaaaaag aaattgcaag atgattttag   1560
ttacgagaca tttgaaacag acttgggtgg gactggctgc tgtttgttaa gcgcaaaaaa   1620
tttgaataaa gatcttaaaa tcaaatccct agtattccaa ttatttgaaa ataaaactac   1680
cacaaagcaa caaattgacg atctattatt gccaggaaac acgaatttac catggacttc   1740
ataagctaat ttgcgatagg cctgcaccct taaggaggaa aaaaacatgt cagagttgag   1800
agccttcagt gccccaggga aagcgttact agctggtgga tatttagttt tagatacaaa   1860
atatgaagca tttgtagtcg gattatcggc aagaatgcat gctgtagccc atccttacgg   1920
ttcattgcaa gggtctgata agtttgaagt gcgtgtgaaa agtaaacaat ttaaagatgg   1980
ggagtggctg taccatataa gtcctaaaag tggcttcatt cctgtttcga taggcggatc   2040
taagaaccct ttcattgaaa aagttatcgc taacgtattt agctacttta aacctaacat   2100
ggacgactac tgcaatagaa acttgttcgt tattgatatt ttctctgatg atgcctacca   2160
ttctcaggag gatagcgtta ccgaacatcg tggcaacaga agattgagtt ttcattcgca   2220
cagaattgaa gaagttccca aaacagggct gggctcctcg gcaggtttag tcacagtttt   2280
aactacagct ttggcctcct tttttgtatc ggacctggaa aataatgtag acaaatatag   2340
agaagttatt cataatttag cacaagttgc tcattgtcaa gctcagggta aaattggaag   2400
cgggtttgat gtagcggcgg cagcatatgg atctatcaga tatagaagat tcccacccgc   2460
attaatctct aatttgccag atattggaag tgctacttac ggcagtaaac tggcgcattt   2520
ggttgatgaa gaagactgga atattacgat taaaagtaac catttacctt cgggattaac   2580
tttatggatg ggcgatatta agaatggttc agaaacagta aaactggtcc agaaggtaaa   2640
aaattggtat gattcgcata tgccagaaag cttgaaaata tatacagaac tcgatcatgc   2700
aaattctaga tttatggatg gactatctaa actagatcgc ttacacgaga ctcatgacga   2760
ttacagcgat cagatatttg agtctcttga gaggaatgac tgtacctgtc aaaagtatcc   2820
tgaaatcaca gaagttagag atgcagttgc cacaattaga cgttccttta gaaaaataac   2880
taaagaatct ggtgccgata tcgaacctcc cgtacaaact agcttattgg atgattgcca   2940
gaccttaaaa ggagttctta cttgcttaat acctggtgct ggtggttatg acgccattgc   3000
agtgattact aagcaagatg ttgatcttag ggctcaaacc gctaatgaca aaagattttc   3060
taaggttcaa tggctggatg taactcaggc tgactggggt gttaggaaag aaaaagatcc   3120
ggaaacttat cttgataaat aacttaaggt agctgcatgc agaattcgcc cttaaggagg   3180
aaaaaaaaat gaccgtttac acagcatccg ttaccgcacc cgtcaacatc gcaaccctta   3240
agtattgggg gaaaagggac acgaagttga atctgcccac caattcgtcc atatcagtga   3300
```

```
ctttatcgca agatgacctc agaacgttga cctctgcggc tactgcacct gagtttgaac   3360
gcgacacttt gtggttaaat ggagaaccac acagcatcga caatgaaaga actcaaaatt   3420
gtctgcgcga cctacgccaa ttaagaaagg aaatggaatc gaaggacgcc tcattgccca   3480
cattatctca atggaaactc cacattgtct ccgaaaataa ctttcctaca gcagctggtt   3540
tagcttcctc cgctgctggc tttgctgcat tggtctctgc aattgctaag ttataccaat   3600
taccacagtc aacttcagaa atatctagaa tagcaagaaa ggggtctggt tcagcttgta   3660
gatcgttgtt tggcggatac gtggcctggg aaatgggaaa agctgaagat ggtcatgatt   3720
ccatggcagt acaaatcgca gacagctctg actggcctca gatgaaagct tgtgtcctag   3780
ttgtcagcga tattaaaaag gatgtgagtt ccactcaggg tatgcaattg accgtggcaa   3840
cctccgaact atttaaagaa agaattgaac atgtcgtacc aaagagattt gaagtcatgc   3900
gtaaagccat tgttgaaaaa gatttcgcca cctttgcaaa ggaaacaatg atggattcca   3960
actctttcca tgccacatgt ttggactctt tccctccaat attctacatg aatgacactt   4020
ccaagcgtat catcagttgg tgccacacca ttaatcagtt ttacggagaa acaatcgttg   4080
catacacgtt tgatgcaggt ccaaatgctg tgttgtacta cttagctgaa aatgagtcga   4140
aactctttgc atttatctat aaattgtttg gctctgttcc tggatgggac aagaaattta   4200
ctactgagca gcttgaggct ttcaaccatc aatttgaatc atctaacttt actgcacgtg   4260
aattggatct tgagttgcaa aaggatgttg ccagagtgat tttaactcaa gtcggttcag   4320
gcccacaaga aacaaacgaa tctttgattg acgcaaagac tggtctacca aaggaataag   4380
atcaattcgc tgcatcgccc ttaggaggta aaaaaaaatg actgccgaca acaatagtat   4440
gccccatggt gcagtatcta gttacgccaa attagtgcaa aaccaaacac ctgaagacat   4500
tttggaagag tttcctgaaa ttattccatt acaacaaaga cctaataccc gatctagtga   4560
gacgtcaaat gacgaaagcg gagaaacatg tttttctggt catgatgagg agcaaattaa   4620
gttaatgaat gaaaattgta ttgttttgga ttgggacgat aatgctattg gtgccggtac   4680
caagaaagtt tgtcatttaa tggaaaatat tgaaaagggt ttactacatc gtgcattctc   4740
cgtctttatt ttcaatgaac aaggtgaatt acttttacaa caaagagcca ctgaaaaaat   4800
aactttccct gatctttgga ctaacacatg ctgctctcat ccactatgta ttgatgacga   4860
attaggtttg aagggtaagc tagacgataa gattaagggc gctattactg cggcggtgag   4920
aaaactagat catgaattag gtattccaga agatgaaact aagacaaggg gtaagtttca   4980
ctttttaaac agaatccatt acatggcacc aagcaatgaa ccatggggtg aacatgaaat   5040
tgattacatc ctattttata agatcaacgc taaagaaaac ttgactgtca acccaaacgt   5100
caatgaagtt agagacttca aatgggtttc accaaatgat ttgaaaacta tgtttgctga   5160
cccaagttac aagtttacgc cttggtttaa gattatttgc gagaattact tattcaactg   5220
gtgggagcaa ttagatgacc tttctgaagt ggaaaatgac aggcaaattc atagaatgct   5280
ataactgcag ctggtaccat atgggaattc gaagctttct agaacaaaaa ctcatctcag   5340
aagaggatct gaatagcgcc gtcgaccatc atcatcatca tcattgagtt taaacggtct   5400
ccagcttggc tgttttggcg gatgagagaa gattttcagc ctgatacaga ttaaatcaga   5460
acgcagaagc ggtctgataa aacagaattt gcctggcggc agtagcgcgg tggtcccacc   5520
tgaccccatg ccgaactcag aagtgaaacg ccgtagcgcc gatggtagtg tggggtctcc   5580
ccatgcgaga gtagggaact gccaggcatc aaataaaacg aaaggctcag tcgaaagact   5640
```

-continued

```
gggcctttcg ttttatctgt tgtttgtcgg tgaacgctct cctgagtagg acaaatccgc   5700
cgggagcgga tttgaacgtt gcgaagcaac ggcccggagg gtggcgggca ggacgcccgc   5760
cataaactgc caggcatcaa attaagcaga aggccatcct gacggatggc ctttttgcgt   5820
ttctacaaac tctttttgtt tatttttcta aatacattca aatatgtatc cgctcatgag   5880
acaataaccc tgataaatgc ttcaataata ttgaaaaagg aagagtatga gtattcaaca   5940
tttccgtgtc gcccttattc ccttttttgc ggcattttgc cttcctgttt ttgctcaccc   6000
agaaacgctg gtgaaagtaa aagatgctga agatcagttg ggtgcacgag tgggttacat   6060
cgaactggat ctcaacagcg gtaagatcct tgagagtttt cgccccgaag aacgttttcc   6120
aatgatgagc acttttaaag ttctgctatg tggcgcggta ttatcccgtg ttgacgccgg   6180
gcaagagcaa ctcggtcgcc gcatacacta ttctcagaat gacttggttg agtactcacc   6240
agtcacagaa aagcatctta cggatggcat gacagtaaga gaattatgca gtgctgccat   6300
aaccatgagt gataacactg cggccaactt acttctgaca acgatcggag gaccgaagga   6360
gctaaccgct tttttgcaca acatggggga tcatgtaact cgccttgatc gttgggaacc   6420
ggagctgaat gaagccatac caaacgacga gcgtgacacc acgatgcctg tagcaatggc   6480
aacaacgttg cgcaaactat taactggcga actacttact ctagcttccc ggcaacaatt   6540
aatagactgg atggaggcgg ataaagttgc aggaccactt ctgcgctcgg cccttccggc   6600
tggctggttt attgctgata aatctggagc cggtgagcgt gggtctcgcg gtatcattgc   6660
agcactgggg ccagatggta agccctcccg tatcgtagtt atctacacga cggggagtca   6720
ggcaactatg gatgaacgaa atagacagat cgctgagata ggtgcctcac tgattaagca   6780
ttggtaactg tcagaccaag tttactcata tatactttag attgatttaa aacttcattt   6840
ttaatttaaa aggatctagg tgaagatcct ttttgataat ctcatgacca aaatccctta   6900
acgtgagttt tcgttccact gagcgtcaga ccccgtagaa aagatcaaag gatcttcttg   6960
agatcctttt tttctgcgcg taatctgctg cttgcaaaca aaaaaaccac cgctaccagc   7020
ggtggtttgt ttgccggatc aagagctacc aactcttttt ccgaaggtaa ctggcttcag   7080
cagagcgcag ataccaaata ctgtccttct agtgtagccg tagttaggcc accacttcaa   7140
gaactctgta gcaccgccta catacctcgc tctgctaatc ctgttaccag tggctgctgc   7200
cagtggcgat aagtcgtgtc ttaccgggtt ggactcaaga cgatagttac cggataaggc   7260
gcagcggtcg ggctgaacgg ggggttcgtg cacacagccc agcttggagc gaacgaccta   7320
caccgaactg agatacctac agcgtgagct atgagaaagc gccacgcttc ccgaagggag   7380
aaaggcggac aggtatccgg taagcggcag ggtcggaaca ggagagcgca cgagggagct   7440
tccaggggga aacgcctggt atctttatag tcctgtcggg tttcgccacc tctgacttga   7500
gcgtcgattt ttgtgatgct cgtcaggggg gcggagccta tggaaaaacg ccagcaacgc   7560
ggccttttta cggttcctgg ccttttgctg gccttttgct cacatgttct ttcctgcgtt   7620
atcccctgat tctgtggata accgtattac cgcctttgag tgagctgata ccgctcgccg   7680
cagccgaacg accgagcgca gcgagtcagt gagcgaggaa gcggaagagc gcctgatgcg   7740
gtattttctc cttacgcatc tgtgcggtat ttcacaccgc atatggtgca ctctcagtac   7800
aatctgctct gatgccgcat agttaagcca gtatacactc cgctatcgct acgtgactgg   7860
gtcatggctg cgccccgaca cccgccaaca cccgctgacg cgccctgacg ggcttgtctg   7920
ctcccggcat ccgcttacag acaagctgtg accgtctccg ggagctgcat gtgtcagagg   7980
ttttcaccgt catcaccgaa acgcgcgagg cagcagatca attcgcgcgc gaaggcgaag   8040
```

-continued

```
cggcatgcat ttacgttgac accatcgaat ggtgcaaaac ctttcgcggt atggcatgat   8100

agcgcccgga agagagtcaa ttcagggtgg tgaatgtgaa accagtaacg ttatacgatg   8160

tcgcagagta tgccggtgtc tcttatcaga ccgtttcccg cgtggtgaac caggccagcc   8220

acgtttctgc gaaaacgcgg gaaaaagtgg aagcggcgat ggcggagctg aattacattc   8280

ccaaccgcgt ggcacaacaa ctggcgggca aacagtcgtt gctgattggc gttgccacct   8340

ccagtctggc cctgcacgcg ccgtcgcaaa ttgtcgcggc gattaaatct cgcgccgatc   8400

aactgggtgc cagcgtggtg gtgtcgatgg tagaacgaag cggcgtcgaa gcctgtaaag   8460

cggcggtgca caatcttctc gcgcaacgcg tcagtgggct gatcattaac tatccgctgg   8520

atgaccagga tgccattgct gtggaagctg cctgcactaa tgttccggcg ttatttcttg   8580

atgtctctga ccagacaccc atcaacagta ttattttctc ccatgaagac ggtacgcgac   8640

tgggcgtgga gcatctggtc gcattgggtc accagcaaat cgcgctgtta gcgggcccat   8700

taagttctgt ctcggcgcgt ctgcgtctgg ctggctggca taaatatctc actcgcaatc   8760

aaattcagcc gatagcggaa cgggaaggcg actggagtgc catgtccggt tttcaacaaa   8820

ccatgcaaat gctgaatgag ggcatcgttc ccactgcgat gctggttgcc aacgatcaga   8880

tggcgctggg cgcaatgcgc gccattaccg agtccgggct gcgcgttggt gcggatatct   8940

cggtagtggg atacgacgat accgaagaca gctcatgtta tatcccgccg tcaaccacca   9000

tcaaacagga ttttcgcctg ctggggcaaa ccagcgtgga ccgcttgctg caactctctc   9060

agggccaggc ggtgaagggc aatcagctgt tgcccgtctc actggtgaaa agaaaaacca   9120

ccctggcgcc caatacgcaa accgcctctc cccgcgcgtt ggccgattca ttaatgcagc   9180

tggcacgaca ggtttcccga ctggaaagcg ggcagtgagc gcaacgcaat taatgtgagt   9240

tagcgcgaat tgatctg                                                  9257
```

<210> SEQ ID NO 52
<211> LENGTH: 36
<212> TYPE: DNA
<213> ORGANISM: Artificial Sequence
<220> FEATURE:
<223> OTHER INFORMATION: Primer (KKDS2_6038-3-2)

<400> SEQUENCE: 52

```
gaggaataaa ccatgtcatt accgttctta acttct                               36
```

<210> SEQ ID NO 53
<211> LENGTH: 55
<212> TYPE: DNA
<213> ORGANISM: Artificial Sequence
<220> FEATURE:
<223> OTHER INFORMATION: Primer (KKMyIA_6038-2-9)

<400> SEQUENCE: 53

```
aagggcgaat tctgcatgca gctaccttaa gttatttatc aagataagtt tccgg          55
```

<210> SEQ ID NO 54
<211> LENGTH: 51
<212> TYPE: DNA
<213> ORGANISM: Artificial Sequence
<220> FEATURE:
<223> OTHER INFORMATION: Primer (KMS_6038-6-1)

<400> SEQUENCE: 54

```
gcagaattcg cccttaagga ggaaaaaaaa atgaccgttt acacagcatc c              51
```

<210> SEQ ID NO 55
<211> LENGTH: 47
<212> TYPE: DNA
<213> ORGANISM: Artificial Sequence
<220> FEATURE:
<223> OTHER INFORMATION: Primer (KDyIA_6038-3-3)

<400> SEQUENCE: 55
ccatatggta ccagctgcag ttatagcatt ctatgaattt gcctgtc 47

<210> SEQ ID NO 56
<211> LENGTH: 11386
<212> TYPE: DNA
<213> ORGANISM: Artificial Sequence
<220> FEATURE:
<223> OTHER INFORMATION: Nucleotide sequence of prepared plasmid
pMW219-KKDyI-TaspA

<400> SEQUENCE: 56
gacagtaaga cgggtaagcc tgttgatgat accgctgcct tactgggtgc attagccagt 60
ctgaatgacc tgtcacggga taatccgaag tggtcagact ggaaaatcag agggcaggaa 120
ctgcagaaca gcaaaaagtc agatagcacc acatagcaga cccgccataa aacgccctga 180
gaagcccgtg acgggctttt cttgtattat gggtagtttc cttgcatgaa tccataaaag 240
gcgcctgtag tgccatttac ccccattcac tgccagagcc gtgagcgcag cgaactgaat 300
gtcacgaaaa agacagcgac tcaggtgcct gatggtcgga gacaaaagga atattcagcg 360
atttgcccga gcttgcgagg gtgctactta agcctttagg gttttaaggt ctgttttgta 420
gaggagcaaa cagcgtttgc gacatccttt tgtaatactg cggaactgac taaagtagtg 480
agttatacac agggctggga tctattcttt ttatcttttt ttattctttc tttattctat 540
aaattataac cacttgaata taaacaaaaa aaacacacaa aggtctagcg gaatttacag 600
agggtctagc agaatttaca agttttccag caaaggtcta gcagaattta cagataccca 660
caactcaaag gaaaaggact agtaattatc attgactagc ccatctcaat tggtatagtg 720
attaaaatca cctagaccaa ttgagatgta tgtctgaatt agttgttttc aaagcaaatg 780
aactagcgat tagtcgctat gacttaacgg agcatgaaac caagctaatt ttatgctgtg 840
tggcactact caaccccacg attgaaaacc ctacaaggaa agaacggacg gtatcgttca 900
cttataacca atacgctcag atgatgaaca tcagtaggga aaatgcttat ggtgtattag 960
ctaaagcaac cagagagctg atgacgagaa ctgtggaaat caggaatcct ttggttaaag 1020
gctttgagat tttccagtgg acaaactatg ccaagttctc aagcgaaaaa ttagaattag 1080
tttttagtga agagatattg ccttatcttt tccagttaaa aaaattcata aaatataatc 1140
tggaacatgt taagtctttt gaaaacaaat actctatgag gatttatgag tggttattaa 1200
aagaactaac acaaaagaaa actcacaagg caaatataga gattagcctt gatgaattta 1260
agttcatgtt aatgcttgaa aataactacc atgagtttaa aaggcttaac caatgggttt 1320
tgaaaccaat aagtaaagat ttaaacactt acagcaatat gaaattggtg gttgataagc 1380
gaggccgccc gactgatacg ttgattttcc aagttgaact agatagacaa atggatctcg 1440
taaccgaact tgagaacaac cagataaaaa tgaatggtga caaaatacca acaaccatta 1500
catcagattc ctacctacat aacggactaa gaaaaacact acacgatgct ttaactgcaa 1560
aaattcagct caccagtttt gaggcaaaat ttttgagtga catgcaaagt aagcatgatc 1620
tcaatggttc gttctcatgg ctcacgcaaa aacaacgaac cacactagag aacatactgg 1680

-continued

```
ctaaatacgg aaggatctga ggttcttatg gctcttgtat ctatcagtga agcatcaaga   1740
ctaacaaaca aaagtagaac aactgttcac cgttacatat caaagggaaa actgtccata   1800
tgcacagatg aaaacggtgt aaaaaagata gatacatcag agcttttacg agtttttggt   1860
gcattcaaag ctgttcacca tgaacagatc gacaatgtaa cagatgaaca gcatgtaaca   1920
cctaatagaa caggtgaaac cagtaaaaca aagcaactag aacatgaaat tgaacacctg   1980
agacaacttg ttacagctca acagtcacac atagacagcc tgaaacaggc gatgctgctt   2040
atcgaatcaa agctgccgac aacacgggag ccagtgacgc ctcccgtggg gaaaaaatca   2100
tggcaattct ggaagaaata gcgccattcg ccattcaggc tgcgcaactg ttgggaaggg   2160
cgatcggtgc gggcctcttc gctattacgc cagctggcga aagggggatg tgctgcaagg   2220
cgattaagtt gggtaacgcc agggttttcc cagtcacgac gttgtaaaac gacggccagt   2280
gaattcgagc tcggtaccct gtttttccac tcttcgttca ctttcgccag gtagctggtg   2340
aagacgaagg aagtcccgga gccatctgcg cggcgtacta cagcaatgtt ttgtgaaggc   2400
agtttcagac ccggattcag tttggcgatg gcttcatcat cccacttctt gattttgccc   2460
aggtagatgt cgccgagggt tttaccatcc agcaccagtt cgccagactt cagccctgga   2520
atgttaaccg ccagcaccac gccgccaatc acggtcggga actggaacag accttcctga   2580
gccagttttt cgtcagacag cggcgcgtca gaggcaccaa aatcaacggt attagcgata   2640
atctgtttta cgccaccgga agaaccgata ccctggtagt taactttatt accggtttct   2700
ttctggtaag tgtcagccca tttggcatac accggcgcag ggaaggttgc acctgcacct   2760
gtcaggcttg cttctgcaaa cacagagaaa gcactcatcg ataaggtcgc ggcgacaaca   2820
gttgcgacgg tggtacgcat aactttcata atgtctcctg ggaggattca taaagcattg   2880
tttgttggct acgagaagca aaataggaca aacaggtgac agttatatgt aaggaatatg   2940
acagttttat gacagagaga taaagtcttc agtctgattt aaataagcgt tgatattcag   3000
tcaattacaa acattaataa cgaagagatg acagaaaaat tttcattctg tgacagagaa   3060
aaagtagccg aagatgacgg tttgtcacat ggagttggca ggatgtttga ttaaaatgaa   3120
gcctgctttt ttatactaag ttggcattat aaaaaagcat tgcttatcaa tttgttgcaa   3180
cgaacaggtc actatcagtc aaaataaaat cattatttga tttcgaattc tcatgtttga   3240
cagcttatca tcgataagct ttaatgcggt agtttatcac agttaaattg ctaacgcagt   3300
caggcaccgt gtatgaaatc taacaatgcg ctcatcgtca tcctcggcac cgtcaccctg   3360
gatgctgtag gcataggctt ggttatgccg gtactgccgg gcctcttgcg ggatatcgtc   3420
cattccgaca gcatcgccag tcactatggc gtgctgctag cgctatatgc gttgatgcaa   3480
tttctatgcg cacccgttct cggagcactg tccgaccgct ttggccgccg cccagtcctg   3540
ctcgcttcgc tacttggagc cactatcgac tacgcgatca tggcgaccac acccgtcctg   3600
tggatctccg gataagtaga cagcctgata agtcgcacga aaaacaggta ttgacaacat   3660
gaagtaacat gcagtaagat acaaatcgct aggtaacact agcagcgtca accgggcgct   3720
ctagctagag ccaagctagc ttggccggat ccgagatttt caggagctaa ggaagctaaa   3780
atggagaaaa aaatcactgg atataccacc gttgatatat cccaatggca tcgtaaagaa   3840
cattttgagg catttcagtc agttgctcaa tgtacctata accagaccgt tcagctggat   3900
attacggcct ttttaaagac cgtaaagaaa aataagcaca agttttatcc ggcctttatt   3960
cacattcttg cccgcctgat gaatgctcat ccggaattcc gtatggcaat gaaagacggt   4020
gagctggtga tatgggatag tgttcaccct tgttacaccg ttttccatga gcaaactgaa   4080
```

```
acgttttcat cgctctggag tgaataccac gacgatttcc ggcagtttct acacatatat   4140

tcgcaagatg tggcgtgtta cggtgaaaac ctggcctatt tccctaaagg gtttattgag   4200

aatatgtttt tcgtctcagc caatccctgg gtgagtttca ccagttttga tttaaacgtg   4260

gccaatatgg acaacttctt cgcccccgtt ttcaccatgg gcaaatatta tacgcaaggc   4320

gacaaggtgc tgatgccgct ggcgattcag gttcatcatg ccgtctgtga tggcttccat   4380

gtcggcagaa tgcttaatga attacaacag tactgcgatg agtggcaggg cggggcgtaa   4440

tttttttaag gcagttattg gtgcccttaa acgcctggtg ctacgcctga ataagtgata   4500

ataagcggat gaatggcaga aattcgtcga agcttaacac agaaaaaagc ccgcacctga   4560

cagtgcgggc tttttttttc gaccactgca gtctgttaca ggtcactaat accatctaag   4620

tagttgattc atagtgactg catatgttgt gttttacagt attatgtagt ctgtttttta   4680

tgcaaaatct aatttaatat attgatattt atatcatttt acgtttctcg ttcagctttt   4740

ttatactaac ttgagcggcc cttgacgatg ccacatcctg agcaaataat tcaaccacta   4800

attgtgagcg gataacacaa ggaggaaaca gctatgtcat taccgttctt aacttctgca   4860

ccgggaaagg ttattatttt tggtgaacac tctgctgtgt acaacaagcc tgccgtcgct   4920

gctagtgtgt ctgcgttgag aacctacctg ctaataagcg agtcatctgc accagatact   4980

attgaattgg acttcccgga cattagcttt aatcataagt ggtccatcaa tgatttcaat   5040

gccatcaccg aggatcaagt aaactcccaa aaattggcca aggctcaaca agccaccgat   5100

ggcttgtctc aggaactcgt tagtcttttg gatccgttgt tagctcaact atccgaatcc   5160

ttccactacc atgcagcgtt ttgtttcctg tatatgtttg tttgcctatg cccccatgcc   5220

aagaatatta agttttcctt aaagtctact ttacccatcg gtgctgggtt gggctcaagc   5280

gcctctattt ctgtatcact ggccttagct atggcctact tgggggggtt aataggatct   5340

aatgacttgg aaaagctgtc agaaaacgat aagcatatag tgaatcaatg ggccttcata   5400

ggtgaaaagt gtattcacgg taccccttca ggaatagata acgctgtggc cacttatggt   5460

aatgccctgc tatttgaaaa agactcacat aatggaacaa taaacacaaa caattttaag   5520

ttcttagatg atttcccagc cattccaatg atcctaacct atactagaat tccaaggtct   5580

acaaaagatc ttgttgctcg cgttcgtgtg ttggtcaccg agaaatttcc tgaagttatg   5640

aagccaattc tagatgccat gggtgaatgt gccctacaag gcttagagat catgactaag   5700

ttaagtaaat gtaaaggcac cgatgacgag gctgtagaaa ctaataatga actgtatgaa   5760

caactattgg aattgataag aataaatcat ggactgcttg tctcaatcgg tgtttctcat   5820

cctggattag aacttattaa aaatctgagc gatgatttga gaattggctc cacaaaactt   5880

accggtgctg gtggcggcgg ttgctctttg actttgttac gaagagacat tactcaagag   5940

caaattgaca gcttcaaaaa gaaattgcaa gatgatttta gttacgagac atttgaaaca   6000

gacttgggtg ggactggctg ctgtttgtta agcgcaaaaa atttgaataa agatcttaaa   6060

atcaaatccc tagtattcca attatttgaa aataaaacta ccacaaagca acaaattgac   6120

gatctattat tgccaggaaa cacgaattta ccatggactt cataagctaa tttgcgatag   6180

gcctgcaccc ttaaggagga aaaaaacatg tcagagttga gagccttcag tgccccaggg   6240

aaagcgttac tagctggtgg atatttagtt ttagatacaa aatatgaagc atttgtagtc   6300

ggattatcgg caagaatgca tgctgtagcc catccttacg gttcattgca agggtctgat   6360

aagtttgaag tgcgtgtgaa aagtaaacaa tttaaagatg ggagtggctg gtaccatata   6420
```

-continued

```
agtcctaaaa gtggcttcat tcctgtttcg ataggcggat ctaagaaccc tttcattgaa   6480
aaagttatcg ctaacgtatt tagctacttt aaacctaaca tggacgacta ctgcaataga   6540
aacttgttcg ttattgatat tttctctgat gatgcctacc attctcagga ggatagcgtt   6600
accgaacatc gtggcaacag aagattgagt tttcattcgc acagaattga agaagttccc   6660
aaaacagggc tgggctcctc ggcaggttta gtcacagttt taactacagc tttggcctcc   6720
ttttttgtat cggacctgga aaataatgta gacaaatata gagaagttat tcataattta   6780
gcacaagttg ctcattgtca agctcagggt aaaattggaa gcgggtttga tgtagcggcg   6840
gcagcatatg gatctatcag atatagaaga ttcccacccg cattaatctc taatttgcca   6900
gatattggaa gtgctactta cggcagtaaa ctggcgcatt tggttgatga agaagactgg   6960
aatattacga ttaaaagtaa ccatttacct tcgggattaa ctttatggat gggcgatatt   7020
aagaatggtt cagaaacagt aaaactggtc cagaaggtaa aaaattggta tgattcgcat   7080
atgccagaaa gcttgaaaat atatacagaa ctcgatcatg caaattctag atttatggat   7140
ggactatcta aactagatcg cttacacgag actcatgacg attacagcga tcagatattt   7200
gagtctcttg agaggaatga ctgtacctgt caaaagtatc ctgaaatcac agaagttaga   7260
gatgcagttg ccacaattag acgttccttt agaaaaataa ctaaagaatc tggtgccgat   7320
atcgaacctc ccgtacaaac tagcttattg gatgattgcc agaccttaaa aggagttctt   7380
acttgcttaa tacctggtgc tggtggttat gacgccattg cagtgattac taagcaagat   7440
gttgatctta gggctcaaac cgctaatgac aaaagatttt ctaaggttca atggctggat   7500
gtaactcagg ctgactgggg tgttaggaaa gaaaaagatc cggaaactta tcttgataaa   7560
taacttaagg tagctgcatg cagaattcgc ccttaaggag gaaaaaaaaa tgaccgttta   7620
cacagcatcc gttaccgcac ccgtcaacat cgcaaccctt aagtattggg ggaaaaggga   7680
cacgaagttg aatctgccca ccaattcgtc catatcagtg actttatcgc aagatgacct   7740
cagaacgttg acctctgcgg ctactgcacc tgagtttgaa cgcgacactt tgtggttaaa   7800
tggagaacca cacagcatcg acaatgaaag aactcaaaat tgtctgcgcg acctacgcca   7860
attaagaaag gaaatggaat cgaaggacgc ctcattgccc acattatctc aatggaaact   7920
ccacattgtc tccgaaaata actttcctac agcagctggt ttagcttcct ccgctgctgg   7980
ctttgctgca ttggtctctg caattgctaa gttataccaa ttaccacagt caacttcaga   8040
aatatctaga atagcaagaa aggggtctgg ttcagcttgt agatcgttgt ttggcggata   8100
cgtggcctgg gaaatgggaa aagctgaaga tggtcatgat tccatggcag tacaaatcgc   8160
agacagctct gactggcctc agatgaaagc ttgtgtccta gttgtcagcg atattaaaaa   8220
ggatgtgagt tccactcagg gtatgcaatt gaccgtggca acctccgaac tatttaaaga   8280
aagaattgaa catgtcgtac caaagagatt tgaagtcatg cgtaaagcca ttgttgaaaa   8340
agatttcgcc acctttgcaa aggaaacaat gatggattcc aactctttcc atgccacatg   8400
tttggactct ttccctccaa tattctacat gaatgacact tccaagcgta tcatcagttg   8460
gtgccacacc attaatcagt tttacggaga aacaatcgtt gcatacacgt ttgatgcagg   8520
tccaaatgct gtgttgtact acttagctga aaatgagtcg aaactctttg catttatcta   8580
taaattgttt ggctctgttc ctggatggga caagaaattt actactgagc agcttgaggc   8640
tttcaaccat caatttgaat catctaactt tactgcacgt gaattggatc ttgagttgca   8700
aaaggatgtt gccagagtga ttttaactca agtcggttca ggcccacaag aaacaaacga   8760
atctttgatt gacgcaaaga ctggtctacc aaaggaataa gatcaattcg ctgcatcgcc   8820
```

```
cttaggaggt aaaaaaaaat gactgccgac aacaatagta tgccccatgg tgcagtatct   8880
agttacgcca aattagtgca aaaccaaaca cctgaagaca ttttggaaga gtttcctgaa   8940
attattccat tacaacaaag acctaatacc cgatctagtg agacgtcaaa tgacgaaagc   9000
ggagaaacat gtttttctgg tcatgatgag gagcaaatta agttaatgaa tgaaaattgt   9060
attgttttgg attgggacga taatgctatt ggtgccggta ccaagaaagt ttgtcattta   9120
atggaaaata ttgaaaaggg tttactacat cgtgcattct ccgtctttat tttcaatgaa   9180
caaggtgaat tacttttaca acaaagagcc actgaaaaaa taactttccc tgatctttgg   9240
actaacacat gctgctctca tccactatgt attgatgacg aattaggttt gaagggtaag   9300
ctagacgata agattaaggg cgctattact gcggcggtga gaaaactaga tcatgaatta   9360
ggtattccag aagatgaaac taagacaagg ggtaagtttc actttttaaa cagaatccat   9420
tacatggcac caagcaatga accatggggt gaacatgaaa ttgattacat cctattttat   9480
aagatcaacg ctaaagaaaa cttgactgtc aacccaaacg tcaatgaagt tagagacttc   9540
aaatgggttt caccaaatga tttgaaaact atgtttgctg acccaagtta caagtttacg   9600
ccttggttta agattatttg cgagaattac ttattcaact ggtgggagca attagatgac   9660
ctttctgaag tggaaaatga caggcaaatt catagaatgc tataacaacg cgtctacaaa   9720
taaaaaaggc acgtcagatg acgtgccttt tttcttgggg ccggggatcc tctagagtcg   9780
acctgcaggc atgcaagctt ggcgtaatca tggtcatagc tgtttcctgt gtgaaattgt   9840
tatccgctca caattccaca caacatacga gccggaagca taaagtgtaa agcctggggt   9900
gcctaatgag tgagctaact cacattaatt gcgttgcgct cactgcccgc tttccagtcg   9960
ggaaacctgt cgtgccagct gcattaatga atcggccaac gcgcggggag aggcggtttg  10020
cgtattgggc gctttctcat agctcacgct gtaggtatct cagttcggtg taggtcgttc  10080
gctccaagct gggctgtgtg ccgaacccca gagtcccgct cagaagaact cgtcaagaag  10140
gcgatagaag gcgatgcgct gcgaatcggg agcggcgata ccgtaaagca cgaggaagcg  10200
gtcagcccat tcgccgccaa gctcttcagc aatatcacgg gtagccaacg ctatgtcctg  10260
atagcggtcc gccacaccca gccggccaca gtcgatgaat ccagaaaagc ggccattttc  10320
caccatgata ttcggcaagc aggcatcgcc atgggtcacg acgagatcct cgccgtcggg  10380
catgcgcgcc ttgagcctgg cgaacagttc ggctggcgcg agcccctgat gctcttcgtc  10440
cagatcatcc tgatcgacaa gaccggcttc catccgagta cgtgctcgct cgatgcgatg  10500
tttcgcttgg tggtcgaatg ggcaggtagc cggatcaagc gtatgcagcc gccgcattgc  10560
atcagccatg atggatactt tctcggcagg agcaaggtga gatgacagga gatcctgccc  10620
cggcacttcg cccaatagca gccagtccct tcccgcttca gtgccaacgt cgagcacagc  10680
tgcgcaagga acgcccgtcg tggccagcca cgatagccgc gctgcctcgt cctgcagttc  10740
attcagggca ccggacaggt cggtcttgac aaaaagaacc gggcgcccct gcgctgacag  10800
ccggaacacg gcggcatcag agcagccgat tgtctgttgt gcccagtcat agccgaatag  10860
cctctccacc caagcggccg gagaacctgc gtgcaatcca tcttgttcaa tcatgcgaaa  10920
cgatcctcat cctgtctctt gatcactacc gcattaaagc atatcgatga taagctgtca  10980
aacatgagcg ttcttcgggg cgaaaactct caaggatctt accgctgttg agatccagtt  11040
cgatgtaacc cactcgtgca cccaactgat cttcagcatc ttttactttc accagcgttt  11100
ctgggtgagc aaaaacagga aggcaaaatg ccgcaaaaaa gggaataagg gcgacacgga  11160
```

-continued

```
aatgttgaat actcatactc ttcctttttc aatattattg aagcatttat cagggttatt  11220

gtctcatgag cggatacata tttgaatgta tttagaaaaa taaacaaata ggggttccgc  11280

gcacatttcc ccgaaaagtg ccacctgacg tctaagaaac cattattatc atgacattaa  11340

cctataaaaa taggcgtatc acgaggccct ttcgtcttca agaatt                11386
```

<210> SEQ ID NO 57
<211> LENGTH: 12232
<212> TYPE: DNA
<213> ORGANISM: Artificial Sequence
<220> FEATURE:
<223> OTHER INFORMATION: Nucleotide sequence of prepared plasmid pMW-Tn7-Pgi-KKDyI-TaspA-Tn7

<400> SEQUENCE: 57

```
gacagtaaga cgggtaagcc tgttgatgat accgctgcct tactgggtgc attagccagt     60

ctgaatgacc tgtcacggga taatccgaag tggtcagact ggaaaatcag agggcaggaa    120

ctgcagaaca gcaaaaagtc agatagcacc acatagcaga cccgccataa aacgccctga    180

gaagcccgtg acgggctttt cttgtattat gggtagtttc cttgcatgaa tccataaaag    240

gcgcctgtag tgccatttac ccccattcac tgccagagcc gtgagcgcag cgaactgaat    300

gtcacgaaaa agacagcgac tcaggtgcct gatggtcgga gacaaaagga atattcagcg    360

atttgcccga gcttgcgagg gtgctactta agcctttagg gttttaaggt ctgttttgta    420

gaggagcaaa cagcgtttgc gacatccttt tgtaatactg cggaactgac taaagtagtg    480

agttatacac agggctggga tctattcttt ttatcttttt ttattctttc tttattctat    540

aaattataac cacttgaata taaacaaaaa aaacacacaa aggtctagcg gaatttacag    600

agggtctagc agaatttaca agttttccag caaaggtcta gcagaattta cagataccca    660

caactcaaag gaaaaggact agtaattatc attgactagc ccatctcaat tggtatagtg    720

attaaaatca cctagaccaa ttgagatgta tgtctgaatt agttgttttc aaagcaaatg    780

aactagcgat tagtcgctat gacttaacgg agcatgaaac caagctaatt ttatgctgtg    840

tggcactact caaccccacg attgaaaacc ctacaaggaa agaacggacg gtatcgttca    900

cttataacca atacgctcag atgatgaaca tcagtaggga aaatgcttat ggtgtattag    960

ctaaagcaac cagagagctg atgacgagaa ctgtggaaat caggaatcct ttggttaaag   1020

gctttgagat ttccagtgg acaaactatg ccaagttctc aagcgaaaaa ttagaattag   1080

tttttagtga agagatattg ccttatcttt tccagttaaa aaaattcata aaatataatc   1140

tggaacatgt taagtctttt gaaaacaaat actctatgag gatttatgag tggttattaa   1200

aagaactaac acaaaagaaa actcacaagg caaatataga gattagcctt gatgaattta   1260

agttcatgtt aatgcttgaa aataactacc atgagtttaa aaggcttaac caatgggttt   1320

tgaaaccaat aagtaaagat ttaaacactt acagcaatat gaaattggtg gttgataagc   1380

gaggccgccc gactgatacg ttgattttcc aagttgaact agatagacaa atggatctcg   1440

taaccgaact tgagaacaac cagataaaaa tgaatggtga caaaatacca acaaccatta   1500

catcagattc ctacctacat aacggactaa gaaaaacact acacgatgct ttaactgcaa   1560

aaattcagct caccagtttt gaggcaaaat ttttgagtga catgcaaagt aagcatgatc   1620

tcaatggttc gttctcatgg ctcacgcaaa aacaacgaac cacactagag aacatactgg   1680

ctaaatacgg aaggatctga ggttcttatg gctcttgtat ctatcagtga agcatcaaga   1740

ctaacaaaca aaagtagaac aactgttcac cgttacatat caaagggaaa actgtccata   1800
```

-continued

```
tgcacagatg aaaacggtgt aaaaaagata gatacatcag agcttttacg agtttttggt   1860
gcattcaaag ctgttcacca tgaacagatc gacaatgtaa cagatgaaca gcatgtaaca   1920
cctaatagaa caggtgaaac cagtaaaaca aagcaactag aacatgaaat tgaacacctg   1980
agacaacttg ttacagctca acagtcacac atagacagcc tgaaacaggc gatgctgctt   2040
atcgaatcaa agctgccgac aacacgggag ccagtgacgc ctcccgtggg gaaaaaatca   2100
tggcaattct ggaagaaata gcgccattcg ccattcaggc tgcgcaactg ttgggaaggg   2160
cgatcggtgc gggcctcttc gctattacgc cagctggcga aagggggatg tgctgcaagg   2220
cgattaagtt gggtaacgcc agggttttcc cagtcacgac gttgtaaaac gacggccagt   2280
gaattcgagc tcggtaccct gtttttccac tcttcgttca ctttcgccag gtagctggtg   2340
aagacgaagg aagtcccgga gccatctgcg cggcgtacta cagcaatgtt ttgtgaaggc   2400
agtttcagac ccggattcag tttggcgatg gcttcatcat cccacttctt gattttgccc   2460
aggtagatgt cgccgagggt tttaccatcc agcaccagtt cgccagactt cagccctgga   2520
atgttaaccg ccagcaccac gccgccaatc acggtcggga actggaacag accttcctga   2580
gccagttttt cgtcagacag cggcgcgtca gaggcaccaa aatcaacggt attagcgata   2640
atctgtttta cgccaccgga agaaccgata ccctggtagt taactttatt accggtttct   2700
ttctggtaag tgtcagccca tttggcatac accggcgcag ggaaggttgc acctgcacct   2760
gtcaggcttg cttctgcaaa cacagagaaa gcactcatcg ataaggtcgc ggcgacaaca   2820
gttgcgacgg tggtacgcat aactttcata atgtctcctg ggaggattca taaagcattg   2880
tttgttggct acgagaagca aaataggaca aacaggtgac agttatatgt aaggaatatg   2940
acagttttat gacagagaga taaagtcttc agtctgattt aaataagcgt tgatattcag   3000
tcaattacaa acattaataa cgaagagatg acagaaaaat tttcattctg tgacagagaa   3060
aaagtagccg aagatgacgg tttgtcacat ggagttggca ggatgtttga ttaaaatgaa   3120
gcctgctttt ttatactaag ttggcattat aaaaaagcat tgcttatcaa tttgttgcaa   3180
cgaacaggtc actatcagtc aaaataaaat cattatttga tttcgaattc tcatgtttga   3240
cagcttatca tcgataagct ttaatgcggt agtttatcac agttaaattg ctaacgcagt   3300
caggcaccgt gtatgaaatc taacaatgcg ctcatcgtca tcctcggcac cgtcaccctg   3360
gatgctgtag gcataggctt ggttatgccg gtactgccgg gcctcttgcg ggatatcgtc   3420
cattccgaca gcatcgccag tcactatggc gtgctgctag cgctatatgc gttgatgcaa   3480
tttctatgcg cacccgttct cggagcactg tccgaccgct ttggccgccg cccagtcctg   3540
ctcgcttcgc tacttggagc cactatcgac tacgcgatca tggcgaccac acccgtcctg   3600
tggatctccg gataagtaga cagcctgata agtcgcacga aaaacaggta ttgacaacat   3660
gaagtaacat gcagtaagat acaaatcgct aggtaacact agcagcgtca accgggcgct   3720
ctagctagag ccaagctagc ttggccggat ccgagatttt caggagctaa ggaagctaaa   3780
atggagaaaa aaatcactgg atataccacc gttgatatat cccaatggca tcgtaaagaa   3840
cattttgagg catttcagtc agttgctcaa tgtacctata accagaccgt tcagctggat   3900
attacggcct ttttaaagac cgtaaagaaa aataagcaca agttttatcc ggcctttatt   3960
cacattcttg cccgcctgat gaatgctcat ccggaattcc gtatggcaat gaaagacggt   4020
gagctggtga tatgggatag tgttcaccct tgttacaccg ttttccatga gcaaactgaa   4080
acgttttcat cgctctggag tgaataccac gacgatttcc ggcagtttct acacatatat   4140
tcgcaagatg tggcgtgtta cggtgaaaac ctggcctatt tccctaaagg gtttattgag   4200
```

-continued aatatgtttt tcgtctcagc caatccctgg gtgagtttca ccagttttga tttaaacgtg 4260
gccaatatgg acaacttctt cgcccccgtt ttcaccatgg gcaaatatta tacgcaaggc 4320
gacaaggtgc tgatgccgct ggcgattcag gttcatcatg ccgtctgtga tggcttccat 4380
gtcggcagaa tgcttaatga attacaacag tactgcgatg agtggcaggg cggggcgtaa 4440
ttttttttaag gcagttattg gtgcccttaa acgcctggtg ctacgcctga ataagtgata 4500
ataagcggat gaatggcaga aattcgtcga agcttaacac agaaaaaagc ccgcacctga 4560
cagtgcgggc ttttttttttc gaccactgca gtctgttaca ggtcactaat accatctaag 4620
tagttgattc atagtgactg catatgttgt gttttacagt attatgtagt ctgtttttta 4680
tgcaaaatct aatttaatat attgatattt atatcatttt acgtttctcg ttcagctttt 4740
ttatactaac ttgagcggcc cttgacgatg ccacatcctg agcaaataat tcaaccacta 4800
attgtgagcg gataacacaa ggaggaaaca gctatgtcat taccgttctt aacttctgca 4860
ccgggaaagg ttattatttt tggtgaacac tctgctgtgt acaacaagcc tgccgtcgct 4920
gctagtgtgt ctgcgttgag aacctacctg ctaataagcg agtcatctgc accagatact 4980
attgaattgg acttcccgga cattagcttt aatcataagt ggtccatcaa tgatttcaat 5040
gccatcaccg aggatcaagt aaactcccaa aaattggcca aggctcaaca agccaccgat 5100
ggcttgtctc aggaactcgt tagtcttttg gatccgttgt tagctcaact atccgaatcc 5160
ttccactacc atgcagcgtt ttgtttcctg tatatgtttg tttgcctatg cccccatgcc 5220
aagaatatta agttttcctt aaagtctact ttacccatcg gtgctgggtt gggctcaagc 5280
gcctctattt ctgtatcact ggccttagct atggcctact tgggggggtt aataggatct 5340
aatgacttgg aaaagctgtc agaaaacgat aagcatatag tgaatcaatg ggccttcata 5400
ggtgaaaagt gtattcacgg taccccttca ggaatagata acgctgtggc cacttatggt 5460
aatgccctgc tatttgaaaa agactcacat aatggaacaa taaacacaaa caattttaag 5520
ttcttagatg atttcccagc cattccaatg atcctaacct atactagaat tccaaggtct 5580
acaaaagatc ttgttgctcg cgttcgtgtg ttggtcaccg agaaatttcc tgaagttatg 5640
aagccaattc tagatgccat gggtgaatgt gccctacaag gcttagagat catgactaag 5700
ttaagtaaat gtaaaggcac cgatgacgag gctgtagaaa ctaataatga actgtatgaa 5760
caactattgg aattgataag aataaatcat ggactgcttg tctcaatcgg tgtttctcat 5820
cctggattag aacttattaa aaatctgagc gatgatttga gaattggctc cacaaaactt 5880
accggtgctg gtggcggcgg ttgctctttg actttgttac gaagagacat tactcaagag 5940
caaattgaca gcttcaaaaa gaaattgcaa gatgatttta gttacgagac atttgaaaca 6000
gacttgggtg ggactggctg ctgtttgtta agcgcaaaaa atttgaataa agatcttaaa 6060
atcaaatccc tagtattcca attatttgaa aataaaacta ccacaaagca acaaattgac 6120
gatctattat tgccaggaaa cacgaattta ccatggactt cataagctaa tttgcgatag 6180
gcctgcaccc ttaaggagga aaaaaacatg tcagagttga gagccttcag tgccccaggg 6240
aaagcgttac tagctggtgg atatttagtt ttagatacaa aatatgaagc atttgtagtc 6300
ggattatcgg caagaatgca tgctgtagcc catccttacg gttcattgca agggtctgat 6360
aagtttgaag tgcgtgtgaa aagtaaacaa tttaaagatg gggagtggct gtaccatata 6420
agtcctaaaa gtggcttcat tcctgtttcg ataggcggat ctaagaaccc tttcattgaa 6480
aaagttatcg ctaacgtatt tagctacttt aaacctaaca tggacgacta ctgcaataga 6540

-continued

```
aacttgttcg ttattgatat tttctctgat gatgcctacc attctcagga ggatagcgtt   6600
accgaacatc gtggcaacag aagattgagt tttcattcgc acagaattga agaagttccc   6660
aaaacagggc tgggctcctc ggcaggttta gtcacagttt taactacagc tttggcctcc   6720
tttttgtat cggacctgga aaataatgta gacaaatata gagaagttat tcataattta    6780
gcacaagttg ctcattgtca agctcagggt aaaattggaa gcgggtttga tgtagcggcg   6840
gcagcatatg gatctatcag atatagaaga ttcccacccg cattaatctc taatttgcca   6900
gatattggaa gtgctactta cggcagtaaa ctggcgcatt tggttgatga agaagactgg   6960
aatattacga ttaaaagtaa ccatttacct tcgggattaa ctttatggat gggcgatatt   7020
aagaatggtt cagaaacagt aaaactggtc cagaaggtaa aaaattggta tgattcgcat   7080
atgccagaaa gcttgaaaat atatacagaa ctcgatcatg caaattctag atttatggat   7140
ggactatcta aactagatcg cttacacgag actcatgacg attacagcga tcagatattt   7200
gagtctcttg agaggaatga ctgtacctgt caaaagtatc ctgaaatcac agaagttaga   7260
gatgcagttg ccacaattag acgttccttt agaaaaataa ctaaagaatc tggtgccgat   7320
atcgaacctc ccgtacaaac tagcttattg gatgattgcc agaccttaaa aggagttctt   7380
acttgcttaa tacctggtgc tggtggttat gacgccattg cagtgattac taagcaagat   7440
gttgatctta gggctcaaac cgctaatgac aaaagatttt ctaaggttca atggctggat   7500
gtaactcagg ctgactgggg tgttaggaaa gaaaaagatc cggaaactta tcttgataaa   7560
taacttaagg tagctgcatg cagaattcgc ccttaaggag gaaaaaaaaa tgaccgttta   7620
cacagcatcc gttaccgcac ccgtcaacat cgcaaccctt aagtattggg ggaaaaggga   7680
cacgaagttg aatctgccca ccaattcgtc catatcagtg actttatcgc aagatgacct   7740
cagaacgttg acctctgcgg ctactgcacc tgagtttgaa cgcgacactt tgtggttaaa   7800
tggagaacca cacagcatcg acaatgaaag aactcaaaat tgtctgcgcg acctacgcca   7860
attaagaaag gaaatggaat cgaaggacgc ctcattgccc acattatctc aatggaaact   7920
ccacattgtc tccgaaaata actttcctac agcagctggt ttagcttcct ccgctgctgg   7980
ctttgctgca ttggtctctg caattgctaa gttataccaa ttaccacagt caacttcaga   8040
aatatctaga atagcaagaa aggggtctgg ttcagcttgt agatcgttgt ttggcggata   8100
cgtggcctgg gaaatgggaa aagctgaaga tggtcatgat tccatggcag tacaaatcgc   8160
agacagctct gactggcctc agatgaaagc ttgtgtccta gttgtcagcg atattaaaaa   8220
ggatgtgagt tccactcagg gtatgcaatt gaccgtggca acctccgaac tatttaaaga   8280
aagaattgaa catgtcgtac caaagagatt tgaagtcatg cgtaaagcca ttgttgaaaa   8340
agatttcgcc acctttgcaa aggaaacaat gatggattcc aactctttcc atgccacatg   8400
tttggactct ttccctccaa tattctacat gaatgacact tccaagcgta tcatcagttg   8460
gtgccacacc attaatcagt tttacggaga aacaatcgtt gcatacacgt ttgatgcagg   8520
tccaaatgct gtgttgtact acttagctga aaatgagtcg aaactctttg catttatcta   8580
taaattgttt ggctctgttc ctggatggga caagaaattt actactgagc agcttgaggc   8640
tttcaaccat caatttgaat catctaactt tactgcacgt gaattggatc ttgagttgca   8700
aaaggatgtt gccagagtga ttttaactca agtcggttca ggcccacaag aaacaaacga   8760
atctttgatt gacgcaaaga ctggtctacc aaaggaataa gatcaattcg ctgcatcgcc   8820
cttaggaggt aaaaaaaaat gactgccgac aacaatagta tgccccatgg tgcagtatct   8880
agttacgcca aattagtgca aaaccaaaca cctgaagaca ttttggaaga gtttcctgaa   8940
```

```
attattccat tacaacaaag acctaatacc cgatctagtg agacgtcaaa tgacgaaagc   9000
ggagaaacat gtttttctgg tcatgatgag gagcaaatta agttaatgaa tgaaaattgt   9060
attgttttgg attgggacga taatgctatt ggtgccggta ccaagaaagt ttgtcattta   9120
atggaaaata ttgaaaaggg tttactacat cgtgcattct ccgtctttat tttcaatgaa   9180
caaggtgaat tacttttaca acaaagagcc actgaaaaaa taactttccc tgatctttgg   9240
actaacacat gctgctctca tccactatgt attgatgacg aattaggttt gaagggtaag   9300
ctagacgata agattaaggg cgctattact gcggcggtga gaaaactaga tcatgaatta   9360
ggtattccag aagatgaaac taagacaagg ggtaagtttc actttttaaa cagaatccat   9420
tacatggcac caagcaatga accatggggt gaacatgaaa ttgattacat cctattttat   9480
aagatcaacg ctaaagaaaa cttgactgtc aacccaaacg tcaatgaagt tagagacttc   9540
aaatgggttt caccaaatga tttgaaaact atgtttgctg acccaagtta caagtttacg   9600
ccttggttta agattatttg cgagaattac ttattcaact ggtgggagca attagatgac   9660
ctttctgaag tggaaaatga caggcaaatt catagaatgc tataacaacg cgtctacaaa   9720
taaaaaaggc acgtcagatg acgtgccttt tttcttgggg ccggggatcc tctagagtcg   9780
aaagaaaaat gccccgctta cgcagggcat ccatttatta ctcaaccgta accgattttg   9840
ccaggttacg cggctggtca acgtcggtgc ctttgatcag cgcgacatgg taagccagca   9900
gctgcagcgg aacggtgtag aagatcggtg caatcacctc ttccacatgc ggcatctcga   9960
tgatgtgcat gttatcgcta cttacaaaac ccgcatcctg atcggcgaag acatacaact  10020
gaccgccacg cgcgcgaact tcttcaatgt tggatttcag tttttccagc aattcgttgt  10080
tcggtgcaac aacaataacc ggcatatcgg catcaattag cgccagcgga ccgtgtttca  10140
gttcgccagc agcgtaggct tcagcgtgaa tgtaagagat ctctttcaac ttcaatgcgc  10200
cttccagcgc gattgggtac tgatcgccac ggcccaggaa cagcgcgtga tgtttgtcag  10260
agaaatcttc tgccagcgct tcaatgcgtt tgtcctgaga cagcatctgc tcaatacggc  10320
tcggcagcgc ctgcagacca tgcacgatgt catgttcaat ggaggcatcc agacctttca  10380
ggcgagacag cttcgccacc agcatcaaca gcacagttaa ctgagtggtg aatgctttag  10440
tggatgccac gccgatttct gtacccgcgt tggtcattag cgccagatcg gattcgcgca  10500
ccagagaaga acccggaacg ttacagattg ccagtgaacc aaggtaaccc agctctttcg  10560
acagacgcag gccagccagg gtatccgcgg tttcgccaga ctgtgacagg ggatcctcta  10620
gagtcgacct gcaggcatgc aagcttggcg taatcatggt catagctgtt tcctgtgtga  10680
aattgttatc cgctcacaat tccacacaac atacgagccg gaagcataaa gtgtaaagcc  10740
tggggtgcct aatgagtgag ctaactcaca ttaattgcgt tgcgctcact gcccgctttc  10800
cagtcgggaa acctgtcgtg ccagctgcat taatgaatcg gccaacgcgc ggggagaggc  10860
ggtttgcgta ttgggcgctt tctcatagct cacgctgtag gtatctcagt tcggtgtagg  10920
tcgttcgctc caagctgggc tgtgtgccga accccagagt cccgctcaga agaactcgtc  10980
aagaaggcga tagaaggcga tgcgctgcga atcgggagcg gcgataccgt aaagcacgag  11040
gaagcggtca gcccattcgc cgccaagctc ttcagcaata tcacgggtag ccaacgctat  11100
gtcctgatag cggtccgcca cacccagccg gccacagtcg atgaatccag aaaagcggcc  11160
attttccacc atgatattcg gcaagcaggc atcgccatgg gtcacgacga gatcctcgcc  11220
gtcgggcatg cgcgccttga gcctggcgaa cagttcggct ggcgcgagcc cctgatgctc  11280
```

```
ttcgtccaga tcatcctgat cgacaagacc ggcttccatc cgagtacgtg ctcgctcgat  11340

gcgatgtttc gcttggtggt cgaatgggca ggtagccgga tcaagcgtat gcagccgccg  11400

cattgcatca gccatgatgg atactttctc ggcaggagca aggtgagatg acaggagatc  11460

ctgccccggc acttcgccca atagcagcca gtcccttccc gcttcagtgc caacgtcgag  11520

cacagctgcg caaggaacgc ccgtcgtggc cagccacgat agccgcgctg cctcgtcctg  11580

cagttcattc agggcaccgg acaggtcggt cttgacaaaa agaaccgggc gcccctgcgc  11640

tgacagccgg aacacggcgg catcagagca gccgattgtc tgttgtgccc agtcatagcc  11700

gaatagcctc tccacccaag cggccggaga acctgcgtgc aatccatctt gttcaatcat  11760

gcgaaacgat cctcatcctg tctcttgatc actaccgcat taaagcatat cgatgataag  11820

ctgtcaaaca tgagcgttct tcggggcgaa aactctcaag gatcttaccg ctgttgagat  11880

ccagttcgat gtaacccact cgtgcaccca actgatcttc agcatctttt actttcacca  11940

gcgtttctgg gtgagcaaaa acaggaaggc aaaatgccgc aaaaaaggga ataagggcga  12000

cacggaaatg ttgaatactc atactcttcc tttttcaata ttattgaagc atttatcagg  12060

gttattgtct catgagcgga tacatatttg aatgtattta gaaaaataaa caaatagggg  12120

ttccgcgcac atttccccga aaagtgccac ctgacgtcta agaaaccatt attatcatga  12180

cattaaccta taaaaatagg cgtatcacga ggccctttcg tcttcaagaa tt          12232
```

<210> SEQ ID NO 58
<211> LENGTH: 9175
<212> TYPE: DNA
<213> ORGANISM: Artificial Sequence
<220> FEATURE:
<223> OTHER INFORMATION: Nucleotide sequence containing genomic sequence encoding downstream enzymes in the mevalonate pathway

<400> SEQUENCE: 58

```
ttagtacagc ggcttaccgc tactgtcttt aatattggtc ttccacgcag cgcgaacctg     60

ttcaactaca ctatccggca ggctggcgta atccaggtcg ttcgcctgtt tagccccggt    120

tttgtacgcc cagtcgaaga atttcagcac ttctgtgcct tgttctggtt tcttctgatc    180

tttgtggatc agaatgaacg tggtagaggt aataggccat gcatcttcgc ctttctggtt    240

ggtcagatcc tgagcgaagg ttttgctcca gtctgcacct tttgctgcat tagcgaagtt    300

ttcttcggtc ggactaaccg gtttaccatc agcggagatc agtttggtgt acgccaggtt    360

gttctgcttc gcgtaagcat attcaacata accaattgca cccggcagac gctgaacgaa    420

cgcggcgata ccgtcgttac ctttaccgcc cagaccgatc ggccatttta cggtagagcc    480

agtaccaacg ttgtttttcc actcttcgtt cactttcgcc aggtagctgg tgaagacgaa    540

ggaagtcccg gagccatctg cgcggcgtac tacagcaatg ttttgtgaag gcagtttcag    600

acccggattc agtttggcga tggcttcatc atcccacttc ttgattttgc ccaggtagat    660

gtcgccgagg gttttaccat ccagcaccag ttcgccagac ttcagccctg gaatgttaac    720

cgccagcacc acgccgccaa tcacggtcgg gaactggaac agaccttcct gagccagttt    780

ttcgtcagac agcggcgcgt cagaggcacc aaaatcaacg gtattagcga taatctgttt    840

tacgccaccg gaagaaccga taccctggta gttaacttta ttaccggttt ctttctggta    900

agtgtcagcc catttggcat acaccggcgc agggaaggtt gcacctgcac ctgtcaggct    960

tgcttctgca aacacagaga aagcactcat cgataaggtc gcggcgacaa cagttgcgac   1020

ggtggtacgc ataactttca taatgtctcc tgggaggatt cataaagcat tgtttgttgg   1080
```

ctacgagaag caaaatagga caaacaggtg acagttatat gtaaggaata tgacagtttt 1140
atgacagaga gataaagtct tcagtctgat ttaaataagc gttgatattc agtcaattac 1200
aaacattaat aacgaagaga tgacagaaaa attttcattc tgtgacagag aaaaagtagc 1260
cgaagatgac ggtttgtcac atggagttgg caggatgttt gattaaaatg aagcctgctt 1320
ttttatacta agttggcatt ataaaaaagc attgcttatc aatttgttgc aacgaacagg 1380
tcactatcag tcaaaataaa atcattattt gatttcgaat tctcatgttt gacagcttat 1440
catcgataag ctttaatgcg gtagtttatc acagttaaat tgctaacgca gtcaggcacc 1500
gtgtatgaaa tctaacaatg cgctcatcgt catcctcggc accgtcaccc tggatgctgt 1560
aggcataggc ttggttatgc cggtactgcc gggcctcttg cgggatatcg tccattccga 1620
cagcatcgcc agtcactatg gcgtgctgct agcgctatat gcgttgatgc aatttctatg 1680
cgcacccgtt ctcggagcac tgtccgaccg ctttggccgc cgcccagtcc tgctcgcttc 1740
gctacttgga gccactatcg actacgcgat catggcgacc acacccgtcc tgtggatctc 1800
cggataagta gacagcctga taagtcgcac gaaaaacagg tattgacaac atgaagtaac 1860
atgcagtaag atacaaatcg ctaggtaaca ctagcagcgt caaccgggcg ctctagctag 1920
agccaagcta gcttggccgg atccgagatt ttcaggagct aaggaagcta aaatggagaa 1980
aaaaatcact ggatatacca ccgttgatat atcccaatgg catcgtaaag aacattttga 2040
ggcatttcag tcagttgctc aatgtaccta taaccagacc gttcagctgg atattacggc 2100
ctttttaaag accgtaaaga aaaataagca caagttttat ccggccttta ttcacattct 2160
tgcccgcctg atgaatgctc atccggaatt ccgtatggca atgaaagacg gtgagctggt 2220
gatatgggat agtgttcacc cttgttacac cgttttccat gagcaaactg aaacgttttc 2280
atcgctctgg agtgaatacc acgacgattt ccggcagttt ctacacatat attcgcaaga 2340
tgtggcgtgt tacggtgaaa acctggccta tttccctaaa gggtttattg agaatatgtt 2400
tttcgtctca gccaatccct gggtgagttt caccagtttt gatttaaacg tggccaatat 2460
ggacaacttc ttcgcccccg ttttcaccat gggcaaatat tatacgcaag gcgacaaggt 2520
gctgatgccg ctggcgattc aggttcatca tgccgtctgt gatggcttcc atgtcggcag 2580
aatgcttaat gaattacaac agtactgcga tgagtggcag ggcggggcgt aattttttta 2640
aggcagttat tggtgccctt aaacgcctgg tgctacgcct gaataagtga taataagcgg 2700
atgaatggca gaaattcgtc gaagcttaac acagaaaaaa gcccgcacct gacagtgcgg 2760
gctttttttt tcgaccactg cagtctgtta caggtcacta ataccatcta agtagttgat 2820
tcatagtgac tgcatatgtt gtgttttaca gtattatgta gtctgttttt tatgcaaaat 2880
ctaatttaat atattgatat ttatatcatt ttacgtttct cgttcagctt ttttatacta 2940
acttgagcgg cccttgacga tgccacatcc tgagcaaata attcaaccac taattgtgag 3000
cggataacac aaggaggaaa cagctatgtc attaccgttc ttaacttctg caccgggaaa 3060
ggttattatt tttggtgaac actctgctgt gtacaacaag cctgccgtcg ctgctagtgt 3120
gtctgcgttg agaacctacc tgctaataag cgagtcatct gcaccagata ctattgaatt 3180
ggacttcccg gacattagct ttaatcataa gtggtccatc aatgatttca atgccatcac 3240
cgaggatcaa gtaaactccc aaaaattggc caaggctcaa caagccaccg atggcttgtc 3300
tcaggaactc gttagtcttt tggatccgtt gttagctcaa ctatccgaat ccttccacta 3360
ccatgcagcg ttttgtttcc tgtatatgtt tgtttgccta tgcccccatg ccaagaatat 3420
taagttttcc ttaaagtcta ctttacccat cggtgctggg ttgggctcaa gcgcctctat 3480

-continued

```
ttctgtatca ctggccttag ctatggccta cttggggggg ttaataggat ctaatgactt   3540
ggaaaagctg tcagaaaacg ataagcatat agtgaatcaa tgggccttca taggtgaaaa   3600
gtgtattcac ggtacccctt caggaataga taacgctgtg gccacttatg gtaatgccct   3660
gctatttgaa aaagactcac ataatggaac aataaacaca aacaatttta agttcttaga   3720
tgatttccca gccattccaa tgatcctaac ctatactaga attccaaggt ctacaaaaga   3780
tcttgttgct cgcgttcgtg tgttggtcac cgagaaattt cctgaagtta tgaagccaat   3840
tctagatgcc atgggtgaat gtgccctaca aggcttagag atcatgacta agttaagtaa   3900
atgtaaaggc accgatgacg aggctgtaga aactaataat gaactgtatg aacaactatt   3960
ggaattgata agaataaatc atggactgct tgtctcaatc ggtgtttctc atcctggatt   4020
agaacttatt aaaaatctga gcgatgattt gagaattggc tccacaaaac ttaccggtgc   4080
tggtggcggc ggttgctctt tgactttgtt acgaagagac attactcaag agcaaattga   4140
cagcttcaaa aagaaattgc aagatgattt tagttacgag acatttgaaa cagacttggg   4200
tgggactggc tgctgtttgt taagcgcaaa aaatttgaat aaagatctta aaatcaaatc   4260
cctagtattc caattatttg aaaataaaac taccacaaag caacaaattg acgatctatt   4320
attgccagga aacacgaatt taccatggac ttcataagct aatttgcgat aggcctgcac   4380
ccttaaggag gaaaaaaaca tgtcagagtt gagagccttc agtgccccag ggaaagcgtt   4440
actagctggt ggatatttag ttttagatac aaaatatgaa gcatttgtag tcggattatc   4500
ggcaagaatg catgctgtag cccatcctta cggttcattg caagggtctg ataagtttga   4560
agtgcgtgtg aaaagtaaac aatttaaaga tggggagtgg ctgtaccata taagtcctaa   4620
aagtggcttc attcctgttt cgataggcgg atctaagaac cctttcattg aaaaagttat   4680
cgctaacgta tttagctact ttaaacctaa catggacgac tactgcaata gaaacttgtt   4740
cgttattgat attttctctg atgatgccta ccattctcag gaggatagcg ttaccgaaca   4800
tcgtggcaac agaagattga gttttcattc gcacagaatt gaagaagttc ccaaaacagg   4860
gctgggctcc tcggcaggtt tagtcacagt tttaactaca gctttggcct cctttttgt    4920
atcggacctg gaaaataatg tagacaaata tagagaagtt attcataatt tagcacaagt   4980
tgctcattgt caagctcagg gtaaaattgg aagcgggttt gatgtagcgg cggcagcata   5040
tggatctatc agatatagaa gattcccacc cgcattaatc tctaatttgc cagatattgg   5100
aagtgctact tacggcagta aactggcgca tttggttgat gaagaagact ggaatattac   5160
gattaaaagt aaccatttac cttcgggatt aactttatgg atgggcgata ttaagaatgg   5220
ttcagaaaca gtaaaactgg tccagaaggt aaaaaattgg tatgattcgc atatgccaga   5280
aagcttgaaa atatatacag aactcgatca tgcaaattct agatttatgg atggactatc   5340
taaactagat cgcttacacg agactcatga cgattacagc gatcagatat ttgagtctct   5400
tgagaggaat gactgtacct gtcaaaagta tcctgaaatc acagaagtta gagatgcagt   5460
tgccacaatt agacgttcct ttagaaaaat aactaaagaa tctggtgccg atatcgaacc   5520
tcccgtacaa actagcttat tggatgattg ccagacctta aaaggagttc ttacttgctt   5580
aatacctggt gctggtggtt atgacgccat tgcagtgatt actaagcaag atgttgatct   5640
tagggctcaa accgctaatg acaaaagatt ttctaaggtt caatggctgg atgtaactca   5700
ggctgactgg ggtgttagga aagaaaaaga tccggaaact tatcttgata aataacttaa   5760
ggtagctgca tgcagaattc gcccttaagg aggaaaaaaa aatgaccgtt tacacagcat   5820
```

```
ccgttaccgc acccgtcaac atcgcaaccc ttaagtattg ggggaaaagg gacacgaagt   5880
tgaatctgcc caccaattcg tccatatcag tgactttatc gcaagatgac ctcagaacgt   5940
tgacctctgc ggctactgca cctgagtttg aacgcgacac tttgtggtta aatggagaac   6000
cacacagcat cgacaatgaa agaactcaaa attgtctgcg cgacctacgc caattaagaa   6060
aggaaatgga atcgaaggac gcctcattgc ccacattatc tcaatggaaa ctccacattg   6120
tctccgaaaa taactttcct acagcagctg gtttagcttc ctccgctgct ggctttgctg   6180
cattggtctc tgcaattgct aagttatacc aattaccaca gtcaacttca gaaatatcta   6240
gaatagcaag aaaggggtct ggttcagctt gtagatcgtt gtttggcgga tacgtggcct   6300
gggaaatggg aaaagctgaa gatggtcatg attccatggc agtacaaatc gcagacagct   6360
ctgactggcc tcagatgaaa gcttgtgtcc tagttgtcag cgatattaaa aaggatgtga   6420
gttccactca gggtatgcaa ttgaccgtgg caacctccga actatttaaa gaaagaattg   6480
aacatgtcgt accaaagaga tttgaagtca tgcgtaaagc cattgttgaa aaagatttcg   6540
ccacctttgc aaaggaaaca atgatggatt ccaactcttt ccatgccaca tgtttggact   6600
ctttccctcc aatattctac atgaatgaca cttccaagcg tatcatcagt tggtgccaca   6660
ccattaatca gttttacgga gaaacaatcg ttgcatacac gtttgatgca ggtccaaatg   6720
ctgtgttgta ctacttagct gaaaatgagt cgaaactctt tgcatttatc tataaattgt   6780
ttggctctgt tcctggatgg gacaagaaat ttactactga gcagcttgag gctttcaacc   6840
atcaatttga atcatctaac tttactgcac gtgaattgga tcttgagttg caaaaggatg   6900
ttgccagagt gattttaact caagtcggtt caggcccaca agaaacaaac gaatctttga   6960
ttgacgcaaa gactggtcta ccaaaggaat aagatcaatt cgctgcatcg cccttaggag   7020
gtaaaaaaaa atgactgccg acaacaatag tatgccccat ggtgcagtat ctagttacgc   7080
caaattagtg caaaaccaaa cacctgaaga cattttggaa gagtttcctg aaattattcc   7140
attacaacaa agacctaata cccgatctag tgagacgtca aatgacgaaa gcggagaaac   7200
atgtttttct ggtcatgatg aggagcaaat taagttaatg aatgaaaatt gtattgtttt   7260
ggattgggac gataatgcta ttggtgccgg taccaagaaa gtttgtcatt taatggaaaa   7320
tattgaaaag ggtttactac atcgtgcatt ctccgtcttt attttcaatg aacaaggtga   7380
attactttta caacaaagag ccactgaaaa aataactttc cctgatcttt ggactaacac   7440
atgctgctct catccactat gtattgatga cgaattaggt ttgaagggta agctagacga   7500
taagattaag ggcgctatta ctgcggcggt gagaaaacta gatcatgaat taggtattcc   7560
agaagatgaa actaagacaa ggggtaagtt tcacttttta aacagaatcc attacatggc   7620
accaagcaat gaaccatggg gtgaacatga aattgattac atcctatttt ataagatcaa   7680
cgctaaagaa aacttgactg tcaacccaaa cgtcaatgaa gttagagact tcaaatgggt   7740
ttcaccaaat gatttgaaaa ctatgtttgc tgacccaagt tacaagttta cgccttggtt   7800
taagattatt tgcgagaatt acttattcaa ctggtgggag caattagatg acctttctga   7860
agtggaaaat gacaggcaaa ttcatagaat gctataacaa cgcgtctaca aataaaaaag   7920
gcacgtcaga tgacgtgcct tttttcttgg ggccgaaaaa tgccccgctt acgcagggca   7980
tccatttatt actcaaccgt aaccgatttt gccaggttac gcggctggtc aacgtcggtg   8040
cctttgatca gcgcgacatg gtaagccagc agctgcagcg gaacggtgta gaagatcggt   8100
gcaatcacct cttccacatg cggcatctcg atgatgtgca tgttatcgct acttacaaaa   8160
cccgcatcct gatcggcgaa gacatacaac tgaccgccac gcgcgcgaac ttcttcaatg   8220
```

```
ttggatttca gtttttccag caattcgttg ttcggtgcaa caacaataac cggcatatcg   8280

gcatcaatta gcgccagcgg accgtgtttc agttcgccag cagcgtaggc ttcagcgtga   8340

atgtaagaga tctctttcaa cttcaatgcg ccttccagcg cgattgggta ctgatcgcca   8400

cggcccagga acagcgcgtg atgtttgtca gagaaatctt ctgccagcgc ttcaatgcgt   8460

ttgtcctgag acagcatctg ctcaatacgg ctcggcagcg cctgcagacc atgcacgatg   8520

tcatgttcaa tggaggcatc cagacctttc aggcgagaca gcttcgccac cagcatcaac   8580

agcacagtta actgagtggt gaatgcttta gtggatgcca cgccgatttc tgtacccgcg   8640

ttggtcatta gcgccagatc ggattcgcgc accagagaag aacccggaac gttacagatt   8700

gccagtgaac caaggtaacc cagctctttc gacagacgca ggccagccag ggtatccgcg   8760

gtttcgccag actgtgacaa ggtgatcatc aggctgttac gacgcacggc agatttgcga   8820

tagcggaatt cagaggcgat ttcgacgtcg cacggaatac ctgctagcga ttcaaaccag   8880

tagcgggaaa ccataccgga gttataagaa gtaccacagg cgaggatctg aatatgctca   8940

accttcgaca gcagttcgtc ggcgttcggt cccagctcgc ttaaatcaac ctgaccgtgg   9000

ctgatgcgtc cggtaagggt gtttttgatc gcgttcggct gttcgtagat ctctttctgc   9060

atgtagtgac ggtaaatgcc tttatcgccc gcgtcatatt gcagattgga ttcgatatcc   9120

tgacgtttta cttccgcgcc agttttatcg aagatgttta ccgaacggcg agtga        9175
```

<210> SEQ ID NO 59
<211> LENGTH: 40
<212> TYPE: DNA
<213> ORGANISM: Artificial Sequence
<220> FEATURE:
<223> OTHER INFORMATION: Primer (Tn7dS_6038-7-1)

<400> SEQUENCE: 59

```
tcgagctcgg taccctgttt ttccactctt cgttcacttt                          40
```

<210> SEQ ID NO 60
<211> LENGTH: 33
<212> TYPE: DNA
<213> ORGANISM: Artificial Sequence
<220> FEATURE:
<223> OTHER INFORMATION: Primer (Tn7dA_6038-7-2)

<400> SEQUENCE: 60

```
aggcttcatt ttaatcaaac atcctgccaa ctc                                 33
```

<210> SEQ ID NO 61
<211> LENGTH: 25
<212> TYPE: DNA
<213> ORGANISM: Artificial Sequence
<220> FEATURE:
<223> OTHER INFORMATION: Primer (Tn7dattLcmS_6038-7-4)

<400> SEQUENCE: 61

```
attaaaatga agcctgcttt tttat                                          25
```

<210> SEQ ID NO 62
<211> LENGTH: 32
<212> TYPE: DNA
<213> ORGANISM: Artificial Sequence
<220> FEATURE:
<223> OTHER INFORMATION: Primer (PgiattRcmA_6038-7-5)

<400> SEQUENCE: 62

-continued

```
ggcatcgtca agggccgctc aagttagtat aa                               32


<210> SEQ ID NO 63
<211> LENGTH: 99
<212> TYPE: DNA
<213> ORGANISM: Artificial Sequence
<220> FEATURE:
<223> OTHER INFORMATION: Primer (gi1.2-MVK-S_6038-7-6)

<400> SEQUENCE: 63

gcccttgacg atgccacatc ctgagcaaat aattcaacca ctaattgtga gcggataaca     60

caaggaggaa acagctatgt cattaccgtt cttaacttc                            99


<210> SEQ ID NO 64
<211> LENGTH: 96
<212> TYPE: DNA
<213> ORGANISM: Artificial Sequence
<220> FEATURE:
<223> OTHER INFORMATION: Primer (pMW-TaspA-yIDIA_6038-7-7)

<400> SEQUENCE: 64

ctctagagga tccccggccc caagaaaaaa ggcacgtcat ctgacgtgcc ttttttattt     60

gtagacgcgt tgttatagca ttctatgaat ttgcct                               96


<210> SEQ ID NO 65
<211> LENGTH: 36
<212> TYPE: DNA
<213> ORGANISM: Artificial Sequence
<220> FEATURE:
<223> OTHER INFORMATION: Primer (Tn7upSv02_6038-24-1)

<400> SEQUENCE: 65

atcctctaga gtcgaaagaa aaatgccccg cttacg                               36


<210> SEQ ID NO 66
<211> LENGTH: 37
<212> TYPE: DNA
<213> ORGANISM: Artificial Sequence
<220> FEATURE:
<223> OTHER INFORMATION: Primer (Tn7upAv02_6038-24-2)

<400> SEQUENCE: 66

atgcctgcag gtcgactgtc acagtctggc gaaaccg                              37


<210> SEQ ID NO 67
<211> LENGTH: 20
<212> TYPE: DNA
<213> ORGANISM: Artificial Sequence
<220> FEATURE:
<223> OTHER INFORMATION: Primer (Tn7v02-F_6038-22-5)

<400> SEQUENCE: 67

acgaactgct gtcgaaggtt                                                 20


<210> SEQ ID NO 68
<211> LENGTH: 20
<212> TYPE: DNA
<213> ORGANISM: Artificial Sequence
<220> FEATURE:
<223> OTHER INFORMATION: Primer (Tn7v02-R_6038-22-6)

<400> SEQUENCE: 68

ggtgtacgcc aggttgttct                                                 20
```

<210> SEQ ID NO 69
<211> LENGTH: 2414
<212> TYPE: DNA
<213> ORGANISM: Artificial Sequence
<220> FEATURE:
<223> OTHER INFORMATION: Nucleotide sequence of genomic fragment containing attL-Tet-attR-Ptac

<400> SEQUENCE: 69

```
tgaagcctgc tttttttatac taagttggca ttataaaaaa gcattgctta tcaatttgtt     60
gcaacgaaca ggtcactatc agtcaaaata aaatcattat ttgatttcga attccccgga    120
tccgtcgacc tgcagggaaa aaggttatgc tgcttttaag acccactttc acatttaagt    180
tgtttttcta atccgcatat gatcaattca aggccgaata agaaggctgg ctctgcacct    240
tggtgatcaa ataattcgat agcttgtcgt aataatggcg gcatactatc agtagtaggt    300
gtttcccttt cttctttagc gacttgatgc tcttgatctt ccaatacgca acctaaagta    360
aaatgcccca cagcgctgag tgcatataat gcattctcta gtgaaaaacc ttgttggcat    420
aaaaaggcta attgattttc gagagtttca tactgttttt ctgtaggccg tgtacctaaa    480
tgtacttttg ctccatcgcg atgacttagt aaagcacatc taaaactttt agcgttatta    540
cgtaaaaaat cttgccagct ttccccttct aaagggcaaa agtgagtatg gtgcctatct    600
aacatctcaa tggctaaggc gtcgagcaaa gcccgcttat tttttacatg ccaatacaat    660
gtaggctgct ctacacctag cttctgggcg agtttacggg ttgttaaacc ttcgattccg    720
acctcattaa gcagctctaa tgcgctgtta atcactttac ttttatctaa tctagacatc    780
attaattcct aatttttgtt gacactctat cattgataga gttattttac cactccctat    840
cagtgataga gaaaagtgaa atgaatagtt cgacaaagat cgcattggta attacgttac    900
tcgatgccat ggggattggc cttatcatgc cagtcttgcc aacgttatta cgtgaattta    960
ttgcttcgga agatatcgct aaccactttg gcgtattgct tgcactttat gcgttaatgc   1020
aggttatctt tgctccttgg cttggaaaaa tgtctgaccg atttggtcgg cgcccagtgc   1080
tgttgttgtc attaataggc gcatcgctgg attacttatt gctggctttt tcaagtgcgc   1140
tttggatgct gtatttaggc cgtttgcttt cagggatcac aggagctact ggggctgtcg   1200
cggcatcggt cattgccgat accacctcag cttctcaacg cgtgaagtgg ttcggttggt   1260
taggggcaag ttttgggctt ggtttaatag cggggcctat tattggtggt tttgcaggag   1320
agatttcacc gcatagtccc ttttttatcg ctgcgttgct aaatattgtc actttccttg   1380
tggttatgtt ttggttccgt gaaaccaaaa atacacgtga taatacagat accgaagtag   1440
gggttgagac gcaatcgaat tcggtataca tcactttatt taaaacgatg cccattttgt   1500
tgattattta tttttcagcg caattgatag gccaaattcc cgcaacggtg tgggtgctat   1560
ttaccgaaaa tcgttttgga tggaatagca tgatggttgg cttttcatta gcgggtcttg   1620
gtcttttaca ctcagtattc caagcctttg tggcaggaag aatagccact aaatggggcg   1680
aaaaaacggc agtactgctc gaatttattg cagatagtag tgcatttgcc tttttagcgt   1740
ttatatctga aggttggtta gatttccctg ttttaatttt attggctggt ggtgggatcg   1800
ctttacctgc attacaggga gtgatgtcta tccaaacaaa gagtcatgag caaggtgctt   1860
tacagggatt attggtgagc cttaccaatg caaccggtgt tattggccca ttactgttta   1920
ctgttattta taatcattca ctaccaattt gggatggctg gatttggatt attggtttag   1980
cgttttactg tattattatc ctgctatcga tgaccttcat gttaacccct caagctcagg   2040
ggagtaaaca ggagacaagt gcttagttat ttcgtcacca aatgatgtta ttccgcgaaa   2100
```

-continued

```
tataatgacc ctcttgataa cccaagaggg catttttttac gataaagaag atttagcttc   2160

tgcagtctgt tacaggtcac taataccatc taagtagttg attcatagtg actgcatatg   2220

ttgtgtttta cagtattatg tagtctgttt tttatgcaaa atctaattta atatattgat   2280

atttatatca ttttacgttt ctcgttcagc ttttttatac taacttgagc gagatctccc   2340

tgttgacaat taatcatcgg ctctataatg tgtggaatcg tgagcggata acaatttcac   2400

acaaggagac tgcc                                                       2414
```

<210> SEQ ID NO 70
<211> LENGTH: 7464
<212> TYPE: DNA
<213> ORGANISM: Artificial Sequence
<220> FEATURE:
<223> OTHER INFORMATION: Nucleotide sequence containing genomic sequence encoding downstream enzymes in the mevalonate pathway under control of tac promoter

<400> SEQUENCE: 70

```
ttagtacagc ggcttaccgc tactgtcttt aatattggtc ttccacgcag cgcgaacctg     60

ttcaactaca ctatccggca ggctggcgta atccaggtcg ttcgcctgtt tagccccggt    120

tttgtacgcc cagtcgaaga atttcagcac ttctgtgcct tgttctggtt tcttctgatc    180

tttgtggatc agaatgaacg tggtagaggt aataggccat gcatcttcgc ctttctggtt    240

ggtcagatcc tgagcgaagg ttttgctcca gtctgcacct tttgctgcat tagcgaagtt    300

ttcttcggtc ggactaaccg gtttaccatc agcggagatc agtttggtgt acgccaggtt    360

gttctgcttc gcgtaagcat attcaacata accaattgca cccggcagac gctgaacgaa    420

cgcggcgata ccgtcgttac ctttaccgcc cagaccgatc ggccatttta cggtagagcc    480

agtaccaacg ttgtttttcc actcttcgtt cactttcgcc aggtagctgg tgaagacgaa    540

ggaagtcccg gagccatctg cgcggcgtac tacagcaatg ttttgtgaag gcagtttcag    600

acccggattc agtttggcga tggcttcatc atcccacttc ttgattttgc ccaggtagat    660

gtcgccgagg gttttaccat ccagcaccag ttcgccagac ttcagccctg gaatgttaac    720

cgccagcacc acgccgccaa tcacggtcgg gaactggaac agaccttcct gagccagttt    780

ttcgtcagac agcggcgcgt cagaggcacc aaaatcaacg gtattagcga taatctgttt    840

tacgccaccg gaagaaccga taccctggta gttaacttta ttaccggttt ctttctggta    900

agtgtcagcc catttggcat acaccggcgc agggaaggtt gcacctgcac ctgtcaggct    960

tgcttctgca aacacagaga aagcactcat cgataaggtc gcggcgacaa cagttgcgac   1020

ggtggtacgc ataactttca taatgtctcc tgggaggatt cataaagcat tgtttgttgg   1080

ctacgagaag caaaatagga caaacaggtg acagttatat gtaaggaata tgacagtttt   1140

atgacagaga gataaagtct tcagtctgat ttaaataagc gttgatattc agtcaattac   1200

tgaagcctgc tttttttatac taacttgagc gagatctccc tgttgacaat taatcatcgg   1260

ctctataatg tgtggaatcg tgagcggata acaatttcac acaaggagac tgccatgtca   1320

ttaccgttct taacttctgc accgggaaag gttattattt ttggtgaaca ctctgctgtg   1380

tacaacaagc ctgccgtcgc tgctagtgtg tctgcgttga gaacctacct gctaataagc   1440

gagtcatctg caccagatac tattgaattg gacttcccgg acattagctt taatcataag   1500

tggtccatca atgatttcaa tgccatcacc gaggatcaag taaactccca aaaattggcc   1560

aaggctcaac aagccaccga tggcttgtct caggaactcg ttagtctttt ggatccgttg   1620
```

-continued

```
ttagctcaac tatccgaatc cttccactac catgcagcgt tttgtttcct gtatatgttt   1680
gtttgcctat gcccccatgc caagaatatt aagttttcct taaagtctac tttacccatc   1740
ggtgctgggt tgggctcaag cgcctctatt tctgtatcac tggccttagc tatggcctac   1800
ttggggggt taataggatc taatgacttg gaaaagctgt cagaaaacga taagcatata   1860
gtgaatcaat gggccttcat aggtgaaaag tgtattcacg gtacccttc aggaatagat    1920
aacgctgtgg ccacttatgg taatgccctg ctatttgaaa aagactcaca taatggaaca   1980
ataaacacaa acaattttaa gttcttagat gatttcccag ccattccaat gatcctaacc   2040
tatactagaa ttccaaggtc tacaaaagat cttgttgctc gcgttcgtgt gttggtcacc   2100
gagaaatttc ctgaagttat gaagccaatt ctagatgcca tgggtgaatg tgccctacaa   2160
ggcttagaga tcatgactaa gttaagtaaa tgtaaaggca ccgatgacga ggctgtagaa   2220
actaataatg aactgtatga acaactattg gaattgataa gaataaatca tggactgctt   2280
gtctcaatcg gtgtttctca tcctggatta gaacttatta aaaatctgag cgatgatttg   2340
agaattggct ccacaaaact taccggtgct ggtggcggcg gttgctcttt gactttgtta   2400
cgaagagaca ttactcaaga gcaaattgac agcttcaaaa agaaattgca agatgatttt   2460
agttacgaga catttgaaac agacttgggt gggactggct gctgtttgtt aagcgcaaaa   2520
aatttgaata aagatcttaa aatcaaatcc ctagtattcc aattatttga aaataaaact   2580
accacaaagc aacaaattga cgatctatta ttgccaggaa acacgaattt accatggact   2640
tcataagcta atttgcgata ggcctgcacc cttaaggagg aaaaaaacat gtcagagttg   2700
agagccttca gtgccccagg gaaagcgtta ctagctggtg gatatttagt tttagataca   2760
aaatatgaag catttgtagt cggattatcg gcaagaatgc atgctgtagc ccatccttac   2820
ggttcattgc aagggtctga taagtttgaa gtgcgtgtga aaagtaaaca atttaaagat   2880
ggggagtggc tgtaccatat aagtcctaaa agtggcttca ttcctgtttc gataggcgga   2940
tctaagaacc ctttcattga aaaagttatc gctaacgtat ttagctactt taaacctaac   3000
atggacgact actgcaatag aaacttgttc gttattgata ttttctctga tgatgcctac   3060
cattctcagg aggatagcgt taccgaacat cgtggcaaca gaagattgag ttttcattcg   3120
cacagaattg aagaagttcc caaaacaggg ctgggctcct cggcaggttt agtcacagtt   3180
ttaactacag ctttggcctc cttttttgta tcggacctgg aaaataatgt agacaaatat   3240
agagaagtta ttcataattt agcacaagtt gctcattgtc aagctcaggg taaaattgga   3300
agcgggtttg atgtagcggc ggcagcatat ggatctatca gatatagaag attcccaccc   3360
gcattaatct ctaatttgcc agatattgga agtgctactt acggcagtaa actggcgcat   3420
ttggttgatg aagaagactg gaatattacg attaaaagta accatttacc ttcgggatta   3480
actttatgga tgggcgatat taagaatggt tcagaaacag taaaactggt ccagaaggta   3540
aaaaattggt atgattcgca tatgccagaa agcttgaaaa tatatacaga actcgatcat   3600
gcaaattcta gatttatgga tggactatct aaactagatc gcttacacga gactcatgac   3660
gattacagcg atcagatatt tgagtctctt gagaggaatg actgtacctg tcaaaagtat   3720
cctgaaatca cagaagttag agatgcagtt gccacaatta gacgttcctt tagaaaaata   3780
actaaagaat ctggtgccga tatcgaacct cccgtacaaa ctagcttatt ggatgattgc   3840
cagaccttaa aaggagttct tacttgctta atacctggtg ctggtggtta tgacgccatt   3900
gcagtgatta ctaagcaaga tgttgatctt agggctcaaa ccgctaatga caaaagattt   3960
tctaaggttc aatggctgga tgtaactcag gctgactggg gtgttaggaa agaaaaagat   4020
```

```
ccggaaactt atcttgataa ataacttaag gtagctgcat gcagaattcg cccttaagga   4080
ggaaaaaaaa atgaccgttt acacagcatc cgttaccgca cccgtcaaca tcgcaaccct   4140
taagtattgg gggaaaaggg acacgaagtt gaatctgccc accaattcgt ccatatcagt   4200
gactttatcg caagatgacc tcagaacgtt gacctctgcg gctactgcac ctgagtttga   4260
acgcgacact ttgtggttaa atggagaacc acacagcatc gacaatgaaa gaactcaaaa   4320
ttgtctgcgc gacctacgcc aattaagaaa ggaaatggaa tcgaaggacg cctcattgcc   4380
cacattatct caatggaaac tccacattgt ctccgaaaat aactttccta cagcagctgg   4440
tttagcttcc tccgctgctg gctttgctgc attggtctct gcaattgcta agttatacca   4500
attaccacag tcaacttcag aaatatctag aatagcaaga aaggggtctg gttcagcttg   4560
tagatcgttg tttggcggat acgtggcctg ggaaatggga aaagctgaag atggtcatga   4620
ttccatggca gtacaaatcg cagacagctc tgactggcct cagatgaaag cttgtgtcct   4680
agttgtcagc gatattaaaa aggatgtgag ttccactcag ggtatgcaat tgaccgtggc   4740
aacctccgaa ctatttaaag aaagaattga acatgtcgta ccaaagagat ttgaagtcat   4800
gcgtaaagcc attgttgaaa aagatttcgc cacctttgca aaggaaacaa tgatggattc   4860
caactctttc catgccacat gtttggactc tttccctcca atattctaca tgaatgacac   4920
ttccaagcgt atcatcagtt ggtgccacac cattaatcag ttttacggag aaacaatcgt   4980
tgcatacacg tttgatgcag gtccaaatgc tgtgttgtac tacttagctg aaaatgagtc   5040
gaaactcttt gcatttatct ataaattgtt tggctctgtt cctggatggg acaagaaatt   5100
tactactgag cagcttgagg ctttcaacca tcaatttgaa tcatctaact ttactgcacg   5160
tgaattggat cttgagttgc aaaaggatgt tgccagagtg attttaactc aagtcggttc   5220
aggcccacaa gaaacaaacg aatctttgat tgacgcaaag actggtctac caaaggaata   5280
agatcaattc gctgcatcgc ccttaggagg taaaaaaaaa tgactgccga caacaatagt   5340
atgccccatg gtgcagtatc tagttacgcc aaattagtgc aaaaccaaac acctgaagac   5400
attttggaag agtttcctga aattattcca ttacaacaaa gacctaatac ccgatctagt   5460
gagacgtcaa atgacgaaag cggagaaaca tgtttttctg gtcatgatga ggagcaaatt   5520
aagttaatga atgaaaattg tattgttttg gattgggacg ataatgctat tggtgccggt   5580
accaagaaag tttgtcattt aatggaaaat attgaaaagg gtttactaca tcgtgcattc   5640
tccgtcttta ttttcaatga acaaggtgaa ttacttttac aacaaagagc cactgaaaaa   5700
ataactttcc ctgatctttg gactaacaca tgctgctctc atccactatg tattgatgac   5760
gaattaggtt tgaagggtaa gctagacgat aagattaagg gcgctattac tgcggcggtg   5820
agaaaactag atcatgaatt aggtattcca gaagatgaaa ctaagacaag gggtaagttt   5880
cactttttaa acagaatcca ttacatggca ccaagcaatg aaccatgggg tgaacatgaa   5940
attgattaca tcctatttta taagatcaac gctaaagaaa acttgactgt caacccaaac   6000
gtcaatgaag ttagagactt caaatgggtt tcaccaaatg atttgaaaac tatgtttgct   6060
gacccaagtt acaagtttac gccttggttt aagattattt gcgagaatta cttattcaac   6120
tggtgggagc aattagatga cctttctgaa gtggaaaatg acaggcaaat tcatagaatg   6180
ctataacaac gcgtctacaa ataaaaaagg cacgtcagat gacgtgcctt ttttcttggg   6240
gccgaaaaat gccccgctta cgcagggcat ccatttatta ctcaaccgta accgattttg   6300
ccaggttacg cggctggtca acgtcggtgc ctttgatcag cgcgacatgg taagccagca   6360
```

gctgcagcgg aacggtgtag aagatcggtg caatcacctc ttccacatgc ggcatctcga 6420
tgatgtgcat gttatcgcta cttacaaaac ccgcatcctg atcggcgaag acatacaact 6480
gaccgccacg cgcgcgaact tcttcaatgt tggatttcag tttttccagc aattcgttgt 6540
tcggtgcaac aacaataacc ggcatatcgg catcaattag cgccagcgga ccgtgtttca 6600
gttcgccagc agcgtaggct tcagcgtgaa tgtaagagat ctctttcaac ttcaatgcgc 6660
cttccagcgc gattgggtac tgatcgccac ggcccaggaa cagcgcgtga tgtttgtcag 6720
agaaatcttc tgccagcgct tcaatgcgtt tgtcctgaga cagcatctgc tcaatacggc 6780
tcggcagcgc ctgcagacca tgcacgatgt catgttcaat ggaggcatcc agacctttca 6840
ggcgagacag cttcgccacc agcatcaaca gcacagttaa ctgagtggtg aatgctttag 6900
tggatgccac gccgatttct gtacccgcgt tggtcattag cgccagatcg gattcgcgca 6960
ccagagaaga acccggaacg ttacagattg ccagtgaacc aaggtaaccc agctctttcg 7020
acagacgcag gccagccagg gtatccgcgg tttcgccaga ctgtgacaag gtgatcatca 7080
ggctgttacg acgcacggca gatttgcgat agcggaattc agaggcgatt tcgacgtcgc 7140
acggaatacc tgctagcgat tcaaaccagt agcgggaaac cataccggag ttataagaag 7200
taccacaggc gaggatctga atatgctcaa ccttcgacag cagttcgtcg gcgttcggtc 7260
ccagctcgct taaatcaacc tgaccgtggc tgatgcgtcc ggtaagggtg tttttgatcg 7320
cgttcggctg ttcgtagatc tctttctgca tgtagtgacg gtaaatgcct ttatcgcccg 7380
cgtcatattg cagattggat tcgatatcct gacgttttac ttccgcgcca gttttatcga 7440
agatgtttac cgaacggcga gtga 7464

<210> SEQ ID NO 71
<211> LENGTH: 70
<212> TYPE: DNA
<213> ORGANISM: Artificial Sequence
<220> FEATURE:
<223> OTHER INFORMATION: Primer (APtacKKDyIv03_6038-36-5)

<400> SEQUENCE: 71
gataaagtct tcagtctgat ttaaataagc gttgatattc agtcaattac tgaagcctgc 60
tttttatac 70

<210> SEQ ID NO 72
<211> LENGTH: 71
<212> TYPE: DNA
<213> ORGANISM: Artificial Sequence
<220> FEATURE:
<223> OTHER INFORMATION: Primer (SPtacKKDyIv02_6038-36-3)

<400> SEQUENCE: 72
tcaccaaaaa taataacctt tcccggtgca gaagttaaga acggtaatga catggcagtc 60
tccttgtgtg a 71